US008188071B2

(12) United States Patent
Jimenez et al.

(10) Patent No.: US 8,188,071 B2
(45) Date of Patent: May 29, 2012

(54) AMINO SUBSTITUTED PYRIDINES AS POTENT KINASE INHIBITORS

(75) Inventors: Juan-Miguel Jimenez, Abingdon (GB); Guy Bemis, Arlington, MA (US); Francois Maltais, Tewksbury, MA (US); Tiansheng Wang, Concord, MA (US); Ronald Knegtel, Abingdon (GB); Chris Davis, Salisbury (GB); Damien Fraysse, Abingdon (GB); Dean Boyall, Faringdon (GB); Luca Settimo, Wood Farm Road (GB); Stephen Young, Oxford (GB); Michael Mortimore, Burford (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 179 days.

(21) Appl. No.: 12/187,909

(22) Filed: Aug. 7, 2008

(65) Prior Publication Data
US 2009/0124602 A1 May 14, 2009

Related U.S. Application Data

(63) Continuation-in-part of application No. PCT/US2008/052443, filed on Jan. 30, 2008.

(60) Provisional application No. 60/898,643, filed on Jan. 31, 2007, provisional application No. 60/913,867, filed on Apr. 25, 2007, provisional application No. 60/969,312, filed on Aug. 31, 2007, provisional application No. 61/014,893, filed on Dec. 19, 2007.

(51) Int. Cl.
A61K 31/551 (2006.01)

(52) U.S. Cl. ........................ 514/218; 540/575
(58) Field of Classification Search ................ 540/575
See application file for complete search history.

(56) References Cited

U.S. PATENT DOCUMENTS

| 3,853,898 | A | 12/1974 | Hardtmann et al. |
| 4,783,472 | A | 11/1988 | Fabre et al. |
| 5,001,137 | A | 3/1991 | Oe et al. |
| 5,100,768 | A | 3/1992 | Niki et al. |
| 5,202,224 | A | 4/1993 | Yamakawa et al. |
| 5,308,854 | A | 5/1994 | Hoffman et al. |
| 5,385,880 | A | 1/1995 | Miyazaki et al. |
| 5,439,916 | A | 8/1995 | Ganguly et al. |
| 5,476,750 | A | 12/1995 | Chu et al. |
| 5,643,744 | A | 7/1997 | Nitta et al. |
| 5,646,330 | A | 7/1997 | Shieh et al. |
| 5,760,032 | A | 6/1998 | Kitajima et al. |
| 5,817,670 | A | 10/1998 | Takayama et al. |
| 5,885,935 | A | 3/1999 | Gates et al. |
| 6,136,810 | A | 10/2000 | Takayama et al. |
| 6,194,581 | B1 | 2/2001 | Cosford et al. |
| 6,225,329 | B1 | 5/2001 | Richter et al. |
| 6,303,655 | B1 | 10/2001 | Takehana et al. |
| 6,436,961 | B1 | 8/2002 | Watson et al. |
| 6,452,008 | B2 | 9/2002 | Muraoka et al. |
| 6,638,935 | B2 | 10/2003 | Emig et al. |
| 6,673,789 | B2 | 1/2004 | Dickinson et al. |
| 6,770,662 | B2 | 8/2004 | Nishide et al. |
| 6,831,175 | B2 | 12/2004 | Li et al. |

| 2002/0115642 | A1 | 8/2002 | Chan et al. |
| 2003/0187026 | A1 | 10/2003 | Li et al. |
| 2004/0058903 | A1 | 3/2004 | Takasugi et al. |
| 2004/0142982 | A1 | 7/2004 | Jimenez Mayorga et al. |
| 2004/0176355 | A1 | 9/2004 | Sasikumar et al. |
| 2004/0176395 | A1 | 9/2004 | Flynn et al. |
| 2005/0004125 | A1 | 1/2005 | Freyne et al. |
| 2005/0049274 | A1 | 3/2005 | Wall et al. |
| 2005/0203067 | A1 | 9/2005 | Hresko et al. |
| 2005/0277640 | A1 | 12/2005 | Dixon et al. |
| 2005/0288286 | A1 | 12/2005 | Flynn et al. |
| 2006/0020034 | A1 | 1/2006 | Garcia et al. |
| 2006/0030583 | A1 | 2/2006 | Arnold et al. |
| 2006/0167251 | A1 | 7/2006 | Fleming et al. |
| 2006/0205739 | A1 | 9/2006 | Eberle et al. |
| 2006/0217387 | A1 | 9/2006 | McArthur et al. |
| 2006/0252764 | A1 | 11/2006 | Guillemont et al. |
| 2006/0276510 | A1 | 12/2006 | Abu-Shakra et al. |
| 2007/0037794 | A1 | 2/2007 | Ungashe et al. |
| 2007/0037811 | A1 | 2/2007 | Lewi et al. |
| 2007/0043068 | A1 | 2/2007 | Arnold et al. |
| 2007/0078140 | A1 | 4/2007 | Borzilleri et al. |
| 2007/0275954 | A1 | 11/2007 | Basarab et al. |
| 2008/0039477 | A1 | 2/2008 | Freyne et al. |
| 2009/0030017 | A1 | 1/2009 | Hanada et al. |
| 2009/0143352 | A1 | 6/2009 | Arnold et al. |
| 2009/0227799 | A1 | 9/2009 | Nakamoto et al. |
| 2011/0118248 | A1 | 5/2011 | Ungashe et al. |

FOREIGN PATENT DOCUMENTS

| EP | 0359547 | 3/1990 |
| GB | 2208862 | 4/1989 |
| WO | 9857957 | 12/1998 |
| WO | 02072571 | 9/2002 |
| WO | 03099773 | 12/2003 |
| WO | 2005000813 | 1/2005 |
| WO | 2005028479 | 3/2005 |
| WO | 2008124849 | 10/2008 |

OTHER PUBLICATIONS

Martinez-Viturro, et al., "Synthesis of aza analogues of the anticancer agent batracylin", www.sciencedirect.com, Tetrahedron letters 48 (2007) 4707-4710.
Geng, et al., "Potent and selective inhibitors of Helicobacter pylori glutamate racemase (MurI): Pyridodiazepine amines", Bioorganic & Medicinal Chemistry Letters (2009) vol. 19, Issue 3, p. 930.
Gungor et al., "Metallation Regioselective en Serie Pyridinique: Synthese Originale D'Amino-2 Aroyl-3 Pyridines", J Organomet Chem 215( ): 139-150 1981.

Primary Examiner — James O Wilson
Assistant Examiner — Brian McDowell
(74) Attorney, Agent, or Firm — Min Lin

(57) ABSTRACT

The present invention relates to compounds useful as inhibitors of protein kinase of the following structural formula:

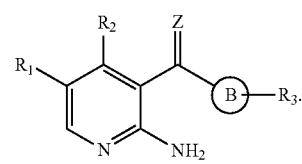

The invention also provides pharmaceutically acceptable compositions comprising said compounds and methods of using the compositions in the treatment of various disease, conditions, or disorders. The invention also provides processes for preparing compounds of the inventions.

14 Claims, No Drawings

AMINO SUBSTITUTED PYRIDINES AS POTENT KINASE INHIBITORS

RELATED APPLICATIONS

This application in a Continuation in Part of PCT Application No. PCT/US2008/052443 filed Jan. 30, 2008 entitled "Kinase Inhibitors", which claims the benefit under 35 U.S.C. §119, U.S. Provisional patent application No. 60/898,643, filed Jan. 31, 2007, entitled "Kinase Inhibitors", and of U.S. Provisional patent application No. 60/913,867, filed Apr. 25, 2007, entitled "Kinase Inhibitors", and of U.S. Provisional patent application No. 60/969,312 filed Aug. 31, 2007, entitled "Kinase Inhibitors", and of U.S. Provisional patent application No. 61/014,893 filed Dec. 19, 2007, entitled "Kinase Inhibitors", the entire contents of these applications are hereby incorporated by reference.

BACKGROUND OF THE INVENTION

Protein kinases constitute a large family of structurally related enzymes that are responsible for the control of a variety of signal transduction processes within the cell (see Hardie, G. and Hanks, S. *The Protein Kinase Facts Book, I and II*, Academic Press, San Diego, Calif.: 1995).

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g. shock, heat shock, ultraviolet radiation, bacterial endotoxin, and $H_2O_2$), cytokines (e.g. interleukin-1 (IL-1) and tumor necrosis factor alpha (TNF-a), and growth factors (e.g. granulocyte macrophage-colony stimulating factor (GM-CSF), and fibroblast growth factor (FGF)). An extracellular stimulus may affect one or more cellular responses related to cell growth, migration, differentiation, secretion of hormones, activation of transcription factors, muscle contraction, glucose metabolism, control of protein synthesis, survival and regulation of the cell cycle.

Kinases may be categorized into families by the substrates they phosphorylate (e.g. protein-tyrosine, protein-serine/threonine, lipids etc). Sequence motifs have been identified that generally correspond to each of these kinase families (See, for example, Hanks, S. K., Hunter, T., *FASEB J.* 1995, 9, 576-596; Knighton et al., *Science* 1991, 253, 407-414; Hiles et al, *Cell* 1992, 70, 419-429; Kunz et al, *Cell* 1993, 73, 585-596; Garcia-Bustos et al, *EMBO J* 1994, 13, 2352-2361).

A serine/threonine kinase, protein kinase C-theta (PKC-theta), is a member of the novel, calcium independent PKC subfamily that is selectively expressed in T cells and skeletal muscle. Several lines of evidence indicate that PKC-theta has an essential role in T cell activation. Upon antigen stimulation of T cells, PKC-theta, but not other PKC isoforms, rapidly translocates from the cytoplasm to the site of cell contact between the T cell and antigen-presenting cell (APC), where it localizes with the T cell receptor (TCR) in a region termed the central supramolecular activation cluster (cSMAC) (Monks et al., 1997, Nature, 385: 83-86; Monks et al., 1998, Nature, 395: 82-86).

It has been reported that PKC-theta selectively activates the transcription factors AP-1 and NF-κB and integrates TCR and CD28 co-stimulatory signals leading to the activation of the CD28 response element (CD28RE) in the IL-2 promotor (Baier-Bitterlich et al., 1996, Mol. Cell. Biol., 16: 1842-1850; Coudronniere et al., 2000, PNAS, 97: 3394-3399). The specific role for PKC-theta in CD3/CD28 co-stimulation of T cells is highlighted in a study where expression of a kinase-dead PKC-theta mutant, or anti-sense PKC-theta dose-dependently inhibited CD3/CD28 co-stimulated NF-κB activation, but not TNF-alpha-stimulated NF-κB activation. This was not seen with other PKC isoforms (Lin et al., 2000, Mol. Cell. Biol., 20: 2933-2940). Recruitment of PKC-theta to the SMAC is reported to be mediated by its N-terminal regulatory domain and is necessary for T cell activation, as an over-expressed PKC-theta catalytic fragment did not translocate and was unable to activate NF-κB, whereas a PKC-theta catalytic domain-Lck membrane-binding domain chimera was able to reconstitute signaling (Bi et al., 2001, Nat. Immunol., 2:556-563).

Translocation of PKC-theta to the SMAC appears to be mediated by a largely PLC-gamma/DAG-independent mechanism, involving Vav and PI3-kinase (Villalba et al., 2002, JCB 157: 253-263), whilst activation of PKC-theta requires input from several signaling components including Lck, ZAP-70, SLP-76, PLC-gamma, Vav and PI3-kinase (Liu et al., 2000, JBC, 275: 3606-3609; Herndon et al., 2001, J. Immunol., 166: 5654-5664; Dienz et al., 2002, J. Immunol., 169: 365-372; Bauer et al., 2001 JBC., 276: 31627-31634). These biochemical studies in human T cells have gained credence from studies in PKC-theta knockout mice, which have confirmed a crucial role for this enzyme in T cell function. PKC-theta−/− mice are healthy and fertile, have a normally developed immune system, but exhibit profound defects in mature T cell activation (Sun et al., 200, Nature, 404:402-407). Proliferative responses to TCR and TCR/CD28 co-stimulation were inhibited (>90%) as were in vivo responses to antigen. In agreement with studies on human T cells, activation of the transcription factors AP-1 and NF-κB was abrogated, resulting in a severe deficit in IL-2 production and IL-2 R upregulation (Baier-Bitterlich et al., 1996, MBC, 16, 1842; Lin et al., 2000, MCB, 20, 2933; Courdonniere, 2000, 97, 3394). More recently, studies in PKC-theta-deficient mice have indicated a role for PKC-theta in the development of mouse models of autoimmune diseases, including multiple sclerosis (MS), rheumatoid arthritis (RA) and irritable bowel disease (IBD) (Salek-Ardakani et al., 2006; Tan et al., 2006; Healy et al., 2006; Anderson et al., 2006). In these models, PKC-theta-deficient mice exhibited a marked reduction in disease severity that was associated with a profound defect in the development and effector function of autoreactive T cells.

In addition to its role in T cell activation, PKC-theta is reported to mediate the phorbol ester-triggered survival signal that protects T cells from Fas- and UV-induced apoptosis (Villalba et al., 2001, J. Immunol. 166: 5955-5963; Berttolotto et al., 2000, 275: 37246-37250). This pro-survival role is of interest because the human PKC-theta gene has been mapped to chromosome 10 (10p15), a region associated with mutations leading to T cell leukaemias and lymphomas (Erdel et al., 1995, Genomics 25: 295-297; Verma et al., 1987, J. Cancer Res. Clin. Oncol., 113: 192-196).

Another serine/threonine protein kinase, Glycogen synthase kinase-3 (GSK-3), is a comprised of □ and □ isoforms that are each encoded by distinct genes [Coghlan et al., Chemistry & Biology 2000, 7, 793-803; and Kim and Kimmel, Curr. Opinion Genetics Dev., 2000 10, 508-514]. GSK-3 has been implicated in various diseases, disorders, and conditions including diabetes, Alzheimer's disease, CNS diseases such as bipolar disorder, schizophrenia, cerebral stroke, Huntington's and other neurodegenerative diseases, leukocytopenia and cardiomyocyte hypertrophy [PCT Application Nos.: WO 99/65897 and WO 00/38675; and Haq et al., J. Cell Biol. 2000, 151, 117-130]. These diseases, disorders, and conditions are associated with the abnormal operation of certain cell signaling pathways in which GSK-3 plays a role. GSK-3 has been found to phosphorylate and modulate the activity of a number of regulatory proteins. These proteins include glycogen synthase, which is the rate limiting enzyme necessary for glycogen synthesis, the microtubule associated protein Tau, the gene transcription factor □-catenin, the translation initiation factor e1F2B, as well as ATP citrate lyase, axin, heat shock factor-1, c-Jun, c-myc, c-myb, CREB, and CEPB□. These diverse protein targets implicate GSK-3 in many aspects of cellular metabolism, proliferation, differentiation, and development.

In a GSK-3 mediated pathway that is relevant for the treatment of type II diabetes, insulin-induced signaling leads to cellular glucose uptake and glycogen synthesis. Along this pathway, GSK-3 is a negative regulator of the insulin-induced signal. Normally, the presence of insulin causes inhibition of GSK-3 mediated phosphorylation and deactivation of glycogen synthase. The inhibition of GSK-3 leads to increased glycogen synthesis and glucose uptake [Klein et al., PNAS 1996, 93, 8455-8459; Cross et al., Biochem. J. 1994, 303, 21-26); Cohen, Biochem. Soc. Trans. 1993, 21, 555-567; and Massillon et al., Biochem J. 1994, 299, 123-128]. However, in a diabetic patient, where the insulin response is impaired, glycogen synthesis and glucose uptake fail to increase despite the presence of relatively high blood levels of insulin. This leads to abnormally high blood levels of glucose with acute and long-term effects that may ultimately result in cardiovascular disease, renal failure and blindness. In such patients, the normal insulin-induced inhibition of GSK-3 fails to occur. It has also been reported that in patients with type II diabetes, GSK-3 is overexpressed [see, PCT Application: WO 00/38675]. Therapeutic inhibitors of GSK-3 are therefore potentially useful for treating diabetic patients suffering from an impaired response to insulin.

GSK-3 activity is associated with Alzheimer's disease. The hallmarks of this disease are the extracellular plaques formed by aggregated □ amyloid peptides and the formation of intracellular neurofibrillary tangles via the tau protein.

It has been shown that GSK-3 inhibition reduces amyloid-□ peptides in an animal model of Alzheimer's disease. See pages 435, 438. Phiel et. al., Nature 423, 435-439 (2003). Mice over-expressing amyloid precursor protein (APP) treated with lithium (a GSK-3□ inhibitor) over a three-week period showed over a 50% decrease in amyloid-□ peptide tissue levels.

The neurofibrillary tangles contain hyperphosphorylated Tau protein, in which Tau is phosphorylated on abnormal sites. GSK-3 is known to phosphorylate these abnormal sites in cell and animal models. Conditional transgenic mice that over-express GSK-3 develop aspects of AD including tau hyperphosphorylation, neuronal apoptosis and spatial learning deficit. Turning off GSK-3 in these mice restores normal behavior, reduces Tau hyperphosphorylation and neuronal apoptosis. (Engel T et al., J Neuro Sci, 2006, 26, 5083-5090 and Lucas et al, EMBO J, 2001, 20, 27-39) Inhibitors of GSK-3 have also been shown to prevent hyperphosphorylation of Tau in cells [Lovestone et al., Current Biology 1994, 4, 1077-86; and Brownlees et al., Neuroreport 1997, 8, 3251-55].

GSK-3 as a target for psychosis and mood disorders, such as schizophrenia and bipolar disease, respectively, have been reported in the literature. AKT haplotype deficiency was identified in a subset of schizophrenic patients which correlated with increased GSK-3 activity. A single allele knockout of GSK-3β resulted in attenuated hyperactivity in response to amphetamine in a behavior model of mania.

Several antipsychotic drugs and mood stabilizers used to treat both schizophrenic and bipolar patients have been shown to inhibit GSK-3 (Emamian et al, Nat Genet, 2004, 36, 131-137; Obrien et al, J Neurosci, 2004, 24, 6791-6798; Beaulieu et al, PNAS, 2004, 101, 5099-5104; Li et al Int J Neuropsychopharmacol, 2006, pp 1-13; Gould T D, Expert Opin Ther Targets, 2006, 10, 377-392). Furthermore, a recent patent, US 2004/0039007 describes GSK 3 inhibitors that show anti-schizophrenic and anxiolytic effects in relevant mouse behavior models.

GSK-3 activity is associated with stroke. Wang et al. showed that IGF-1 (insulin growth factor-1), a known GSK 3 inhibitor, reduced infarct size in rat brains after transient middle cerebral artery occlusion (MCAO), a model for stroke in rats. [Wang et al., Brain Res 2000, 859, 381-5; Sasaki et al., Neurol Res 2001, 23, 588-92; Hashimoto et al., J. Biol. Chem 2002, 277, 32985-32991]. US 2004/0039007 describes the effect of GSK 3 inhibitors in MCAO, a stroke model in rats. These GSK 3 inhibitors significantly reduced striatal ischemic damage and reduce edema formation in rats. Additionally, the rats "demonstrated marked improvement in neurological function over the time course of the experiment."

Accordingly, there is a great need to develop compounds useful as inhibitors of protein kinases. In particular, it would be desirable to develop compounds that are useful as inhibitors of GSK-3 and PKC-theta, particularly given the inadequate treatments currently available for the majority of the disorders implicated in their activation.

SUMMARY OF THE INVENTION

This invention provides, in general, compounds that are useful as kinase inhibitors.

In one embodiment the compounds of the present invention are represented by structural formula I:

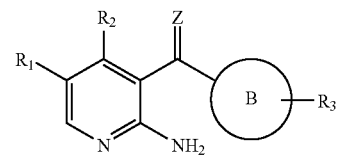

or a pharmaceutically acceptable salt thereof.

B is a monocyclic heteroaromatic ring, a 6,6 bicyclic heteroaromatic ring, or a 6,5 bicyclic heteroaromatic ring wherein the heteroaromatic ring is optionally and independently substituted with one or more $R_{12}$ groups in addition to $R_3$ (additionally B is independently optionally substituted with $R_{12'}$).

Z is O or S.

$R_1$ is —H, halogen, —CN, —NO$_2$, or -T1-Q1.

T1 is a bond (absent) or C1-6 aliphatic (or alternatively C1-10 aliphatic), wherein up to three methylene units of T1 are optionally and independently replaced by G wherein G is —O—, —S—, —S(O)—, —S(O)$_2$—, —N(R$^4$)—, or —C(O)—; T1 is optionally and independently substituted with one or more JT1.

Q1 is —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J1 and independently optionally and independently substituted with one or more $R_{13}$ groups (additionally Q1 can be absent, additionally Q1 is not —H).

J1 is —Y1-M1.

Y1 is a bond (absent) or C1-6 aliphatic (or alternatively C1-10 aliphatic) wherein up to three methylene units of Y1 are optionally and independently replaced with G1 wherein G1 is —N(R$^\$$)—, —O—, —S—, —C(O)—, —S(O)—, or —S(O)$_2$— (additionally Y1 can be oxo, and when Y1 is a C1-6 or C1-10 aliphatic as described above it can additionally be optionally and independently substituted with one or more JT1).

M1 is —H, C1-6 aliphatic, C3-8 cycloaliphatic, halo C1-4 aliphatic, —O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, —NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$; M1 is optionally and independently substituted with one or more J (additionally M1 can be absent, additionally M1 is not —H).

$R_2$ is —H, halogen, —CN, —N(O)$_2$, or optionally substituted C1-C6 alkyl.

$R_3$ is halogen, —CN, —NO$_2$, or -T2-Q2.

T2 is a bond (absent) or C1-6 aliphatic (or alternatively C1-10 aliphatic), wherein up to three methylene units of T2 are optionally and independently replaced by G' wherein G' is —O—, —S—, —S(O)—, —S(O)$_2$—, —N(R$_4$)—, or —C(O)—; T2 is optionally and independently substituted with one or more JT2.

Q2 is —H, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more $R_{13}$ groups (additionally Q2 can be absent, additionally Q2 is not —H), (additionally, wherein when $R_1$ and $R_2$ are —H, $R_{12}$ is absent and $R_3$ is -T2-Q2 then -T2-Q2 is not —H, —NHCH$_2$CH(OH)CH$_2$OH, or

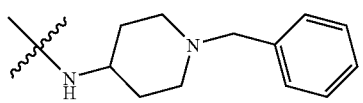

(alternatively, wherein when $R_1$ and $R_2$ are —H, $R_{12}$ is absent, $R_{12'}$ is absent, Z is O, $R_3$ is -T2-Q2 then -T2-Q2 is not absent, NHCH$_2$CH(OH)CH$_2$OH or

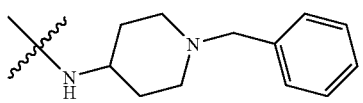

(alternatively, wherein when $R_1$ and $R_2$ are —H, $R_{12}$ is absent, $R_{12'}$ is absent, Z is O, $R_3$ is -T2-Q2 then -T2-Q2 is not absent).

J2 is —Y2-M2.

Y2 is a bond (absent) or C1-6 aliphatic (or alternatively C1-10 aliphatic), wherein up to three methylene units of Y2 are optionally and independently replaced with G1' wherein G1' is —N(R$^\$$)—, —O—, —S—, —C(O)—, —S(O)—, or —S(O)$_2$— (additionally Y2 can be oxo, and when Y2 is a C1-6 (or C1-10) aliphatic as described above it can additionally be optionally and independently substituted with one or more JT2).

M2 is —H, C1-6 aliphatic, C3-8 cycloaliphatic, haloC1-4 aliphatic, —O(haloC1-4 aliphatic), 3-8 membered heterocyclyl, 5-6 membered heteroaryl (alternatively heteroaryl), phenyl (alternatively aryl), halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, —NR$^\$$C(O)N(R$^\$$)$_2$, SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$; wherein M2 is optionally substituted with one or more J (additionally M2 can be absent, additionally M2 is not —H).

Each J is independently —H, halogen, C1-6 aliphatic, C3-6 cycloaliphatic, —NO$_2$, —CN, —N(R$^\$$)$_2$, —OR$^\$$, —C(O)R$^\$$, —C(O)N(R$^\$$)$_2$, —C(O)$_2$R$^\$$, oxo, —O(haloC1-4 aliphatic), or haloC1-4 aliphatic (additionally J is not —H).

$R_4$ is —H or an optionally (and independently) substituted C1-C6 alkyl.

Each JT1 is independently halogen, —CN, —N(O)$_2$, or hydroxy.

Each JT2 is independently halogen, —CN, —N(O)$_2$, or hydroxy.

each R$^\$$ is independently —H or C1-C6 alkyl.

Each $R_{12}$ is independently halogen, amino, aminoalkyl, alkylaminoalkyl, alkoxy, hydroxy, —CN, —NO$_2$, or optionally (and independently) substituted C1-C6 alkyl.

Each $R_{12}'$ is independently halogen, amino, aminoalkyl, alkylaminoalkyl, alkoxy, hydroxy, —CN, —NO$_2$, or optionally and independently substituted C1-C10 aliphatic wherein up to three methylene units are optionally and independently replaced by G' wherein G' is —O—, —S(O)$_p$—, —N(R$^4$)—, or —C(O)—, and each methylene unit is optionally and independently substituted with one or more JT3; or $R_{12'}$ is cycloaliphatic, or phenyl, (additionally wherein the cycloaliphatic or phenyl groups are optionally and independently substituted with one or more JT4, and additionally wherein $R_{12'}$ is heteroaryl optionally and independently substituted with one or more JT4); p is 0, 1 or 2.

Each JT3 is optionally and independently halogen, —CN, —NO$_2$, cycloaliphatic, or phenyl.

Each JT4 is optionally and independently halogen, C1-C6 alkyl, or C1-C6 alkoxy.

Each $R_{13}$ is independently halogen, amino, aminoalkyl, alkylaminoalkyl, alkoxy, hydroxy, —CN, —NO$_2$, oxo or optionally and independently substituted C1-C6 alkyl.

In one embodiment, the present invention is a method of treating or preventing protein kinase-mediated condition in a subject, comprising administering to the subject an effective amount of a compound, a pharmaceutically acceptable salt thereof, or composition of the present invention.

In one embodiment the present invention is the manufacture of a compound, a pharmaceutically acceptable salt thereof, or composition of the present invention for use in treating or preventing a protein kinase-mediated condition in a subject.

In another embodiment, the compounds, pharmaceutically acceptable salts thereof, and compositions of the present invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention relates to compounds, pharmaceutically acceptable salts thereof, and compositions (such as, pharmaceutical compositions) useful as protein kinase inhibitors.

In one embodiment, the compounds, pharmaceutically acceptable salts thereof, and compositions of the present invention are effective as inhibitors of PKCtheta.

In one embodiment, the compounds, pharmaceutically acceptable salts thereof, and compositions of the present invention are effective as inhibitors of GSK-3.

Compounds of this invention include those described generally herein, and are further illustrated by the classes, subclasses, and species disclosed herein. As used herein, the definitions defined herein shall apply unless otherwise indicated. For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

In one embodiment the present invention is a compound represented by structural formula I:

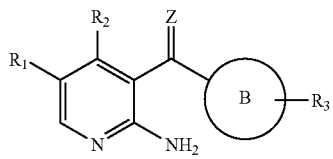

I or a pharmaceutically acceptable salt thereof.

B is a monocyclic heteroaromatic ring, a 6,6 bicyclic heteroaromatic ring, or a 6,5 bicyclic heteroaromatic ring wherein the heteroaromatic ring is optionally substituted with one or more R' groups in addition to $R_3$. In certain embodiments, B is a monocyclic heteroaromatic ring, a 6,6 bicyclic heteroaromatic ring, or a 6,5 bicyclic heteroaromatic ring wherein the heteroaromatic ring is independently optionally and independently substituted with one or more $R_{12}$ groups in addition to $R_3$. In certain embodiments, B is a monocyclic heteroaromatic ring, a 6,6 bicyclic heteroaromatic ring, or a 6,5 bicyclic heteroaromatic ring wherein the heteroaromatic ring is optionally substituted with $R_{12}$' and independently and optionally and independently substituted with one or more $R_{12}$ groups in addition to $R_3$. In certain embodiments, B is a monocyclic heteroaromatic ring, a 6,6 bicyclic heteroaromatic ring, or a 6,5 bicyclic heteroaromatic ring substituted with $R_3$ and independently optionally and independently substituted with one or more $R_{12}$ groups. The point of attachment of the 6,5 bicyclic ring to —C(Z)— is on the 6 membered ring. In certain embodiments, B is a monocyclic heteroaromatic ring substituted with $R_3$ and independently optionally and independently substituted with one or more $R_{12}$ groups. In certain embodiments, B is pyridyl, pyrazinyl, pyrimidinyl, pyridazinyl, imidazolyl, pyrrolyl, pyrazolyl, triazolyl, tetrazolyl, thienyl, oxazolyl, isoxazolyl, oxadiazolyl, thiazolyl, isothiazolyl or thiadiazolyl substituted with $R_3$ and independently optionally and independently substituted with one or more $R_{12}$ groups (additionally B is optionally substituted with $R_{12}$'). In certain embodiments, B is thienyl substituted with $R_3$ and independently optionally and independently substituted with one or more $R_{12}$ groups (additionally B is optionally substituted with $R_{12}$'). In certain embodiments, B is represented by the following structural formula:

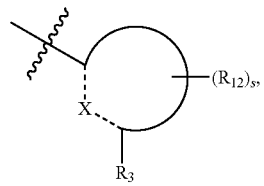

X is, —O—, —S—, or —NR$^x$—. R$^x$ is absent or —H. s is 0, 1 or 2. In certain embodiments, X is —O—. In certain alternative embodiments, X is —S—. In certain alternative embodiments, X is —NR$^x$—. In certain embodiments, B is represented by the following structural formula:

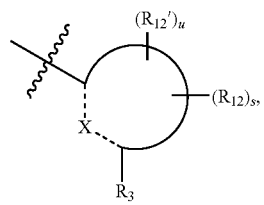

X is, —O—, —S—, or —NR$^x$—. R$^x$ is absent or —H. s is 0, 1 or 2. u is 0 or 1. The dashed lines represent a direct (aromatic) bond between X and carbon atoms which form part of the aromatic ring. In certain embodiments, ring B is thiadiazolyl. In certain embodiments, ring B is thiazolyl. In certain embodiments, ring B is thienyl. In certain embodiments, B is a monocyclic nitrogen containing heteroaromatic ring.

In certain embodiments, B is represented by the following structural formula:

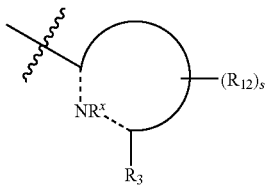

R$^x$ is absent or —H. s is 0, 1 or 2. Each dashed line represents a direct (aromatic) bond between the nitrogen and carbon atoms which form part of the aromatic ring. In certain embodiments, B is represented by the following structural formula:

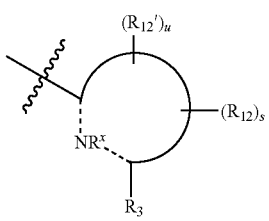

R$^x$ is absent or —H. s is 0, 1 or 2. u is 0 or 1. In certain embodiments, ring B is pyridyl. In certain embodiments, ring B is imidazolyl. In certain embodiments, ring B is pyrrolyl. In certain embodiments, ring B is pyrazinyl. In certain embodiments, ring B is pyrimidinyl. In certain embodiments ring B is oxazolyl. In certain embodiments, ring B is oxadiazolyl. In certain embodiments, ring B is thiazolyl. In certain embodiments, ring B is thiadiazolyl.

In certain embodiments, B is represented by the following structural formula:

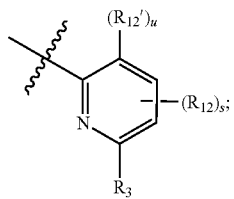

s is 0 or 1. u is 0 or 1. Each dashed line represents a direct (aromatic) bond between the nitrogen and carbon atoms which form part of the aromatic ring.

In certain embodiments, B is represented by the following structural formula:

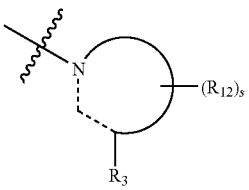

s is 0, 1 or 2 (additionally B is optionally substituted with $R_{12}'$). Each dashed line represents a direct (aromatic) bond between the atoms which form part of the aromatic ring.

In certain embodiments, B is represented by the following structural formula:

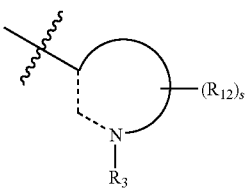

s is 0, 1 or 2 (additionally B is optionally substituted with $R_{12}'$). Each dashed line represents a direct (aromatic) bond between the atoms which form part of the aromatic ring. In certain embodiments, ring B is pyrimidinyl. In certain embodiments, ring B is imidazolyl.

In certain embodiments, B is represented by the following structural formula:

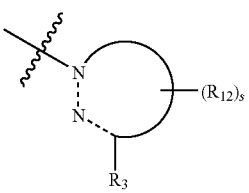

s is 0, 1 or 2 (additionally B is optionally substituted with $R_{12}'$). Each dashed line represents a direct (aromatic) bond between the atoms which form part of the aromatic ring. In certain embodiments, ring B is oxadiazolyl. In certain embodiments, ring B is pyrazolyl. In certain embodiments, ring B is pyradazinyl.

In certain embodiments, B is represented by the following structural formula:

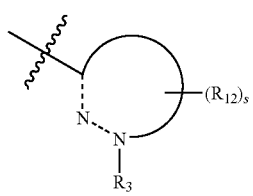

s is 0, 1 or 2 (additionally B is optionally substituted with $R_{12}'$). Each dashed line represents a direct (aromatic) bond between the atoms which form part of the aromatic ring. In certain embodiments, ring B is oxadiazolyl. In certain embodiments, ring B is pyrazolyl.

In certain embodiments, ring B is a 6,6 bicyclic heteroaromatic ring substituted with $R_3$ (additionally B is optionally substituted with $R_{12}'$ and independently optionally substituted with one or more $R_{12}$). In certain embodiments, ring B is isoquinolinyl, cinnolinyl, quinazolinyl, pyridopyridyl, or pyridopyradazinyl (additionally B is substituted with $R_3$ and optionally substituted with $R_{12}'$ and independently optionally and independently substituted with one or more $R_{12}$.

As used herein, each substitutable ring atom on B can be substituted with $R_3$, $R_{12}$, or $R_{12}'$. In certain embodiments, ring B is substituted with 0-5 $R_{12}$ groups, 0-3 $R_{12}$ groups, 0-2 $R_{12}$ groups, or 0-1 $R_{12}$ groups.

Z is O or S. In certain embodiments Z is O.

$R_1$ is —H, halogen, —CN, —NO$_2$, or -T1-Q1. In certain embodiments $R_1$ is —H, halogen, or -T1-Q1. In certain embodiments, $R_1$ is -T1-Q1. In certain alternative embodiments, $R_1$ is —H, or halogen. In certain embodiments, $R_1$ is —H, or bromine, additionally $R_1$ is chlorine. In certain embodiments, $R_1$ is —H, or bromine, chlorine, —CN, or T1-Q1. In certain embodiments, $R_1$ is —H.

T1 is absent or C1-10 aliphatic, wherein up to three methylene units of T1 are optionally and independently replaced by G wherein G is —O—, —S—, —S(O)—, —S(O)$_2$—, —N(R$_4$)—, or —C(O)—; T1 is optionally substituted with one or more JT1. T1 is a bond (absent) or C1-6 aliphatic, wherein up to three methylene units of T1 are optionally and independently replaced by G wherein G is —O—, —S—, —S(O)—, —S(O)$_2$—, —N(R$_4$)—, or —C(O)—; T1 is optionally substituted with one or more JT1. In certain embodiments two or more G groups may optionally replace adjacent methylene units of T1 to give groups which include, but are not limited to: —CO$_2$—, —N(R$_4$)CO—, —C(O)N(R$_4$)—, —N(R$_4$)C(O)O—, —OC(O)N(R$_4$)—, —N(R$_4$)CON(R$_4$)—, —N(R$_4$)SO$_2$—, —SO$_2$N(R$_4$)—, —N(R$_4$)SO$_2$N(R$_4$)—, and —N(R$_4$)N(R$_4$)—. In certain embodiments the methylene units of T1 are optionally replaced by —, —CO—, —N(R$_4$)—, —CO$_2$—, —S(O)$_2$—, —N(R$_4$)CO—, or —C(O)N(R$_4$)—. In certain embodiments the methylene units of T1 are optionally replaced by —CO—, —N(R$_4$)—, —CO$_2$—, —N(R$_4$)CO—, or —C(O)N(R$_4$)—. In certain embodiments the methylene units of T1 are optionally replaced by —CO—, —N(R$_4$)—, —N(R$_4$)CO—, or —C(O)N(R$_4$)—. In certain embodiments, T1 is not substituted. In certain embodiments G is absent. In certain embodiments, T1 is absent or C1-10 aliphatic, wherein up to three methylene units of T1 are optionally and independently replaced by G wherein G is —O—, —N(R$_4$)—, or —C(O)—; additionally T1 is optionally substituted with one or more JT1. In certain embodiments, T1 is absent or C1-10 aliphatic, wherein up to three methylene units of T1 are optionally and independently replaced by G wherein G is —O—, or —N(R$_4$)—; additionally T1 is optionally substituted with one or more JT1. In certain embodiments, T1 is a bond (absent) or C1-6 aliphatic, wherein up to three methylene units of T1 are optionally and independently replaced by G wherein G is —O—, —N(R$_4$)—, or —C(O)—; additionally T1 is optionally substituted with one or more JT1. In certain embodiments, T1 is absent or C1-6 aliphatic, wherein up to three methylene units of T1 are optionally and independently replaced by G wherein G is —O—, or —N(R$_4$)—; additionally T1 is optionally substituted with one or more JT1. In certain embodiments, T1 is absent or C1-6 alkyl, C2-C6 alkenyl, or C2-C6 alkynyl, wherein up to three methylene units of T1 are optionally and independently replaced by G wherein G is —O—, or —N(R$_4$)—; additionally T1 is optionally substituted with one or more JT1. In certain embodiments, T1 is absent or C1-10 alkyl, C2-C10 alkenyl, or C2-C10 alkynyl, wherein up to three methylene units of T1 are optionally and independently replaced by G wherein G is —O—, or —N(R$_4$)—; additionally T1 is optionally substituted with one or more JT1. In certain embodiments, T1 is absent or C1-6 aliphatic, wherein up to two methylene units of T1 are optionally and independently replaced by G wherein G is —O—, or —N(R$_4$)—; additionally T1 is optionally substituted with one or more JT1. In certain embodiments, T1 is absent or C1-10 aliphatic, wherein up to two methylene units of T1 are optionally and independently replaced by G wherein G is —O—, or —N(R$_4$)—; additionally T1 is optionally substituted with one or more JT1. In certain embodiments, T1 is a bond (absent) or C1-6 aliphatic, wherein up to three methylene units of T1 are optionally and independently replaced by G wherein G is —O—; T1 is optionally substituted with one or more JT1. In certain embodiments, T1 is a bond (absent) or C1-6 aliphatic. In certain embodiments, T1 is a bond (absent), C1-C6 alkyl, C2-C6 alkenyl, or C2-C6 alkynyl. In certain embodiments, T1 is a bond (absent) or C2-C6 alkenyl. In alternative embodiments T1 is represented by a structural formula selected from the following structural formulas:

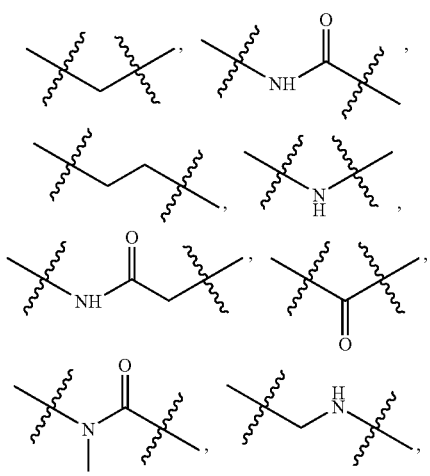

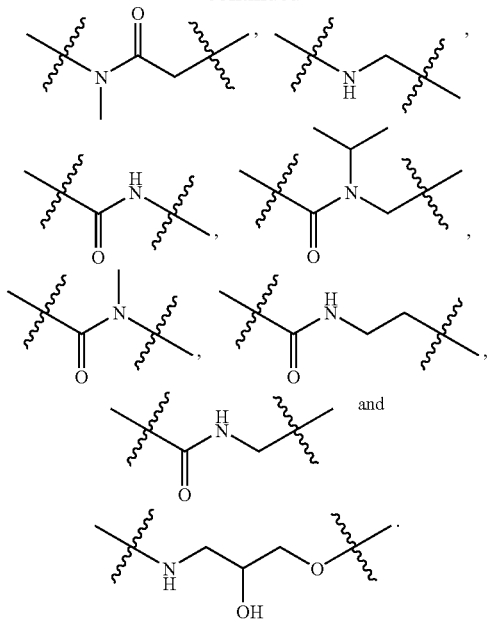

additional examples of T1 include:

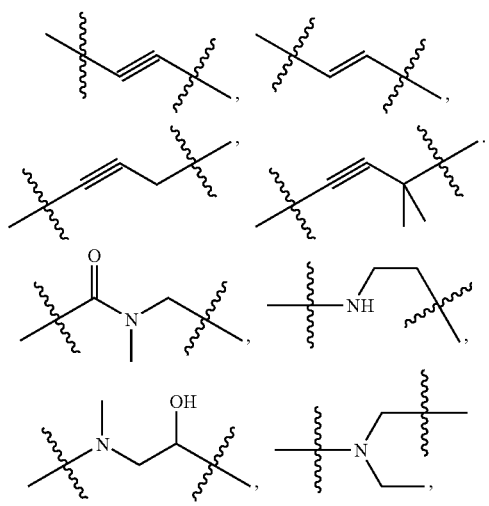

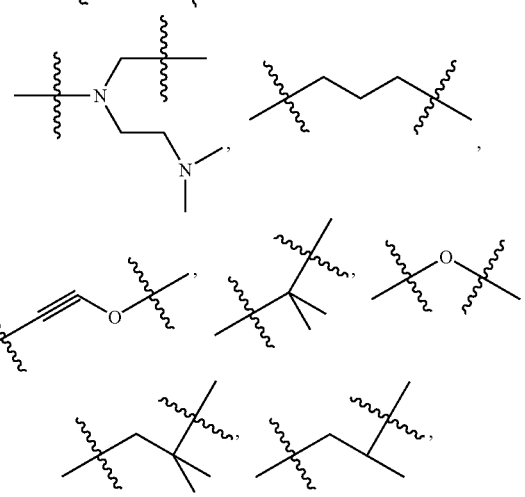

-continued

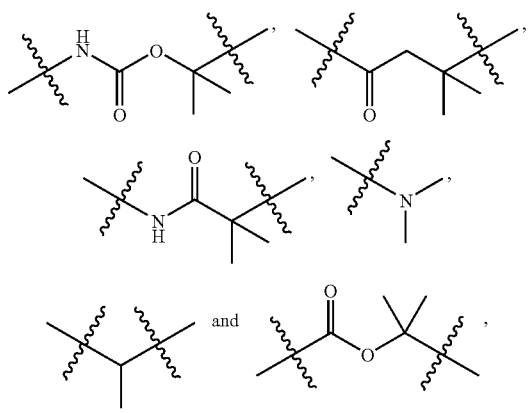

additionally, T1 can be:

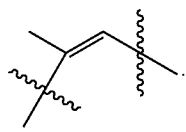

In one embodiment T1 is a bond (absent) or represented by a structural formula selected from the group consisting of:

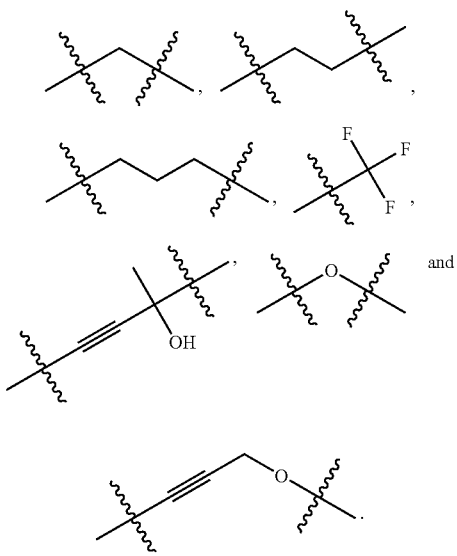

Preferably, T1 is joined to compounds of the invention as represented by the below example.

For example, when T1 is:

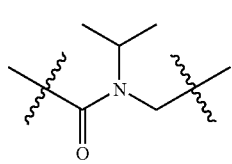

it is joined to compounds of the invention as follows:

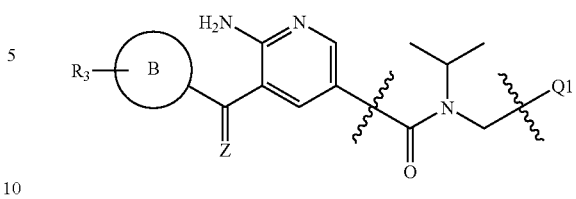

or the alternative representation:

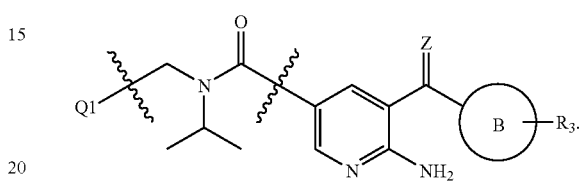

Q1 is —H, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J1 and independently optionally substituted with one or more R" groups. In certain embodiments, Q1 is absent, —H, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J1 and independently optionally substituted with one or more R" groups. In certain embodiments, Q1 is —H, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J1 and independently optionally substituted with one or more $R_{13}$ groups. In certain embodiments, Q1 is absent, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J1 and independently optionally substituted with one or more $R_{13}$ groups. In certain embodiments, Q1 is absent, —H, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J1 and independently optionally substituted with one or more $R_{13}$ groups. In certain embodiments, Q1 is —H, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is independently optionally substituted with J1. In certain embodiments, Q1 is absent, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is independently optionally substituted with J1. In certain embodiments, Q1 is absent, —H, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is independently optionally substituted with J1. In certain embodiments, Q1 is —H, a 3-8-membered saturated, partially unsaturated, or fully unsaturated monocyclic ring having 0-3 heteroatoms independently selected from nitrogen, oxygen, and sulfur; Q1 is optionally substituted with J1. In certain embodiments, Q1 is absent, —H, or a 3-8-membered saturated, partially unsaturated, or fully unsaturated monocyclic ring having 0-3 heteroatoms independently selected from nitrogen, oxygen, and sulfur; Q1 is optionally substituted with J1. In certain embodiments, Q1 is —H, or a 3-8-membered saturated, partially unsaturated, or fully unsaturated monocyclic ring having 0-3 nitrogen atoms optionally substituted with J1. In certain embodiments, Q1 is absent, —H, or a 3-8-membered saturated, partially unsaturated, or fully unsaturated monocyclic ring having 0-3 nitrogen atoms or an 8-12 membered saturated, partially unsaturated, or fully unsaturated bicyclic ring system having 0-3 nitrogen atoms wherein Q1 is optionally substituted with J1.

In certain embodiments Q1 is selected from the group consisting of absent, cyclopropyl, cyclopentyl, cyclobutyl, cyclohexyl, cyclohexenyl, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, thienyl, furyl, benzofuryl, benzothienyl, indolyl, indazolyl, isoindolyl, benzimidazolyl, quinolyl, quinoxalyl, isoquinolyl, indolinyl, oxazolidinyl, isoxazolidinyl, thiazolidinyl, isothiazolidinyl, oxazocanyl, oxazepanyl, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, thiazepanyl, and thiazocanyl wherein each ring is independently optionally and independently substituted with J1. In certain embodiments, Q1 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl each optionally and independently substituted with J1, additionally Q1 is thienyl, furyl, benzofuryl, benzothienyl, imidazolyl, pyrazinyl, pyrimidinyl, isoindolyl, isoquinolyl, indazolyl, or pyrazolyl, each optionally and independently substituted with J1. In certain embodiments, Q1 is halogen, phenyl optionally substituted with J1, or pyridyl optionally substituted with J1. In certain embodiments, Q1 is absent, indolyl optionally substituted with J1, quinolyl optionally substituted with J1, cyclohexyl optionally substituted with J1, cyclohexenyl optionally substituted with J1, pyrrolyl optionally substituted with J1, imidazolyl optionally substituted with J1, cyclopropyl optionally substituted with J1, piperidinyl optionally substituted with J1, pyrrolidinyl optionally substituted with J1, phenyl optionally substituted with J1, or pyridyl optionally substituted with J1. In certain embodiments, Q1 is absent, phenyl optionally substituted with C1-C4 alkyl, or pyridyl optionally substituted with C1-C4 alkyl. In certain embodiments, Q1 is absent, indolyl, pyrrolyl, cyclopropyl, cyclohexyl, cyclohexenyl, piperidinyl, pyrrolidinyl phenyl or pyridyl each optionally substituted with —OR$^\$$, —N(R$^\$$)$_2$, or C1-C4 alkyl. In certain embodiments, Q1 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with haolgen, —CN, —OR$^\$$, —N(R$^\$$)$_2$, C1-C4 haloalkyl, or C1-C4 alkyl, additionally Q1 is thienyl, furyl, benzofuryl, or benzothienyl, each optionally and independently substituted with haolgen, —CN, —OR$^\$$, —N(R$^\$$)$_2$, C1-C4 haloalkyl, or C1-C4 alkyl. In certain embodiments, Q1 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with halogen, —OH, —NH$_2$, —CN, C1-C4 haloalkyl, or C1-C4 alkyl, additionally Q1 is thienyl, furyl, benzofuryl, or benzothienyl, each optionally and independently substituted with halogen, —OH, —NH$_2$, —CN, C1-C4 haloalkyl, or C1-C4 alkyl. In certain embodiments, Q1 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with —OH, —NH$_2$, or C1-C4 alkyl, additionally Q1 is thienyl, furyl, benzofuryl, or benzothienyl, each optionally and independently substituted with halogen, —OH, —NH$_2$, or C1-C4 alkyl. In certain embodiments, Q1 is phenyl optionally substituted with C1-C4 alkyl, or pyridyl optionally substituted with C1-C4 alkyl. In certain embodiments, Q2 is absent, indolyl, phenyl optionally substituted with —OH, —NH$_2$, or C1-C4 alkyl, or pyridyl optionally substituted with C1-C4 alkyl. —OR$^\$$, —N(R$^\$$)$_2$, or C1-C4 alkyl.

In certain alternative embodiments, Q1 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, and thiazocanyl wherein each ring is independently optionally substituted with J1. In certain embodiments, Q1 is selected from the group consisting of absent, phenyl, cyclopropyl, cyclobutyl, cyclopentyl, cyclohexyl, cyclohexenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, indolyl, indazolyl, benzimidazolyl, quniolyl, quinoxalyl, indolinyl, oxazolidinyl, isoxazolidinyl, thiazolidinyl, isothiazolidinyl, oxazocanyl, oxazepanyl, thiazepanyl, and thiazocanyl and bridged bicyclic rings such as, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, wherein each ring is independently optionally substituted with J1.

In certain embodiments, Q1 is selected from the group consisting of phenyl, cyclopropyl, cyclopentyl, cyclohexyl, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, indolyl, indazolyl, benzimidazolyl, quinolyl, quinoxalyl, indolinyl, oxazolidinyl, isoxazolidinyl, thiazolidinyl, isothiazolidinyl, oxazocanyl, oxazepanyl, thiazepanyl, and thiazocanyl wherein each ring is independently optionally substituted with J1. In certain embodiments, Q1 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, diazepanyl, and oxazepanyl wherein each ring is independently optionally substituted with J1. In certain embodiments, Q1 is selected from the group consisting of absent, cyclohexyl, diazabicyclooctyl, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, pyrrolidinyl, diazepanyl, and oxazepanyl wherein each ring is independently optionally substituted with J1. In certain embodiments, Q1 is selected from the group consisting of cyclohexyl, diazabicyclooctyl, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, pyrrolidinyl, diazepanyl, and oxazepanyl wherein each ring is independently optionally substituted with J1. In certain embodiments, Q1 is selected from the group consisting of phenyl, pyridyl, piperidinyl, piperazinyl, diazepanyl, and oxazepanyl wherein each ring is independently optionally substituted with J1. In certain embodiments, Q1 is selected from the group consisting of absent, cyclohexyl, diazabicyclooctyl, phenyl, pyridyl, piperidinyl, piperazinyl, pyrrolidinyl, diazepanyl, and oxazepanyl wherein each ring is independently optionally substituted with J1. In certain embodiments, Q1 is selected from the group consisting of cyclohexyl, 3,8-diazabicyclo[3.2.1.]octyl, phenyl, pyridyl, piperidinyl, piperazinyl, pyrrolidinyl, diazepanyl, and oxazepanyl wherein each ring is independently optionally substituted with J1. In certain embodiments, Q1 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, diazepanyl, and oxazepanyl wherein each ring is independently optionally substituted with J1. In certain embodiments, Q1 is selected from the group consisting of absent, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, pyrrolidinyl, diazepanyl, and oxazepanyl wherein each ring is independently optionally substituted with J1. In certain embodiments, Q1 is selected from the group consisting of phenyl, pyridyl, piperidinyl, piperazinyl, diazepanyl, and oxazepanyl wherein each ring is independently optionally substituted with J1. In certain embodiments, Q1 is selected from the group consisting of absent, phenyl, pyridyl, piperidinyl, piperazinyl, pyrrolidinyl, diazepanyl, and oxazepanyl wherein each ring is independently optionally substituted with J1. In certain embodiments, Q1 is represented by the following structural formula:

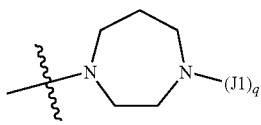

q is 0 or 1. In certain embodiments Q1 is not substituted with $R_{12}$. In certain embodiments Q1 is not substituted with $R_{13}$. In certain embodiments Q1 is not substituted.

J1 is —Y1-M1.

Y1 is absent, oxo or C1-10 aliphatic wherein up to three methylene units of Y1 are optionally and independently replaced with G1 wherein G1 is —N($R^\$$)—, —O—, —S—, —C(O)—, —S(O)—, or —S(O)$_2$—. In one embodiment, Y1 is a bond (absent), or C1-6 aliphatic wherein up to three methylene units of Y1 are optionally and independently replaced with G1 wherein G1 is —N($R^\$$)—, —O—, —S—, —C(O)—, —S(O)—, or —S(O)$_2$—. In certain embodiments, Y1 is a bond (absent), oxo, or C1-6 aliphatic wherein up to three methylene units of Y1 are optionally and independently replaced with G1 wherein G1 is —N($R^\$$)—, —O—, —S—, —C(O)—, —S(O)—, or —S(O)$_2$—. In certain embodiments two or more G1 groups may optionally replace adjacent methylene units of Y1 to give groups which include, but are not limited to: —CO$_2$—, —N($R^\$$)CO—, —C(O)N($R^\$$)—, —N($R^\$$)C(O)O—, —OC(O)N($R^\$$)—, —N($R^\$$)CON($R^\$$)—, —N($R^\$$)SO$_2$—, —SO$_2$N($R^\$$)—, —N($R^\$$)SO$_2$N($R^\$$)—, and —N($R^\$$)N($R^\$$)—. In certain embodiments the methylene units of Y1 are optionally replaced by —O—, —CO—, —N($R^\$$)—, —CO$_2$—, —S(O)$_2$—, —N($R^\$$)CO—, or —C(O)N($R^\$$)—. In certain embodiments the methylene units of Y1 are optionally replaced by —CO—, —N($R^\$$)—, —CO$_2$—, —S(O)$_2$—, —N($R^\$$)CO—, or —C(O)N($R^\$$)—. In certain embodiments the methylene units of Y1 are optionally replaced by —O—, —CO$_2$—, —CO—, —S(O)$_2$— or —N($R^\$$)—. In certain embodiments, Y1 is a bond (absent), or C1-10 aliphatic wherein up to three methylene units of Y1 are optionally and independently replaced with G1 wherein G1 is —N($R^\$$)—, —O—, —C(O)—, or —S(O)$_2$—. In certain embodiments, Y1 is a bond (absent), or C1-6 aliphatic wherein up to three methylene units of Y1 are optionally and independently replaced with G1 wherein G1 is —N($R^\$$)—, —O—, —C(O)—, or —S(O)$_2$—. In certain embodiments, Y1 is a bond (absent), oxo, or C1-10 aliphatic wherein up to three methylene units of Y1 are optionally and independently replaced with G1 wherein G is —N($R^\$$)—, —O—, —C(O)—, or —S(O)$_2$—. In certain embodiments, Y1 is a bond (absent), oxo, or C1-6 aliphatic wherein up to three methylene units of Y1 are optionally and independently replaced with G1 wherein G1 is —N($R^\$$)—, —O—, —C(O)—, or —S(O)$_2$— where Y1 is optionally and independently substituted with one or more JT1. In certain embodiments, Y1 is a bond (absent) or C1-6 aliphatic wherein up to three methylene units of Y1 are optionally and independently replaced with G1 wherein G1 is —O— or —C(O)—. In certain embodiments, Y1 is a bond (absent), oxo, or C1-6 aliphatic wherein up to three methylene units of Y1 are optionally and independently replaced with G1 wherein G1 is —O— or —C(O)—. In certain embodiments, Y1 is a bond (absent) or C1-10 alkyl group wherein up to three methylene units of Y1 are optionally and independently replaced with G1 wherein G1 is —O—. In certain embodiments, Y1 is a bond (absent) or C1-6 alkyl group wherein up to three methylene units of Y1 are optionally and independently replaced with G1 wherein G1 is —O— optionally. In certain embodiments, Y1 is a bond (absent) or C1-6 alkyl group wherein up to two methylene units of Y1 are optionally and independently replaced with G1 wherein G1 is —O—. In certain embodiments, Y1 is a bond (absent) or C1-6 alkyl group wherein up to one methylene unit of Y1 are optionally and independently replaced with G1 wherein G1 is —O—. In certain embodiments, Y1 is a bond (absent), oxo, or C1-6 alkyl group. In certain embodiments, G1 is absent. Additionally, in all the preceding recitations of Y1 in this paragraph, Y1 is optionally and independently substituted with one or more JT1. Alternatively, in all the preceding recitations of Y1 in this paragraph Y1 is not substituted.

M1 is —H, C1-6 aliphatic, C3-8 cycloaliphatic, haloC1-4 aliphatic, O(haloC1-4 aliphatic), 3-8 membered heterocyclyl, 5-6 membered aryl (e.g., heteroaryl or aryl), halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more R". In certain embodiments, M1 is absent, —H, C1-6 aliphatic, C3-8 cycloaliphatic, haloC1-4 aliphatic, O(haloC1-4 aliphatic), 3-8 membered heterocyclyl, heteroaryl, aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more R". In certain embodiments, M1 is —H, C1-6 aliphatic, C3-8 cycloaliphatic, haloC1-4 aliphatic, O(haloC1-4 aliphatic), 3-8 membered heterocyclyl, 5-6 membered heteroaryl, 5-6 membered aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more J. In certain embodiments, M1 is absent, —H, C1-6 aliphatic, C3-8 cycloaliphatic, haloC1-4 aliphatic, O(haloC1-4 aliphatic), 3-8 membered heterocyclyl, heteroaryl, aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more J. In certain embodiments, M1 is —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more R". In certain embodiments, M1 is absent, —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more R". In certain embodiments, M1 is —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more J. In certain embodiments, M1 is absent, —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more J. In certain embodiments, M1 is absent, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more J. M1 is C3-8 cycloaliphatic, 3-8 membered heterocyclyl, 5-6 membered heteroaryl, phenyl, —OR$^\$$, —SR$^\$$, —N(R$^\$$)$_2$, —P(O)R$^\$$, —P(O)$_2$R$^\$$, P(O)(R$^\$$)$_2$, or PO(OR$^\$$)$_2$, wherein M1 is optionally and independently substituted with one or more J; or M1 is absent, —CN, —NO$_2$, or halogen. M1 is C3-8 cycloaliphatic, 3-8 membered heterocyclyl, 5-6 membered heteroaryl, phenyl, —N(R$^\$$)$_2$, or —OR$^\$$; wherein M1 is optionally and independently substituted with one or more J; or M1 is absent, —CN, or halogen. M1 is phenyl, —N(R$^\$$)$_2$, or —OR$^\$$; wherein M1 is optionally and independently substituted with one or more J; or M1 is absent, or —CN.

In certain alternate embodiments, M1 is —H, C3-8 cycloaliphatic, 3-8 membered heterocyclyl, 5-6 membered heteroaryl, phenyl, halogen, —NO$_2$, —CN, —P(O)R$^\$$, —P(O)$_2$R$^\$$, P(O)(R$^\$$)$_2$, or PO(OR$^\$$)$_2$, wherein M1 is optionally and independently substituted with one or more J. In certain embodiments, M1 is absent, —H, C3-8 cycloaliphatic, 3-8 membered heterocyclyl, 5-6 membered heteroaryl, phenyl, halogen, —NO$_2$, —CN, —P(O)R$^\$$, —P(O)$_2$R$^\$$, P(O)(R$^\$$)$_2$, or PO(OR$^\$$)$_2$, wherein M1 is optionally and independently substituted with one or more J. In certain embodiments, M1 is —H, C3-8 cycloaliphatic, 3-8 membered heterocyclyl, 5-6 membered heteroaryl, phenyl, halogen, —NO$_2$, or —CN; M1 is optionally and independently substituted with one or more J. In certain embodiments, M1 is —H. In certain embodiments, M1 is absent, —H, C3-8 cycloaliphatic, 3-8 membered heterocyclyl, 5-6 membered heteroaryl, phenyl, halogen, —NO$_2$, or —CN; M1 is optionally and independently substituted with one or more J. In certain embodiments, M1 is —H. In certain alternative embodiments, M1 is absent, H, halogen, —CN, —OR$^\$$, —SR$^\$$, or —N(R$^\$$)$_2$. In certain embodiments, M1 is absent, —H, —OR$^\$$, or —N(R$^\$$)$_2$. R$_2$ is —H, halogen, —CN, —N(O)$_2$, or optionally substituted C1-C6 alkyl. In certain embodiments, R$_2$ is —H, halogen, —CN, —N(O)$_2$, or C1-C6 alkyl optionally and independently substituted with one or more R$_{13}$. In certain embodiments, R$_2$ is —H, halogen, or C1-C6 alkyl optionally substituted with halogen. In certain embodiments, R$_2$ is —H, F, Br, Cl or C1-C6 alkyl optionally substituted with F or Br, additionally R$_2$ is Cl. In certain embodiments, $R_2$ is —H, Br, C1-C6 alkyl or $CF_3$, additionally $R_2$ is Cl. In certain embodiments, $R_2$ is —H.

$R_3$ is halogen, —CN, —$NO_2$, or -T2-Q2. In certain embodiments $R_3$ is halogen or -T2-Q2. In certain embodiments $R_3$ is -T2-Q2. In certain alternative embodiments $R_3$ is halogen. In certain embodiments, -T2-Q2 is not —H. In one embodiment, when $R_1$ and $R_2$ are —H, $R_{12}$ is absent and $R_3$ is -T2-Q2 then -T2-Q2 is not —H, —$NHCH_2CH(OH)CH_2OH$, or

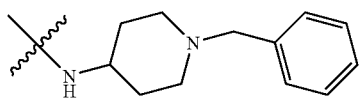

(alternatively, wherein when $R_1$ and $R_2$ are —H, $R_{12}$ is absent, $R_{12'}$ is absent, Z is O, $R_3$ is -T2-Q2 then -T2-Q2 is not absent, $NHCH_2CH(OH)CH_2OH$, or

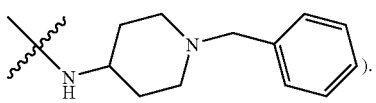

Alternatively, wherein when $R_1$ and $R_2$ are —H, $R_{12}$ is absent, $R_{12'}$ is absent, Z is O, $R_3$ is -T2-Q2 then -T2-Q2 is not absent.

T2 is absent or C1-10 aliphatic, wherein up to three methylene units of T2 are optionally and independently replaced by G' wherein G' is —O—, —S—, —S(O)—, —$S(O)_2$—, —$N(R_4)$—, or —C(O)—; T2 is optionally substituted with one or more JT2. T2 is a bond (absent) or C1-6 aliphatic, wherein up to three methylene units of T2 are optionally and independently replaced by G' wherein G' is —O—, —S—, —S(O)—, —$S(O)_2$—, —$N(R_4)$—, or —C(O)—; T2 is optionally substituted with one or more JT2. In certain embodiments two or more G groups may optionally replace adjacent methylene units of T2 to give groups which include, but are not limited to: —$CO_2$—, —$N(R_4)CO$—, —C(O)N($R_4$)—, —$N(R_4)C(O)O$—, —$OC(O)N(R_4)$—, —$N(R_4)CON(R_4)$—, —$N(R_4)SO_2$—, —$SO_2N(R_4)$—, —$N(R_4)SO_2N(R_4)$—, and —$N(R_4)N(R_4)$—. In certain embodiments the methylene units of T2 are optionally replaced by —O—, —CO—, —$N(R_4)$—, —$CO_2$—, —$S(O)_2$—, —$N(R_4)CO$—, or —$C(O)N(R_4)$—. In certain embodiments the methylene units of T2 are optionally replaced by —CO—, —$N(R_4)$—, —$CO_2$—, —$N(R_4)CO$—, or —$C(O)N(R_4)$—. In certain embodiments the methylene units of T2 are optionally replaced by —CO—, —$N(R_4)$—, —$N(R_4)CO$—, or —$C(O)N(R_4)$—. In certain embodiments, T2 is a bond (absent) or C1-10 aliphatic, wherein up to three methylene units of T2 are optionally and independently replaced by G' wherein G' is —O—, —$N(R_4)$—, or —C(O)—; T2 is optionally and independently substituted with one or more JT2. In certain embodiments, T2 is a bond (absent) or C1-6 aliphatic, wherein up to three methylene units of T2 are optionally and independently replaced by G' wherein G' is —O—, —$N(R_4)$—, or —C(O)—; T2 is optionally and independently substituted with one or more JT2. In certain embodiments, T2 is a bond (absent) or C1-10 aliphatic, wherein up to three methylene units of T2 are optionally and independently replaced by G' wherein G' is —$N(R_4)$—, or —C(O)—; T2 is optionally and independently substituted with one or more JT2. In certain embodiments, T2 is a bond (absent) or C1-6 aliphatic, wherein up to three methylene units of T2 are optionally and independently replaced by G' wherein G' is —$N(R_4)$—, or —C(O)—; T2 is optionally and independently substituted with one or more JT2. In certain embodiments, T2 is absent or C1-10 alkyl, wherein up to three methylene units of T2 are optionally and independently replaced by G' wherein G' is —$N(R_4)$—, or —C(O)—; T2 is optionally and independently substituted with one or more JT2. In certain embodiments, T2 is absent or C1-10 alkyl, wherein up to three methylene units of T2 are optionally and independently replaced by G' wherein G' is —$N(R_4)$—, or —C(O)—. In certain embodiments, T2 is absent or C1-10 alkyl, wherein up to two methylene units of T2 are optionally and independently replaced by G' wherein G' is —$N(R_4)$—, or —C(O)—. In certain embodiments, T2 is absent. In alternative embodiments T2 is absent or represented a structural formula selected from the following structural formulas:

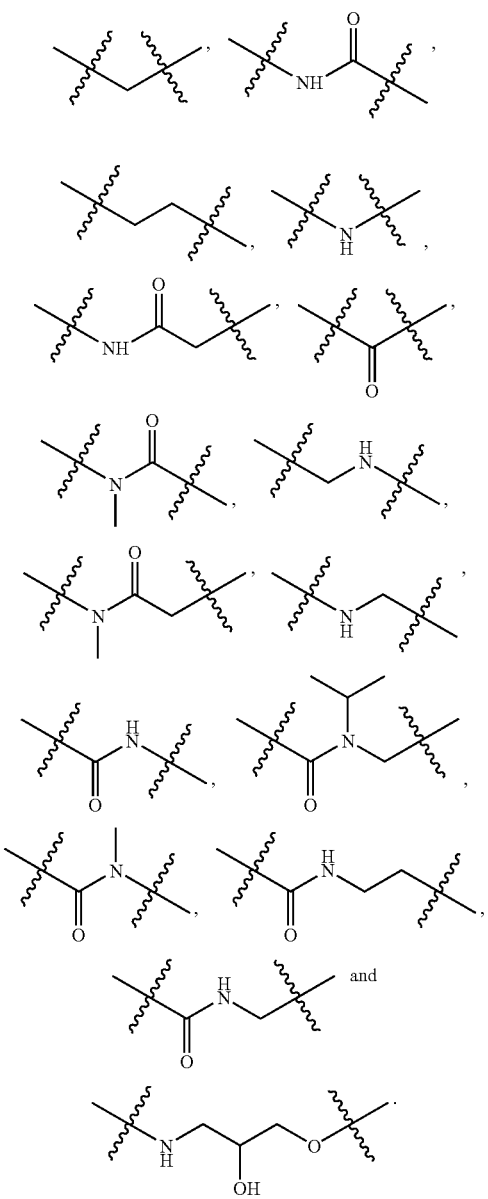

Additional values of 12 include:

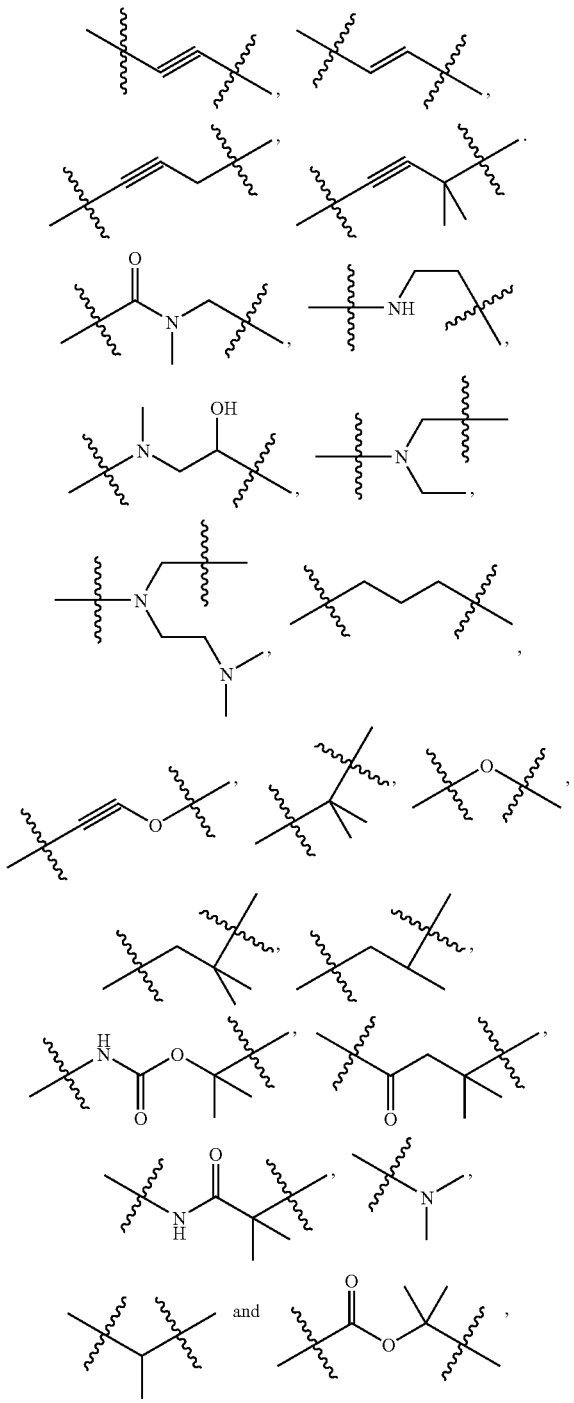

additionally T2 is represented by a structural formula selected from the group consisting of:

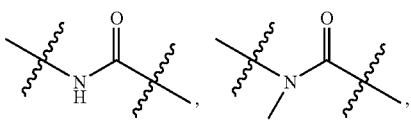

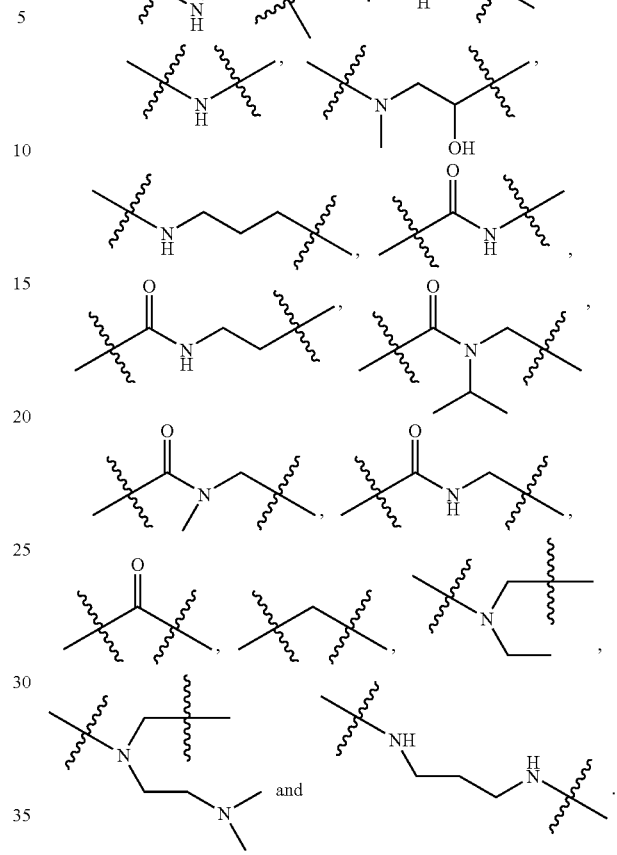

In certain embodiments T2 is not substituted.

In certain embodiments, T2 is absent, or C1-4 aliphatic, wherein one methylene unit of T2 is optionally replaced by G' wherein G' is —N(R$_4$)—, —O—, —S—, or —C(O)—; T2 is optionally and independently substituted with one or more JT2, preferably T2 is C1-4 aliphatic, wherein one methylene unit of T2 is replaced by G' wherein G' is —N(R$_4$)—; T2 is optionally and independently substituted with one or more JT2.

In alternative embodiments, T2 is absent.

In alternative embodiments, T2 is C1-10 aliphatic, wherein two methylene units of T2 are independently replaced by G' wherein G' is —N(R$_4$)—, —O—, —S—, or —C(O)—; T2 is optionally and independently substituted with one or more JT2, preferably, T2 is C1-10 aliphatic, wherein two methylene units of T2 are independently replaced by G' wherein G' is —N(R$_4$)—, —O—, or —S—; T2 is optionally and independently substituted with one or more JT2 more preferably, T2 is C1-10 aliphatic, wherein two methylene units of T2 are replaced by G' wherein G' is —N(R$_4$)—; T1 is optionally and independently substituted with one or more JT2.

Q2 is —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more R"

groups. In certain embodiments, Q2 is absent, —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more R" groups. In certain embodiments, Q2 is —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more $R_{13}$ groups. In certain embodiments, Q2 is absent, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more $R_{13}$ groups. In certain embodiments, Q2 is absent, —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more $R_{13}$ groups.

In certain embodiments, Q2 is absent, —H, or a 3-8-membered saturated, partially unsaturated, or fully unsaturated monocyclic ring having 0-3 heteroatoms independently selected from nitrogen, oxygen, and sulfur or an 8-12 membered saturated, partially unsaturated, or fully unsaturated bicyclic ring system having 0-5 heteroatoms independently selected from nitrogen, oxygen, and sulfur; Q2 is optionally substituted with J2. In certain embodiments, Q2 is —H, or a 3-8-membered saturated, partially unsaturated, or fully unsaturated monocyclic ring having 0-3 heteroatoms independently selected from nitrogen, oxygen, and sulfur; Q2 is optionally substituted with J2. In certain embodiments, Q2 is absent, —H, or a 3-8-membered saturated, partially unsaturated, or fully unsaturated monocyclic ring having 0-3 heteroatoms independently selected from nitrogen, oxygen, and sulfur; Q2 is optionally substituted with J2. In certain embodiments, Q2 is —H, or a 3-8-membered saturated, partially unsaturated, or fully unsaturated monocyclic ring having 0-3 nitrogen atoms optionally substituted with J2. In certain embodiments, Q2 is absent, —H, or a 3-8-membered saturated, partially unsaturated, or fully unsaturated monocyclic ring having 0-3 nitrogen atoms or an 8-12 membered saturated, partially unsaturated, or fully unsaturated bicyclic ring system having 0-3 nitrogen atoms wherein Q2 is optionally substituted with J2. In certain embodiments, Q2 is phenyl optionally substituted with J2 or pyridyl optionally substituted with J2. In certain embodiments, Q2 is absent, indolyl optionally substituted with J2, phenyl optionally substituted with J2 or pyridyl optionally substituted with J2. In certain embodiments, Q2 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with J2. In certain embodiments, Q2 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with haolgen, —CN, —OR$^\$$, —N(R$^\$$)$_2$, C1-C4 haloalkyl, or C1-C4 alkyl. In certain embodiments, Q2 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with halogen, —OH, —NH$_2$, —CN, C1-C4 haloalkyl, or C1-C4 alkyl. In certain embodiments, Q2 is absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with —OH, —NH$_2$, or C1-C4 alkyl. In certain embodiments, Q2 is phenyl optionally substituted with C1-C4 alkyl, or pyridyl optionally substituted with C1-C4 alkyl. In certain embodiments, Q2 is absent, indolyl, phenyl optionally substituted with —OH, —NH$_2$, or C1-C4 alkyl, or pyridyl optionally substituted with C1-C4 alkyl.

In certain alternative embodiments, Q2 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, and thiazocanyl wherein each ring is independently optionally substituted with J2. In certain embodiments, Q2 is selected from the group consisting of absent, phenyl, cyclopropyl, cyclobutyl, cyclopentyl, cyclohexyl, cyclohexenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, indolyl, indazolyl, benzimidazolyl, quinolyl, quinoxalyl, indolinyl, oxazolidinyl, isoxazolidinyl, thiazolidinyl, isothiazolidinyl, oxazocanyl, oxazepanyl, thiazepanyl, and thiazocanyl, bridged bicyclic rings, such as, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, wherein each ring is independently optionally substituted with J2, additionally Q2 is independently optionally substituted with one or more $R_{13}$ groups, additional values for Q2 include azetidinyl, isoindolinyl, isoindolyl, dihydroindazolyl, dihydrobenzimidazolyl, morpholinyl, tetrahydropyridyl, dihydropyridyl, tetrahydropyrazinyl, dihydropyrazinyl, tetrahydropyrimidinyl, dihydropyrimidinyl, dihydropyrrolyl, dihydropyrazolyl, dihydroimidazolyl, teoctahydropyrrolopyrazyl, octahydropyrrolopyridyl, octahydropyridopyrazyl, or octahydropyridopyridyl each independently optionally substituted with J2, and additionally independently optionally substituted with one or more $R_{13}$ groups. In certain embodiments, Q2 is selected from the group consisting of phenyl, cyclopropyl, cyclopentyl, cyclohexyl, zabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, indolyl, indazolyl, benzimidazolyl, quinolyl, quinoxalyl, indolinyl, oxazolidinyl, isoxazolidinyl, thiazolidinyl, isothiazolidinyl, oxazocanyl, oxazepanyl, thiazepanyl, and thiazocanyl wherein each ring is independently optionally substituted with J2. In certain embodiments, Q2 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, diazepanyl, and oxazepanyl wherein each ring is independently optionally substituted with J2. In certain embodiments, Q2 is selected from the group consisting of absent, cyclohexyl, diazabicyclooctyl, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, pyrrolidinyl, diazepanyl, and oxazepanyl wherein each ring is independently optionally substituted with J2, additionally Q2 is independently optionally substituted with one or more $R_{13}$ groups, additional values for Q2 include azetidinyl, morpholinyl, azepanyl, diazabicycloheptyl, diazabicyclooctyl, indolyl, tetrahydropyridyl, dihydropyridyl, octahydropyrrolopyrazyl, octahydropyrrolopyridyl, octahydropyridopyrazyl, or octahydropyridopyridyl each independently optionally substituted with J2, and additionally independently optionally substituted with one or more $R_{13}$ groups. In certain embodiments, Q2 is selected from the group consisting of cyclohexyl, diazabicyclooctyl, phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, pyrrolidinyl, diazepanyl, and oxazepanyl wherein each ring is independently optionally substituted with J2. In certain embodiments, Q2 is selected from the group consisting of phenyl, pyridyl, piperidinyl, piperazinyl, diazepanyl, and oxazepanyl wherein each ring is independently optionally substituted with J2. In certain embodiments, Q2 is selected from the group consisting of absent, cyclohexyl, diazabicyclooctyl, phenyl, pyridyl, piperidinyl, piperazinyl, pyrrolidinyl, diazepanyl, and oxazepanyl wherein each ring is independently optionally substituted with J2, additionally Q2 is independently optionally substituted with one or more $R_{13}$ groups, additional values for Q2 include azetidinyl, morpholinyl, azepanyl, diazabicycloheptyl, diazabicyclooctyl, indolyl, tetrahydropyridyl, dihydropyridyl, octahydropyrrolopyrazyl, or octahydropyrrolopyridyl each independently optionally substituted with J2, and additionally independently optionally substituted with one or more $R_{13}$ groups. In certain embodiments, Q2 is selected from the group consisting of cyclohexyl, 3,8-diazabicyclo[3.2.1.]octyl, phenyl, pyridyl, piperidinyl, piperazinyl, pyrrolidinyl, diazepanyl, and oxazepanyl wherein each ring is independently optionally substituted with J2, additionally Q2 is independently optionally substituted with one or more $R_{13}$ groups, additional values for Q2 include absent, azetidinyl, morpholinyl, azepanyl, 2,5 diazabicycloheptyl, diazabicyclooctyl, indolyl, tetrahydropyridyl, octahydro-1H-pyrrolo[2,3-b]pyrazyl, or octahydropyrrolo[1,2-a]pyrazyl each independently optionally substituted with J2, and additionally independently optionally substituted with one or more $R_{13}$ groups. In certain embodiments, Q2 is represented by the following structural formula:

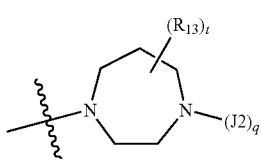

t is 0 or 1, and q is 0 or 1. In certain alternative embodiments, Q2 is represented by a structural formula represented by:

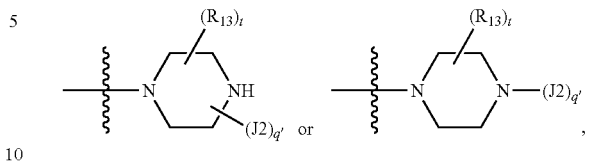

t is 0 or 1, and q' is 0, 1 or 2.

In certain embodiments, Q2 is represented by the following structural formula:

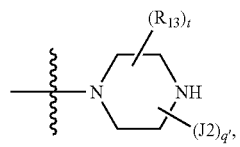

t is 0 or 1, and q' is 0, 1 or 2.

In certain embodiments, Q2 is represented by the following structural formula:

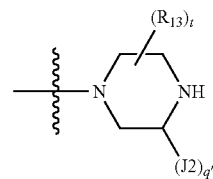

t is 0 or 1, and q' is 0, 1 or 2.

In certain embodiments, Q2 is represented by the following structural formula:

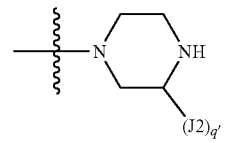

q' is 0, 1 or 2.

In certain embodiments Q2 is not substituted with $R_{13}$. In certain embodiments Q2 is substituted with J2. In certain embodiments Q2 is not —H.

In certain embodiments, Q2 is a 3-8 membered saturated, partially saturated or fully unsaturated monocyclic ring having 0-3 heteroatoms independently selected from nitrogen, oxygen and sulfur, wherein Q2 is optionally substituted with J2 and independently optionally and independently substituted with one or more $R_{13}$ groups, preferably Q2 is a 3-8 membered saturated, partially saturated or fully unsaturated monocyclic ring having 0-3 nitrogen atoms, wherein Q2 is optionally substituted with J2.

In certain alternative embodiments, Q2 is a 3-8 membered saturated, partially saturated or fully unsaturated monocyclic ring having 1-3 nitrogen atoms, wherein Q2 is optionally substituted with J2.

In certain alternative embodiments, Q2 is absent.

J2 is —Y2-M2.

Y2 is a bond (absent) or C1-6 aliphatic (alternatively C1-10), wherein up to three methylene units of Y2 are optionally replaced with G1' wherein G1' is —N($R^\$$)—, —O—, —S—, —C(O)—, —S(O)—, or —S(O)$_2$—. Y2 is a bond (absent), oxo, or C1-6 aliphatic, wherein up to three methylene units of Y2 are optionally replaced with G1' wherein G1' is —N($R^\$$)—, —O—, —S—, —C(O)—, —S(O)—, or —S(O)$_2$—. Y2 is absent, oxo, or C1-10 aliphatic, wherein up to three methylene units of Y2 are optionally replaced with G1' wherein G1' is —N($R^\$$)—, —O—, —S—, —C(O)—, —S(O)—, or —S(O)$_2$—. In certain embodiments two or more G1' groups may optionally replace adjacent methylene units of Y2 to give groups which include, but are not limited to: —CO$_2$—, —N($R^\$$)CO—, —C(O)N($R^\$$)—, —N($R^\$$)C(O)O—, —OC(O)N($R^\$$)—, —N($R^\$$)CON($R^\$$)—, —N($R^\$$)SO$_2$—, —SO$_2$N($R^\$$)—, —N($R^\$$)SO$_2$N($R^\$$)—, and —N($R^\$$)N($R^\$$)—. In certain embodiments the methylene units of Y2 are optionally replaced by —O—, CO—, —N($R^\$$)—, —CO$_2$—, —S(O)$_2$—, —N($R^\$$)CO—, or —C(O)N($R^\$$)—. In certain embodiments the methylene units of Y2 are optionally replaced by —CO—, —N($R^\$$)—, —CO$_2$—, —S(O)$_2$—, —N($R^\$$)CO—, or —C(O)N($R^\$$)—. In certain embodiments the methylene units of Y2 are optionally replaced by —O—, —CO$_2$—, —CO—, —S(O)$_2$— or —N($R^\$$)—. In certain embodiments, Y2 is a bond (absent), oxo or C1-6 aliphatic wherein up to three methylene units of Y2 are independently and optionally replaced with G1 wherein G1 is —N($R^\$$)—, —O—, —C(O)—, or —S(O)$_2$—. In certain embodiments, Y2 is absent, oxo or C1-10 aliphatic wherein up to three methylene units of Y2 are independently and optionally replaced with G1' wherein G1' is —N($R^\$$)—, —O—, —C(O)—, or —S(O)$_2$—. In certain embodiments, Y2 is a bond (absent) or C1-6 aliphatic wherein up to three methylene units of Y2 are independently and optionally replaced with G1' wherein G1' is —N($R^\$$)—, —O—, —C(O)—, or —S(O)$_2$—. In certain embodiments, Y2 is a bond (absent), oxo, or C1-6 aliphatic wherein up to three methylene units of Y2 are optionally and independently replaced with G1' wherein G1' is —O—, —C(O)—, or —SO$_2$—. In certain embodiments, Y2 is absent, oxo, or C1-10 aliphatic wherein up to three methylene units of Y2 are optionally and independently replaced with G1' wherein G1' is —N($R^\$$)—, —O—, or —C(O)—. In certain embodiments, Y2 is a bond (absent) or C1-6 aliphatic wherein up to three methylene units of Y2 are optionally and independently replaced with G1' wherein G1' is —O—, or —C(O)—, or —SO$_2$—. Additionally, in all the preceding recitations of Y2 in this paragraph Y2 is optionally and independently substituted with one or more JT2. Alternatively, in all the preceding recitiaitons of Y2 in this paragraph Y2 is not substituted.

In one embodiment Y2 is a bond (absent) or represented by a structural formula selected from the group consisting of:

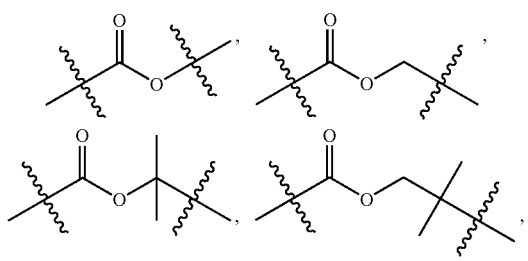

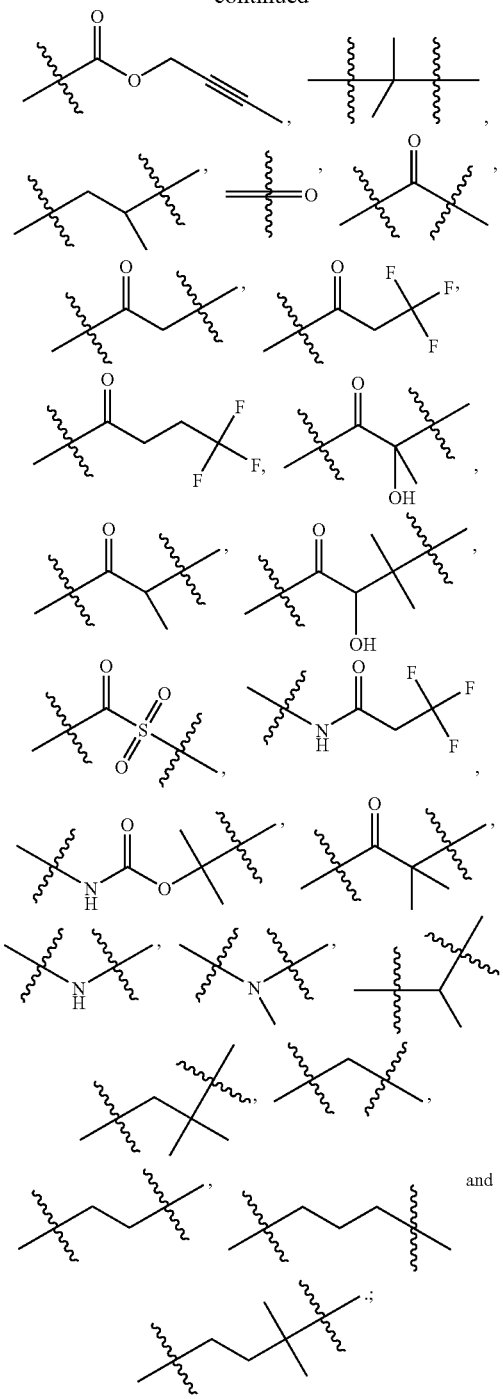

additionally Y2 can be:

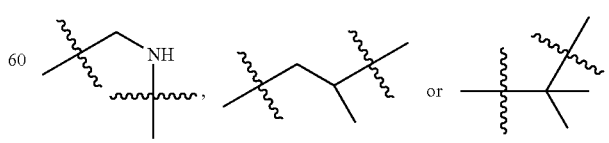

M2 is —H, C1-6 aliphatic, C3-8 cycloaliphatic, haloC1-4 aliphatic, O(haloC1-4 aliphatic), 3-8 membered heterocyclyl, 5-6 membered heteroaryl, 5-6 membered aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$, wherein M2 is optionally substituted with one or more R". M2 is absent, —H, C1-6 aliphatic, C3-8 cycloaliphatic, haloC1-4 aliphatic, O(haloC1-4 aliphatic), 3-8 membered heterocyclyl, heteroaryl, aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$, wherein M2 is optionally substituted with one or more R$^\$$. In certain embodiments, M2 is —H, C1-6 aliphatic, C3-8 cycloaliphatic, haloC1-4 aliphatic, O(haloC1-4 aliphatic), 3-8 membered heterocyclyl, 5-6 membered heteroaryl, 5-6 membered aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M2 is optionally substituted with one or more J. In certain embodiments, M2 is absent, —H, C1-6 aliphatic, C3-8 cycloaliphatic, haloC1-4 aliphatic, O(haloC1-4 aliphatic), 3-8 membered heterocyclyl, 5-6 membered heteroaryl, 5-6 membered aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or PO(OR$^\$$)$_2$, wherein M2 is optionally substituted with one or more J. In certain embodiments, M2 is absent, —H, C1-6 aliphatic, C3-8 cycloaliphatic, haloC1-4 aliphatic, O(haloC1-4 aliphatic), 3-8 membered heterocyclyl, heteroaryl, aryl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$, wherein M2 is optionally substituted with one or more J; additionally M2 is not —H. In certain embodiments, M2 is —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR)$_2$, wherein M2 is optionally substituted with one or more R". In certain embodiments, M2 is absent, —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$, wherein M2 is optionally substituted with one or more R". In certain embodiments, M2 is —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$, wherein M2 is optionally substituted with one or more J. In certain embodiments, M2 is absent, —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$, wherein M2 is optionally substituted with one or more J. In certain embodiments, M2 is absent, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$, wherein M2 is optionally substituted with one or more J. In certain embodiments, M2 is absent, C1-6 aliphatic, C3-8 cycloaliphatic, 3-8 membered heterocyclyl, 5-6 membered heteroaryl, phenyl, —N(O)$_2$, —CN, —OR$^\$$, —N(R$^\$$)$_2$, —C(O)R$^\$$, —C(O)$_2$R$^\$$, —S(O)R$^\$$, or —S(O)$_2$R$^\$$ wherein M2 is optionally substituted with one or more J. In certain embodiments, M2 is C1-6 aliphatic, C3-8 cycloaliphatic, 3-8 membered heterocyclyl, 5-12 membered heteroaryl, 5-12 membered aryl, —N(R$^\$$)$_2$, —OR$^\$$, —C(O)R$^\$$, —C(O)$_2$R$^\$$, —S(O)R$^\$$, or —S(O)$_2$R$^\$$ wherein M2 is optionally and independently substituted with one or more J; or M2 is absent, —NO$_2$, or —CN. In certain embodiments, M2 is —OR$^\$$, —N(R$^\$$)$_2$, —C(O)R$^\$$, —C(O)$_2$R$^\$$, —S(O)R$^\$$, or —S(O)$_2$R$^\$$ pyridyl, pyrazinyl, pyrimidinyl, pyrrolyl, imidazolyl, pyrazolyl, furyl, tetrahydrofuryl, thienyl, tetrahydrothienyl, pyranyl, tetrahydropyranyl, isooxazolyl, piperidinyl, pyrrolidinyl, cyclopentyl, cyclohexyl, cyclopropyl, naphthyl, or phenyl, wherein M2 is optionally and independently substituted with one or more J; or M2 is absent, —N(O)$_2$, or —CN. In certain embodiments, M2 is absent, phenyl, pyridyl, pyrazinyl, pyrimidinyl, pyrrolyl, imidazolyl, pyrazolyl, furyl, tetrahydrofuryl, thienyl, tetrahydrothienyl, pyranyl, tetrahydropyranyl, isooxazolyl, piperidinyl, pyrrolidinyl, cyclopentyl, cyclohexyl, cyclopropyl, —N(O)$_2$, —CN, —OR$^\$$, —N(R$^\$$)$_2$, —C(O)R$^\$$, —C(O)$_2$R$^\$$, —S(O)R$^\$$, or —S(O)$_2$R$^\$$ wherein M2 is optionally substituted with one or more J. In certain embodiments, M2 is —H, C3-8 cycloaliphatic, 3-8 membered heterocyclyl, 5-6 membered heteroaryl, phenyl, halogen, —NO$_2$, —CN, —P(O)R$^\$$, —P(O)$_2$R$^\$$, —P(O)(R$^\$$)$_2$, or —PO(OR$^\$$)$_2$, wherein M2 is optionally and independently substituted with one or more J. In certain embodiments, M2 is absent, —H, C3-8 cycloaliphatic, 3-8 membered heterocyclyl, 5-6 membered heteroaryl, phenyl, halogen, —NO$_2$, —CN, —OR$^\$$, —SR$^\$$, —N(R$^\$$)$_2$, —P(O)R$^\$$, —P(O)$_2$R$^\$$, —P(O)(R$^\$$)$_2$, or —PO(OR$^\$$)$_2$, wherein M2 is optionally and independently substituted with one or more J. In certain embodiments, M2 is —H, C3-8 cycloaliphatic, 3-8 membered heterocyclyl, 5-6 membered heteroaryl, phenyl, halogen, —NO$_2$, or —CN, wherein M2 is optionally and independently substituted with one or more J. In certain embodiments, M2 is absent, —H, C3-8 cycloaliphatic, 3-8 membered heterocyclyl, 5-6 membered heteroaryl, phenyl, halogen, —OR$^\$$, —SR$^\$$, —N(R$^\$$)$_2$, or —CN, wherein M2 is optionally and independently substituted with one or more J.

Each J is independently halogen, C1-6 aliphatic, C3-6 cycloaliphatic, —NO$_2$, —CN, —N(R$^\$$)$_2$, —OR$^\$$, —C(O)R$^\$$, —CON(R$^\$$)$_2$, —C(O)$_2$R$^\$$, oxo, —O(haloC1-4 aliphatic), or halo(C1-4 aliphatic). Each J is independently —H, halogen, C1-6 aliphatic, C3-6 cycloaliphatic, —NO$_2$, —CN, —N(R$^\$$)$_2$, —OR$^\$$, —C(O)R$^\$$, —CON(R$^\$$)$_2$, —C(O)$_2$R$^\$$, oxo, —O(haloC1-4 aliphatic), or halo(C1-4 aliphatic). In certain embodiments, each J is independently halogen, C1-6 aliphatic, —NO$_2$, —CN, —N(R$^\$$)$_2$, —OR$^\$$, —C(O)R$^\$$, —C(O)N(R$^\$$)$_2$, —C(O)$_2$R$^\$$, oxo, or halo(C1-4 aliphatic). In certain embodiments, each J is independently —H, halogen, C1-6 aliphatic, —NO$_2$, —CN, —N(R$^\$$)$_2$, —OR$^\$$, —C(O)R$^\$$, —C(O)N(R$^\$$)$_2$, —C(O)$_2$R$^\$$, oxo, or halo(C1-4 aliphatic). In certain embodiments, each J is independently —H, halogen, C1-6 aliphatic, —NO$_2$, —CN, —N(R$^\$$)$_2$, —OR$^\$$, oxo, or halo(C1-4 aliphatic). In certain embodiments, J is halogen, alkyl, haloalkyl, —NH$_2$, —OH, or oxo.

$R_4$ is —H or an optionally substituted C1-C6 alkyl. $R_4$ is —H or an optionally substituted C1-C6 alkyl independently and optionally substituted with one or more $R_{13}$. In certain embodiments, $R_4$ is —H or C1-C6 alkyl.

Each JT1 is independently R". In certain embodiments each JT1 is independently halogen, cyano, nitro, amino, aminoalkyl, alkylaminoalkyl, alkoxy or hydroxy. In certain embodiments, each JT1 is independently halogen, —CN, —N(O)$_2$, or hydroxy. In certain embodiments each JT1 is independently halogen or hydroxy.

Each JT2 is independently R". In certain embodiments each JT2 is independently halogen, cyano, nitro, amino, aminoalkyl, alkylaminoalkyl, alkoxy or hydroxy. In certain embodiments, each JT2 is independently halogen, —CN, —N(O)$_2$, or hydroxy. In certain embodiments, each JT2 is independently halogen, —CN, amino, or hydroxy. In certain embodiments each JT2 is independently halogen or hydroxy.

Each R$^\$$ is independently —H or C1-C6 alkyl.

Each $R_{12}$ is independently R'. In certain embodiments, each $R_{12}$ is independently halogen, amino, aminoalkyl, alkylaminoalkyl, alkoxy, hydroxy, —CN, —NO$_2$, or C1-C6 alkyl independently and optionally substituted with one or more JT1. In certain embodiments, each $R_{12}$ is independently halogen, amino, aminoalkyl, alkylaminoalkyl, alkoxy, hydroxy, —CN, —NO$_2$, or optionally substituted C1-C6 alkyl. In certain embodiments, each $R_{12}$ is independently halogen, —CN, —NO$_2$, or C1-C6 alkyl independently and optionally substituted with one or more JT1. In certain embodiments, each $R_{12}$ is independently halogen, —CN, —NO$_2$, or optionally substituted C1-C6 alkyl. In certain embodiments, each $R_{12}$ is independently Br, Cl, F, or C1-C6 alkyl optionally substituted with halogen.

Each $R_{12'}$ is independently R'. Each $R_{12}$ is independently halogen, amino, aminoalkyl, alkylaminoalkyl, alkoxy, hydroxy, —CN, —NO$_2$, or optionally and independently substituted C1-C10 aliphatic wherein up to three methylene units are optionally and independently replaced by G' wherein G' is —O—, —S(O)$_p$—, —N(R$_4$)—, or —C(O)—, and each methylene unit is optionally and independently substituted with one or more JT3, or each $R_{12}$ is cycloaliphatic, or phenyl; p is 0, 1 or 2. In certain embodiments, each $R_{12}$ is independently halogen, amino, aminoalkyl, alkylaminoalkyl, alkoxy, hydroxy, —CN, —NO$_2$, or optionally and independently substituted C1-C10 aliphatic wherein up to three methylene units are optionally and independently replaced by G' wherein G' is —O—, —S(O)$_p$—, —N(R$_4$)—, or —C(O)—, and each methylene unit is optionally and independently substituted with one or more JT3, or each $R_{12'}$ is cycloaliphatic, phenyl, or heteroaryl, each optionally and independently substituted with one or more JT4. In certain embodiments, each $R_{12}$ is independently halogen, amino, aminoalkyl, alkylaminoalkyl, alkoxy, hydroxy, —CN, —NO$_2$, or optionally and independently substituted C1-C10 aliphatic wherein up to three methylene units are optionally and independently replaced by G' wherein G' is —O—, —S(O)$_p$—, —N(R$_4$)—, or —C(O)—, and each methylene unit is optionally and independently substituted with one or more JT3, or each $R_{12'}$ is C3-C8 cycloaliphatic, phenyl, or a monocyclic heteroaryl, each optionally and independently substituted with one or more JT4.

Each $R_{13}$ is independently R". In certain embodiments, each $R_{13}$ is independently halogen, amino, aminoalkyl, alkylaminoalkyl, alkoxy or hydroxy, oxo, —CN, —NO$_2$, or C1-C6 alkyl independently and optionally substituted with one or more JT1. In certain embodiments, each $R_{13}$ is independently halogen, amino, aminoalkyl, alkylaminoalkyl, alkoxy or hydroxy, oxo, —CN, —NO$_2$, or optionally substituted C1-C6 alkyl. In certain embodiments, each $R_{13}$ is independently halogen, —CN, —NO$_2$, or C1-C6 alkyl independently and optionally substituted with one or more JT1, additionally $R_{13}$ is alkoxy independently and optionally substituted with one or more JT1 or hydroxy. In certain embodiments, each $R_{13}$ is independently halogen, —CN, —NO$_2$, or optionally substituted C1-C6 alkyl, additionally $R_{13}$ is alkoxy or hydroxy. In certain embodiments, each $R_{13}$ is independently Br, Cl, F, or C1-C6 alkyl optionally substituted with halogen, additionally $R_{13}$ is alkoxy or hydroxy.

In certain embodiments, B is represented by the following structural formula:

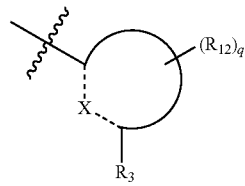

q is 0 or 1. X is, —O—, —S—, or —NR$^x$—. R$^x$ is absent or —H, and the remainder of the variables are as described above for structural formula I.

In certain embodiments, B is represented by the following structural formula:

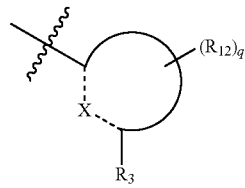

q is 0 or 1. X is, —O—, —S—, or —NR$^x$—. R$^x$ is absent or —H; $R_3$ is halogen, or T2-Q2; T2 is a bond; Q2 is —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more $R_{13}$ groups; and the remainder of the variables are as described above for structural formula I.

In certain embodiments, the compound of the present invention is not:

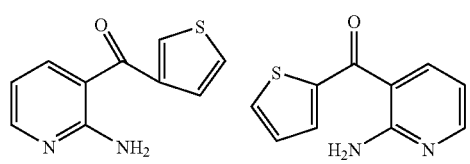

(2-aminopyridin-3-yl)(thiophen-3-yl)methanone, 2-amino-3-(2-thenoyl)pyridine,

(2-amino-5-bromopyridin-3-yl)(6-fluoropyridin-3-yl)methanone,

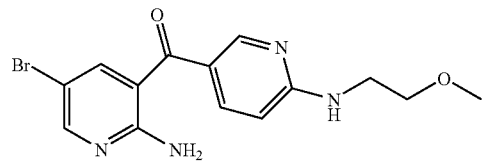

(2-amino-5-bromopyridin-3-yl)(6-(2-methoxyethylamino)pyridin-3-yl)methanone

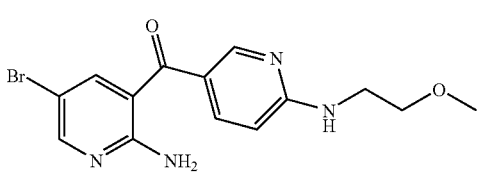

(2-amino-5-(3,4-dimethoxyphenyl)pyridin-3-yl)(6-aminopyridin-3-yl)methanone

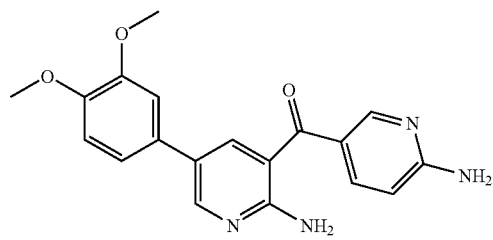

(2-amino-5-(3,4-dim ethoxyphenyl)pyridin-3-yl)(6-(2-methoxyethylamino)pyridin-3-yl)methanone

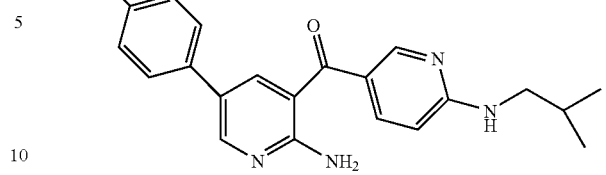

(2-amino-5-(3,4-dimethoxyphenyl)pyridin-3-yl)(6-(isobutylamino)pyridin-3-yl)methanone, additionally the compound of the present invention is not:

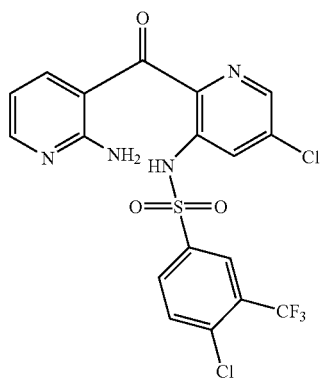

benzenesulfonamide, N-[2-[(2-amino-3pyridinyl)carbonyl]-5-chloro-3-pyridinyl]-4-chloro-(trifluoromethyl),

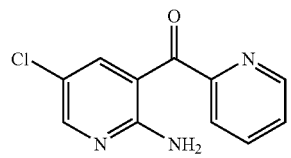

Methanone, (2-amino-5-chloro-3-pyridinyl)-4-pyridinyl-;

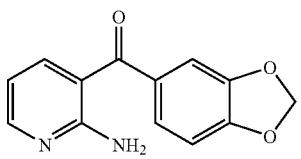

Methanone, (2-amino-3-pyridinyl)-1,3-benzodioxol-5-yl, or

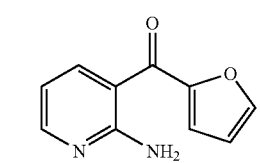

Methanone, (2-amino-3-pyridinyl)-2-furanyl-.

In certain embodiments, the present invention is a compound of structural formula I as described above wherein the compound is not: with the proviso the compound is not (2-amino-5-(3,4-dimethoxyphenyl)pyridin-3-yl)(6-aminopyridin-3-yl)methanone, (2-amino-5-bromopyridin-3-yl)(6-(2-methoxyethylamino)pyridin-3-yl)methanone, (2-amino-5-(3,4-dimethoxyphenyl)pyridin-3-yl)(6-(2-methoxyethylamino)pyridin-3-yl)methanone, (2-amino-5-(3,4-dimethoxyphenyl)pyridin-3-yl)(6-(isobutylamino)pyridin-3-yl)methanone In one embodiment when $R_1$ is —H, halogen, CN, $NO_2$, or T1-Q1; T1 is a bond or C1-6 aliphatic additionally up to three methylene units of T1 are optionally and independently replaced by G wherein G is —O—; Q1 is —H, or a 3-8-membered saturated, partially unsaturated, or fully unsaturated monocyclic ring having 0-3 heteroatoms independently selected from nitrogen, oxygen, and sulfur (additional values for Q1 include absent or an 8-12 membered saturated, partially saturated or fully unsaturated bicyclic ring system having 0-5 heteroatoms independently selected from nitrogen, oxygen and sulfur); Q1 is optionally substituted with J1; J1 is Y1-M1; Y1 is a bond or C1-6 alkyl group (additionally up to three methylene units of Y1 are optionally and independently replaced by G1 wherein G1 is —O—, and Y1 is optionally substituted with JT1); M1 is —H, C3-8 cycloaliphatic, 3-8 membered heterocyclyl, 5-6 membered heteroaryl, phenyl, halogen, —$NO_2$, or —CN (additionally M1 can be absent, —$OR^\$$, or —$N(R^\$)_2$); M1 is optionally and independently substituted with one or more J; $R_3$ is T2-Q2; T2-Q2 is not —H; T2 is a bond or C1-6 aliphatic, wherein up to three methylene units of T2 are optionally and independently replaced by G' wherein G' is —O—, —S—, —S(O)—, —$S(O)_2$—, —$N(R_4)$—, or —C(O)—; T2 is optionally substituted with one or more JT2; Q2 is —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J2 and independently optionally substituted with one or more $R_{13}$ groups (additionally Q2 can be absent); J2 is Y2-M2; Y2 is a bond or C1-6 aliphatic, wherein up to three methylene units of Y2 are optionally replaced with G1' wherein G1' is —$N(R^\$)$—, —O—, —S—, —C(O)—, —S(O)—, or —$S(O)_2$— (additionally Y2 is oxo and additionally Y2 is optionally substituted with JT2); and M2 is —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —$N(O)_2$, —CN, —$OR^\$$, —$SR^\$$, —$N(R^\$)_2$, —$C(O)R^\$$, —$C(O)_2R^\$$, —C(O)N$(R^\$)_2$, —$OC(O)R^\$$, —$OC(O)N(R^\$)_2$, —$NR^\$C(O)R^\$$, —$NR^\$C(O)_2R^\$$, $NR^\$C(O)N(R^\$)_2$, —$SO_2N(R^\$)_2$, —$NR^\$S(O)_2R^\$$, —$S(O)R^\$$, —$S(O)_2R^\$$, —$P(O)R^\$$, —$P(O)_2R^\$$, P(O)$(R^\$)_2$, or PO$(OR^\$)_2$, wherein M2 is optionally substituted with one or more J (additionally M2 can be absent); and the remainder of the variables are as described above for structural formula I.

Preferably, $R_1$ is —H, halogen, or -Q1-T1, where T1 is a bond, C1-C6 alkyl, C2-C6 alkenyl, or C2-C6 alkynyl additionally up to three methylene units of T1 are optionally and independently replaced by G wherein G is —O—; Q1 is —H, or a 3-8-membered saturated, partially unsaturated, or fully unsaturated monocyclic ring having 0-3 nitrogen atoms optionally substituted with J1 (additional values for Q1 include absent or an 8-12 membered saturated, partially saturated or fully unsaturated bicyclic ring system having 0-3 nitrogen atoms); T2 is a bond or C1-6 aliphatic, wherein up to three methylene units of T2 are optionally and independently replaced by G' wherein G' is —O—, —$N(R_4)$—, or —C(O)—; T2 is optionally and independently substituted with one or more JT2; Q2 is —H, or a 3-8-membered saturated, partially unsaturated, or fully unsaturated monocyclic ring having 0-3 heteroatoms independently selected from nitrogen, oxygen, and sulfur (additionally Q2 can be absent); Q2 is optionally substituted with J2; Y2 is a bond or C1-6 aliphatic wherein up to three methylene units of Y2 are independently and optionally replaced with G1' wherein G1' is —$N(R^\$)$—, —O—, —C(O)—, or —$S(O)_2$-(additionally Y2 is oxo and additionally Y2 is optionally substituted with JT2); M2 is —H, C3-8 cycloaliphatic, 3-8 membered heterocyclyl, 5-6 membered heteroaryl, phenyl, halogen, —$NO_2$, —CN, —$P(O)R^\$$, —$P(O)_2R^\$$, —$P(O)(R^\$)_2$, or —$PO(OR^\$)_2$, wherein M2 is optionally and independently substituted with one or more J (additionally M2 can be absent), and the remainder of the variables are as described above for structural formula I.

More preferably, $R_1$ is —H, halogen, or -Q1-T1, where T1 is as described above; Q1 is halogen, phenyl optionally substituted with J1, or pyridyl optionally substituted with J1, (additional values for Q1 include absent or cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with J1) (even more preferably, Q1 is phenyl optionally substituted with C1-C4 alkyl, or pyridyl optionally substituted with C1-C4 alkyl (additional values for Q1 include absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with C1-C4 alkyl, C1-C4 haloalkyl, —OH or $NH_2$); T2 is a bond or C1-6 aliphatic, wherein up to three methylene units of T2 are optionally and independently replaced by G' wherein G' is —$N(R_4)$—, or —CO—; T2 is optionally and independently substituted with one or more JT2 (even more preferably, T2 is represented a structural formula selected from the following structural formulas:

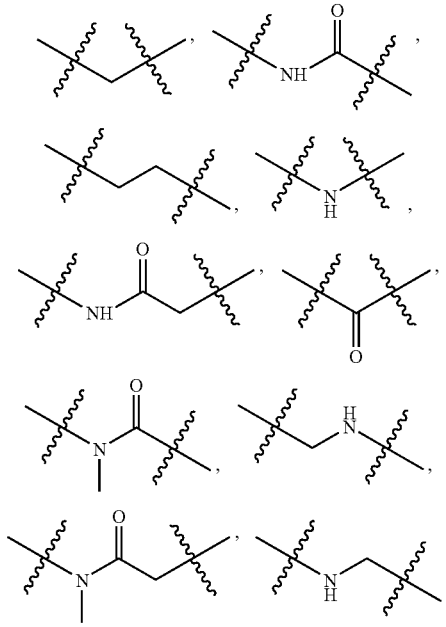

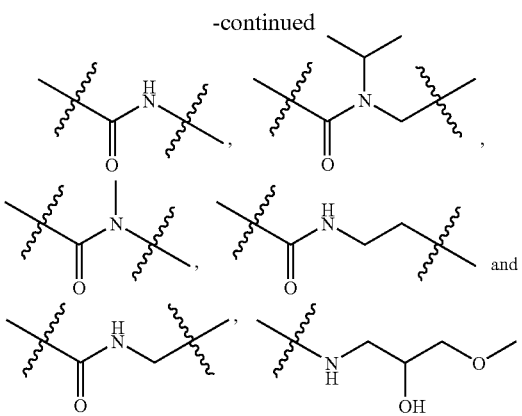

Additional values of T2 include:

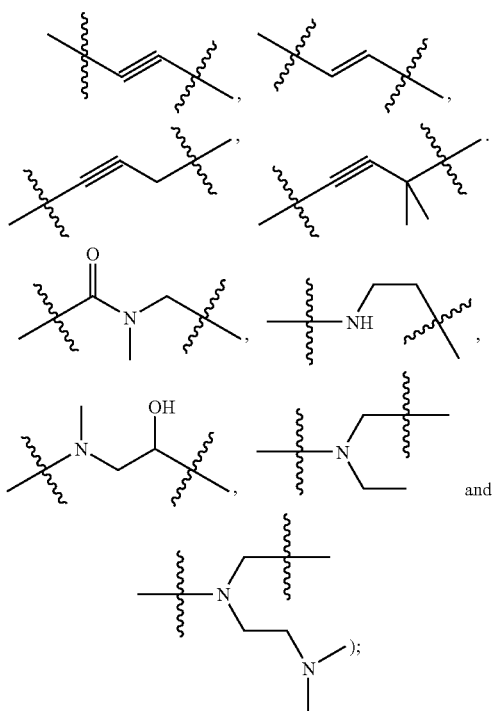

Q2 is —H, or a 3-8-membered saturated, partially unsaturated, or fully unsaturated monocyclic ring having 0-3 nitrogen atoms optionally substituted with J2 (additionally Q2 can be absent) (even more preferably Q2 is selected from the group consisting of phenyl, pyridyl, pyrazinyl, pyrimidinyl, pyrrolyl, imidazolyl, pyrazolyl, oxazolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, and thiazocanyl wherein each ring is independently optionally substituted with J2 (additional values for Q2 include cyclopropyl, cyclobutyl, cyclopentyl, cyclohexyl, cyclohexenyl, indolyl, indazolyl, benzimidazolyl, quinolyl, quinoxalyl, indolinyl, azabicyclopentyl, azabicyclohexyl, azabicycloheptyl, azabicyclooctyl, azabicyclodecyl, azabicyclohexyl, diazabicycloheptyl, diazabicyclooctyl, diazabicyclononyl, and diazabicyclodecyl, each optionally and independently substituted with J2); still more preferably, Q2 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, diazepanyl, and oxazepanyl wherein each ring is independently optionally substituted with J2 (an additional value for Q2 includes pyrrolidinyl, cyclopropyl, cyclobutyl, cyclopentyl, cyclohexyl, cyclohexenyl, indolyl, indazolyl, benzimidazolyl, quinolyl, quinoxalyl, indolinyl, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, each optionally and independently substituted with J2); still more preferably, Q2 is selected from the group consisting of phenyl, pyridyl, piperidinyl, piperazinyl, diazepanyl, and oxazepanyl wherein each ring is independently optionally substituted with J2 (an additional value for Q2 includes absent pyrrolidinyl, cyclohexyl, 3,8-diazobicyclo[3.2.1.]octyl); still more preferably, Q2 is represented by the following structural formula:

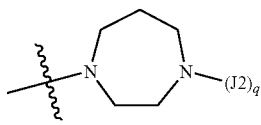

q is 0 or 1); Y2 is a bond or C1-6 aliphatic wherein up to three methylene units of Y2 are optionally and independently replaced with G1' wherein G1' is —O—, or —C(O)—, or —SO$_2$— (additionally Y2 is oxo and additionally Y2 optionally substituted with JT2); and M2 is —H, C3-8 cycloaliphatic, 3-8 membered heterocyclyl, 5-6 membered heteroaryl, phenyl, halogen, —NO$_2$, or —CN, wherein M2 is optionally and independently substituted with one or more J (additionally M2 can be absent, —OR$^\$$, or —N(R$^\$$)$_2$), and the remainder of the variables are as described above for structural formula I.

In an alternative embodiment when R$_3$ is —H, halogen, CN, NO$_2$, or T2-Q2; T2 is a bond or C1-6 aliphatic additionally up to three methylene units of T1 are optionally and independently replaced by G' wherein G' is —O—; Q2 is —H, or a 3-8-membered saturated, partially unsaturated, or fully unsaturated monocyclic ring having 0-3 heteroatoms independently selected from nitrogen, oxygen, and sulfur; (additional values/for Q2 include absent or an 8-12 membered saturated, partially saturated or fully unsaturated bicyclic ring system having 0-5 heteroatoms independently selected from nitrogen, oxygen and sulfur) Q2 is optionally substituted with J2; J2 is Y2-M2; Y2 is a bond or C1-6 alkyl group (additionally up to three methylene units of Y2 are optionally and independently replaced by G1' wherein G1' is —O—, and Y2 is optionally substituted with JT2); M2 is —H, C3-8 cycloaliphatic, 3-8 membered heterocyclyl, 5-6 membered heteroaryl, phenyl, halogen, —NO$_2$, or —CN; M2 is optionally and independently substituted with one or more J (additionally M2 can be absent, —OR$^\$$, or —N(R$^\$$)$_2$); R$^1$ is T1-Q1; T1-Q1 is not —H; T1 is a bond or C1-6 aliphatic, wherein up to three methylene units of T1 are optionally and independently replaced by G wherein G is —O—, —S—, —S(O)—, —S(O)$_2$—, —N(R$^4$)—, or —C(O)—; T1 is optionally substituted with one or more JT1; Q1 is —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is optionally substituted with J1 and independently optionally substituted with one or more $R_{13}$ groups (additionally Q1 can be absent); J1 is Y1-M1; Y1 is a bond or C1-6 aliphatic, wherein up to three methylene units of Y1 are optionally replaced with G1 wherein G1 is —N(R$^\$$)—, —O—, —S—, —C(O)—, —S(O)—, or —S(O)$_2$— (additionally Y1 is oxo optionally substituted with JT1); and M1 is —H, C1-6 aliphatic, C3-8 cycloaliphatic, haloC1-4 aliphatic, O(haloC1-4 aliphatic), 3-8 membered heterocyclyl, 5-6 membered heteroaryl, phenyl, halogen, —N(O)$_2$, —CN, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, P(O)(R$^\$$)$_2$, or PO(OR$^\$$)$_2$, wherein M1 is optionally substituted with one or more J (additionally M1 is absent) and the remainder of the variables are as described above for structural formula I.

Preferably, $R_3$ is —H, halogen, or T2-Q2; T2 is a bond, C1-C6 alkyl, C2-C6 alkenyl, or C2-C6 alkynyl additionally up to three methylene units of T1 are optionally and independently replaced by G wherein G is —O—; Q2 is —H, or a 3-8-membered saturated, partially unsaturated, or fully unsaturated monocyclic ring having 0-3 nitrogen atoms optionally substituted with J2 (additional values for Q2 include absent or an 8-12 membered saturated, partially saturated or fully unsaturated bicyclic ring system having 0-3 nitrogen atoms); T1 is a bond or C1-6 aliphatic, wherein up to three methylene units of T1 are optionally and independently replaced by G wherein G is —O—, —N(R$_4$)—, or —C(O)—; T1 is optionally and independently substituted with one or more JT1; Q1 is —H, or a 3-8-membered saturated, partially unsaturated, or fully unsaturated monocyclic ring having 0-3 heteroatoms independently selected from nitrogen, oxygen, and sulfur (additionally Q1 can be absent); Q1 is optionally substituted with J1; Y1 is a bond or C1-6 aliphatic wherein up to three methylene units of Y1 are independently and optionally replaced with G1 wherein G1 is —N(R$^\$$)—, —O—, —C(O)—, or —S(O)$_2$— (additionally Y1 is oxo and additionally Y1 is optionally substituted with JT1); M1 is —H, C3-8 cycloaliphatic, 3-8 membered heterocyclyl, 5-6 membered heteroaryl, phenyl, halogen, —NO$_2$, —CN, —P(O)R$^\$$, —P(O)$_2$R$^\$$, —P(O)(R$^\$$)$_2$, or —PO(OR$^\$$)$_2$, wherein M1 is optionally and independently substituted with one or more J (additionally M1 can be absent), and the remainder of the variables are as described above for structural formula I.

More preferably, $R_3$ is —H, halogen, or T2-Q2; T2 is as described above; Q2 is halogen, phenyl optionally substituted with J2, or pyridyl optionally substituted with J2 (additional values for Q2 include absent or cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with J1), (even more preferably, Q1 is phenyl optionally substituted with C1-C4 alkyl, or pyridyl optionally substituted with C1-C4 alkyl (additional values for Q2 include absent, cyclopropyl, cyclobutyl, cyclopentyl, cyclohexyl, cyclohexenyl, indolyl, quinolyl, pyridyl, pyrrolyl, piperidinyl, piperizinyl, pyrrolidinyl, or phenyl optionally substituted with C1-C4 alkyl, C1-C4 haloalkyl, —OH or NH$_2$); T1 is a bond or C1-6 aliphatic, wherein up to three methylene units of T1 are optionally and independently replaced by G wherein G is —N(R$_4$)—, or —CO—; T1 is optionally and independently substituted with one or more JT1 (even more preferably, T1 is represented a structural formula selected from the following structural formulas:

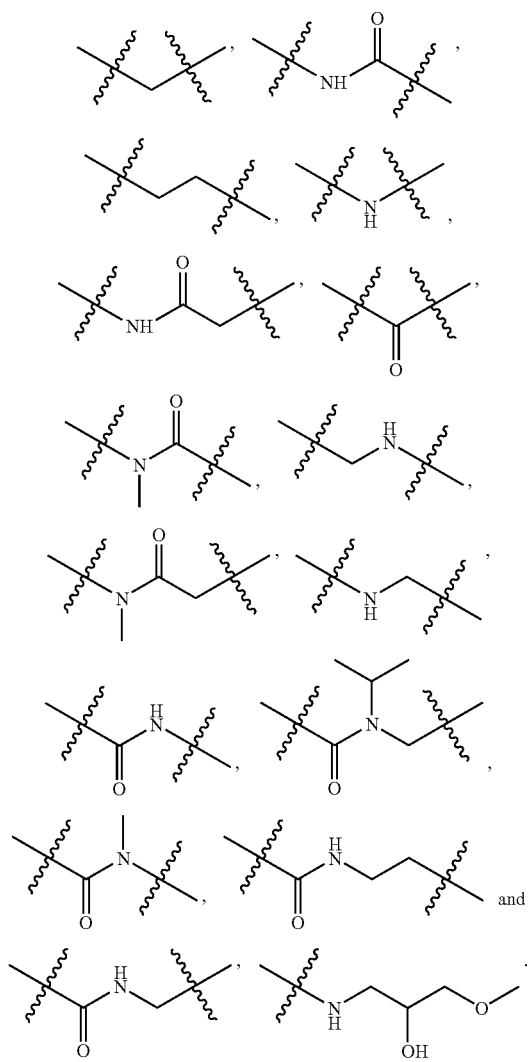

Additional values of T1 include:

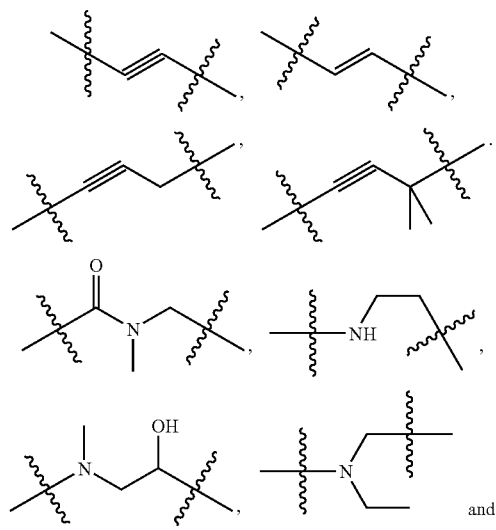

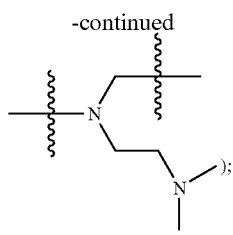

Q1 is —H, or a 3-8-membered saturated, partially unsaturated, or fully unsaturated monocyclic ring having 0-3 nitrogen atoms optionally substituted with J2 (additionally Q1 can be absent) (even more preferably Q1 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, and thiazocanyl wherein each ring is independently optionally substituted with J1 (additionally values for Q1 include cyclopropyl, cyclobutyl, cyclopentyl, cyclohexyl, cyclohexenyl, indolyl, indazolyl, benzimidazolyl, quinolyl, quinoxalyl, indolinyl, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, each optionally and independently substituted with J2); still more preferably, Q1 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, diazepanyl, and oxazepanyl wherein each ring is independently optionally substituted with J1 (an additional value for Q1 includes pyrrolidinyl, cyclopropyl, cyclobutyl, cyclopentyl, cyclohexyl, cyclohexenyl, indolyl, indazolyl, benzimidazolyl, quinolyl, quinoxalyl, indolinyl, azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, and diazabicyclodecyl, each optionally and independently substituted with J2); still more preferably, Q1 is selected from the group consisting of phenyl, pyridyl, piperidinyl, piperazinyl, diazepanyl, and oxazepanyl wherein each ring is independently optionally substituted with J1 (an additional value for Q1 includes pyrrolidinyl, cyclohexyl, 3,8-diazobicyclo[3.2.1.]octyl) still more preferably, Q1 is represented by the following structural formula:

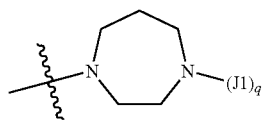

q is 0 or 1); Y1 is a bond or C1-6 aliphatic wherein up to three methylene units of Y1 are optionally and independently replaced with G1 wherein G1 is —O—, or —C(O)—, or —SO$_2$— (additionally Y1 is optionally substituted with JT1); and M2 is —H, C3-8 cycloaliphatic, 3-8 membered heterocyclyl, 5-6 membered heteroaryl, phenyl, halogen, —NO$_2$, or —CN, wherein M1 is optionally and independently substituted with one or more J (additionally M1 is absent, —OR$^\$$, or —N(R$^\$$)$_2$), and the remainder of the variables are as described above for structural formula I.

In a first embodiment, the present invention is, a compound represented by structural formula I wherein, B is a monocyclic heteroaromatic ring, a 6,6 bicyclic heteroaromatic ring, or a 6,5 bicyclic heteroaromatic ring (additionally wherein B is substituted with R$_3$ and independently optionally and independently substituted with one or more R$_{12}$ (and additionally independently optionally substituted with R$_{12}$'), and the remainder of the variables are as described above for structural formula I.

In a second embodiment, the present invention is, a compound represented by structural formula I wherein, Z is O and the remainder of the variables are as described above for the first embodiment.

In a third embodiment, the present invention is, a compound represented by structural formula I wherein, R$_2$ is —H, halogen, —CN, —N(O)$_2$, or C1-C6 alkyl optionally and independently substituted with one or more R$_{13}$, preferably R$_2$ is —H, and the remainder of the variables are as described above for the first or second embodiments.

In a fourth embodiment, the present invention is, a compound represented by structural formula I wherein, R$_1$ is —H, halogen, or -T1-Q1;

T1 is a bond (absent) or C1-6 aliphatic (alternatively C1-10 aliphatic), wherein up to three methylene units of T1 are optionally and independently replaced by G wherein G is —O—, —N(R$_4$)—, or —C(O)—, (additionally T1 is optionally and independently substituted with one or more JT1);

Q1 is —H, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is independently optionally substituted with J1 (additionally Q1 can be absent, additionally Q1 is not —H);

J1 is —Y1-M1;

Y1 is a bond (absent) or C1-6 aliphatic (alternatively C1-10 aliphatic) wherein up to three methylene units of Y1 are optionally and independently replaced with G1 wherein G1 is —N(R$^\$$)—, —O—, —C(O)—, or —S(O)$_2$— (additionally Y1 can be optionally and independently substituted with one or more JT1 additionally Y1 can be oxo); and M1 is —H, C3-8 cycloaliphatic, 3-8 membered heterocyclyl, 5-6 membered heteroaryl, phenyl, halogen, —NO$_2$, —CN, —P(O)R$^\$$, —P(O)$_2$R$^\$$, P(O)(R$^\$$)$_2$, or PO(OR$^\$$)$_2$, wherein M1 is optionally and independently substituted with one or more J (additionally M1 can be absent, —OR$^\$$, —SR$^\$$, —N(R$^\$$)$_2$, additionally M1 is not —H), and the remainder of the variables are as described above for the first, second, or third embodiments.

In a fifth embodiment, the present invention is, a compound represented by structural formula I wherein, R$_1$ is —H, halogen, or -T1-Q1;

T1 is a bond (absent) or C1-6 aliphatic (alternatively C1-10 aliphatic), (additionally up to three methylene units of T1 can be optionally and independently replaced by G wherein G is —O— (additionally G can be —N(R$_4$)—)). Additionally, in this embodiment T1 can additionally be optionally and independently substituted with one or more JT1;

Q1 is —H, or a 3-8-membered saturated, partially unsaturated, or fully unsaturated monocyclic ring having 0-3 heteroatoms independently selected from nitrogen, oxygen, and sulfur (additionally Q1 is absent or an 8-12 membered saturated, partially unsaturated or fully unsaturated bicyclic ring system having 0-5 heteroatoms independently selected from nitrogen, oxygen and sulfur (wherein Q1 is additionally optionally substituted with J1); Q1 is optionally substituted with J1, alternatively Q1 is as in the fourth embodiment;

Y1 is a bond (absent) or C1-6 aliphatic (alternatively C1-10 aliphatic) wherein up to three methylene units of Y1 are optionally and independently replaced with G1 wherein G1 is —O— or —C(O)— (additionally G1 can be —N(R$^\$$), —S(O)$_2$—), and additionally in this embodiment Y1 can be optionally and independently substituted with one or more JT1); and M1 is —H, C3-8 cycloaliphatic, 3-8 membered heterocyclyl, 5-6 membered heteroaryl, phenyl, halogen, —NO$_2$, or —CN; M1 is optionally and independently substituted with one or more J (additionally M1 can be absent, —OR$^\$$, —N(R$^\$$)$_2$ additionally M1 is not —H or —NO$_2$) and the remainder of the variables are as described above for the first, second, third or fourth embodiments.

In a sixth embodiment, the present invention is, a compound represented by structural formula I wherein, Q1 is —H, or a 3-8-membered saturated, partially unsaturated, or fully unsaturated monocyclic ring having 0-3 nitrogen atoms optionally substituted with J1 (additionally Q1 is absent or an 8-12 membered saturated, partially unsaturated or fully unsaturated bicyclic ring system having 0-3 nitrogen atoms wherein each ring is optionally substituted with J1) alternatively Q1 is as in the fourth embodiment; and each J is independently —H, halogen, C1-6 aliphatic, —NO$_2$, —CN, —N(R$^\$$)$_2$, —OR$^\$$, —C(O)R$^\$$, —C(O)N(R$^\$$)$_2$, —C(O)$_2$R$^\$$, oxo, or halo(C1-4 aliphatic) (additionally J is not —H) and the remainder of the variables are as described above for any of the first through fifth embodiments.

In a seventh embodiment, the present invention is, a compound represented by structural formula I wherein, R$_1$ is -T1-Q1, (alternatively R$_1$ is as described in the fourth embodiment);

T1 is a bond (absent), C1-C6 alkyl (alternatively C1-10 alkyl), C2-C6 alkenyl (alternatively C2-10 alkenyl), or C2-C6 alkynyl (alternatively C2-10 alkynyl), (additionally up to three methylene units of T1 can be optionally and independently replaced by G wherein G is —O— (additionally G is —N(R$_4$)—)). Additionally, in this embodiment T1 can additionally be optionally and independently substituted with one or more JT1;

Q1 is halogen, phenyl optionally substituted with J1, or pyridyl optionally substituted with J1 (additionally Q1 is absent, indolyl, quinolyl, cyclohexyl, cyclohexenyl, cyclopropyl, pyrrolyl, imidazolyl, piperidinyl, or pyrrolidinyl optionally substituted with J1; additionally Q1 is cyclobutyl, cyclopentyl, piperazinyl, thienyl, furyl, benzofuryl, benzothienyl, pyrazinyl, pyrimidinyl, isoindolyl, isoquinolyl, indazolyl, piperizinyl, or pyrazolyl, optionally substituted with J1, additionally Q1 is not halogen);

Y1 is a bond (absent) or C1-6 alkyl (alternatively C1-10 alkyl) group (additionally up to three methylene units of Y1 can be replaced by G1 where G1 can be —O—, and Y1 can be optionally and independently substituted with one or more JT1 in this embodiment); and M1 is —H (additionally M1 can be absent, alternatively M1 is not —H) (alternatively M1 is as described in the fifth embodiment or alternatively M1 is phenyl, —N(R$^\$$)$_2$, or —OR$^\$$; wherein M1 is optionally and independently substituted with one or more J; or M1 is absent, or —CN), and the remainder of the variables are as described above for any of the first through sixth embodiments.

In an eighth embodiment, the present invention is, a compound represented by structural formula I wherein, R$_1$ is —H, or halogen and the remainder of the variables are as described above for the first, second, or third embodiments.

In a ninth embodiment, the present invention is, a compound represented by structural formula I wherein, ring B is pyridyl, pyrazinyl, pyrimidinyl, pyridazinyl, imidazolyl, pyrrolyl, pyrazolyl, triazolyl, tetrazolyl, thienyl, oxazolyl, isoxazolyl, oxadiazolyl, thiazolyl, isothiazolyl or thiadiazolyl (additionally ring B is isoquinolyl, cinnolinyl, quinazolinyl, pyridopyridyl, or pyridopyradazinyl) (additionally wherein ring B in this embodiment is substituted with R$_3$ and independently, optionally and independently substituted with one or more R$_{12}$ (and additionally independently optionally substituted with R$_{12}$'), and the remainder of the variables are as described above for any of the first through eighth embodiments.

In an tenth embodiment, the present invention is, a compound represented by structural formula I wherein, B is thienyl (additionally wherein B is substituted with R$_3$ and independently, optionally and independently substituted with one or more R$_{12}$ (and additionally optionally substituted with R$_{12}$')) (alternatively ring B is thiazolyl, substituted with R$_3$ and optionally and independently substituted with one or more R$_{12}$ (and additionally independently optionally substituted with R$_{12}$') and the remainder of the variables are as described above for the ninth embodiment.

In an eleventh embodiment, the present invention is, a compound represented by structural formula I wherein, ring B is a nitrogen containing heteroaromatic ring (additionally wherein B is substituted with R$_3$ and independently, optionally and independently substituted with one or more R$_{12}$ and additionally optionally substituted with R$_{12}$'). In one embodiment ring B is imidazolyl (additionally wherein ring B is substituted with R$_3$ and independently, optionally and independently substituted with one or more R$_{12}$ (and additionally optionally substituted with R$_{12}$')); and the remainder of the variables are as described above for the ninth embodiment. In another embodiment ring B is pyrazolyl substituted with R$_3$ and independently, optionally and independently substituted with one or more R$_{12}$ (and additionally optionally substituted with R$_{12}$'); and the remainder of the variables are as described above for the ninth embodiment.

In a twelfth embodiment, the present invention is, a compound represented by structural formula I wherein, ring B is represented by the following structural formula:

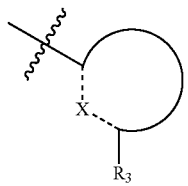

X is, —O—, —S— or —NR$^x$—. R$^x$ is absent or —H. The dashed lines represent a direct bond between X and carbon atoms which form part of the aromatic ring. Preferably X is —S—. Alternatively B is:

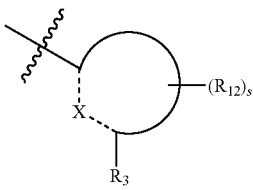

X is, —O—, —S—, or —NR$^x$—. R$^x$ is absent or —H. s is 0, 1 or 2. The dashed lines represent a direct bond between X and carbon atoms which form part of the aromatic ring. Preferably X is —S—, and B is thiazolyl, thiadiazolyl, or thienyl and the remainder of the variables are as described above for the ninth embodiment. Alternatively B is:

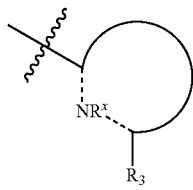

R$^x$ is absent or —H, and the remainder of the variables are as described above for the ninth embodiment. Alternatively B is:

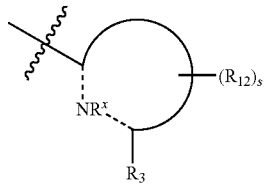

R$^x$ is absent or —H. s is 0, 1 or 2; and the remainder of the variables are as described above for the ninth embodiment. Alternatively B is:

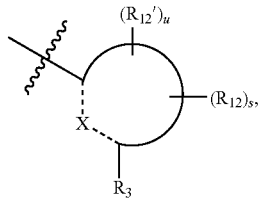

u is 0 or 1. R$^x$ is absent or —H. s is 0, 1 or 2; and the remainder of the variables are as described above for the ninth embodiment.

Alternatively B is

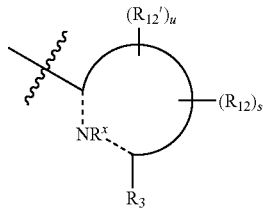

u is 0 or 1. R$^x$ is absent or —H. s is 0, 1 or 2; and the remainder of the variables are as described above for the ninth embodiment.

In a thirteenth embodiment, the present invention is a compound represented by structural formula I wherein, wherein ring B is pyridyl (additionally wherein ring B is substituted with R$_3$ and independently, optionally and independently substituted with one or more R$_{12}$ (and additionally independently optionally substituted with R$_{12}$')) and the remainder of the variables are as described above for the ninth embodiment.

In a fourteenth embodiment, the present invention is, a compound represented by structural formula I wherein, ring B is imidazolyl (additionally wherein ring B is substituted with R$_3$ and independently, optionally and independently substituted with one or more R$_{12}$ (and additionally independently optionally substituted with R$_{12}$')) and the remainder of the variables are as described above for the ninth embodiment.

In a fifteenth embodiment, the present invention is, a compound represented by structural formula I wherein, ring B is pyrrolyl (additionally wherein ring B is substituted with R$_3$ and independently, optionally and independently substituted with one or more R$_{12}$ (and additionally independently optionally substituted with R$_{12}$')) alternatively ring B is pyrazolyl substituted with R$_3$ and independently, optionally and independently substituted with one or more R$_{12}$ (and additionally independently optionally substituted with R$_{12}$') and the remainder of the variables are as described above for the ninth embodiment.

In a sixteenth embodiment, the present invention is, a compound represented by structural formula I wherein, ring B is pyrazinyl (additionally wherein ring B is substituted with R$_3$ and independently, optionally and independently substituted with one or more R$_{12}$ (and additionally independently optionally substituted with R$_{12}$')) and the remainder of the variables are as described above for the ninth embodiment. Alternatively, the present invention is, a compound represented by structural formula I wherein, ring B is pyrimidinyl substituted with R$_3$ and independently, optionally and independently substituted with one or more R$_{12}$ (and additionally independently optionally substituted with R$_{12}$') and the remainder of the variables are as described above for the ninth embodiment.

In a seventeenth embodiment, the present invention is, a compound represented by structural formula I wherein, ring B is oxazolyl (additionally wherein ring B is substituted with R$_3$ and independently, optionally and independently substituted with one or more R$_{12}$ (or alternatively independently optionally substituted with R$_{12}$'). Alternatively ring B is isoxazolyl substituted with R$_3$ and independently, optionally and independently substituted with one or more R$_{12}$ (or alternatively optionally substituted with R$_{12}$') and the remainder of the variables are as described above for the ninth embodiment.

In an eighteenth embodiment, the present invention is, a compound represented by structural formula I wherein, ring B is isoquinolyl, substituted with R$_3$ and independently, optionally and independently substituted with one or more R$_{12}$ (and additionally independently optionally substituted with R$_{12}$') and the remainder of the variables are as described above for the ninth embodiment.

In a nineteenth embodiment, the present invention is, a compound represented by structural formula I wherein, ring B is oxadiazolyl and the remainder of the variables are as described above for the ninth embodiment.

In a twentieth embodiment, the present invention is, a compound represented by structural formula I wherein, ring B is thiazolyl (additionally wherein ring B is substituted with R$_3$ and independently, optionally and independently substituted with one or more R$_{12}$ (or alternatively independently optionally substituted with R$_{12}$') and the remainder of the variables are as described above for the ninth embodiment.

In a twenty first embodiment, the present invention is, a compound represented by structural formula I wherein, ring B is isothiazolyl (additionally wherein ring B is substituted with $R_3$ and independently, optionally and independently substituted with one or more $R_{12}$ (or alternatively optionally substituted with $R_{12}'$)) and the remainder of the variables are as described above for the ninth embodiment.

In a twenty second embodiment, the present invention is, a compound represented by structural formula I wherein, ring B is thiadiazolyl (additionally wherein ring B is substituted with $R_3$) and the remainder of the variables are as described above for the ninth embodiment.

In a twenty third embodiment, the present invention is, a compound represented by structural formula I wherein, $R_3$ is halogen or -T2-Q2. Preferably, $R_3$ is T2-Q2;

T2 is a bond (absent) or C1-6 aliphatic (alternatively C1-10 aliphatic), wherein up to three methylene units of T2 are optionally and independently replaced by G' wherein G' is —O—, —N($R_4$)—, or —C(O)— (additionally G' is —S—); T2 is optionally and independently substituted with one or more JT2. Preferably, T2 is a bond (absent);

Q2 is —H, or a 3-8-membered saturated, partially unsaturated, or fully unsaturated monocyclic ring having 0-3 heteroatoms independently selected from nitrogen, oxygen, and sulfur (additionally Q2 is absent or an 8-12 membered saturated, partially saturated or fully unsaturated bicyclic ring system having 0-5 heteroatoms independently selected from nitrogen, oxygen and sulfur); Q2 is optionally substituted with J2, alternatively Q2 is as described above for Structural Formula I;

J2 is —Y2-M2;

Y2 is a bond (absent) or C1-6 aliphatic (alternatively C1-C10 aliphatic) wherein up to three methylene units of Y2 are independently and optionally replaced with G1' wherein G1' is —N($R^\$$)—, —O—, —C(O)—, or —S(O)$_2$— (additionally Y2 is oxo and in this embodiment is optionally and independently substituted with one or more JT2);

M2 is —H, C3-8 cycloaliphatic, 3-8 membered heterocyclyl, 5-6 membered heteroaryl, phenyl, halogen, —NO$_2$, —CN, —P(O)$R^\$$, —P(O)$_2R^\$$, —P(O)($R^\$$)$_2$, or —PO(O$R^\$$)$_2$, wherein M2 is optionally and independently substituted with one or more J (additionally M2 can be absent, —N($R^\$$)$_2$, —O$R^\$$, or —S$R^\$$; additionally M2 can be C1-6 aliphatic, —C(O)$R^\$$, —C(O)$_2R^\$$, —S(O)$R^\$$, or —S(O)$_2R^\$$ wherein M2 is optionally and independently substituted with one or more J; additionally M2 is not halogen, —P(O)$R^\$$, —P(O)$_2R^\$$, —P(O)($R^\$$)$_2$, —PO(O$R^\$$)$_2$ —SRS or —H) (alternatively, M2 is C1-6 aliphatic, C3-8 cycloaliphatic, 3-8 membered heterocyclyl, 5-12 membered heteroaryl, 5-12 membered aryl, —N($R^\$$)$_2$, —O$R^\$$, —C(O)$R^\$$, —C(O)$_2R^\$$, —S(O)$R^\$$, or —S(O)$_2R^\$$ wherein M2 is optionally and independently substituted with one or more J);

each J is independently —H, halogen, C1-6 aliphatic, —NO$_2$, —CN, —N($R^\$$)$_2$, —O$R^\$$, —CO$R^\$$, —CON($R^\$$)$_2$, —CO$_2R^\$$, oxo or halo(C1-4 aliphatic) (additionally J is not —H) and the remainder of the variables are as described above in any one of the tenth through the twenty second embodiments.

Alternatively, in the twenty third embodiment, T2 is absent, or C1-4 aliphatic, wherein one methylene unit of T2 is optionally replaced by G' wherein G' is —N($R_4$)—, —O—, —S—, or —C(O)—; T2 is optionally and independently substituted with one or more JT2, preferably T2 is C1-4 aliphatic, wherein one methylene unit of T2 is replaced by G' wherein G' is —N($R_4$)—; T1 is optionally and independently substituted with one or more JT2; and Q2 is a 3-8 membered saturated, partially saturated or fully unsaturated monocyclic ring having 0-3 heteroatoms independently selected from nitrogen, oxygen and sulfur, wherein Q2 is optionally substituted with J2 and independently optionally and independently substituted with one or more $R_{13}$ groups, preferably Q2 is a 3-8 membered saturated, partially saturated or fully unsaturated monocyclic ring having 0-3 nitrogen atoms, wherein Q2 is optionally substituted with J2 and the remainder of the variables are as described in twenty third embodiment.

Alternatively in the twenty third embodiment, T2 is absent; and Q2 is Q2 is a 3-8 membered saturated, partially saturated or fully unsaturated monocyclic ring having 1-3 nitrogen atoms, wherein Q2 is optionally substituted with J2, and the remainder of the variables are as described in twenty third embodiment. In the above two alternative embodiment, T2, Q2 and J2 together comprise at least two heteroatoms.

Alternatively in the twenty third embodiment, Q2 is absent; and T2 is C1-10 aliphatic, wherein two methylene units of T2 are independently replaced by G' wherein G' is —N($R_4$)—, —O—, —S—, or —C(O)—; T2 is optionally and independently substituted with one or more JT2, preferably, T2 is C1-10 aliphatic, wherein two methylene units of T2 are independently replaced by G' wherein G' is —N($R_4$)—, —O—, or —S—; T1 is optionally and independently substituted with one or more JT2 more preferably, T2 is C1-10 aliphatic, wherein two methylene units of T2 are replaced by G' wherein G' is —N($R_4$)—; T2 is optionally and independently substituted with one or more JT2 and the remainder of the variables are as described in twenty third embodiment.

In a twenty fourth embodiment, the present invention is, a compound represented by structural formula I wherein, T2 is a bond (absent) or C1-6 aliphatic (alternatively C1-10 aliphatic), wherein up to three methylene units of T2 are optionally and independently replaced by G' wherein G' is —N($R_4$)—, or —C(O)— (additionally G' is —O—, or —S—); T2 is optionally and independently substituted with one or more JT2. Preferably, T2 is a bond (absent);

Q2 is —H, or a 3-8-membered saturated, partially unsaturated, or fully unsaturated monocyclic ring having 0-3 nitrogen atoms optionally substituted with J2 (additionally Q2 is absent or an 8-12 membered saturated, partially unsaturated or fully unsaturated bicyclic ring system having 0-3 nitrogen atoms wherein each ring is optionally substituted with J2); alternatively Q2 is as described above for Structural Formula I;

Y2 is a bond (absent) or C1-6 aliphatic (alternatively C1-C10 aliphatic) wherein up to three methylene units of Y2 are optionally and independently replaced with G1' wherein G1' is —O—, or —C(O)—, or —SO$_2$— (additionally G1' can be —N($R^\$$), (additionally Y2 is oxo and additionally in this embodiment Y2 is optionally and independently substituted with one or more JT2; additionally G1' is not —SO$_2$—);

M2 is —H, C3-8 cycloaliphatic (including cyclopentyl, cyclohexyl, cyclopropyl), 3-8 membered heterocyclyl (including tetrahydrofuryl, tetrahydrothienyl, tetrahydropyranyl, piperidinyl, and pyrrolidinyl), 5-6 membered heteroaryl (including, pyridyl, pyrazinyl, pyrimidinyl, pyrrolyl, imidazolyl, pyrazolyl, furnayl, thienyl, pyranyl, and isooxazolyl), phenyl, halogen, —NO$_2$ or —CN, wherein M2 is optionally and independently substituted with one or more J (additionally M2 can be absent, —N($R^\$$)$_2$, —O$R^\$$, or —S$R^\$$; additionally M2 can be —C(O)$R^\$$, —C(O)$_2R^\$$, —S(O)$R^\$$, or —S(O)$_2R^\$$ wherein M2 is optionally and independently substituted with one or more J, additionally M2 is not halogen, —SRS or —H) (alternatively M2 is —O$R^\$$, —N($R^\$$)$_2$, C(O)$R^\$$, —C(O)$_2 R^\$$, —S(O)$R^\$$, or —S(O)$_2R^\$$, pyridyl, pyrazinyl, pyrimidinyl, pyrrolyl, imidazolyl, pyrazolyl, furyl, tetrahydrofuryl, thienyl, tetrahydrothienyl, pyranyl, tetrahydropyranyl, isooxazolyl, piperidinyl, pyrrolidinyl, cyclopentyl, cyclohexyl, cyclopropyl, naphthyl, or phenyl, wherein M2 is optionally and independently substituted with one or more J; or M2 is absent, —N(O)$_2$, or —CN);

each J is independently —H, halogen, C1-6 aliphatic, —NO$_2$, —CN, —N(R$^S$)$_2$, OR$^S$, oxo, or halo(C1-4 aliphatic) (alternatively J is not —H) and the remainder of the variables are as described above for the twenty third embodiment.

In a twenty fifth embodiment, the present invention is, a compound represented by structural formula I wherein, Q2 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, and thiazocanyl wherein each ring is independently optionally substituted with J2 (additionally Q2 is independently optionally substituted with one or more R$_{13}$ groups) (additionally Q2 can be absent, cyclopropyl, cyclopentyl, cyclobutyl, cyclohexyl, cyclohexenyl, indolyl, indazolyl, benzimidazolyl, quinolyl, quinoxalyl, indolinyl azabicyclopentyl, azabicyclohexyl, azabicycloheptyl, azabicyclooctyl, azabicyclononyl, azabicyclodecyl, diazabicyclohexyl, diazabicycloheptyl, diazabicyclooctyl, diazabicyclononyl, or diazabicyclodecyl and other additional values for Q2 include azetidinyl, isoindolinyl, isoindolyl, dihydroindazolyl, dihydrobenzimidazolyl, morpholinyl, tetrahydropyridyl, dihydropyridyl, tetrahydropyrazinyl, dihydropyrazinyl, tetrahydropyrimidinyl, dihydropyrimidinyl, dihydropyrrolyl, dihydropyrazolyl, dihydroimidazolyl, octahydropyrrolopyrazyl, octahydropyrrolopyridyl, octahydropyridopyrazyl, or octahydropyridopyridyl each independently optionally substituted with J2, and additionally independently optionally substituted with one or more R$_{13}$ groups) and the remainder of the variables are as described above for the twenty fourth embodiment.

In a twenty sixth embodiment, the present invention is, a compound represented by structural formula I wherein, Q2 is selected from the group consisting of phenyl, pyridyl, pyrazinyl, pyrimidinyl, pyrrolyl, imidazolyl, pyrazolyl, oxazalolyl, oxadiazolyl, thiazolyl, thiadiazolyl, piperidinyl, piperazinyl, diazepanyl, and oxazepanyl wherein each ring is independently optionally substituted with J2 (additionally Q2 is independently optionally substituted with one or more R$_{13}$ groups), (additionally Q2 can be absent, cyclohexyl, diazabicycloocty, or pyrrolidinyl and other additional values for Q2 include azetidinyl, morpholinyl, azepanyl, diazabicycloheptyl, diazabicyclooctyl, indolyl, tetrahydropyridyl, dihydropyridyl, octahydropyrrolopyrazyl, octahydropyrrolopyridyl, octahydropyridopyrazyl, or octahydropyridopyridyl each independently optionally substituted with J2, and additionally independently optionally substituted with one or more R$_{13}$ groups) and the remainder of the variables are as described above for the twenty fourth embodiment.

In a twenty seventh embodiment, the present invention is, a compound represented by structural formula I wherein, Q2 is selected from the group consisting of phenyl, pyridyl, piperidinyl, piperazinyl, diazepanyl, and oxazepanyl wherein each ring is independently optionally substituted with J2 (additionally Q2 is independently optionally substituted with one or more R$_{13}$ groups) (additionally Q2 can be absent, cyclohexyl, 3,8-diazabicyclo[3.2.1]octyl, or pyrrolidinyl additionally Q2 is independently optionally substituted with one or more R$_{13}$ groups, additional values for Q2 include azetidinyl, morpholinyl, azepanyl, 2,5 diazabicycloheptyl, diazabicyclooctyl, indolyl, tetrahydropyridyl, octahydro-1H-pyrrolo[2,3-b]pyrazyl, or octahydropyrrolo[1,2-a]pyrazyl, each independently optionally substituted with J2, and additionally independently optionally substituted with one or more R$_{13}$ groups) (additionally Q2 can be pyrrolyl, or pyrazolyl, each independently optionally substituted with J2, and additionally independently optionally substituted with one or more R$_{13}$ groups) and the remainder of the variables are as described above for the twenty fourth embodiment.

In one embodiment the compounds of the present invention are represented by structural formula II:

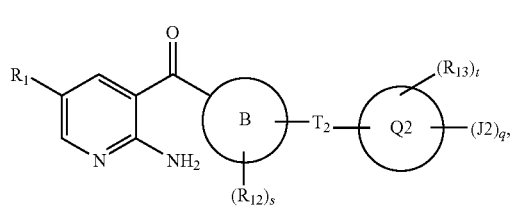

t is 0 or 1, s is 0, 1 or 2, q is 0 or 1, and the remainder of the variables are as described above for structural formula I or any of the first through twenty seventh embodiments, unless otherwise described in the above structure.

In one embodiment the compounds of the present invention are represented by structural formula III:

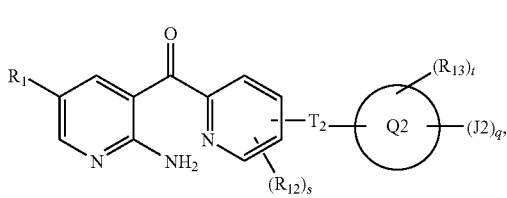

t is 0 or 1 s is 0, 1 or 2, q is 0 or 1, and the remainder of the variables are as described above for structural formula I or any of the first through twenty seventh embodiments unless otherwise described in the above structure.

In a twenty eighth embodiment, the present invention is, a compound represented by structural formula I, II, or III wherein Q2 is represented by the following structural formula:

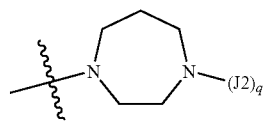

q is 0 or 1, wherein when q is 0, the nitrogen to which (J2)$_q$ is attached is —NH—, and the remainder of the variables are as described above for any one of the twenty fourth through twenty seventh embodiments alternatively, Q2 is represented by the following structural formula:

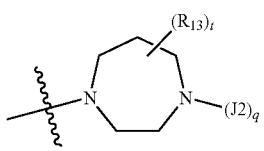

t is 0 or 1, q is 0 or 1, wherein when q is 0, the nitrogen to which $(J2)_q$ is attached is —NH—, and the remainder of the variables are as described above for any one of the twenty fourth through twenty seventh embodiments.

In one embodiment the compounds of the present invention are represented by structural formula IV:

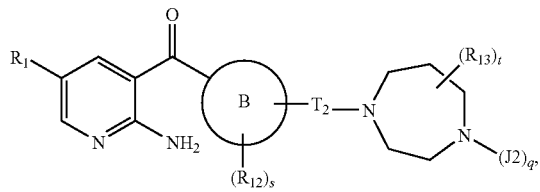

t is 0 or 1, s is 0, 1 or 2, and q is 0 or 1, wherein when q is 0, the nitrogen to which $(J2)_q$ is attached is —NH—, and the remainder of the variables are as described above for structural formula I or any of the first through twenty eighth embodiments unless otherwise described in the above structure.

In one embodiment the compounds of the present invention are represented by structural formula V:

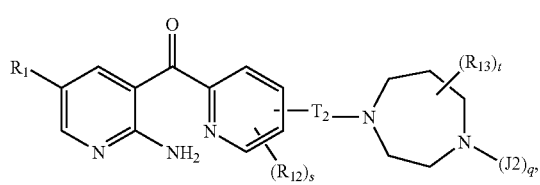

t is 0 or 1, s is 0, 1 or 2, q is 0 or 1, wherein when q is 0, the nitrogen to which $(J2)_q$ is attached is —NH—, and the remainder of the variables are as described above for structural formula I or any of the first through twenty eighth embodiments unless otherwise described in the above structure.

In one embodiment the compounds of the present invention are represented by structural formula VI:

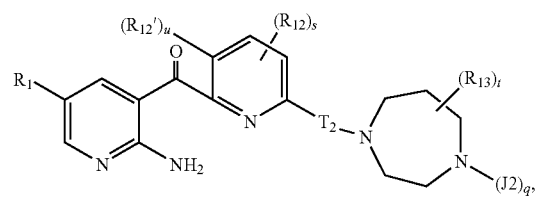

u is 0 or 1, s is 0, 1, or 2, t is 0 or 1 q is 0 or 1, wherein when q is 0, the nitrogen to which $(J2)_q$ is attached is —NH—, and the remainder of the variables are as described above for structural formula I or any of the first through twenty eighth embodiments unless otherwise described in the above structure.

In a twenty ninth embodiment, the present invention is, a compound represented by structural formula I, II, or III wherein Q2 is phenyl, independently optionally substituted with J2 (and additionally independently optionally and independently substituted with $R_{13}$), and the remainder of the variables are as described above for any one of the twenty fourth through twenty seventh embodiments.

In a thirtieth embodiment, the present invention is, a compound represented by structural formula I, II, or III wherein Q2 is pyridyl, independently optionally substituted with J2 (and additionally independently optionally and independently substituted with $R_{13}$), and the remainder of the variables are as described above for any one of the twenty fourth through twenty seventh embodiments.

In a thirty first embodiment, the present invention is, a compound represented by structural formula I, II, or III wherein Q2 is piperidinyl, independently optionally substituted with J2 (and additionally independently optionally and independently substituted with $R_{13}$), and the remainder of the variables are as described above for any one of the twenty fourth through twenty seventh embodiments In a thirty second embodiment, the present invention is, a compound represented by structural formula I, II, or III wherein Q2 is piperazinyl, independently optionally substituted with J2 (and additionally independently optionally and independently substituted with $R_{13}$), in particular Q2 is:

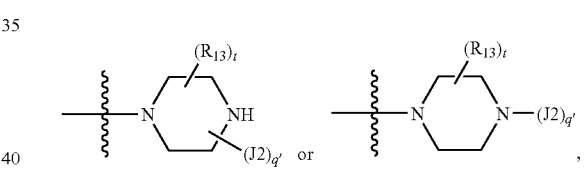

t is 0 or 1; and q' is 0, 1 or 2; alternatively t is 0, 1 or 2, q' is 0, or 1, wherein $R_{13}$ and J2 can be bound to the same carbon atom, and wherein when $(J2)_{q'}$ is attached is —NH— and q is 0, the nitrogen to which $(J2)_{q'}$ is attached is —NH—, and the remainder of the variables are as described above for any one of the twenty fourth through twenty seventh embodiments; in one embodiment Q2 is

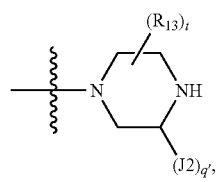

t is 0 or 1; and q' is 0, 1 or 2; alternatively t is 0, 1 or 2, q' is 0, or 1, wherein $R_{13}$ and J2 can be bound to the same carbon atom, and the remainder of the variables are as described above for any one of the twenty fourth through twenty seventh embodiments.

In one embodiment the compounds of the present invention are represented by structural formula VII:

VII

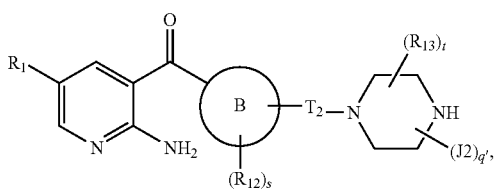

t is 0 or 1; s is 0, 1 or 2, and q' is 0, 1 or 2 alternatively t is 0, 1 or 2, and q' is 0, or 1, wherein $R_{13}$ and J2 can be bound to the same carbon atom, and the remainder of the variables are as described above for structural formula I or any of the first through twenty seventh embodiments unless otherwise described in the above structure.

In one embodiment the compounds of the present invention are represented by structural formula VIII:

VIII

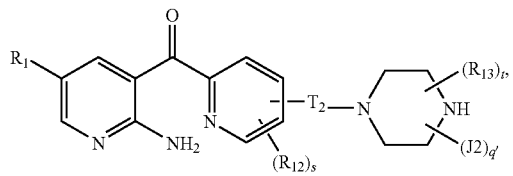

t is 0 or 1; s, is 0, 1 or 2, and q' is 0, 1 or 2, alternatively t is 0, 1 or 2, and q' is 0, or 1, wherein $R_{13}$ and J2 can be bound to the same carbon atom; and the remainder of the variables are as described above for structural formula I or any of the first through twenty seventh embodiments unless otherwise described in the above structure.

In one embodiment the compounds of the present invention are represented by structural formula IX:

IX

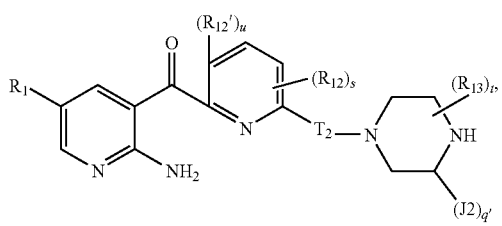

u is 0 or 1, s is 0, 1 or 2, t is 0 or 1; and q' is 0, 1 or 2; alternatively t is 0, 1 or 2, q' is 0, or 1, wherein $R_{13}$ and J2 can be bound to the same carbon atom, and the remainder of the variables are as described above for structural formula I or any of the first through twenty seventh embodiments unless otherwise described in the above structure.

In one embodiment the compounds of the present invention are represented by structural formula X:

X

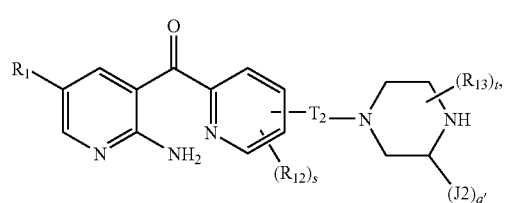

t is 0 or 1; s is 0, 1 or 2 and q' is 0, 1 or 2; alternatively t is 0, 1 or 2, q' is 0, wherein $R_{13}$ and J2 can be bound to the same carbon atom, and the remainder of the variables are as described above for structural formula I or any of the first through twenty seventh or thirty second embodiments unless otherwise described in the above structure.

In one embodiment the compounds of the present invention are represented by structural formula XI:

XI

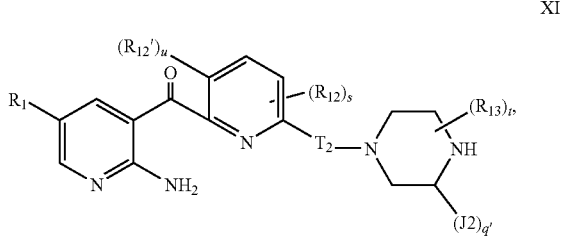

u is 0 or 1; s is 0, 1, or 2, t is 0 or 1; and q' is 0, 1 or 2; alternatively t is 0, 1 or 2, q' is 0, or 1, wherein $R_{13}$ and J2 can be bound to the same carbon atom, and the remainder of the variables are as described above for structural formula I or any of the first through twenty seventh or thirty second embodiments unless otherwise described in the above structure.

In one embodiment the compounds of the present invention are represented by structural formula XII:

XII

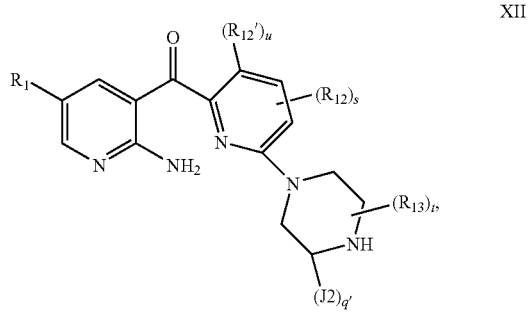

u is 0 or 1, t is 0 or 1; s is 0 or 1; and q' is 0, 1 or 2; alternatively t is 0, 1 or 2, q' is 0, or 1, wherein $R_{13}$ and J2 can be bound to the same carbon atom, and the remainder of the variables are as described above for structural formula I or any of the first through twenty seventh or thirty second embodiments unless otherwise described in the above structure.

In one embodiment, for structural formulas VI, IX, X, XI, and XII:

$R_1$ is —H, halogen, or -T1-Q1;

T1 is absent or C1-10 aliphatic, wherein up to three methylene units of T1 are optionally and independently replaced by G wherein G is —, —N($R_4$)—, or —C(O)—; T1 is optionally and independently substituted with one or more JT1;

Q1 is absent or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein each ring is independently optionally substituted with J1;

J1 is —Y1-M1;

Y1 is a absent, oxo, or C1-10 aliphatic wherein up to three methylene units of Y1 are optionally and independently replaced with G1 wherein G1 is —N(R$^\$$)—, —O—, —C(O)—, or —S(O)$_2$—; Y1 is optionally and independently substituted with one or more JT1; and M1 is C3-8 cycloaliphatic, 3-8 membered heterocyclyl, 5-6 membered heteroaryl, phenyl, —OR$^\$$, —SR$^\$$, —N(R$^\$$)$_2$, —P(O)R$^\$$, —P(O)$_2$R$^\$$, P(O)(R$^\$$)$_2$, or PO(OR$^\$$)$_2$, wherein M1 is optionally and independently substituted with one or more J; or M1 is absent, halogen, —NO$_2$, or —CN,), and the remainder of the variables are as described above for structural formula I.

In another embodiment, for structural formulas VI, IX, X, XI, and XII:

T1 is absent or C1-10 aliphatic wherein up to three methylene units of T1 can be optionally and independently replaced by G wherein G is —O— or —N(R$_4$)—; T1 is optionally and independently substituted with one or more JT1;

Y1 is absent or C1-10 aliphatic wherein up to three methylene units of Y1 are optionally and independently replaced with G1 wherein G1 is —O—-C(O)—, —N(R$^\$$), or —S(O)$_2$—); Y1 is optionally and independently substituted with one or more JT1;

M1 is C3-8 cycloaliphatic, 3-8 membered heterocyclyl, 5-6 membered heteroaryl, phenyl, —OR$^\$$, or —N(R$^\$$)$_2$; M1 is optionally and independently substituted with one or more J; or M1 is absent, halogen or —CN; and each J is independently —H, halogen, C1-6 aliphatic, —NO$_2$, —CN, —N(R$^\$$)$_2$, —OR$^\$$, —C(O)R$^\$$, —C(O)N(R$^\$$)$_2$, —C(O)$_2$R$^\$$, oxo, or halo(C1-4 aliphatic) (additionally J is not —H) and the remainder of the variables are as described above for structural formula I.

In another embodiment, for structural formulas VI, IX, X, XI, and XII:

T1 is absent, C1-C10 alkyl, C2-C10 alkenyl, or C2-C10 alkynyl, wherein up to three methylene units of T1 can be optionally and independently replaced by G wherein G is —O— or —N(R$_4$)—; T1 is optionally and independently substituted with one or more JT1;

Q1 is absent, phenyl, indolyl, quinolyl, cyclohexyl, cyclohexenyl, cyclopropyl, pyrrolyl, imidazolyl, piperidinyl, or pyrrolidinyl optionally substituted with J1; additionally Q1 is cyclobutyl, cyclopentyl, piperazinyl, thienyl, furyl, benzofuryl, benzothienyl, pyrazinyl, pyrimidinyl, isoindolyl, isoquinolyl, indazolyl, piperizinyl, or pyrazolyl, optionally substituted with J1;

Y1 is absent or C1-10 alkyl group wherein up to three methylene units of Y1 can be replaced by G1 where G1 can be —O—, Y1 is optionally and independently substituted with one or more JT1; and M1 is phenyl, —N(R$^\$$)$_2$, or —OR$^\$$; wherein M1 is optionally and independently substituted with one or more J; or M1 is absent, or —CN;

each J is independently —H, halogen, C1-6 aliphatic, —NO$_2$, —CN, —N(R$^\$$)$_2$, —OR$^\$$, —C(O)R$^\$$, —C(O)N(R$^\$$)$_2$, —C(O)$_2$R$^\$$, oxo, or halo(C1-4 aliphatic) (additionally J is not —H) and the remainder of the variables are as described above for structural formula I.

In another embodiment, for structural formulas VI, IX, X, XI, and XII:

Y2 is absent, oxo, or C1-10 aliphatic wherein up to three methylene units of Y2 are independently and optionally replaced with G1' wherein G1' is —N(R$^\$$)—, —O—, —C(O)—, or —S(O)$_2$—, Y2 is optionally and independently substituted with one or more JT2;

M2 is C1-6 aliphatic, C3-8 cycloaliphatic, 3-8 membered heterocyclyl, 5-12 membered heteroaryl, 5-12 membered aryl, —N(R$^\$$)$_2$, —OR$^\$$, —C(O)R$^\$$, —C(O)$_2$R$^\$$, —S(O)R$^\$$, or —S(O)$_2$R$^\$$ wherein M2 is optionally and independently substituted with one or more J; or M2 is absent, —NO$_2$, or —CN; and each J is independently halogen, C1-6 aliphatic, —NO$_2$, —CN, N(R$^\$$)$_2$, —OR$^\$$, —COR$^\$$, —CON(R$^\$$)$_2$, —CO$_2$R$^\$$, oxo or haloC1-4 aliphatic;

In this embodiment for structural formulas VI, IX, X, and XI, T2 is absent or C1-10 aliphatic, wherein up to three methylene units of T2 are optionally and independently replaced by G' wherein G' is —O—, —S—, —N(R$^4$)—, or —C(O)—; T2 is optionally and independently substituted with one or more JT2; and the remainder of the variables are as described above for any of the above three embodiments for structural formulas VI, IX, X, XI, and XII.

In another embodiment, for structural formulas VI, IX, X, XI, and XII:

M2 is —OR$^\$$, —N(R$^\$$)$_2$, —C(O)R$^\$$, —C(O)$_2$R$^\$$, —S(O)R$^\$$, or —S(O)$_2$R$^\$$, pyridyl, pyrazinyl, pyrimidinyl, pyrrolyl, imidazolyl, pyrazolyl, furyl, tetrahydrofuryl, thienyl, tetrahydrothienyl, pyranyl, tetrahydropyranyl, isooxazolyl, piperidinyl, pyrrolidinyl, cyclopentyl, cyclohexyl, cyclopropyl, naphthyl, or phenyl, wherein M2 is optionally and independently substituted with one or more J; or M2 is absent, —N(O)$_2$, or —CN; and each J is independently halogen, C1-6 aliphatic, —NO$_2$, —CN, —N(R$^\$$)$_2$, —OR$^\$$, oxo, or halo C1-4 aliphatic.

In this embodiment for structural formulas VI, IX, X, and XI, T2 is absent or C1-10 aliphatic, wherein up to three methylene units of T1 T2 are optionally and independently replaced by G' wherein G' is —N(R$^4$)—, —O—, —S—, or —C(O)—; T1 T2 is optionally and independently substituted with one or more JT2; and the remainder of the variables are as described above for any of the above first three embodiments for structural formulas VI, IX, X, XI, and XII.

In a thirty third embodiment, the present invention is, a compound represented by structural formula I, II, or III wherein Q2 is piperidinyl, independently optionally substituted with J2 and independently optionally and independently substituted with R$_{13}$, and the remainder of the variables are as described above for any one of the twenty fourth through twenty seventh or thirty second embodiments.

In a thirty fourth embodiment, the present invention is, a compound represented by structural formula I, II, or III wherein Q2 is oxazepanyl independently optionally substituted with J2 (and additionally independently optionally and independently substituted with R$_{13}$), and the remainder of the variables are as described above for any one of the twenty fourth through twenty seventh or thirty second embodiments.

In a thirty fifth embodiment, the present invention is, a compound represented by structural formula I, II, or III wherein Q2 is indolyl independently optionally substituted with J2 and independently optionally and independently substituted with R$_{13}$, and the remainder of the variables are as described above for any one of the twenty fourth through twenty seventh or thirty second embodiments.

In a thirty sixth embodiment, the present invention is, a compound represented by structural formula I, II, or III wherein Q2 is pyrrolidinyl, cyclohexyl, diazobicyclooctyl, morpholinyl, azepanyl, diazabicycloheptyl, octahydropyrrolopyrazinyl, azetidinyl or tetrahydropyridyl each independently optionally substituted with J2 and independently optionally and independently substituted with R$_{13}$, and the remainder of the variables are as described above for any one of the twenty fourth through twenty seventh or thirty second embodiments.

In a thirty seventh embodiment, the present invention is a compound represented by structural formula I wherein T2 is a bond, and the remainder of the variables are as described above for any of the twenty fifth through the thirty sixth embodiments.

As described herein, a specified number range of atoms includes any integer therein. For example, a group having from 1-4 atoms could have 1, 2, 3, or 4 atoms.

As used here the terms "absent" and "a bond" can be used interchangeably to mean the variable does not exits in that embodiment, that is the variable does not represent an atom or groups of atoms.

The term "stable", as used herein, refers to compounds that are not substantially altered when subjected to conditions to allow for their production, detection, recovery, storage, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", as used herein, means a straight-chain (i.e., unbranched), or branched, hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear or branched alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds.

The term "cycloaliphatic" (or "carbocycle" or "carbocyclyl" or "carbocyclic") refers to a non-aromatic monocyclic carbon containing ring which can be saturated or contain one or more units of unsaturation, having three to fourteen ring carbon atoms. The term includes polycyclic fused, spiro or bridged carbocyclic ring systems. The term also includes polycyclic ring systems in which the carbocyclic ring can be fused to one or more non-aromatic carbocyclic or heterocyclic rings or one or more aromatic rings or combination thereof, wherein the radical or point of attachment is on the carbocyclic ring. Fused bicyclic ring systems comprise two rings which share two adjoining ring atoms, bridged bicyclic group comprise two rings which share three or four adjacent ring atoms, spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic") as used herein means refers to a non-aromatic monocyclic ring which can be saturated or contain one or more units of unsaturation, having three to fourteen ring atoms in which one or more ring carbons is replaced by a heteroatom such as, N, S, or O. The term includes polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 3-piperazinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, dihydro-benzimidazol-2-onyl, and 1,3-dihydro-imidazol-2-onyl, azabicyclopentyl, azabicyclohexyl, azabicycloheptyl, azabicyclooctyl, azabicyclononyl, azabicyclodecyl, diazabicyclohexyl, diazabicycloheptyl, dihydroindazolyl, dihydrobenzimidazolyl, tetrahydropyridyl, dihydropyridyl, tetrahydropyrazinyl, dihydropyrazinyl, tetrahydropyrimidinyl, dihydropyrimidinyl, dihydropyrrolyl, dihydropyrazolyl, dihydroimidazolyl, octahydropyrrolopyrazyl, octahydropyrrolopyridyl, octahydropyridopyrazyl, octahydropyridopyridyl, diazabicyclooctyl, diazabicyclononyl, and diazabicyclodecyl.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the molecule through an oxygen ("alkoxy" e.g., —O-alkyl) or sulfur ("thioalkyl" e.g., —S-alkyl) atom.

The terms "haloalkyl", "haloalkenyl", "haloaliphatic", and "haloalkoxy" (or "aminoalkyl", "hydroxyalkyl" etc.,) mean alkyl, alkenyl or alkoxy, as the case may be, substituted with one or more halogen atoms. This term includes perfluorinated alkyl groups, such as —$CF_3$ and —$CF_2CF_3$.

The terms "halogen", "halo", and "hal" mean F, Cl, Br, or I. The term haloaliphatic and —O(haloaliphatic) include, mono- di- and tri-halo substituted aliphatic groups.

The term "aryl" used alone or as part of a larger moiety as in "aralkyl", "aralkoxy", "aryloxyalkyl", or "heteroaryl" refers to carbocyclic and or heterocyclic aromatic ring systems. The term "aryl" may be used interchangeably with the term "aryl ring".

Carbocyclic aromatic ring groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is fused to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. G in "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

In some embodiments, where indicated a methylene unit of an aliphatic chain is optionally replaced with another atom or group. Examples of such atoms or groups include, but are not limited to, —N(R$^\$$)—, —O—, —C(O)—, —C(=N—CN)—, —C(=NR$^\$$)—, —C(=NOR$^\$$)—, —S—, —S(O)—, and —S(O)$_2$—. These atoms or groups can be combined to form larger groups. Examples of such larger groups include, but are not limited to, —OC(O)—, —C(O)CO—, —CO$_2$—, —C(O)NR$^\$$—, —C(=N—CN), —N(R$^\$$)C(O)—, —N(R$^\$$)C(O)O—, —S(O)$_2$N(R$^\$$)—, —N(R$^\$$)SO$_2$—, —N(R$^\$$)C(O)N(R$^\$$)—, —OC(O)N(R$^\$$)—, and —N(R$^\$$)SO$_2$N(R$^\$$)—, wherein R$^\$$ is defined herein.

Only those replacement and combinations of groups that result in a stable structure are contemplated. Optional replacements can occur both within the chain and/or at either end of the chain; i.e. both at the point of attachment and/or also at the terminal end. Two optional replacements can also be adjacent to each other within a chain so long as it results in a chemically stable compound. The optional replacements can also completely replace all of the carbon atoms in a chain. For example, a C$_3$ aliphatic can be optionally replaced by —N(R$^\$$)—, —C(O)—, and —N(R$^\$$)— to form —N(R$^\$$)C(O)N(R$^\$$)— (a urea), or a C$_1$ aliphatic can be optionally replaced by, for example, —OH, NH$_2$ etc.

Unless otherwise indicated, if the replacement occurs at the terminal end, the replacement atom is bound to an H on the terminal end. For example, if —CH$_2$CH$_2$CH$_3$ were optionally replaced with —O—, the resulting compound could be —OCH$_2$CH$_3$, —CH$_2$OCH$_3$, or —CH$_2$CH$_2$OH.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

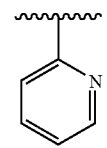

also represents

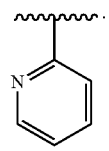

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

As described herein, where indicated compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Only those choices and combinations of substituents that result in a stable structure are contemplated. Such choices and combinations will be apparent to those of ordinary skill in the art and may be determined without undue experimentation.

The term "ring atom" is an atom such as C, N, O or S that is in the ring of an aromatic group, cycloalkyl group or non-aromatic heterocyclic ring.

A "substitutable ring atom" in an aromatic or non-aromatic ring group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

An aryl group as defined herein may contain one or more substitutable ring atoms, which may be bonded to a suitable substituent. Examples of suitable substituents on a substitutable ring carbon atom of an aryl group includes R'. R' is —Ra, —Br, —Cl, —I, —F, —ORa, —SRa, —O—CORa, —CORa, —CSRa, —CN, —NO$_2$, —NCS, —SO$_3$H, —N(RaRb), —COORa, —NRcNRcCORa, —NRcNRcCO$_2$Ra, —CHO, —CON(RaRb), —OC(O)N(RaRb), —CSN(RaRb), —NRc-CORa, —NRcCOORa, —NRcCSRa, —NRcCON(RaRb), —NRcNRcC(O)N(RaRb), —NRcCSN(RaRb), —C(=NRc)—N(RaRb), —C(=S)N(RaRb), —NRd-C(=NRc)—N(RaRb), —NRcNRaRb, —S(O)$_p$NRaRb, —NRcSO$_2$N(RaRb), —NRcS(O)$_p$Ra, —S(O)$_p$Ra, —OS(O)$_p$NRaRb or —OS(O)$_p$Ra; wherein p is 1 or 2.

Ra-Rd are each independently —H, an aliphatic group, aromatic group, non-aromatic carbocyclic or heterocyclic group or —N(RaRb), taken together, form a non-aromatic heterocyclic group. The aliphatic, aromatic and non-aromatic heterocyclic group represented by Ra-Rd and the non-aromatic heterocyclic group represented by —N(RaRb) are each optionally and independently substituted with one or more groups represented by R$^\#$. Preferably Ra-Rd are unsubstituted.

R$^\#$ is halogen, R$^+$, —OR$^+$, —SR$^+$, —NO$_2$, —CN, —N(R$^+$)$_2$, —COR$^+$, —COOR$^+$, —NHCO$_2$R$^+$, —NHC(O)R$^+$, —NHNHC(O)R$^+$, —NHC(O)N(R$^+$)$_2$, —NHNHC(O)N(R$^+$)$_2$, —NHNHCO$_2$R$^+$, —C(O)N(R$^+$)$_2$, —OC(O)R$^+$, —OC(O)N(R$^+$)$_2$, —S(O)$_2$R$^+$, —SO$_2$N(R$^+$)$_2$, —S(O)R$^+$, —NHSO$_2$N(R$^+$)$_2$, —NHSO$_2$R$^+$, —C(=S)N(R$^+$)$_2$, or —C(=NH)—N(R$^+$)$_2$.

R$^+$ is —H, a C1-C4 alkyl group, a monocyclic aryl group, a non-aromatic carbocyclic or heterocyclic group each optionally substituted with alkyl, haloalkyl, alkoxy, haloalkoxy, halogen, —CN, —NO$_2$, amine, alkylamine or dialkylamine. Preferably R+ is unsubstituted.

An aliphatic or a non-aromatic heterocyclic or carbocyclic group as used herein may contain one or more substituents. Examples of suitable substituents for an aliphatic group or a ring carbon of a non-aromatic heterocyclic group is R". R" includes those substituents listed above for R' and =O, =S, =NNHR, =NN(R)$_2$, =NNHC(O)R, =NNHCO2 (alkyl), =NNHSO2 (alkyl), =NR, spiro cycloalkyl group or fused cycloalkyl group. Each R is independently selected from hydrogen, an unsubstituted alkyl group or a substituted alkyl group. Examples of substituents on the alkyl group represented by R include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

A preferred position for substitution of a non-aromatic nitrogen-containing heterocyclic group is the nitrogen ring atom. Suitable substituents on the nitrogen of a non-aromatic heterocyclic group or heteroaryl group include —R$^\wedge$, —N(R$^\wedge$)$_2$, C(O)R$^\wedge$, CO$_2$R$^\wedge$, —C(O)C(O)R$^\wedge$, —SO$_2$R$^\wedge$, SO$_2$N(R$^\wedge$)$_2$, C(=S)N(R$^\wedge$)$_2$, C(=NH)—N(R$^\wedge$)$_2$, and —NR$^\wedge$SO$_2$R$^\wedge$; wherein R$^\wedge$ is hydrogen, an aliphatic group, a substituted aliphatic group, aryl, substituted aryl, heterocyclic or carbocyclic ring or a substituted heterocyclic or carbocyclic ring. Examples of substituents on the group represented by R$^\wedge$ include alkyl, haloalkoxy, haloalkyl, alkoxyalkyl, sulfonyl, alkylsulfonyl, halogen, nitro, cyano, hydroxy, aryl, carbocyclic or heterocyclic ring, oxo, amino, alkylamino, dialkylamino, aminocarbonyl, alkylaminocarbonyl, dialkylaminocarbonyloxy, alkoxy, carboxy, alkoxycarbonyl, or alkylcarbonyl. Preferably R$^\wedge$ is not substituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

As used herein an optionally substituted aralkyl can be substituted on both the alkyl and the aryl portion. Unless otherwise indicated as used herein optionally substituted aralkyl is optionally substituted on the aryl portion.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds of this invention, pharmaceutically acceptable solvates (e.g., hydrates) and clathrates of the compounds of this invention may also be employed in compositions to treat or prevent the herein identified disorders.

As used herein, the term "pharmaceutically acceptable solvate," is a solvate formed from the association of one or more pharmaceutically acceptable solvent molecules to one of the compounds the invention. The term solvate includes hydrates (e.g., hemihydrate, monohydrate, dihydrate, trihydrate, tetrahydrate, and the like).

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

In addition to the compounds of this invention, pharmaceutically acceptable derivatives or prodrugs of the compounds of this invention may also be employed in compositions to treat or prevent the herein identified disorders.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —NO2, —ONO, or —ONO2 moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" includes any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

In one embodiment the present invention is a pharmaceutical composition comprising a compound of the present invention and a pharmaceutically acceptable carrier, diluent, adjuvant or vehicle. In one embodiment the present invention is a pharmaceutical composition comprising an effective amount of compound of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to a subject as defined herein. These pharmaceutical compositions, which comprise an amount of the protein inhibitor effective to treat or prevent a protein kinase-mediated condition and a pharmaceutically acceptable carrier, are another embodiment of the present invention.

In one embodiment the present invention is a method of treating or preventing a protein kinase-mediated disorder in a subject in need thereof, comprising administering to the subject an effective amount of a compound or composition of the present invention.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, an "effective amount" refers to an amount sufficient to elicit the desired biological response. In the present invention the desired biological response is to reduce or ameliorate the severity, duration, progression, or onset of a protein kinase-mediated condition, prevent the advancement of a protein kinase-mediated condition, cause the regression of a protein kinase-mediated condition, prevent the recurrence, development, onset or progression of a symptom associated with a protein kinase-mediated condition, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of protein kinase-mediated condition, and the mode of administration. The skilled artisan will be able to determine appropriate dosages depending on these and other factors. When co-administered with other agents, e.g., when co-administered with an protein kinase-mediated condition agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a protein kinase-mediated condition, or the amelioration of one or more symptoms (preferably, one or more discernible symptoms) of a protein kinase-mediated condition resulting from the administration of one or more therapies (e.g., one or more therapeutic agents such as a compound of the invention). In specific embodiments, the terms "treat", "treatment" and "treating" refer to the amelioration of at least one measurable physical parameter of a protein kinase-mediated condition. In other embodiments the terms "treat", "treatment" and "treating" refer to the inhibition of the progression of a protein kinase-mediated condition, either physically by, e.g., stabilization of a discernible symptom, physiologically by, e.g., stabilization of a physical parameter, or both. In other embodiments the terms "treat", "treatment" and "treating" refer to the reduction or stabilization of a protein kinase-mediated condition.

As used herein, the terms "prevent", "prevention" and "preventing" refer to the reduction in the risk of acquiring or developing a given protein kinase-mediated condition, or the reduction or inhibition of the recurrence or a protein kinase-mediated condition. In one embodiment, a compound of the invention is administered as a preventative measure to a patient, preferably a human, having a genetic predisposition to any of the conditions, diseases or disorders described herein.

In one aspect, the present invention provides a method for treating or lessening the severity of a disease, condition, or disorder where a protein kinase is implicated in the disease state. In another aspect, the present invention provides a method for treating or lessening the severity of a kinase disease, condition, or disorder where inhibition of enzymatic activity is implicated in the treatment of the disease. In another aspect, this invention provides a method for treating or lessening the severity of a disease, condition, or disorder with compounds that inhibit enzymatic activity by binding to the protein kinase. Another aspect provides a method for treating or lessening the severity of a kinase disease, condition, or disorder by inhibiting enzymatic activity of the kinase with a protein kinase inhibitor. In some embodiments, said protein kinase inhibitor is a PKCtheta or GSK-3 inhibitor.

The term "protein kinase-mediated condition", as used herein means any disease or other deleterious condition in which a protein kinase plays a role. Such conditions include, without limitation, autoimmune diseases, inflammatory diseases, proliferative and hyperproliferative diseases, immunologically-mediated diseases, immuno-deficiency disorders, immunomodulatory or immunosuppressive disorder, bone diseases, metabolic diseases, neurological and neurodegenerative diseases, cardiovascular diseases, hormone related diseases, diabetes, allergies, asthma, and Alzheimer's disease.

The term "GSK-3-mediated condition", as used herein means any disease or other deleterious condition in which GSK 3 plays a role. Such conditions include, without limitation, diabetes, neurodegenerative diseases (e.g., Alzheimer's disease, Huntington's disease, Parkinson's disease, AIDS-associated dementia, bipolar disorder), amyotrophic lateral sclerosis (ALS, Lou Gehrig's disease), multiple sclerosis (MS), schizophrenia, leukocytopenia, cardiomyocyte hypertrophy, stroke, and rheumatoid arthritis.

The term "PKCtheta-mediated condition", as used herein means any disease or other deleterious condition in which PKCtheta plays a role. Such conditions include, without limitation, autoimmune diseases: including MS, RA and IBD, proliferative diseases: including without limitation T cell leukaemias and lymphomas.

Proliferative or hyperproliferative disease are characterized by excessive or abnormal cell proliferation. Such diseases include, without limitation, cancer and myeloproliferative disorders.

The term "cancers" includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer.

The term "Aurora-mediated condition" or "Aurora-mediated disease" as used herein means any disease or other deleterious condition in which Aurora (Aurora A, Aurora B, and Aurora C) is known to play a role. Such conditions include, without limitation, cancer such as colorectal, thyroid, and breast cancer; and myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

Thus, the term "cancerous cell" as provided herein, includes a cell afflicted by any one of the above-identified conditions. In some embodiments, the cancer is selected from colorectal, thyroid, or breast cancer.

The term "myeloproliferative disorders", includes disorders such as polycythemia vera, thrombocythemia, myeloid metaplasia with myelofibrosis, hypereosinophilic syndrome, juvenile myelomonocytic leukaemia, systemic mast cell disease, and hematopoietic disorders, in particular, acute-myelogenous leukemia (AML), chronic-myelogenous leukemia (CML), acute-promyelocytic leukemia (APL), and acute lymphocytic leukemia (ALL).

Examples of neurodegenerative diseases include, without limitation, Alzheimer's disease Huntington's disease, Parkinson's disease, AIDS-associated dementia, and bipolar disorder.

Examples of autoimmune diseases include, without limitation, multiple sclerosis, rheumatoid arthritis and irritable bowel disease.

In one embodiment, the present invention is a method of treating or preventing a disease or disorder, described herein, in a subject in need thereof, comprising administering to the subject an effective amount of a compound, composition or a pharmaceutically acceptable salt described herein. In another embodiment, the present invention is the use of an effective amount of a compound, composition or a pharmaceutically acceptable salt described herein for treating or preventing a disease or disorder, described herein, in a subject in need thereof. In one embodiment, the present invention is the use of an effective amount of a compound, composition or a pharmaceutically acceptable salt described herein for the manufacture of a medicament method for the treatment or prevention of a disease or disorder, described herein, in a subject in need thereof. In one embodiment, the disease or disorder is cancer. In another embodiment, the disease or disorder is cancer, such as, colorectal, thyroid, and breast cancer; or myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, or systemic mast cell disease. In another embodiment the disease or disorder is a neurodegenerative disease (e.g., Alzheimer's disease, Huntington's disease, Parkinson's disease, AIDS-associated dementia, bipolar disorder), amyotrophic lateral sclerosis (ALS, Lou Gehrig's disease), multiple sclerosis (MS), schizophrenia, leukocytopenia, cardiomyocyte hypertrophy, stroke, or rheumatoid arthritis (RA) In another embodiment the disease or disorder is MS, RA or irritable bowel disease (IBD). In another embodiment, the disease or disorder is MS. The terms, "disease", "disorder" and "condition" may be used interchangeably here to refer to a protein kinase-mediated condition.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intraarticular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The dosage regimen utilizing the compounds of Structural Formula I can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compound of Structural Formula I required to treat, for example, to prevent, inhibit (fully or partially) or arrest the progress of the disease.

Dosages of the compounds of Structural Formula I can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosings such as twice, three or four times per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

An effective amount can be achieved in the method or pharmaceutical composition of the invention employing a compound of Structural Formula I or a pharmaceutically acceptable salt or solvate (e.g., hydrate) thereof alone or in combination with an additional suitable therapeutic agent, for example, a cancer-therapeutic agent. When combination therapy is employed, an effective amount can be achieved using a first amount of a compound of Structural Formula I or a pharmaceutically acceptable salt or solvate (e.g., hydrate) thereof and a second amount of an additional suitable therapeutic agent.

In one embodiment, the compound of Structural Formula I and the additional therapeutic agent, are each administered in an effective amount (i.e., each in an amount which would be therapeutically effective if administered alone). In another embodiment, the compound of Structural Formula I and the additional therapeutic agent, are each administered in an amount which alone does not provide a therapeutic effect (a sub-therapeutic dose). In yet another embodiment, the compound of Structural Formula I can be administered in an effective amount, while the additional therapeutic agent is administered in a sub-therapeutic dose. In still another embodiment, the compound of Structural Formula I can be administered in a sub-therapeutic dose, while the additional therapeutic agent, for example, a suitable cancer-therapeutic agent is administered in an effective amount.

As used herein, the terms "in combination" or "coadministration" can be used interchangeably to refer to the use of more than one therapies (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

When coadministration involves the separate administration of the first amount of a compound of Structural Formula I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Structural Formula I and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of coadministration of a first amount of a compound of Structural Formula I and a second amount of an additional therapeutic agent can result in an enhanced or synergistic therapeutic effect, wherein the combined effect is greater than the additive effect that would result from separate administration of the first amount of the compound of Structural Formula I and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S, and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

In some embodiments, said additional therapeutic agent is selected from a cancer-therapeutic agent, such as, an anti-cancer agent, an anti-proliferative agent, or a chemotherapeutic agent.

In some embodiments, said additional therapeutic agent is selected from camptothecin, the MEK inhibitor: U0126, a KSP (kinesin spindle protein) inhibitor, adriamycin, interferons, and platinum derivatives, such as Cisplatin.

In other embodiments, said additional therapeutic agent is selected from taxanes; inhibitors of bcr-abl (such as Gleevec, dasatinib, and nilotinib); inhibitors of EGFR (such as Tarceva and Iressa); DNA damaging agents (such as cisplatin, oxaliplatin, carboplatin, topoisomerase inhibitors, and anthracyclines); and antimetabolites (such as AraC and 5-FU).

In yet other embodiments, said additional therapeutic agent is selected from camptothecin, doxorubicin, idarubicin, Cisplatin, taxol, taxotere, vincristine, tarceva, the MEK inhibitor, U0126, a KSP inhibitor, vorinostat, Gleevec, dasatinib, and nilotinib.

In another embodiment, said additional therapeutic agent is selected from Her-2 inhibitors (such as Herceptin); HDAC inhibitors (such as vorinostat), VEGFR inhibitors (such as Avastin), c-KIT and FLT-3 inhibitors (such as sunitinib), BRAF inhibitors (such as Bayer's BAY 43-9006) MEK inhibitors (such as Pfizer's PD0325901); and spindle poisons (such as Epothilones and paclitaxel protein-bound particles (such as Abraxane®).

Other therapies or anticancer agents that may be used in combination with the inventive agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., anti-emetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, adriamycin, dexamethasone, and cyclophosphamide.

A compound of the instant invention may also be useful for treating cancer in combination with any of the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®);

idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglist-frame.htm, and The Merck Manual, Seventeenth Ed. 1999, the entire contents of which are hereby incorporated by reference.

Other examples of agents the compounds of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

As inhibitors of protein kinases, the compounds and compositions of this invention are also useful in biological samples. One aspect of the invention relates to inhibiting protein kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of protein kinase activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention is set forth in the Examples below.

Another aspect of this invention relates to the use of the compounds described here (in particular those with moderate observed affinity for biochemical targets (IC50 1-10 µM)) as start points for chemistry optimisation. In particular, one aspect of this invention relates to routine inhibition studies against a target enzyme for chemical optimisation.

Another aspect of this invention relates to the use of the compounds described herein for crystallography (in particular those with moderate observed affinity for biochemical targets): In particular, the one aspect of this invention relates to the generation of co-complex crystal structures with compounds described herein.

Another aspect of this invention relates to the use of the compounds described herein as chemical tools to probe target biology in vitro and in vivo: In particular inhibitors with moderate affinity in biochemical assays can be used to probe the biological impact of inhibiting a target enzyme in cells and in whole animal models of disease.

Another aspect of the invention provides a method for modulating enzyme activity by contacting a compound of formula I with a protein kinase.

ABBREVIATIONS

The following abbreviations are used:
DMSO dimethyl sulfoxide
TCA trichloroacetic acid
ATP adenosine triphosphate
BSA bovine serum albumin DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time In some embodiments, the compounds of this invention are represented in Table 1. In certain embodiments, the variables: B, Z, $R_1$, T1, G, Q1, J1, Y1, G1, M1, $R_2$, $R_3$, T2, G', Q2, J2, Y2, G1', M2, J, $R_4$, JT1, JT2, $R^\$$, $R_{12}$, $R_{12'}$, JT3, JT4, and $R_{13}$ are as defined in the specific embodiments as shown in Table 1.

TABLE 1

1

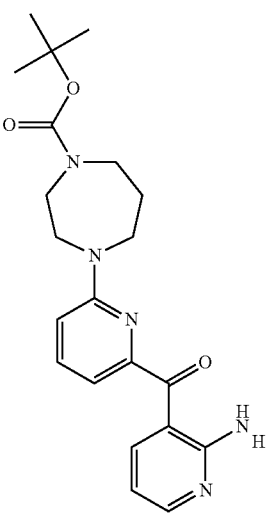

2

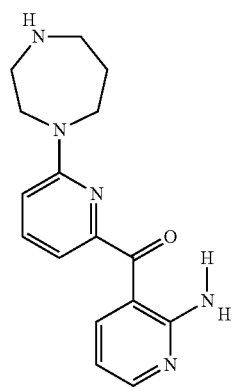

TABLE 1-continued

3

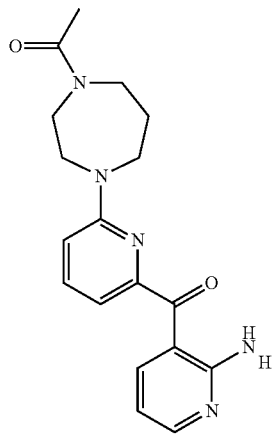

4

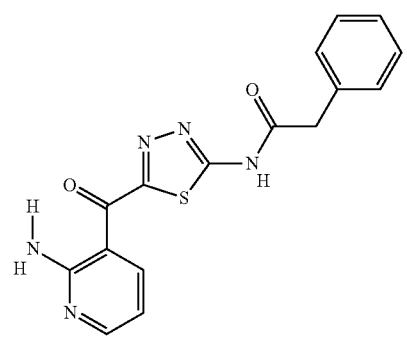

5

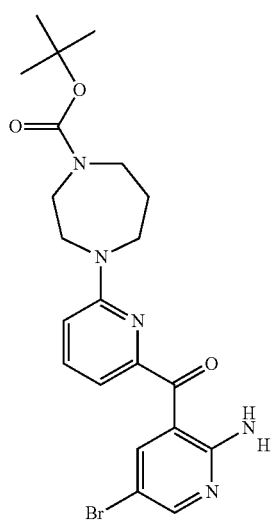

TABLE 1-continued
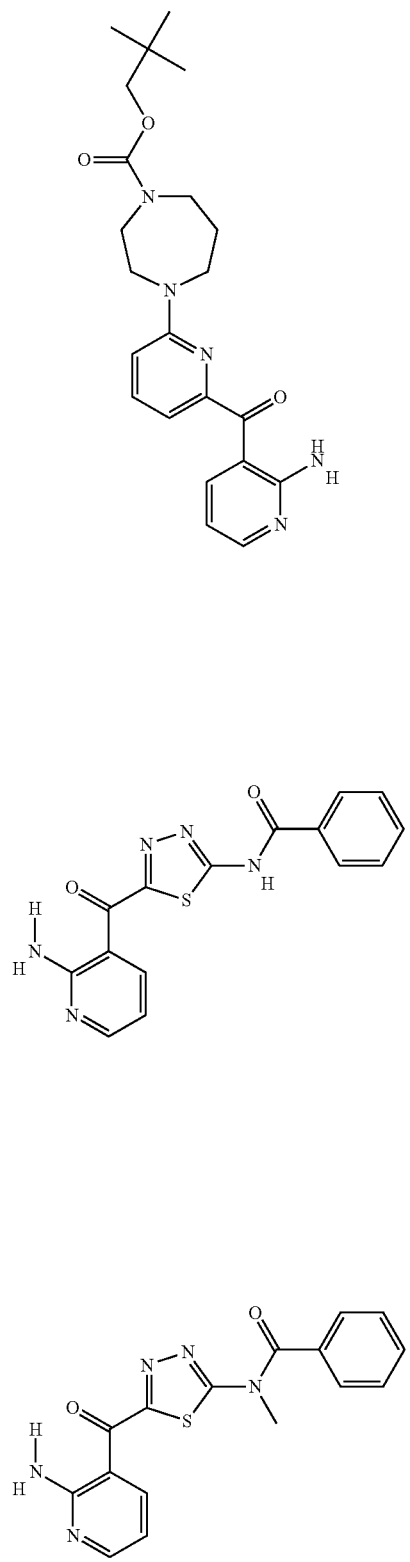
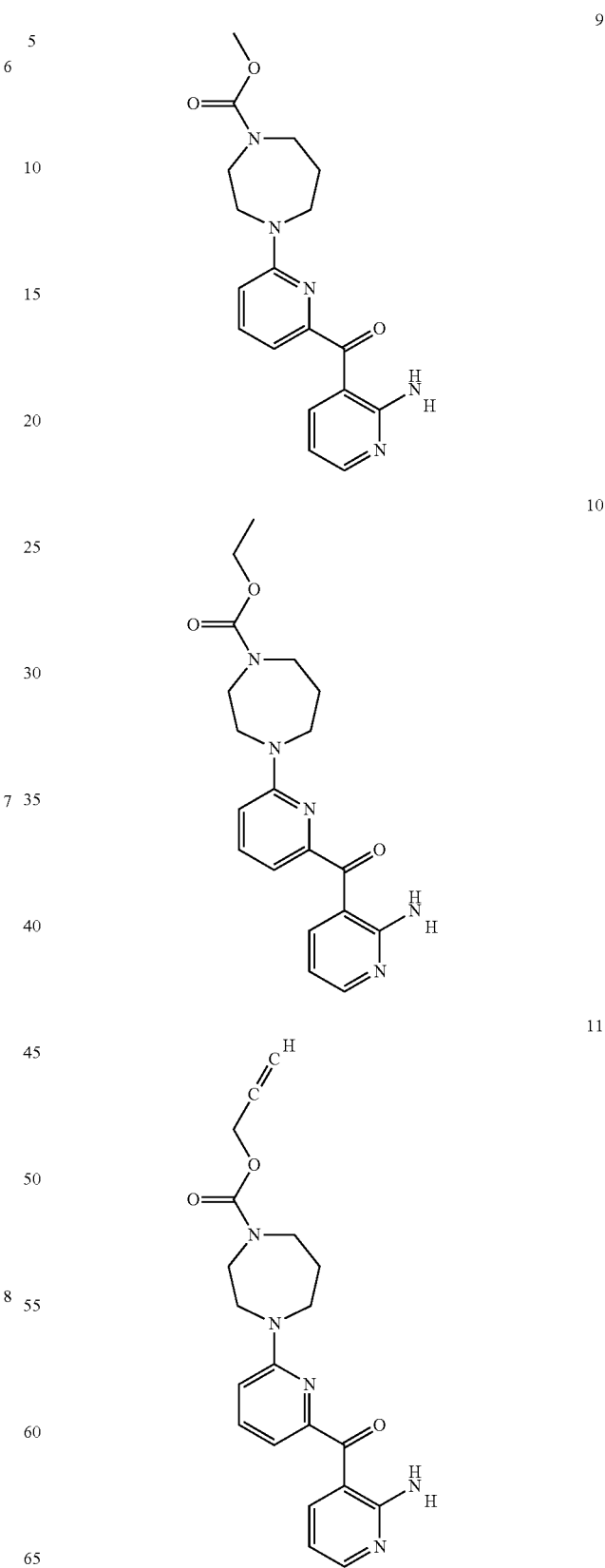

TABLE 1-continued
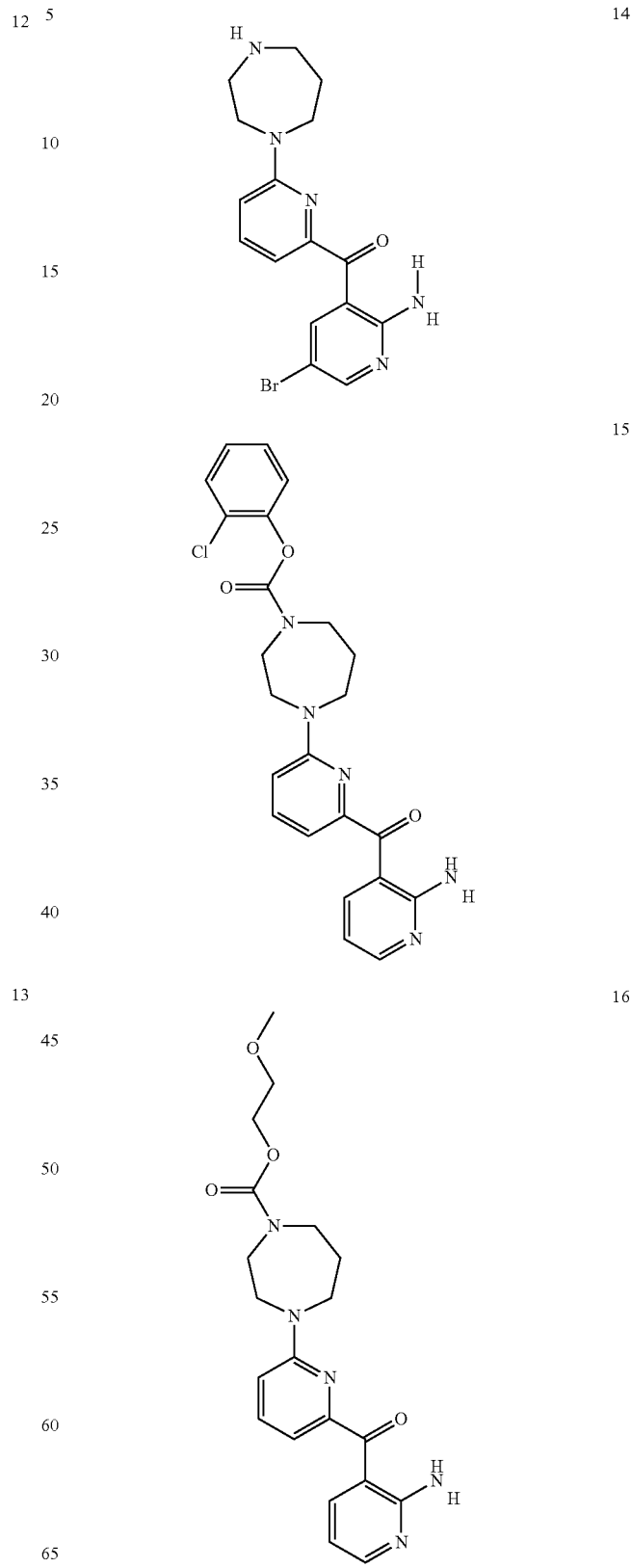

TABLE 1-continued
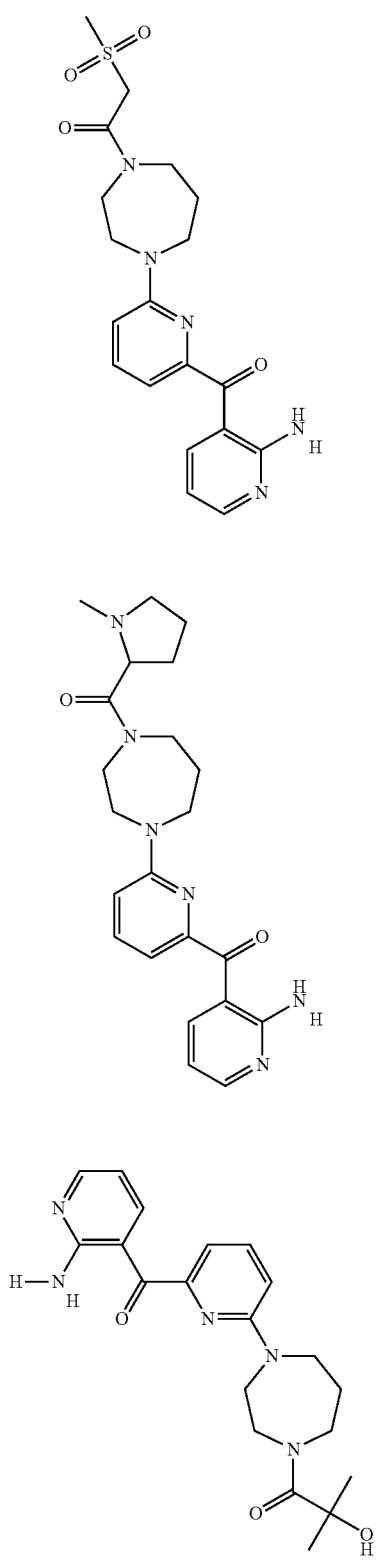
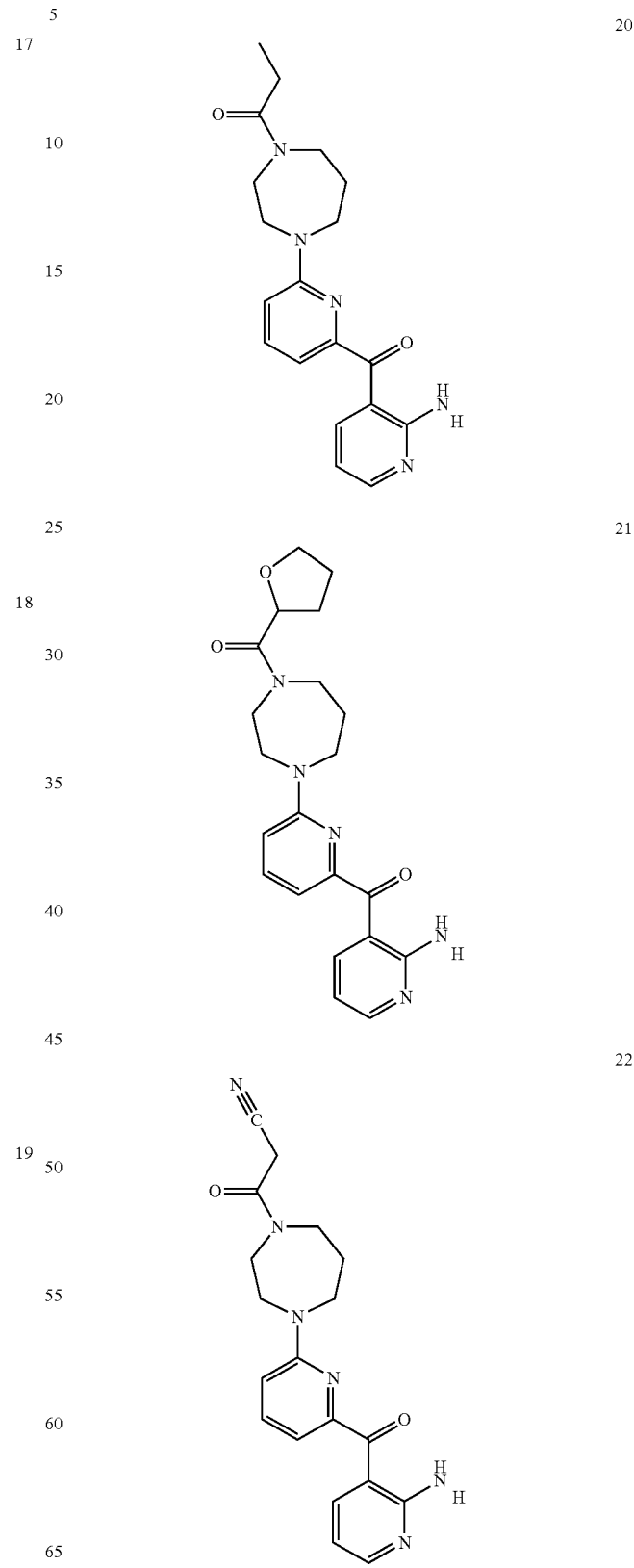

TABLE 1-continued
| | |
|---|---|
| 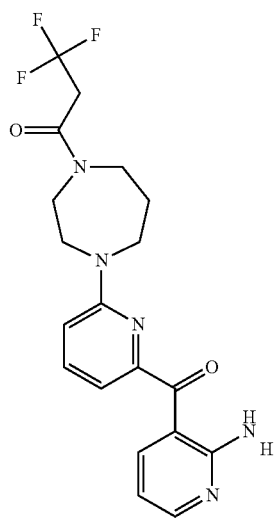 | 23 |
| 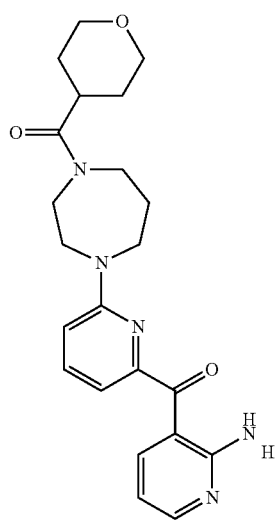 | 24 |
| 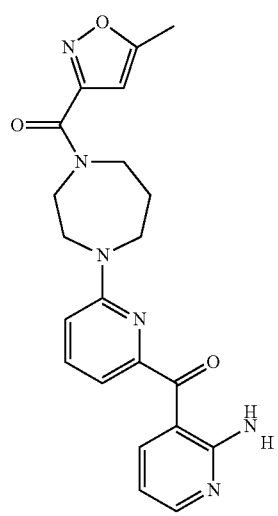 | 25 |
| | |
|---|---|
| 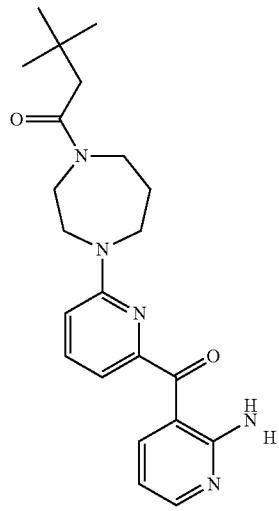 | 26 |
| 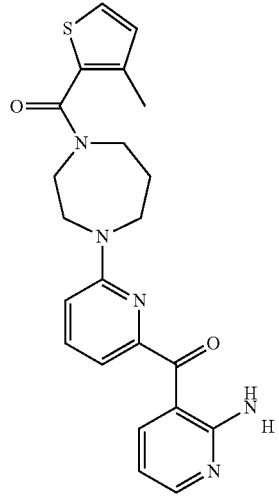 | 27 |
| 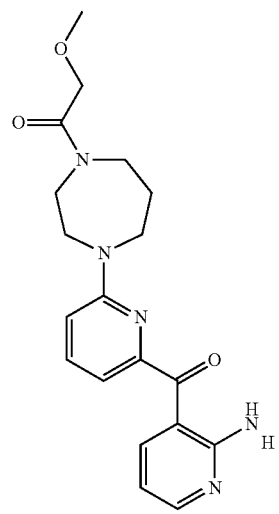 | 28 |

TABLE 1-continued
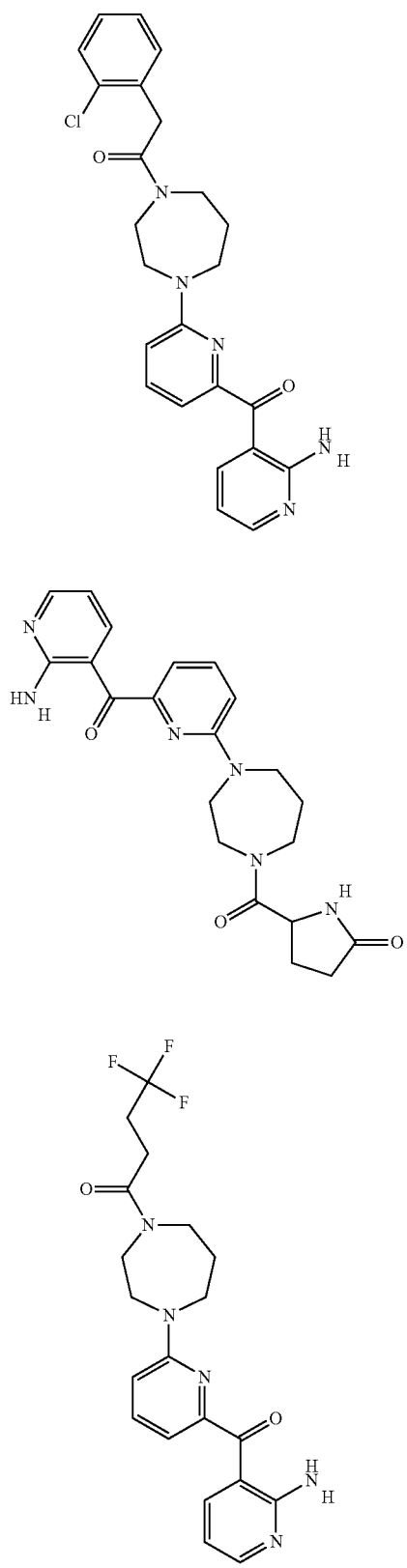
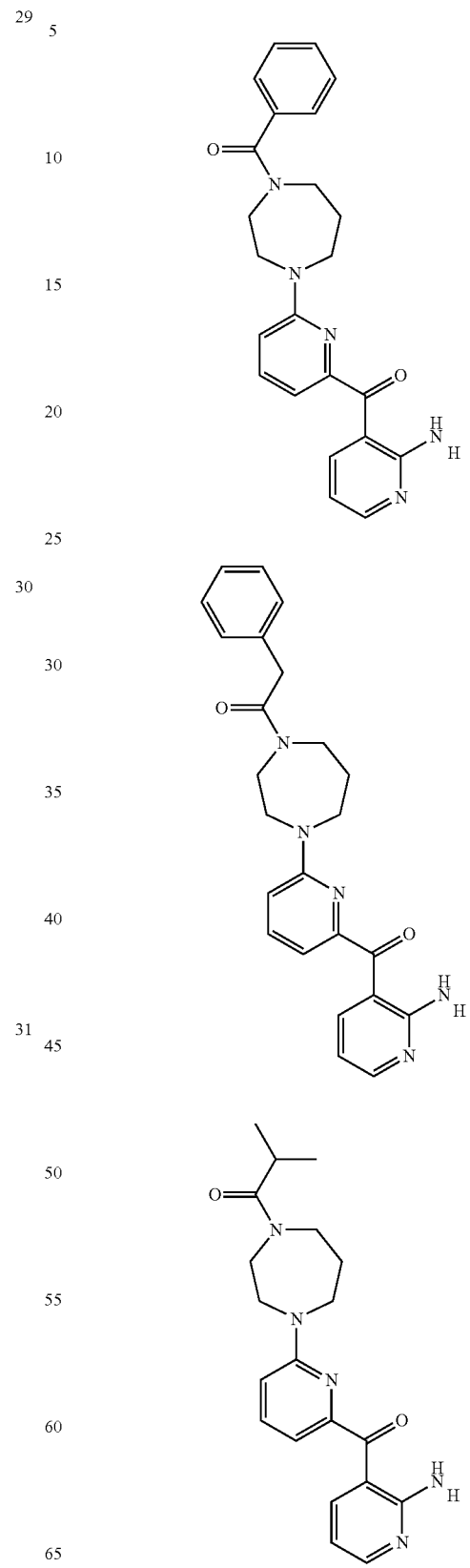

TABLE 1-continued
35 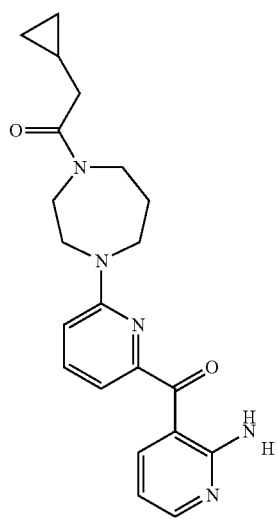
36
37
5 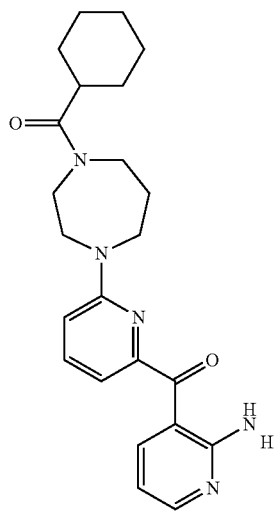
38
10
15
20
25
30 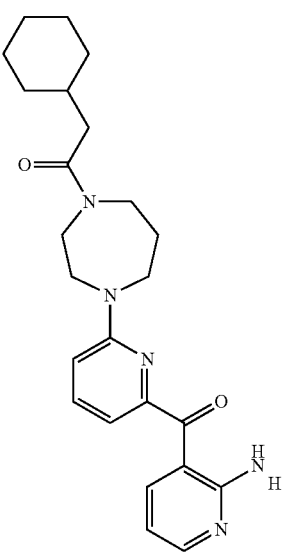
39
35
40
45
50 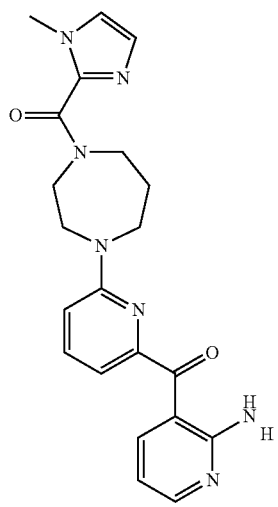
40
55
60
65

TABLE 1-continued
41
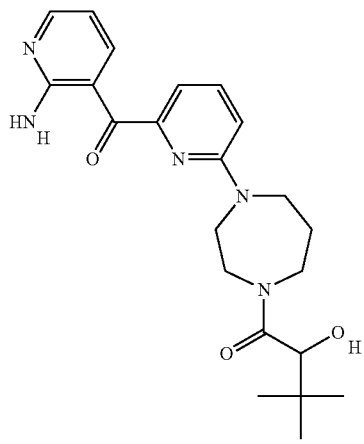
42
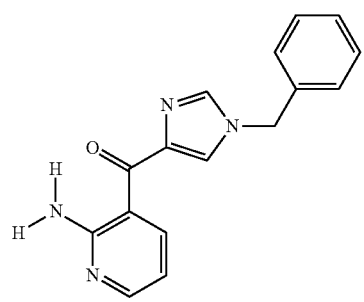
43
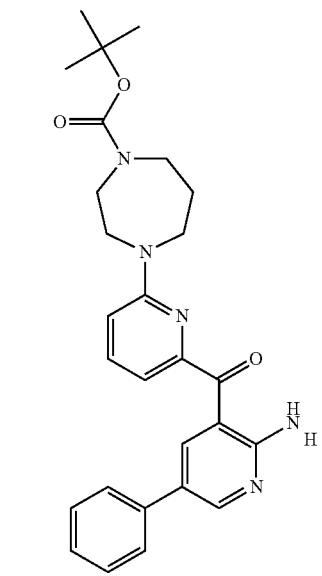
TABLE 1-continued
44
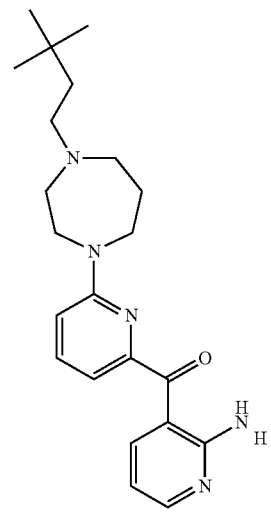
45
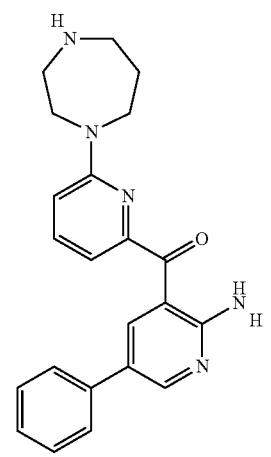
46
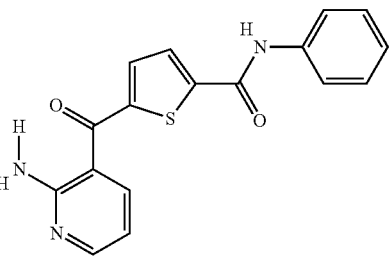
47
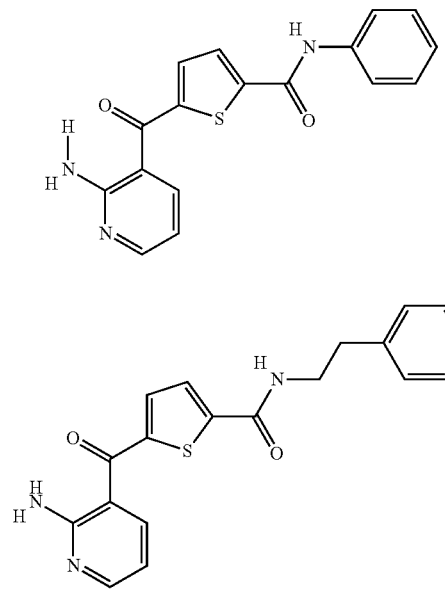

| 48 | 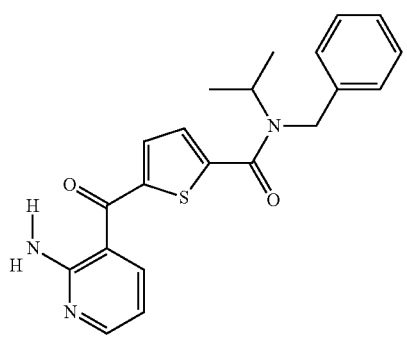 |
| 49 | 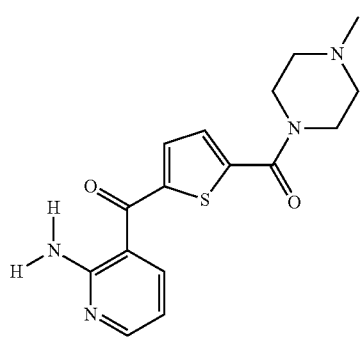 |
| 50 | 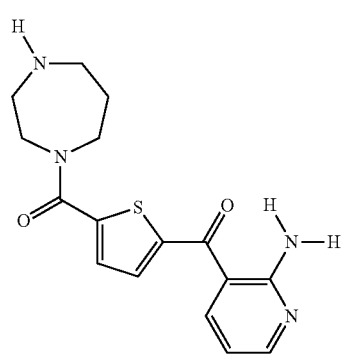 |
| 51 | 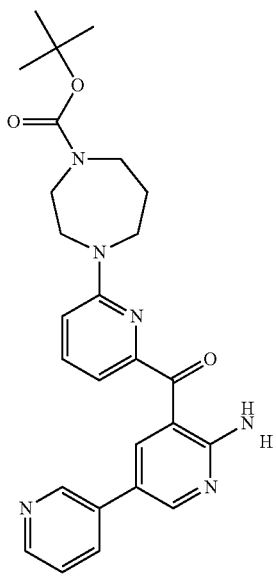 |
| 52 | 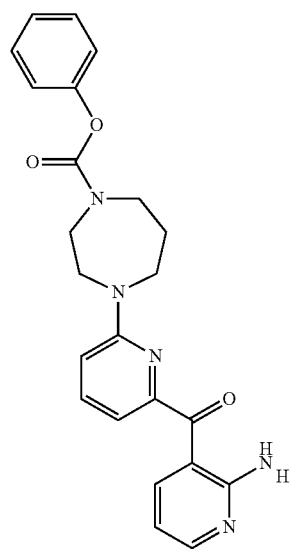 |
| 53 | 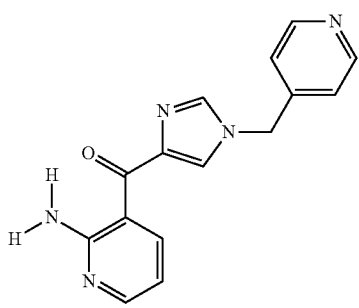 |

TABLE 1-continued
| | |
|---|---|
| 54 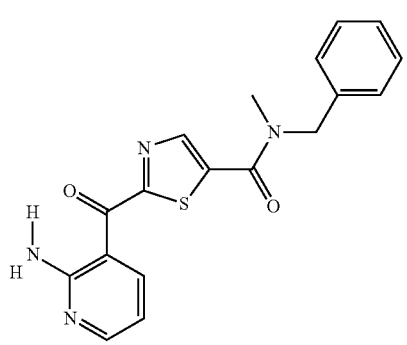 | 57 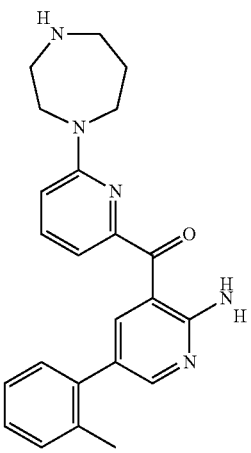 |
| 55 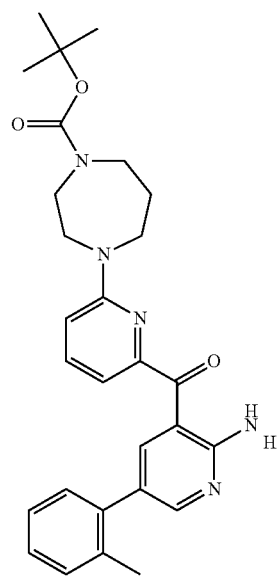 | 58 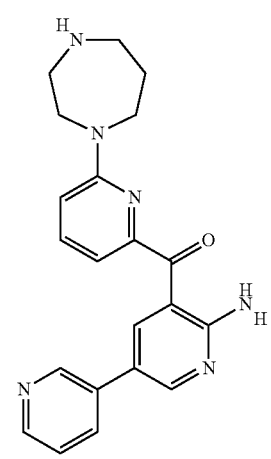 |
| 56 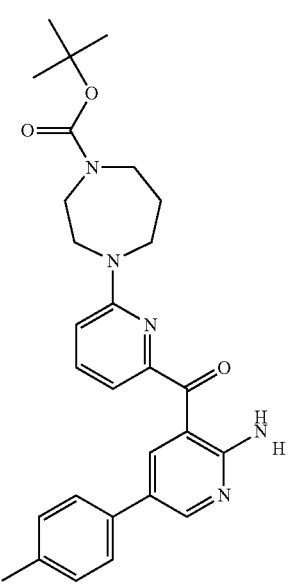 | 59 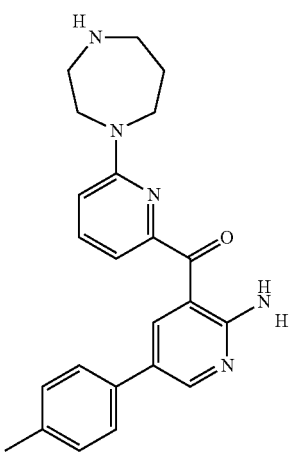 |

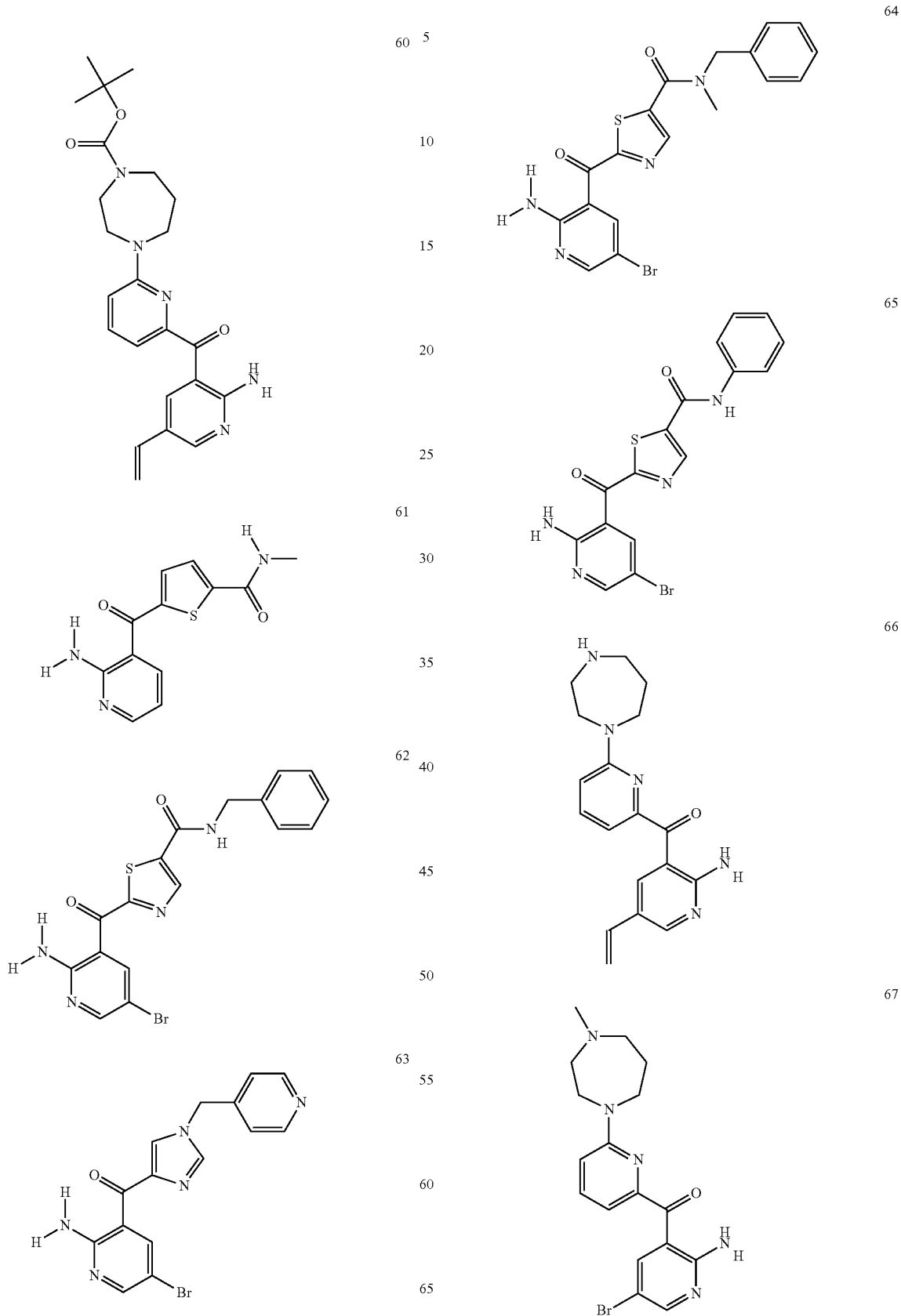

TABLE 1-continued
| | |
|---|---|
| 68 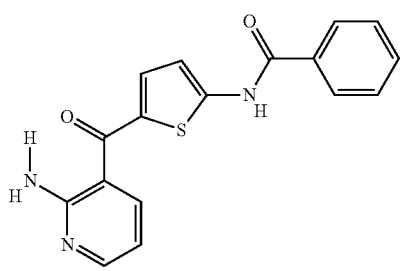 | 71 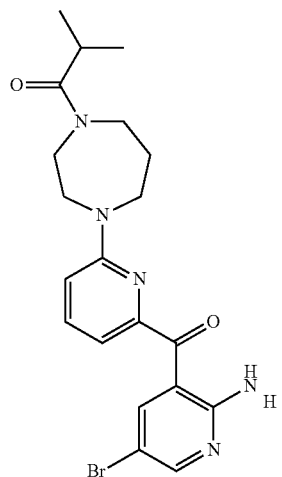 |
| 69 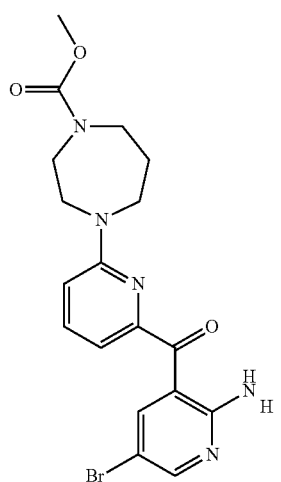 | 72 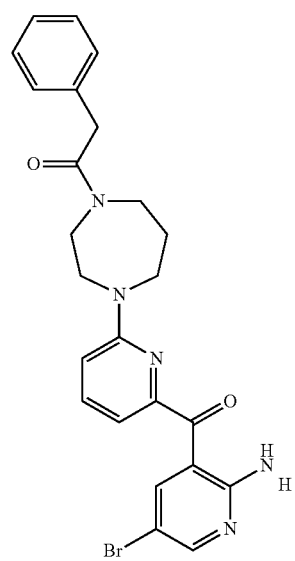 |
| 70 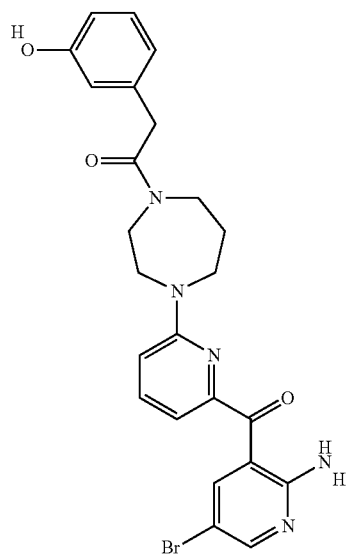 | 73 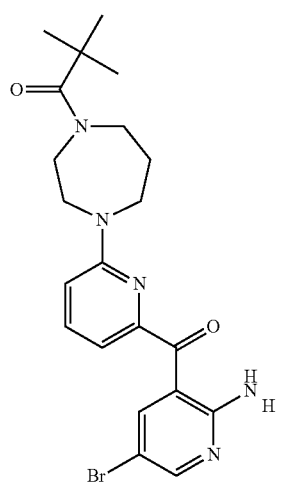 |

TABLE 1-continued
74 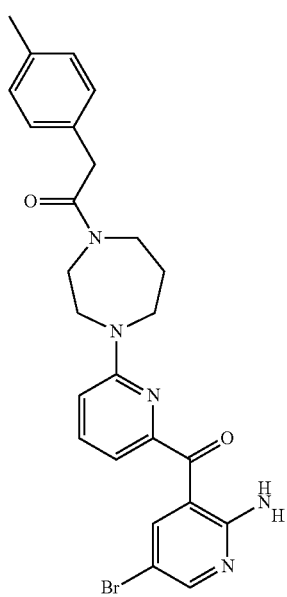
75 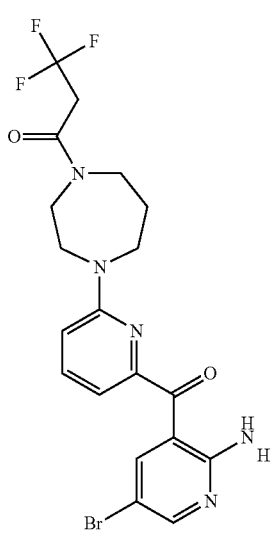
76 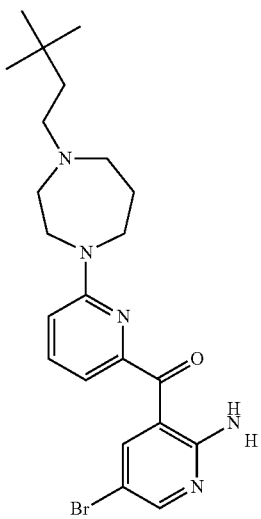
77 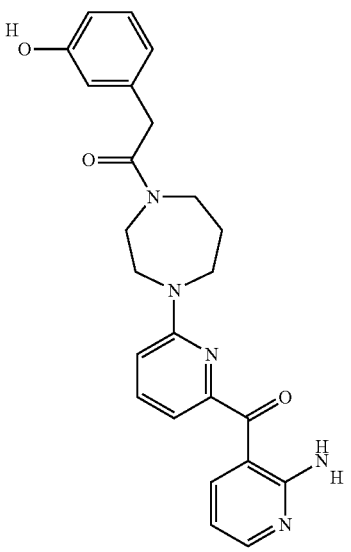
78 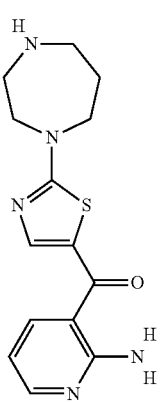

TABLE 1-continued
79
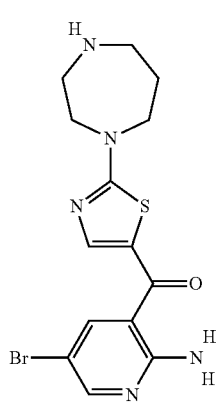
80
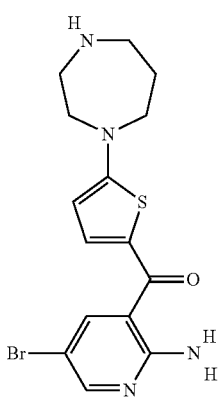
81
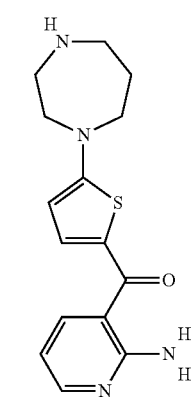
TABLE 1-continued
82
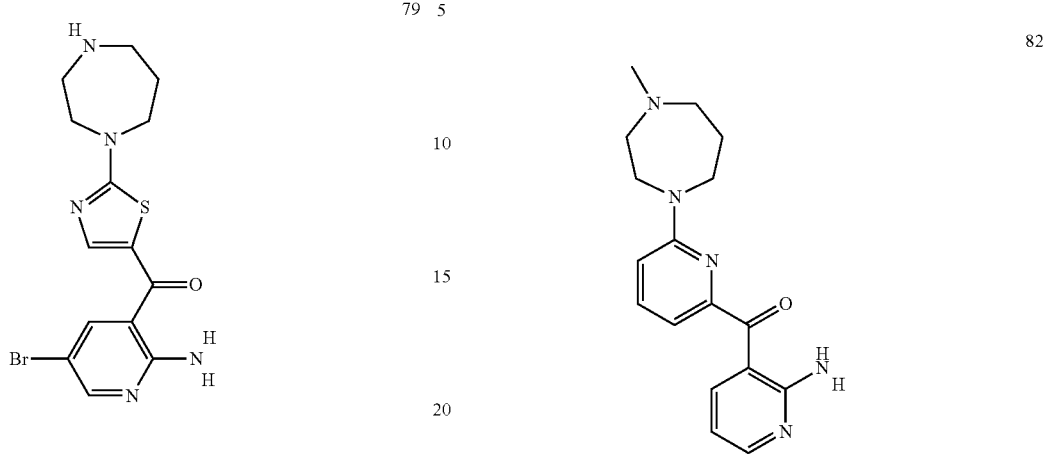
83
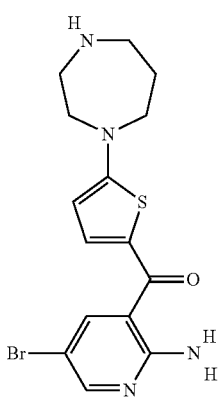
84
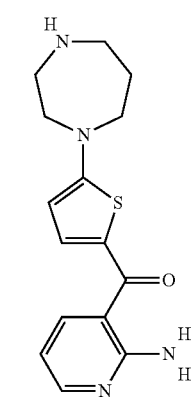
85
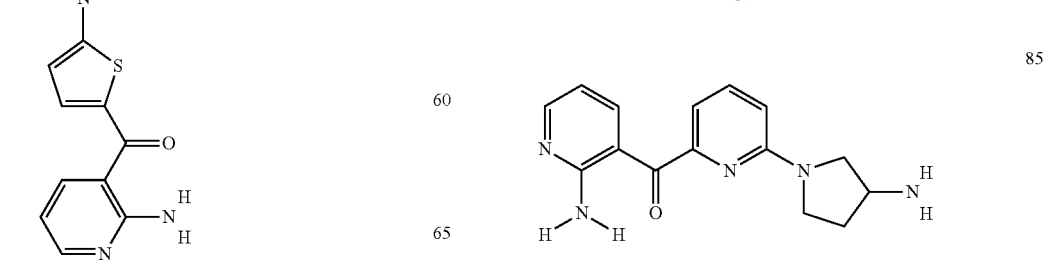

TABLE 1-continued
| | |
|---|---|
| 86 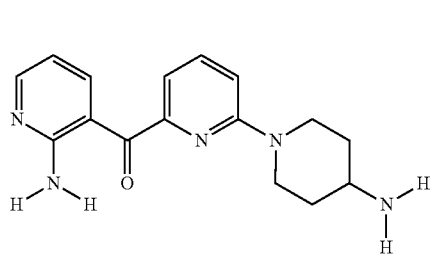 | 90 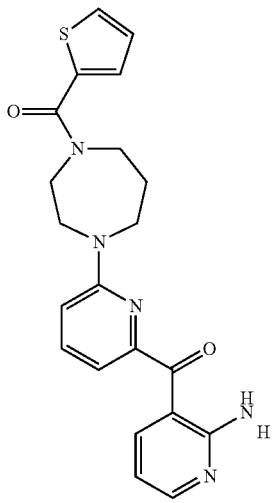 |
| 87 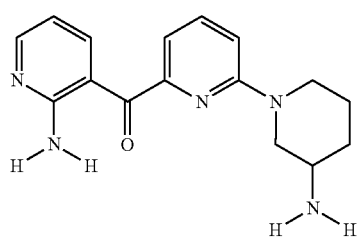 | 91 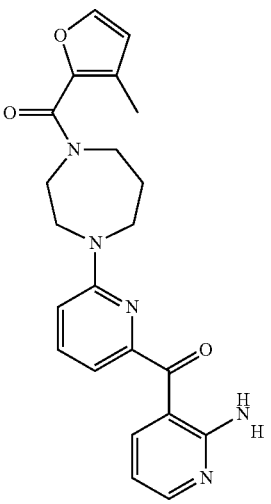 |
| 88 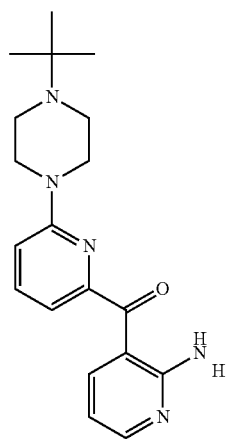 | 92 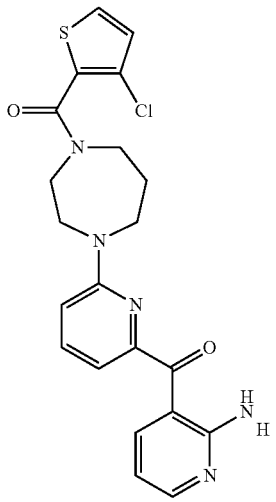 |
| 89 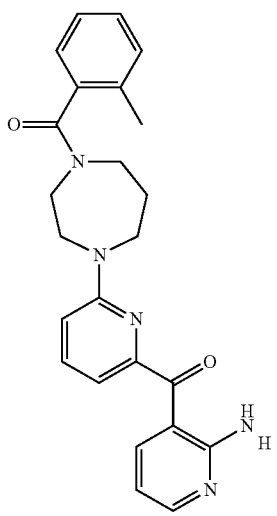 | |

TABLE 1-continued
93
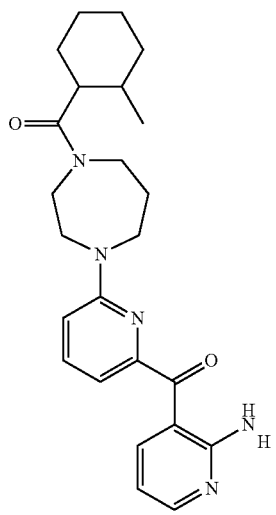
94
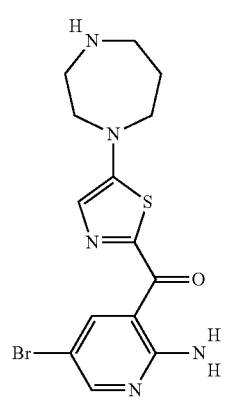
95
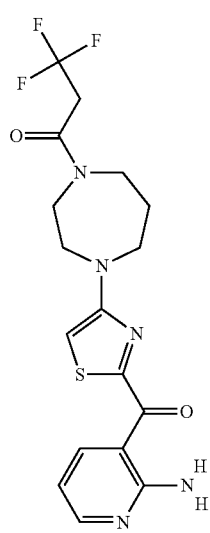
TABLE 1-continued
96
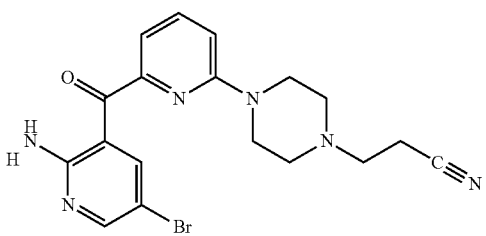
97
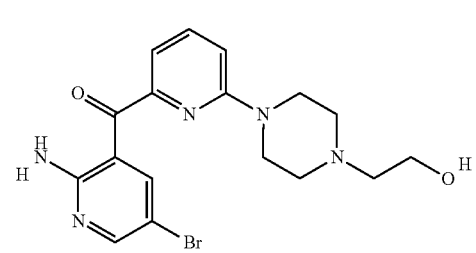
98
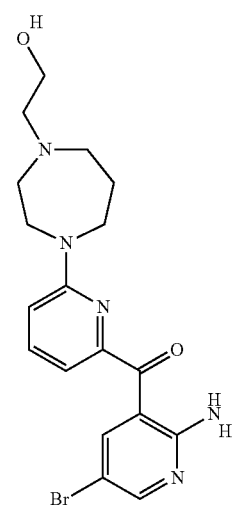
99
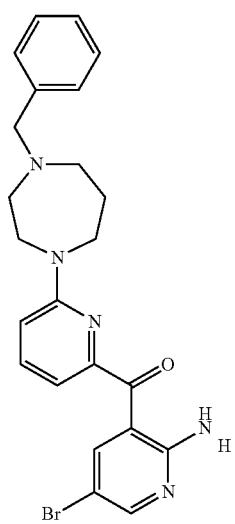

TABLE 1-continued
100
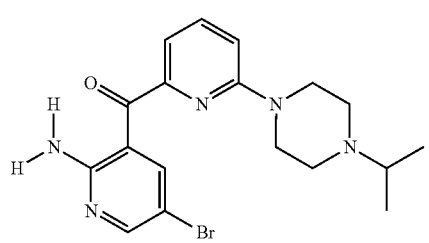
101
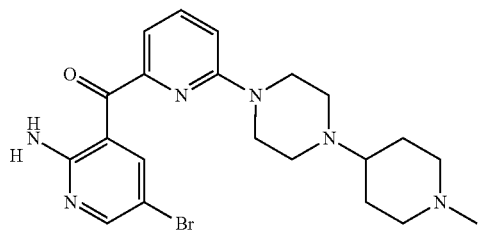
102
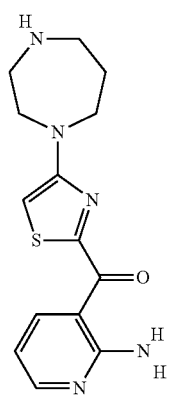
103
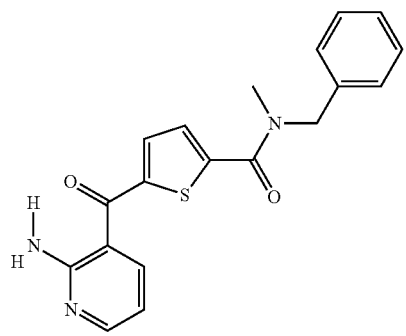
TABLE 1-continued
104
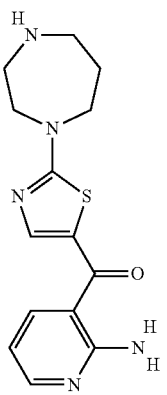
105
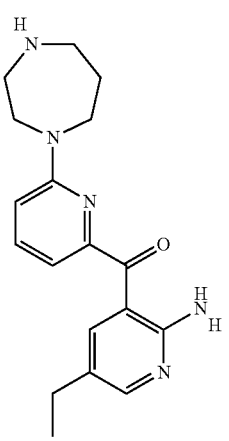
106
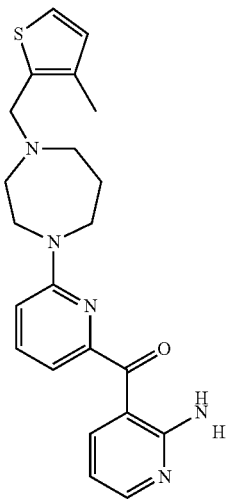

TABLE 1-continued
107 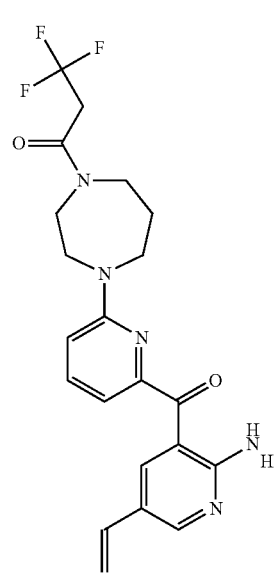
108 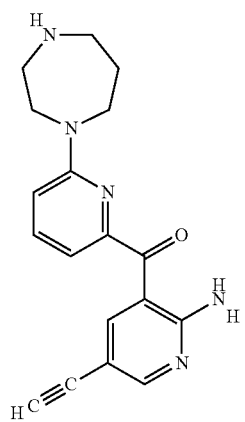
109 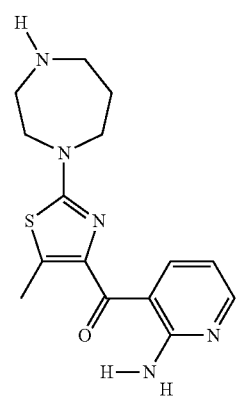
110 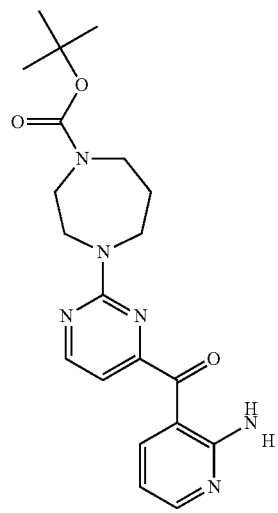
111 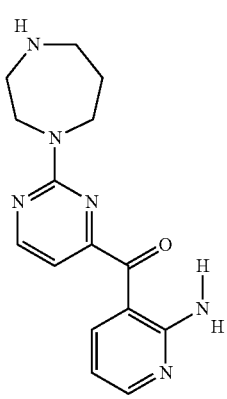
112 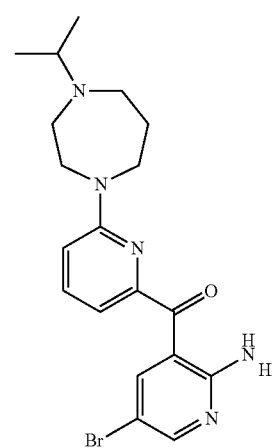

TABLE 1-continued
113
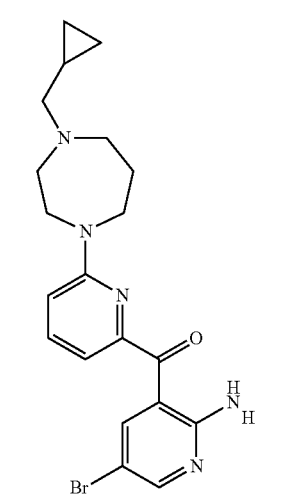
114
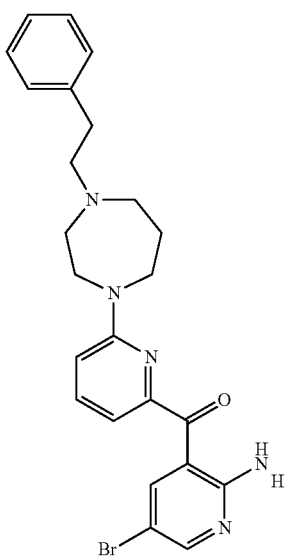
115
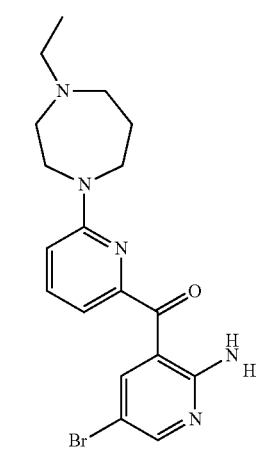
TABLE 1-continued
116
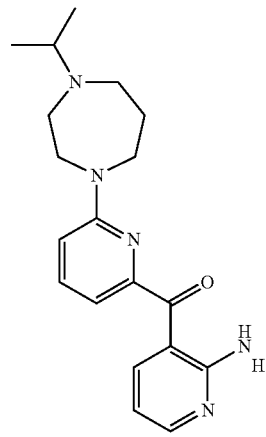
117
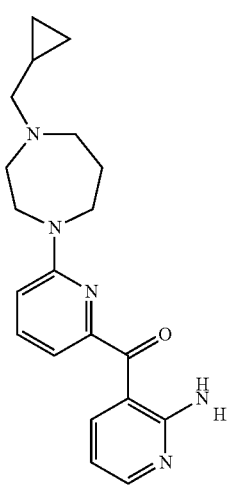
118
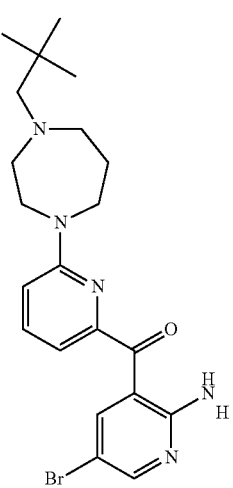

TABLE 1-continued
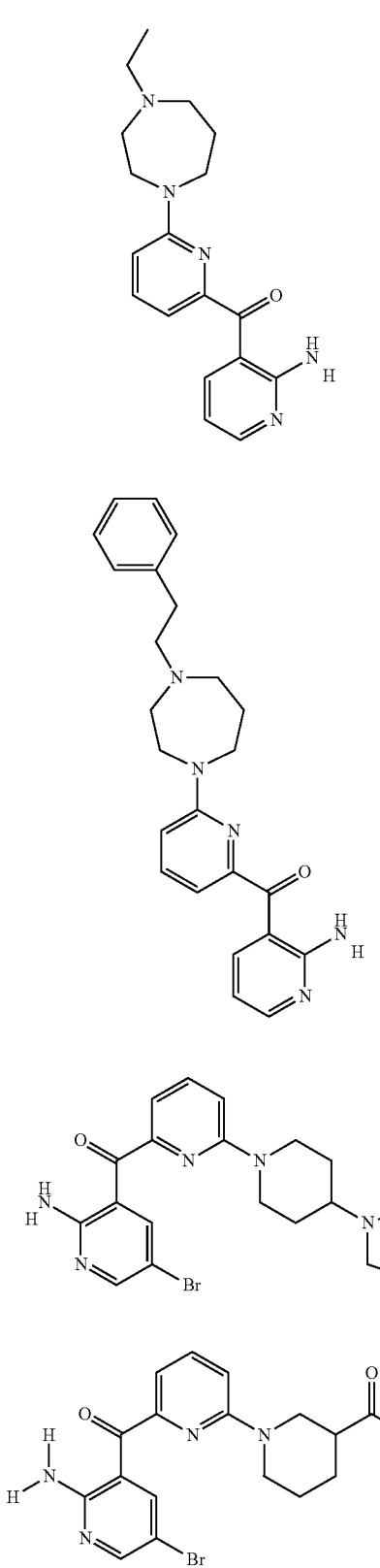
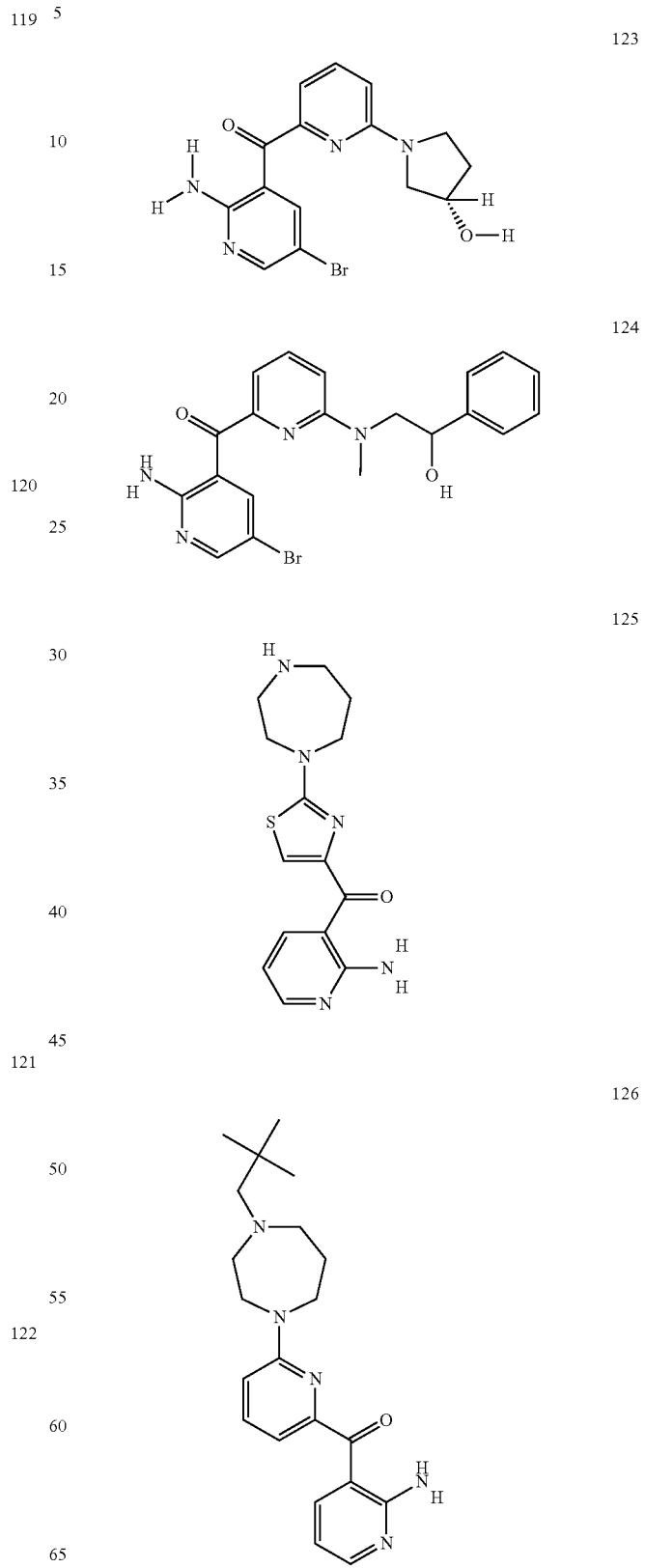

TABLE 1-continued
127 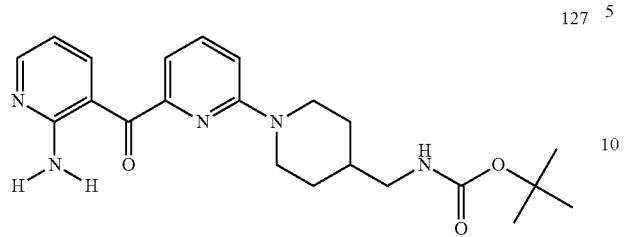
128 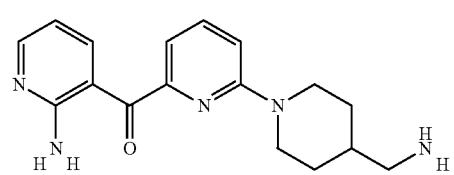
129 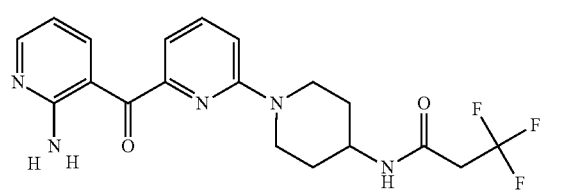
130 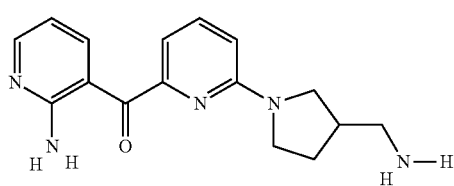
131 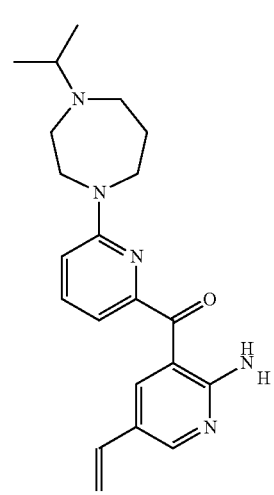
TABLE 1-continued
132 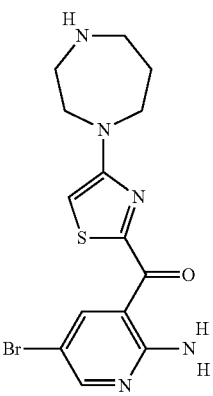
133 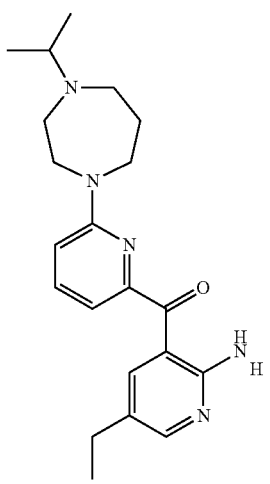
134 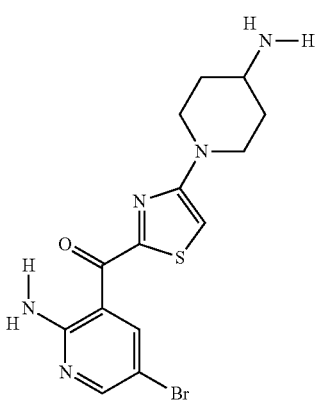

TABLE 1-continued
| | |
|---|---|
| 135 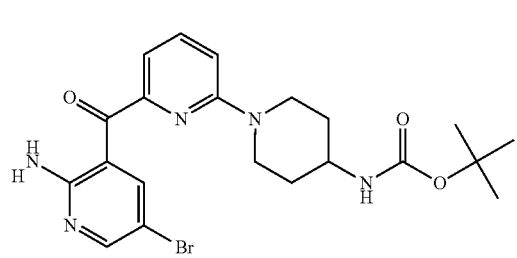 | 139 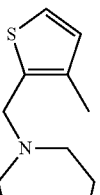 |
| 136 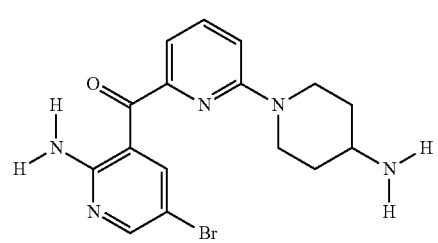 | 140 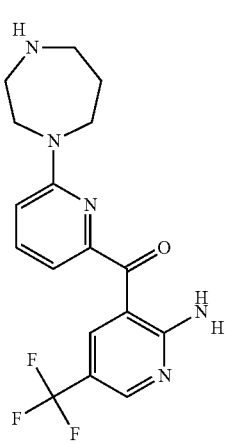 |
| 137 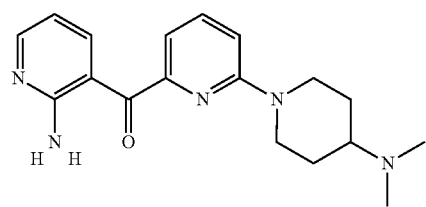 | 141 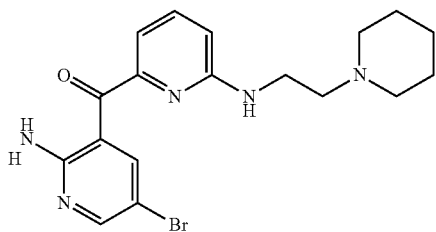 |
| 138 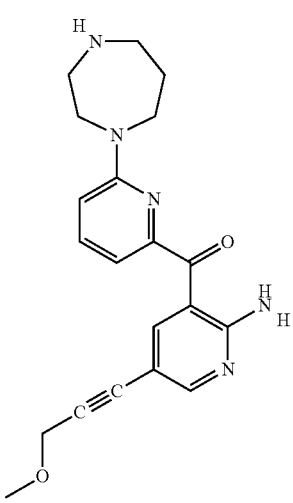 | 142 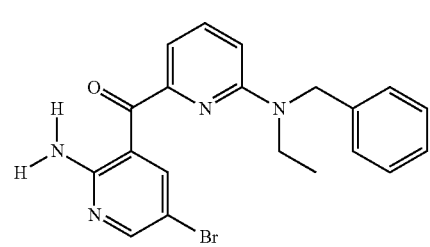 |

TABLE 1-continued
143 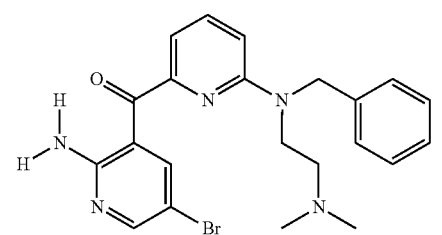
144 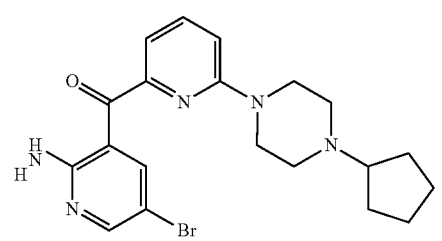
145 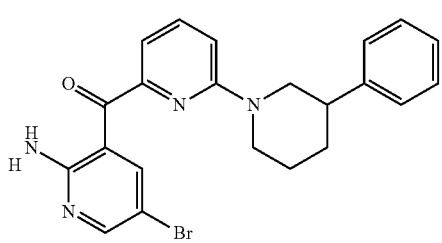
146 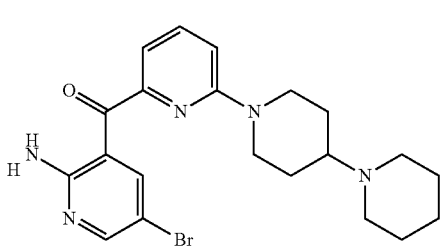
147 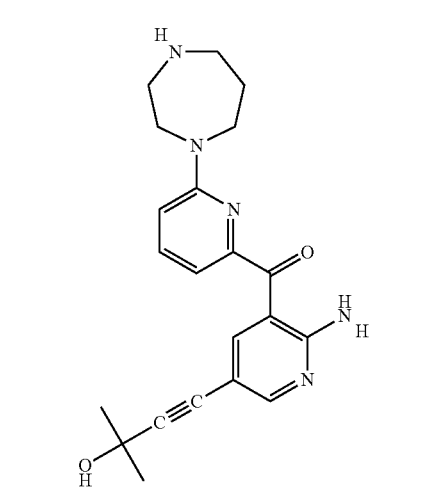
TABLE 1-continued
148 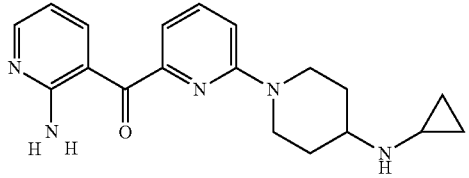
149 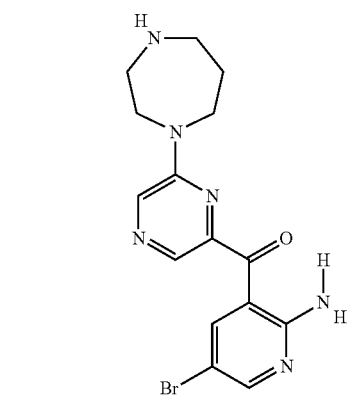
150 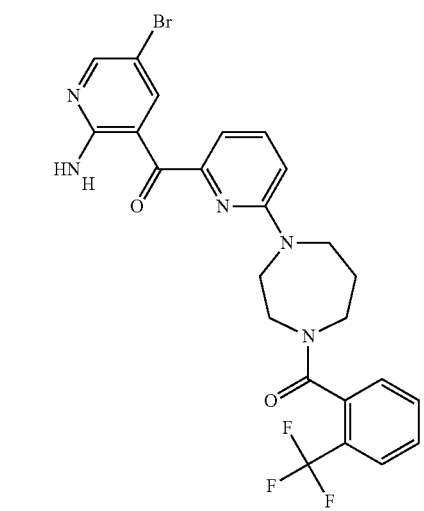

TABLE 1-continued
151 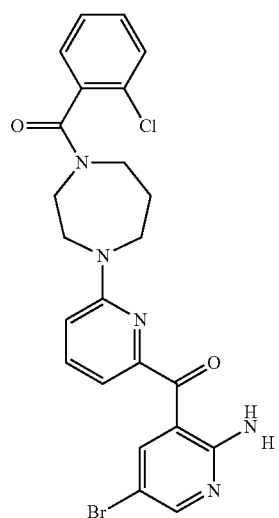
152 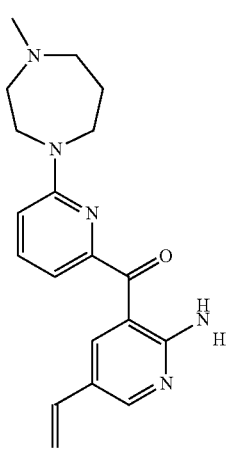
153 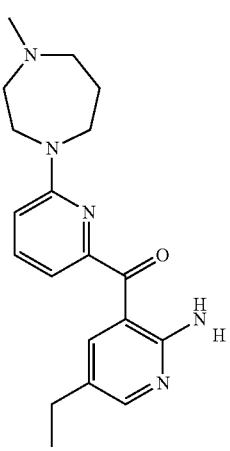
TABLE 1-continued
154 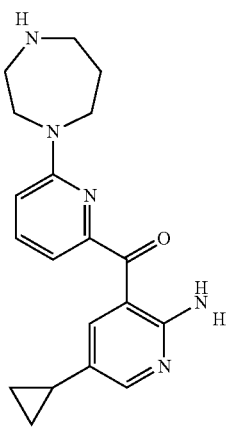
155 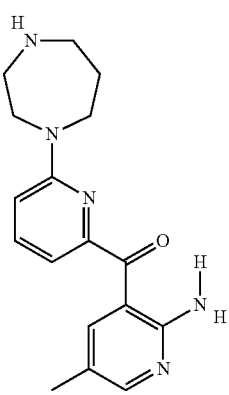
156 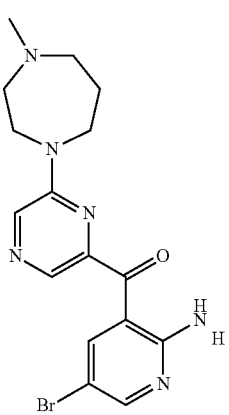

TABLE 1-continued
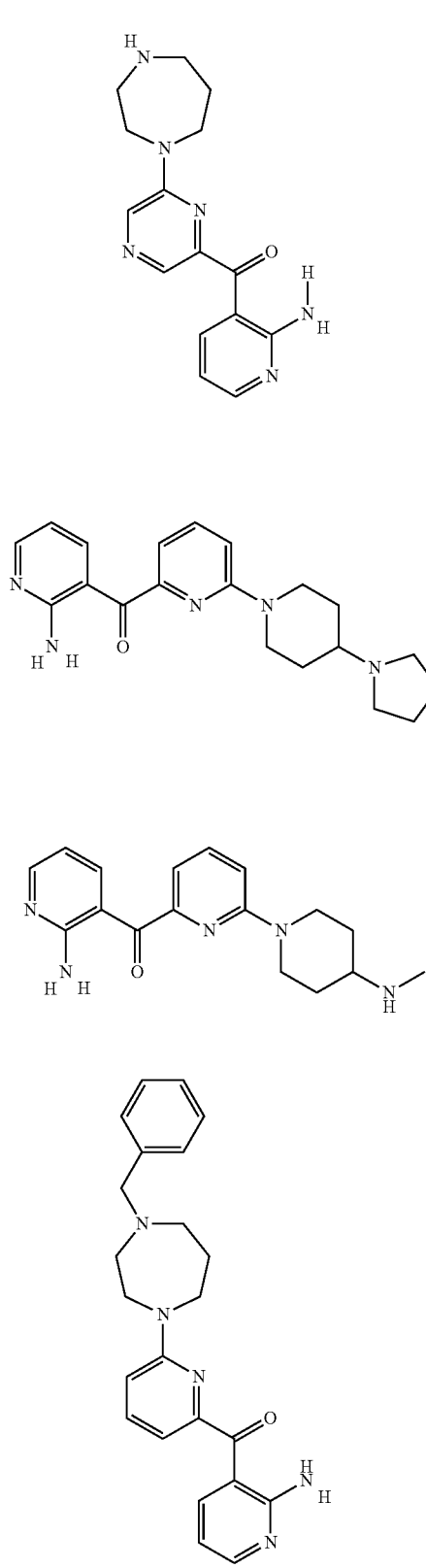
157
158
159
160
TABLE 1-continued
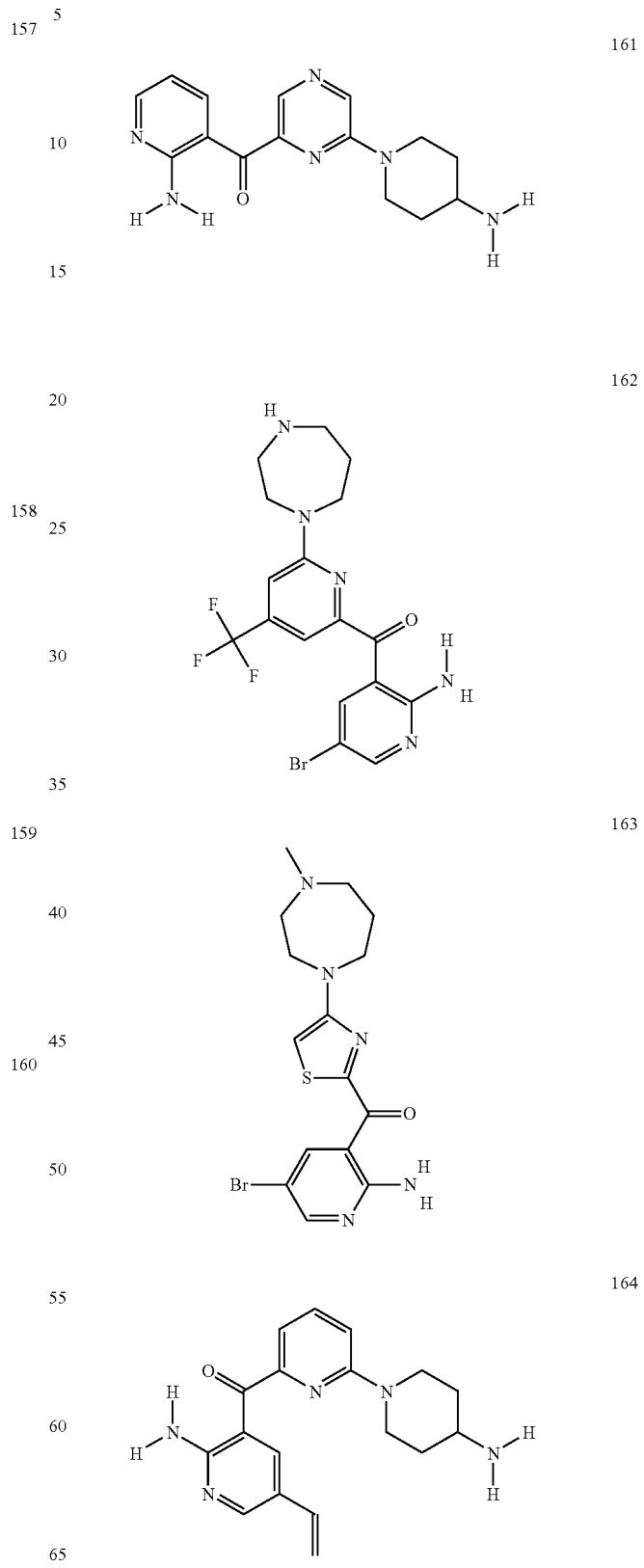
161
162
163
164

TABLE 1-continued
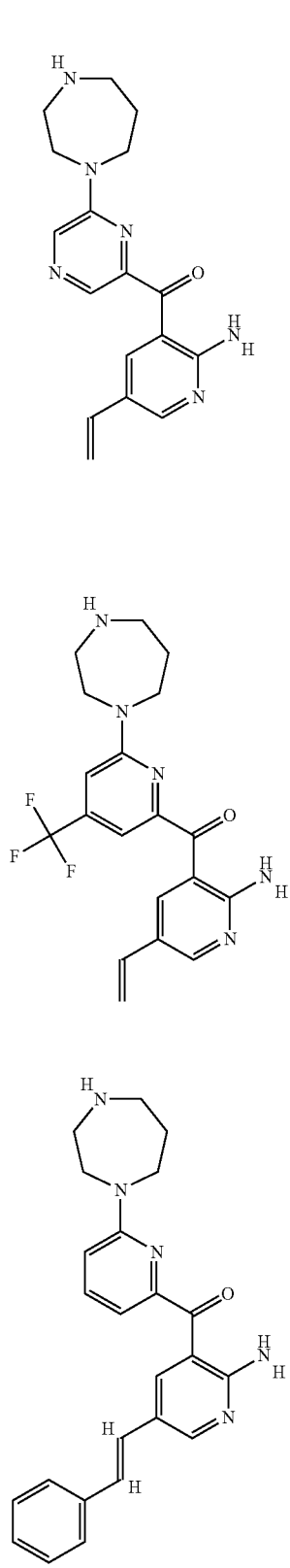
165
166
167
TABLE 1-continued
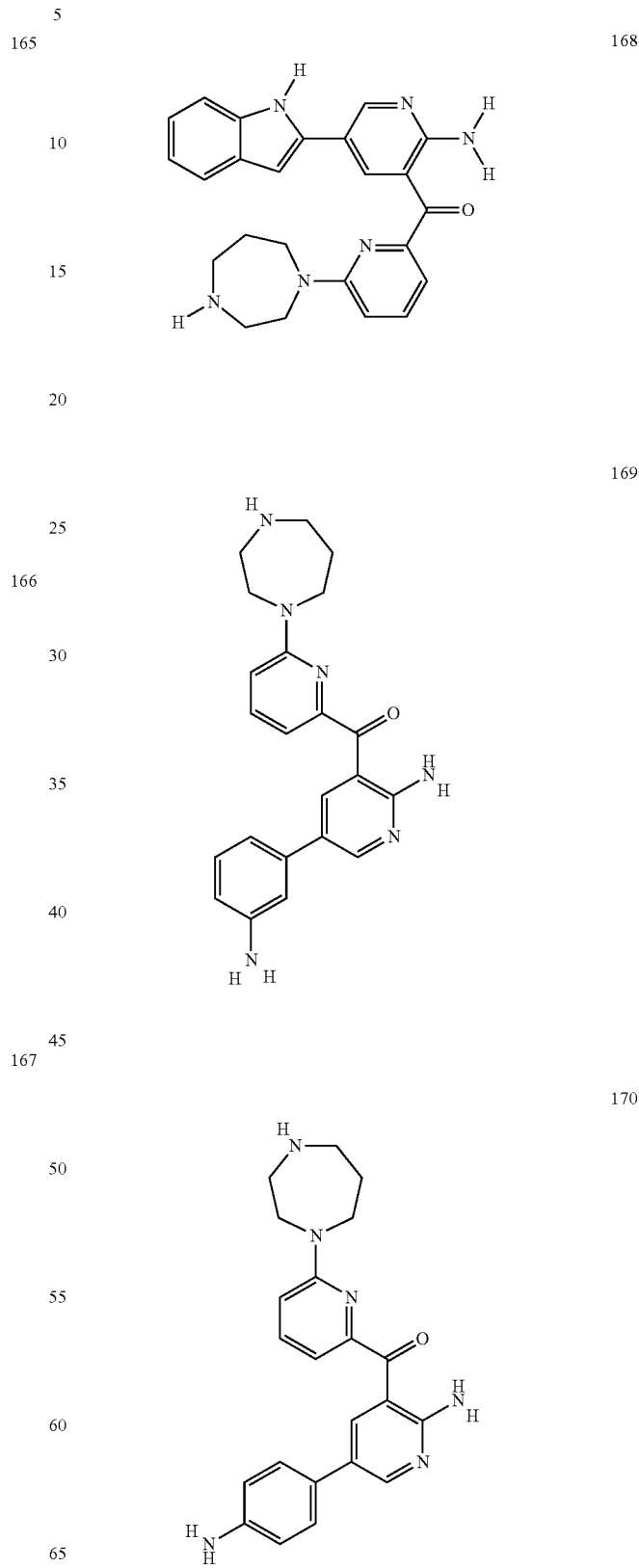
168
169
170

TABLE 1-continued
| | |
|---|---|
| 171 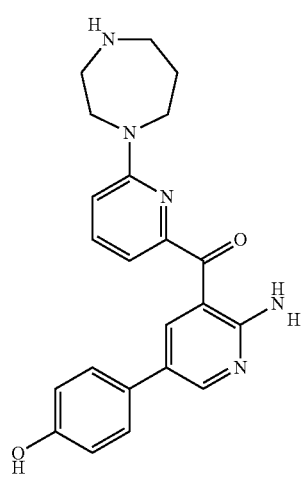 | 175 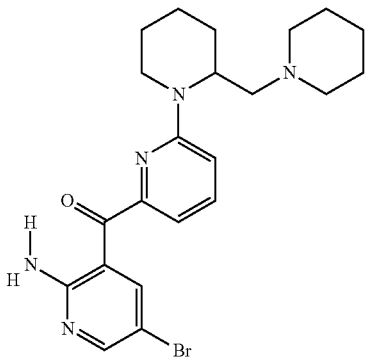 |
| 172 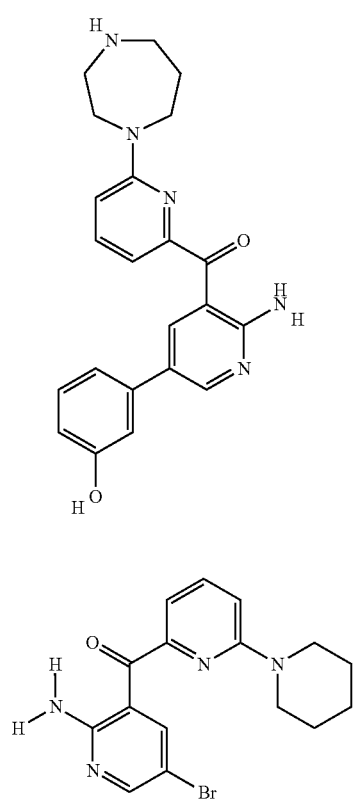 | 176 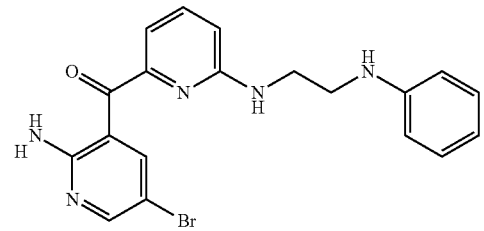 |
| | 177 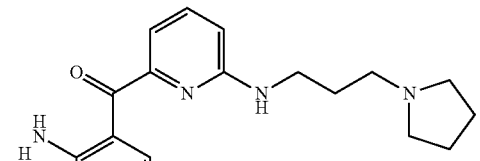 |
| 173 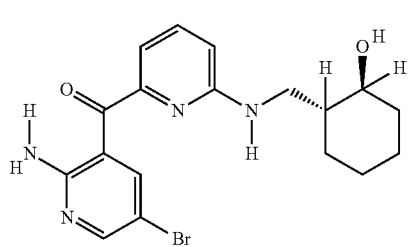 | |
| 174 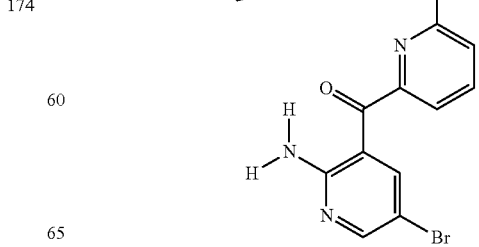 | 178 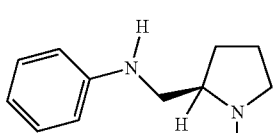 |

TABLE 1-continued
179
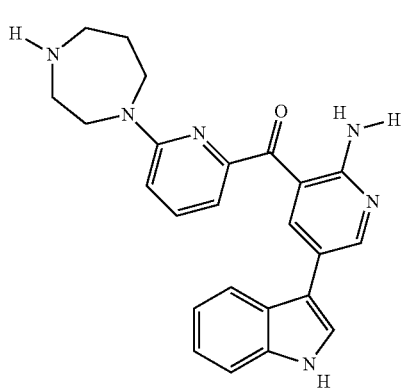
180
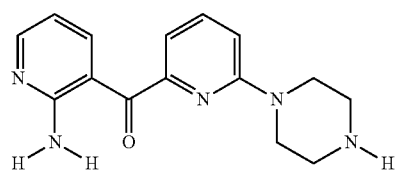
181
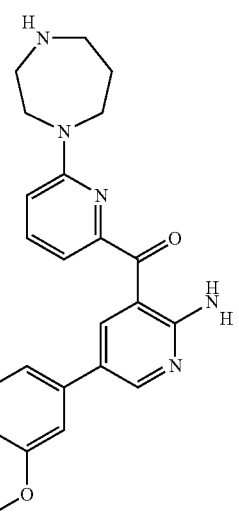
182
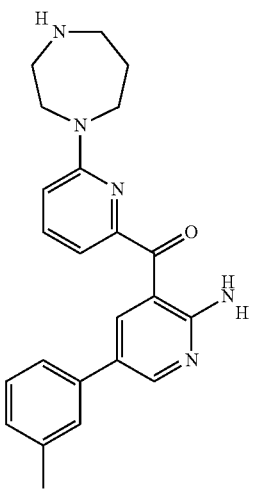
183
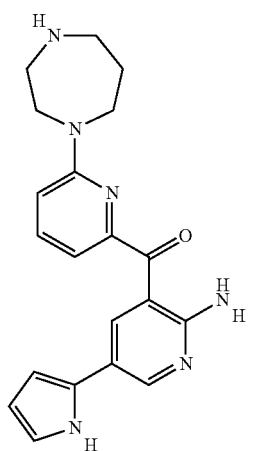
184
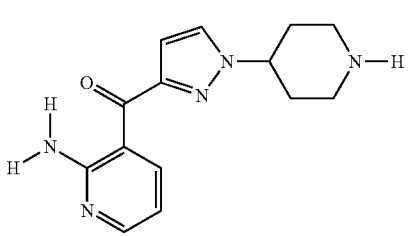

TABLE 1-continued
| 185 | 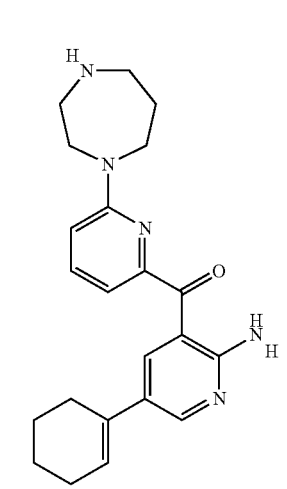 |
| --- | --- |
| 186 | 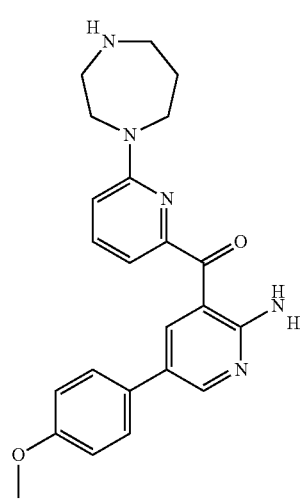 |
| 187 | 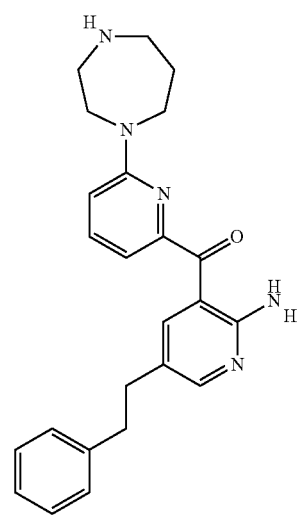 |
TABLE 1-continued
| 188 | 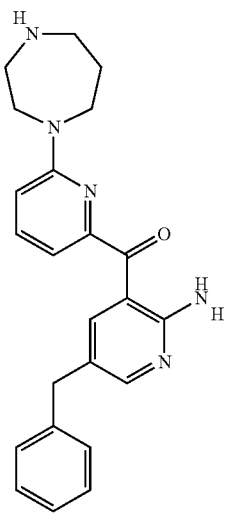 |
| --- | --- |
| 189 | 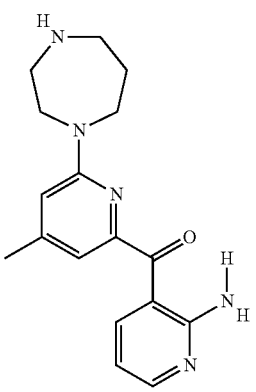 |
| 190 | |

TABLE 1-continued
191 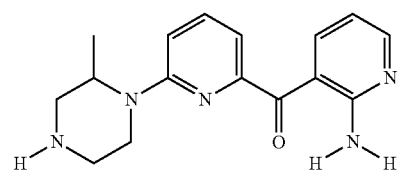
192 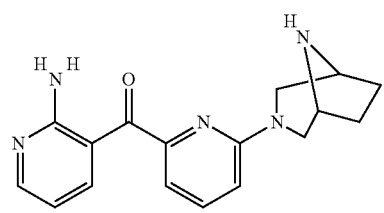
193 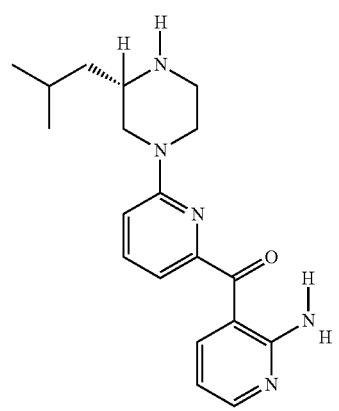
194 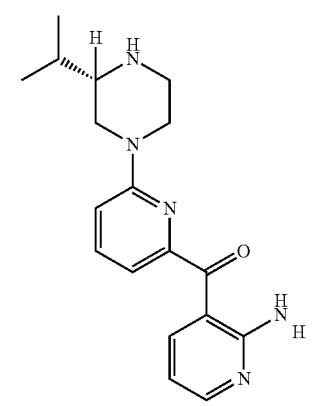
195 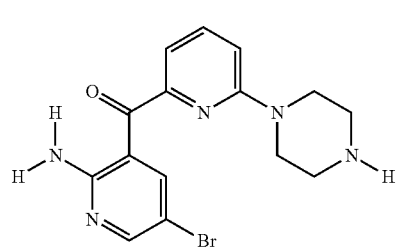
TABLE 1-continued
196 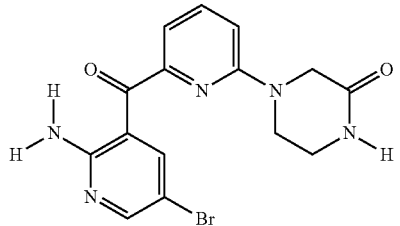
197
198
199 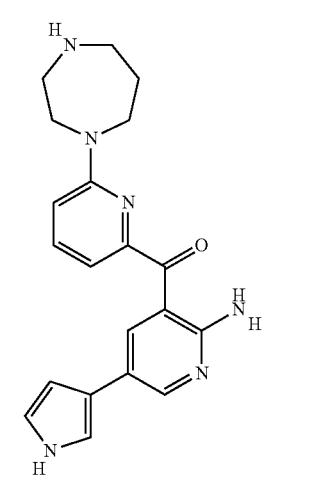

TABLE 1-continued
200 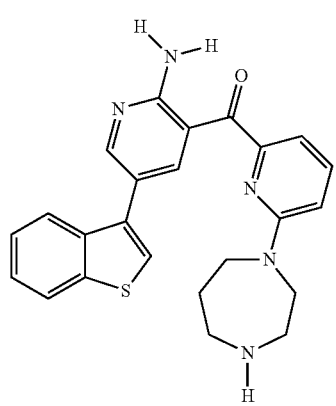
201 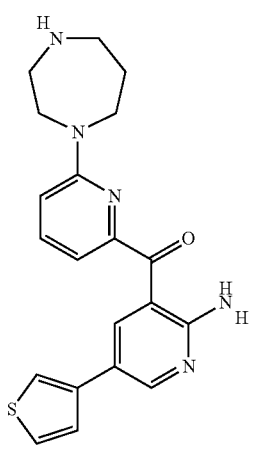
202 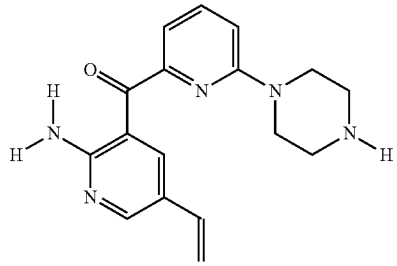
203 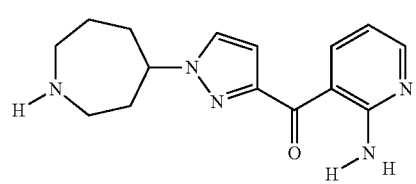
TABLE 1-continued
204 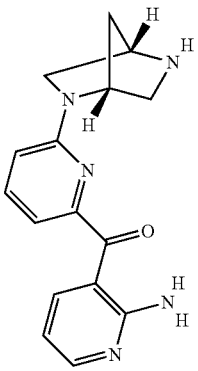
205 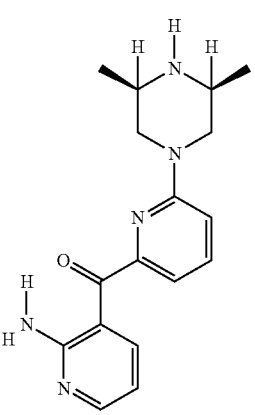
206 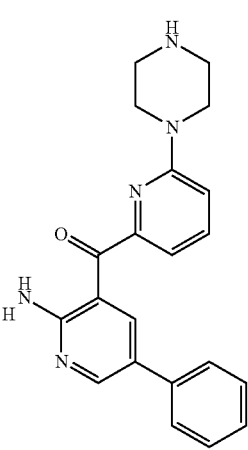

TABLE 1-continued
207 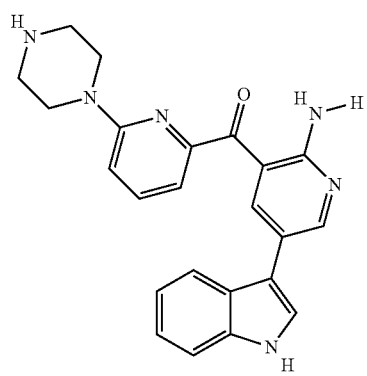
208 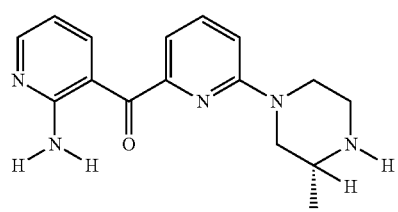
209 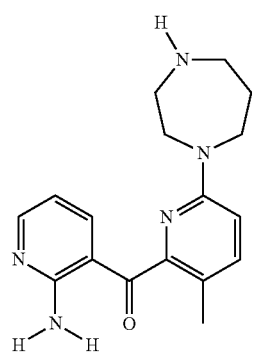
210 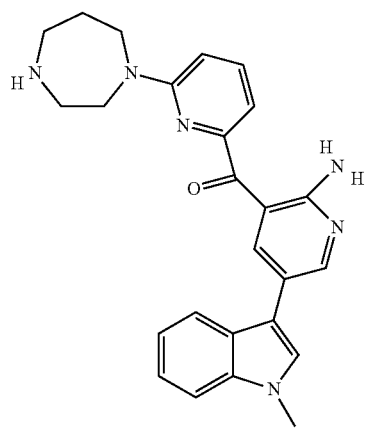
TABLE 1-continued
211 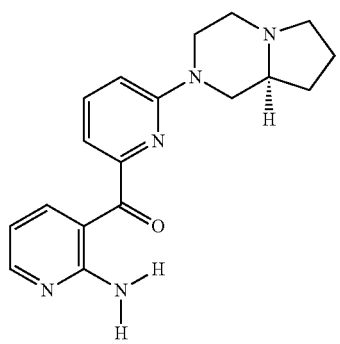
212 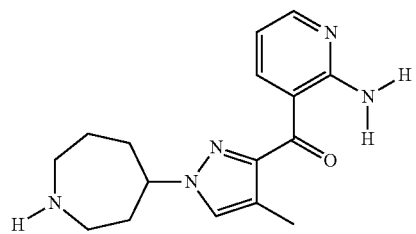
213 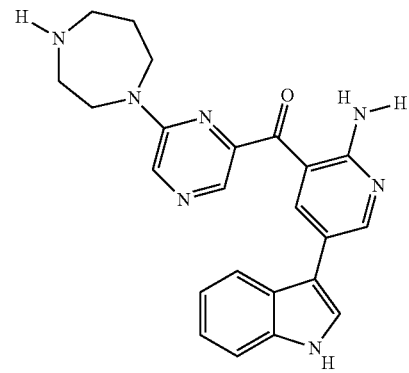
214 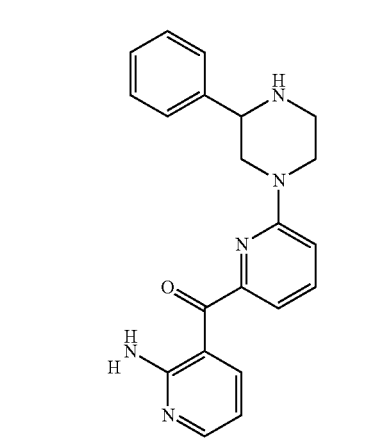

TABLE 1-continued
215 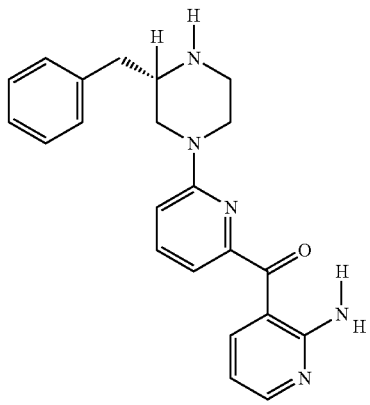
216 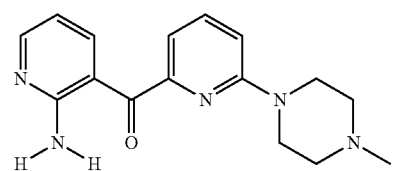
217 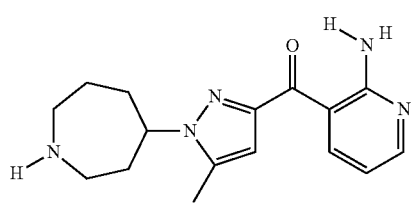
218 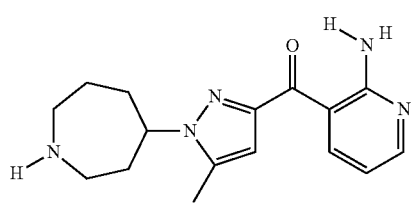
219 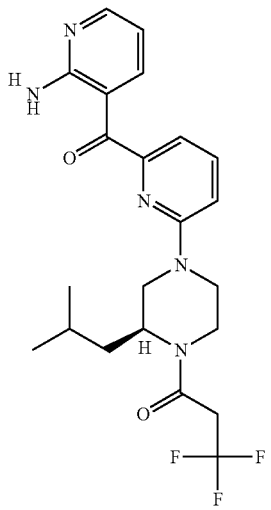
220 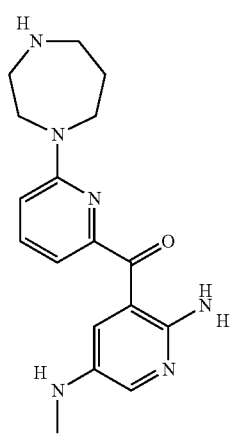
221 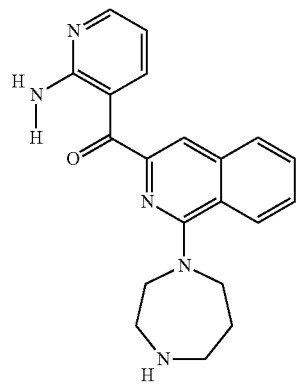

TABLE 1-continued

| | |
|---|---|
| 222 | (structure) |
| 223 | (structure) |
| 224 | (structure) |
| 225 | (structure) |
| 226 | (structure) |
| 227 | (structure) |
| 228 | (structure) |
| 229 | (structure) |
| 230 | (structure) |

TABLE 1-continued
| 231 | 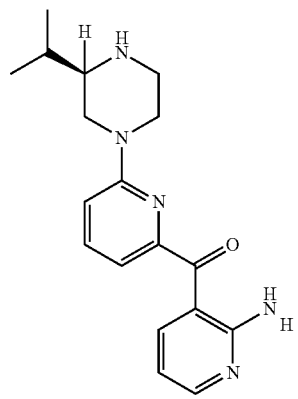 |
| 232 | 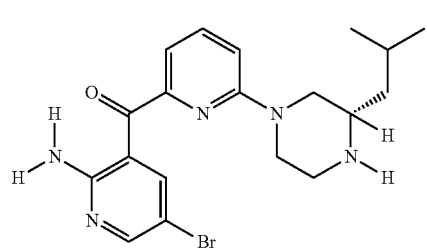 |
| 233 | 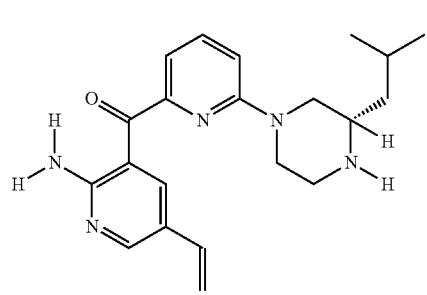 |
| 234 | 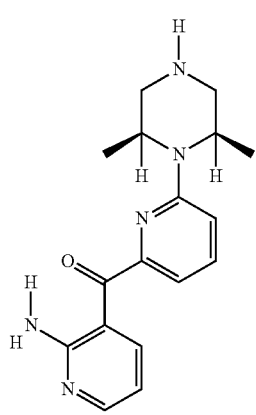 |
TABLE 1-continued
| 235 | 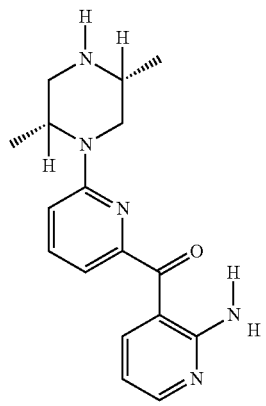 |
| 236 | 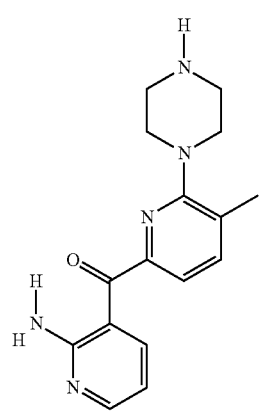 |
| 237 | |

TABLE 1-continued
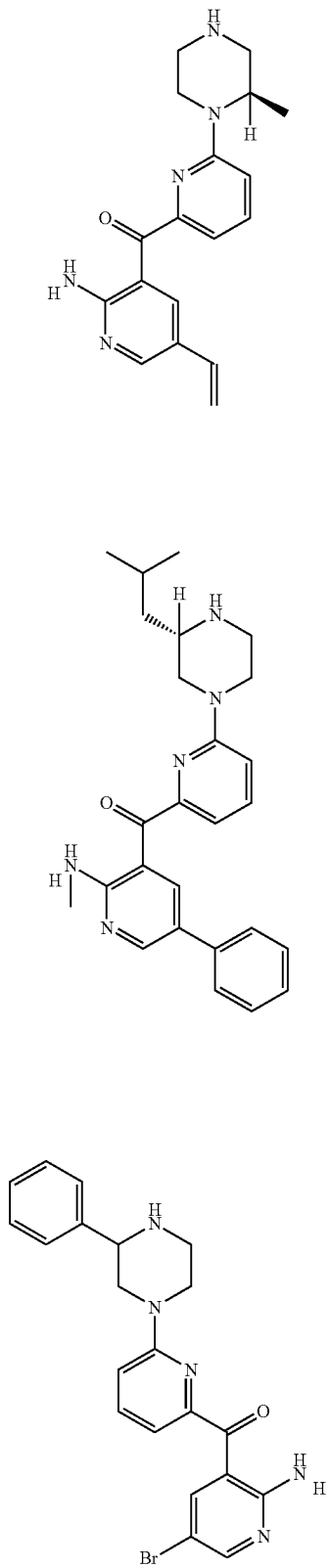
238
239
240
TABLE 1-continued
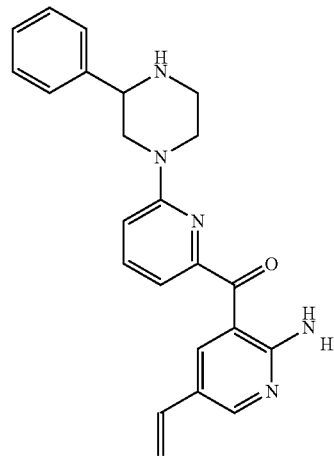
241
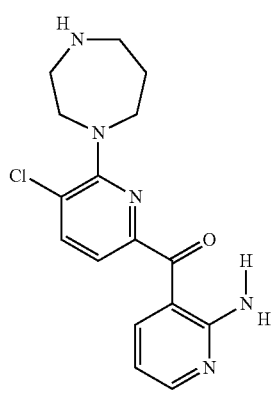
242
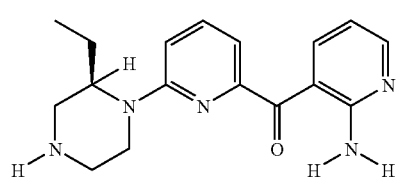
243
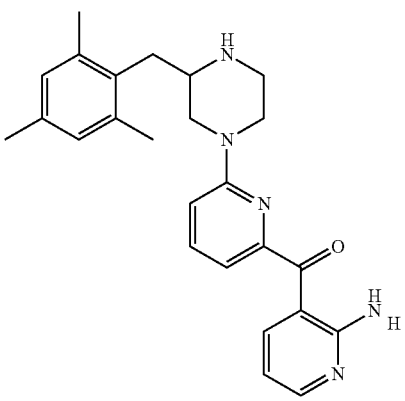
244

TABLE 1-continued
245 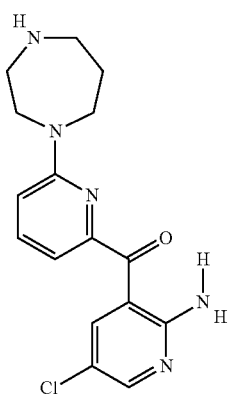
246 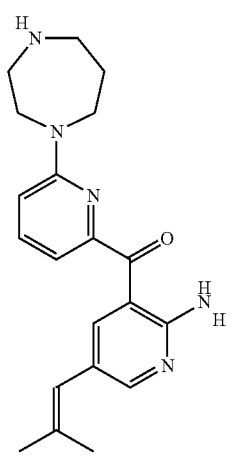
247 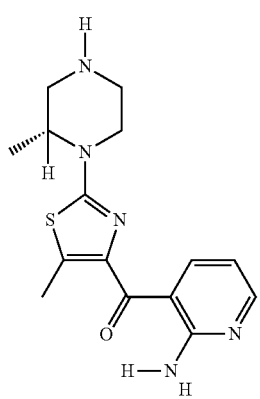
248 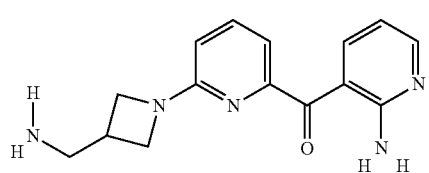
TABLE 1-continued
249 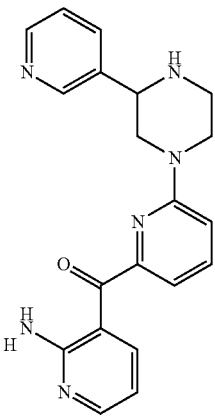
250 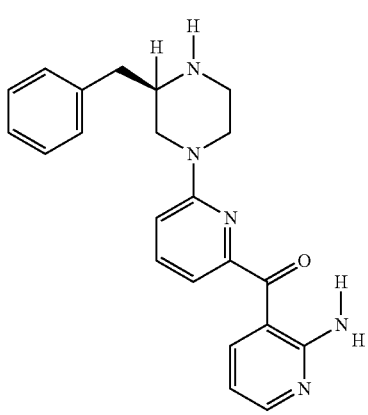
251 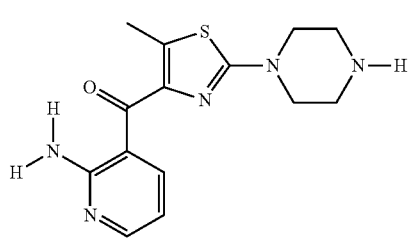
252 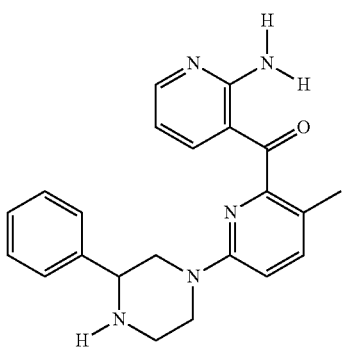

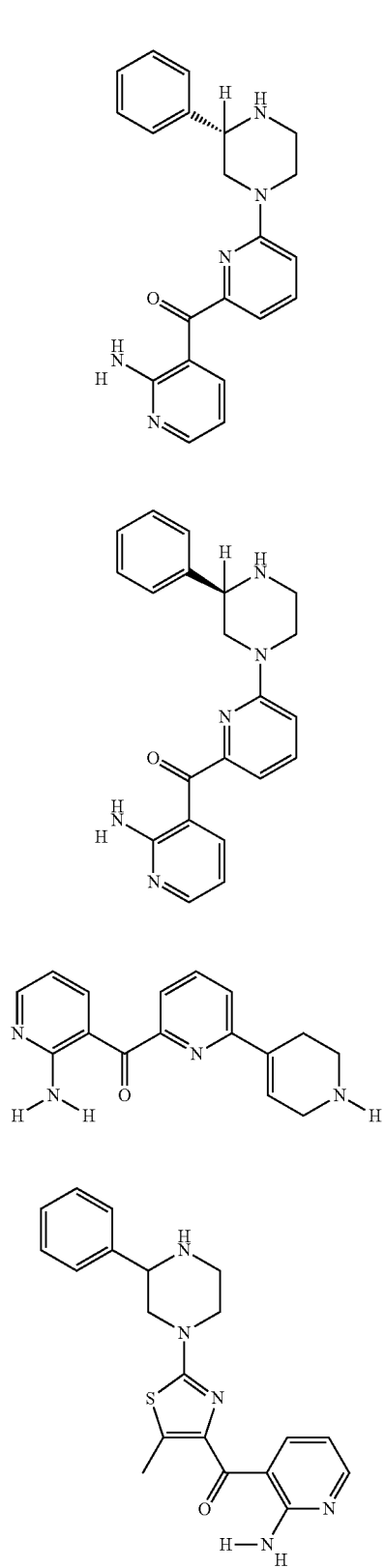

| | |
|---|---|
| 261 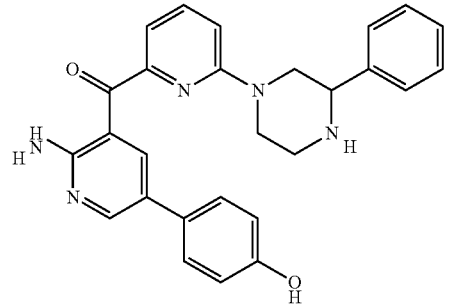 | 265 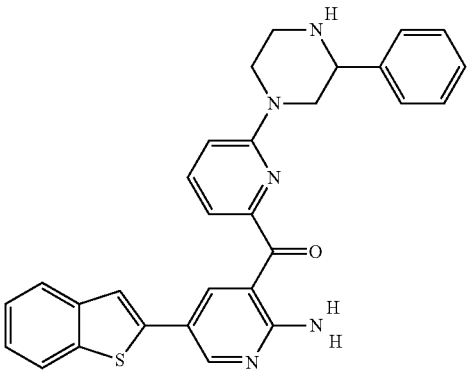 |
| 262 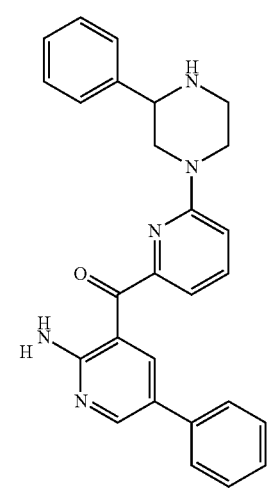 | 266 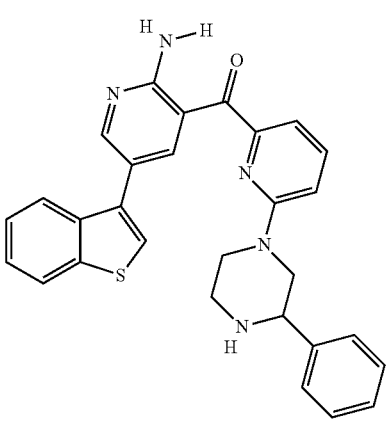 |
| 263 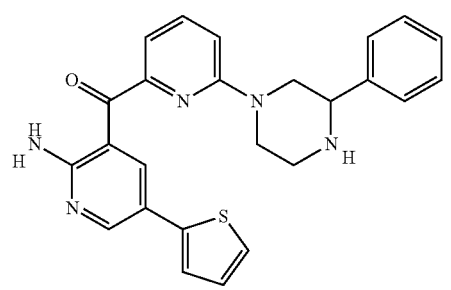 | 267 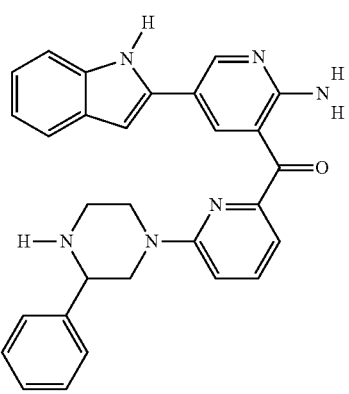 |
| 264 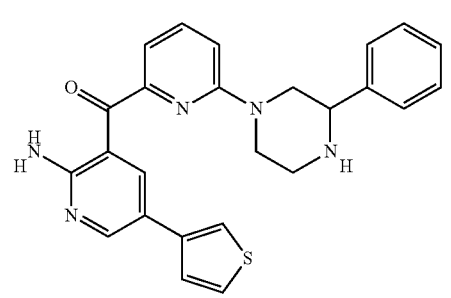 | 268 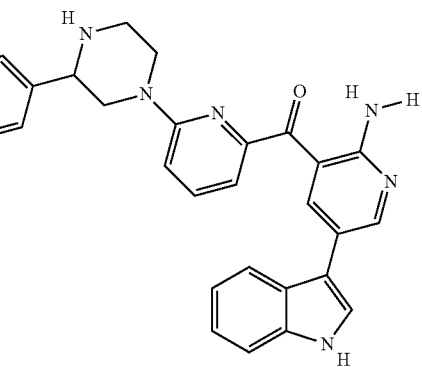 |

TABLE 1-continued
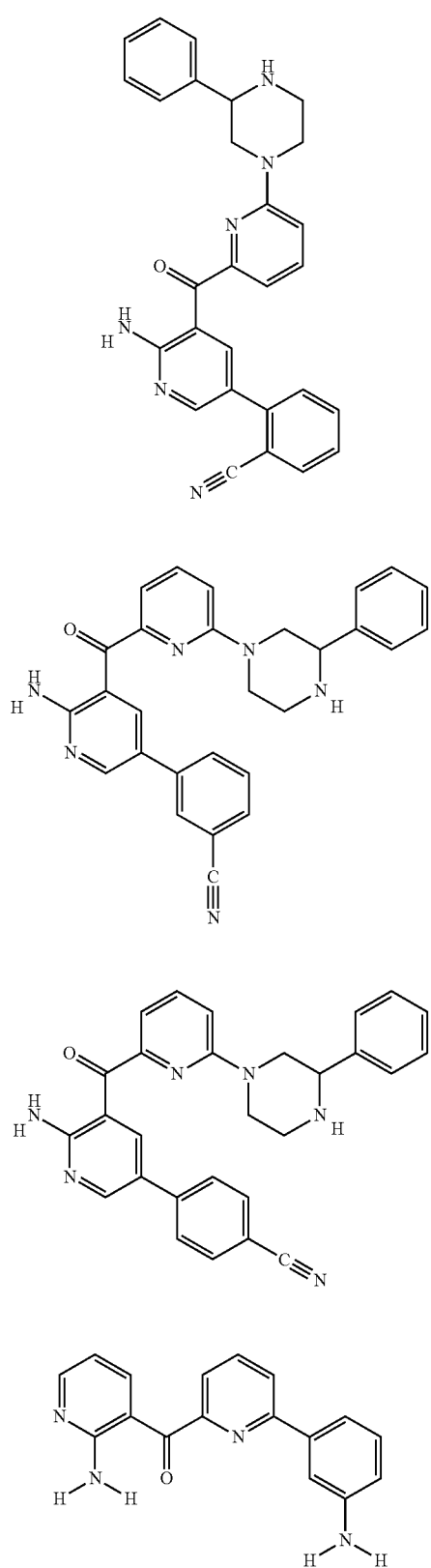
269
270
271
272
TABLE 1-continued
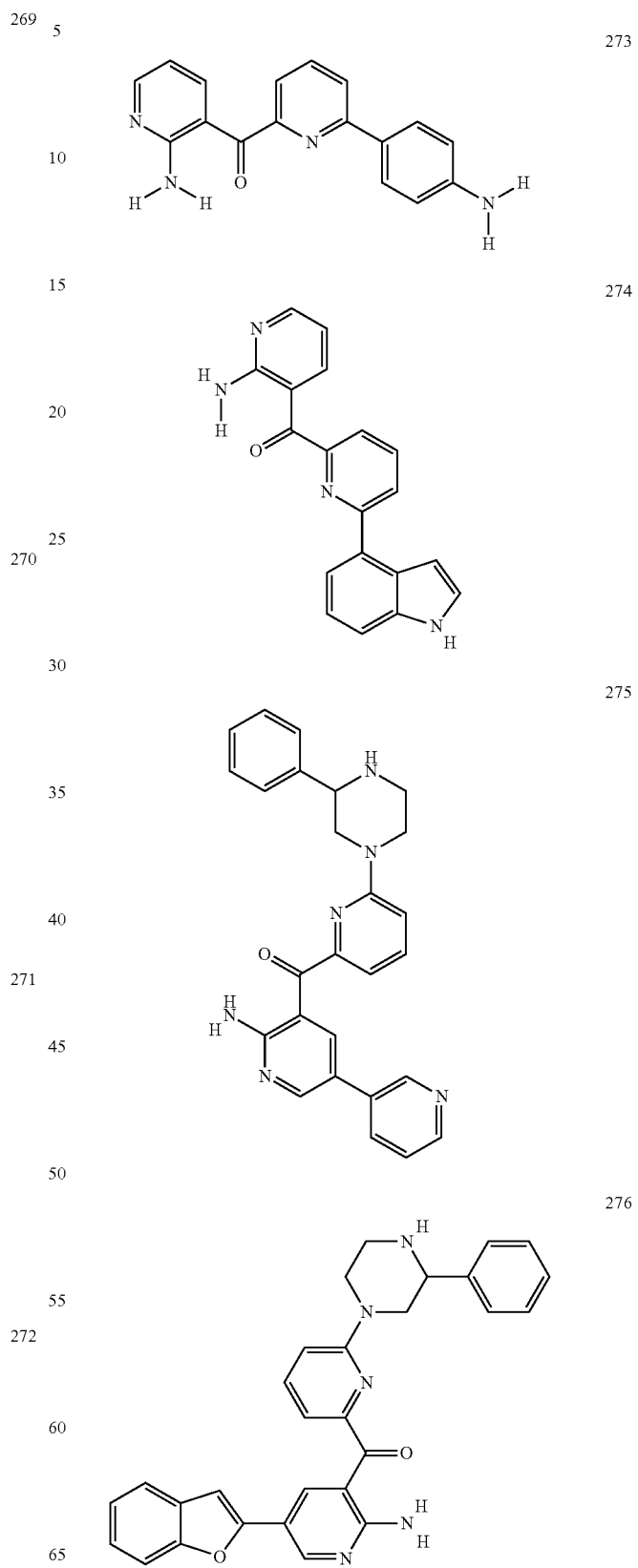
273
274
275
276

TABLE 1-continued
| 277 | 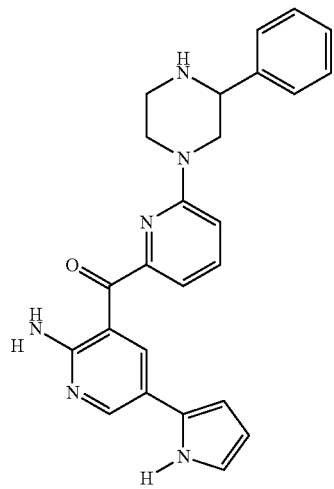 |
| --- | --- |
| 278 | 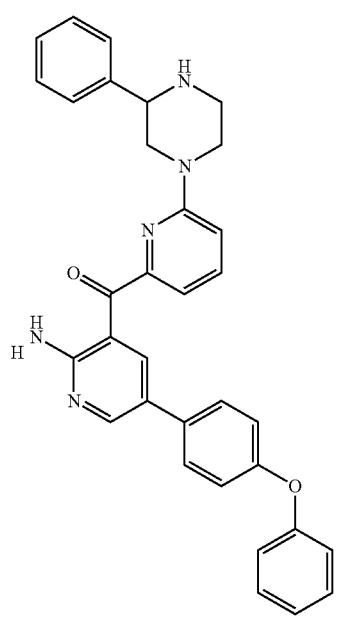 |
| 279 | 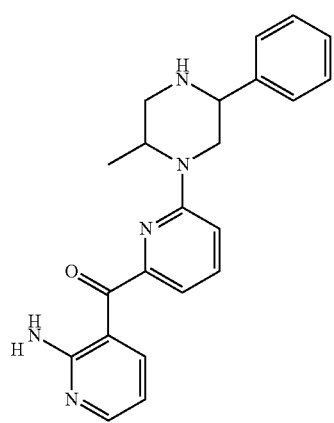 |
TABLE 1-continued
| 280 | 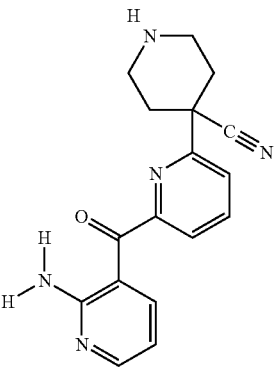 |
| --- | --- |
| 281 | 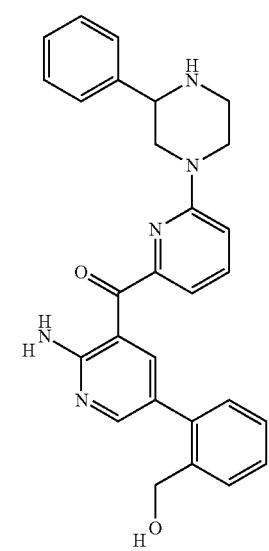 |
| 282 | 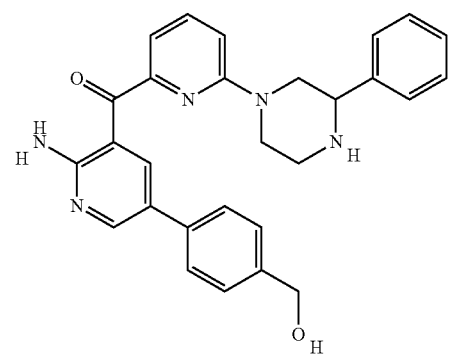 |

TABLE 1-continued
283 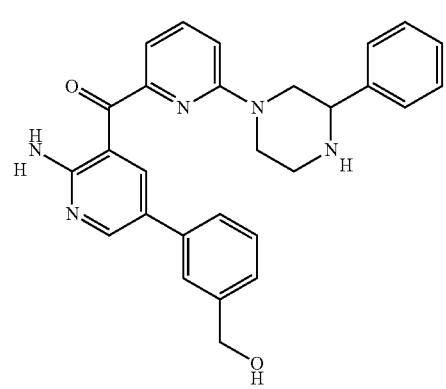
284 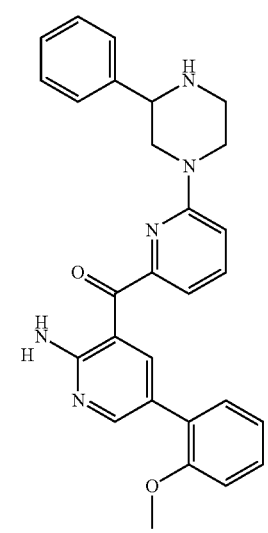
285 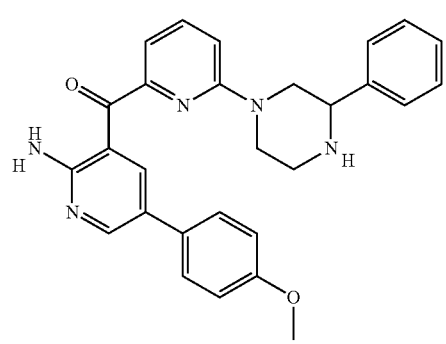
TABLE 1-continued
286 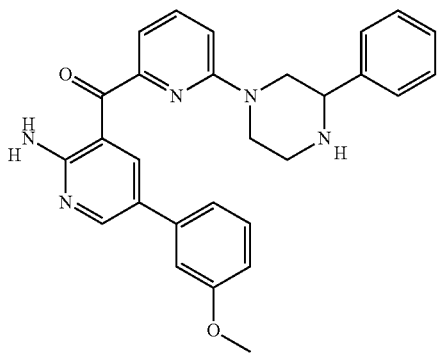
287 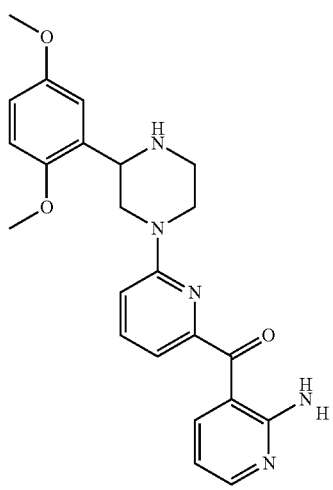
288 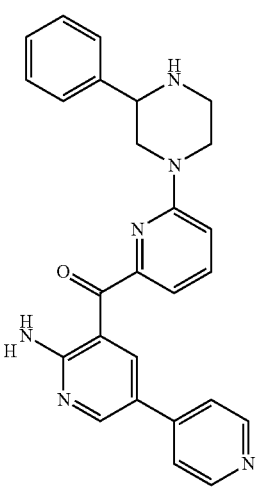

TABLE 1-continued
289 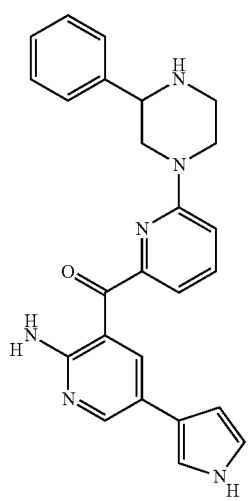
290 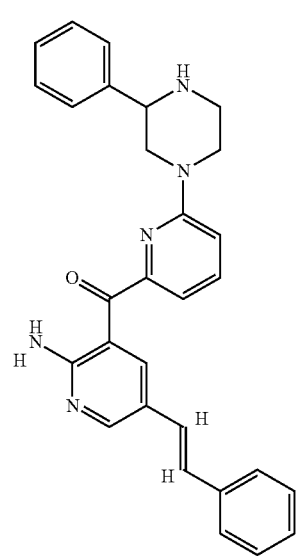
291 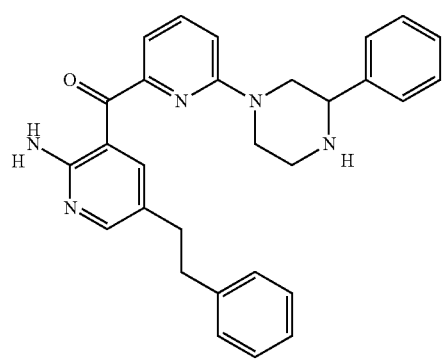
TABLE 1-continued
292 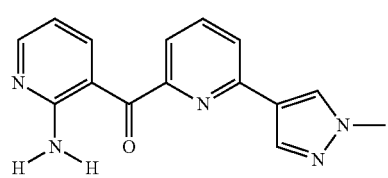
293 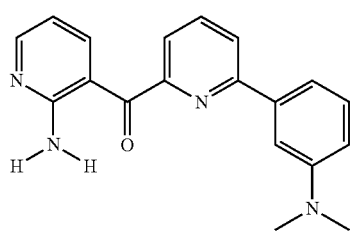
294 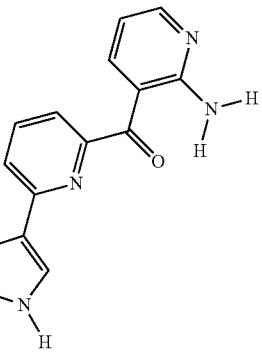
295 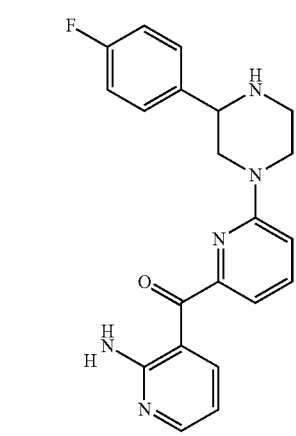

TABLE 1-continued
296 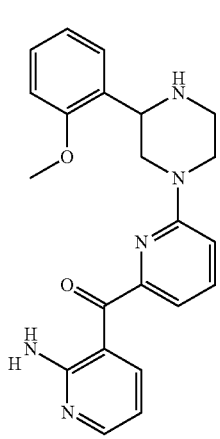
297 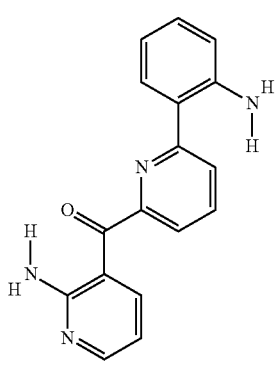
298 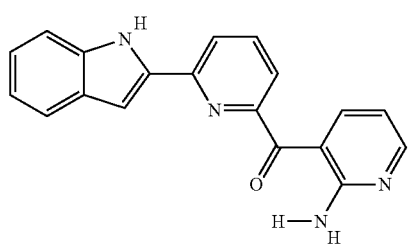
299 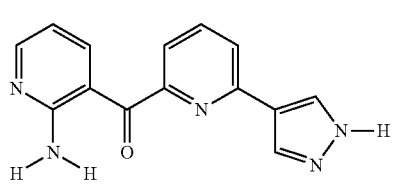
300 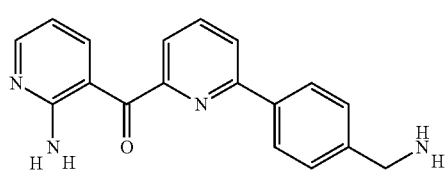
TABLE 1-continued
301 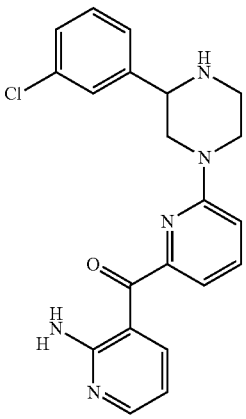
302 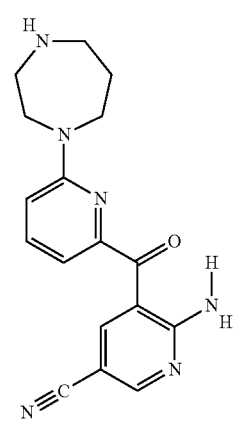
303 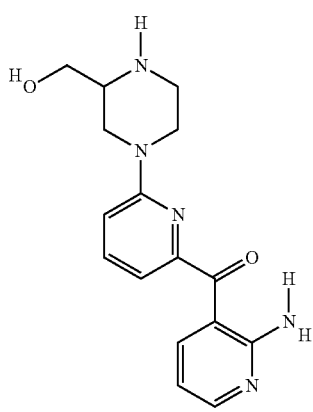

TABLE 1-continued
| 304 | 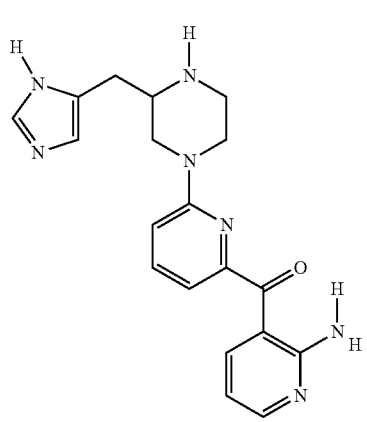 |
| --- | --- |
| 305 | 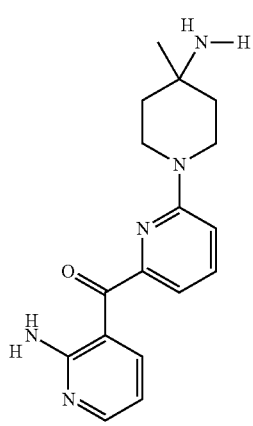 |
| 306 | 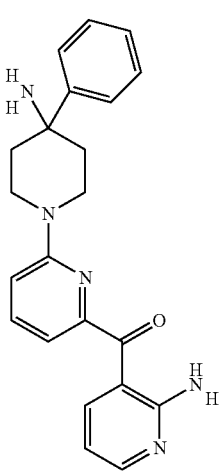 |
TABLE 1-continued
| 307 | 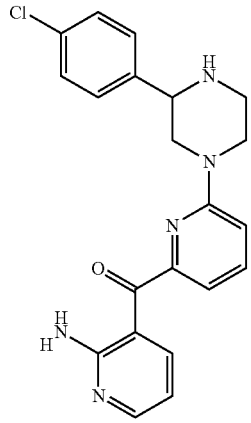 |
| --- | --- |
| 308 | 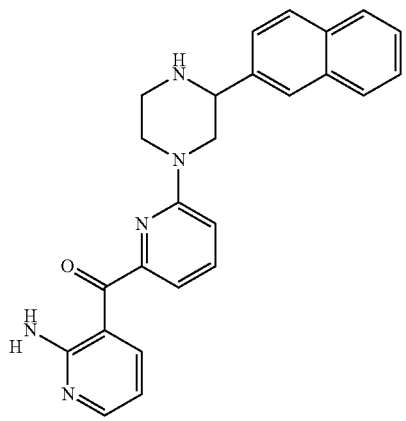 |
| 309 | 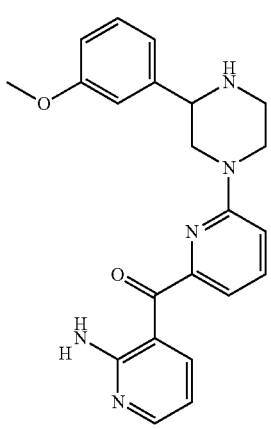 |

TABLE 1-continued
310
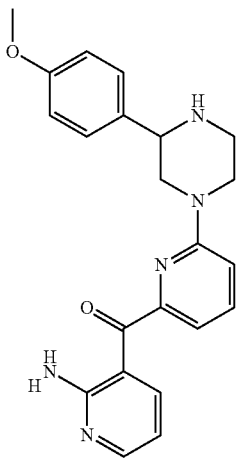
311
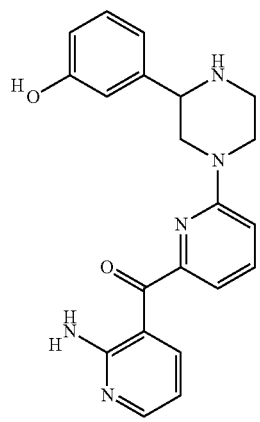
312
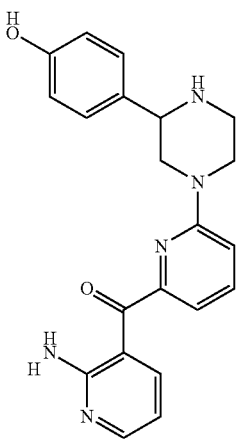
TABLE 1-continued
313
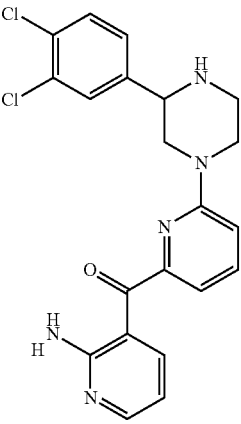
314
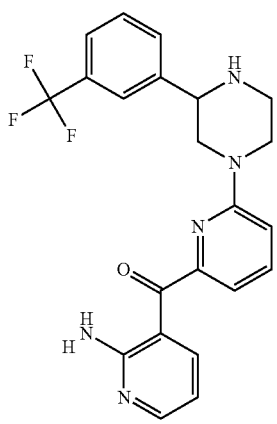
315
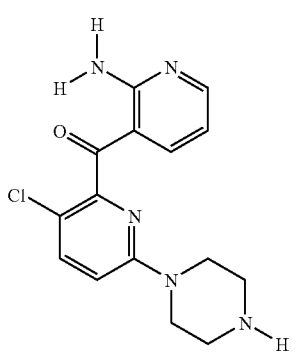
316
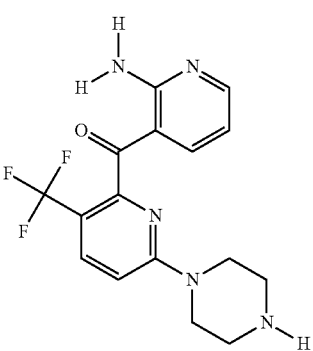

TABLE 1-continued
317 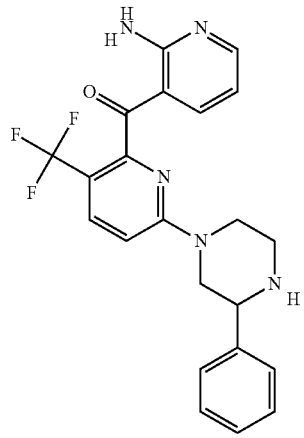
318 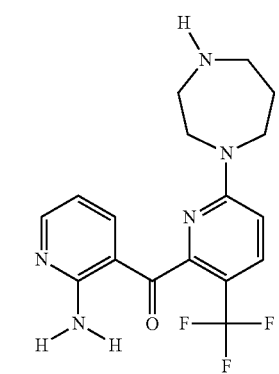
319 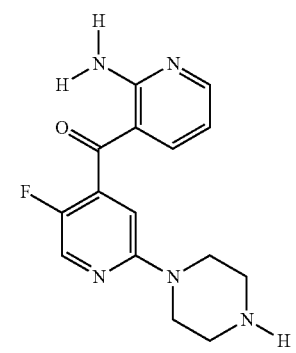
320 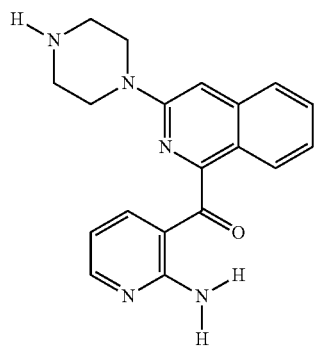
TABLE 1-continued
321 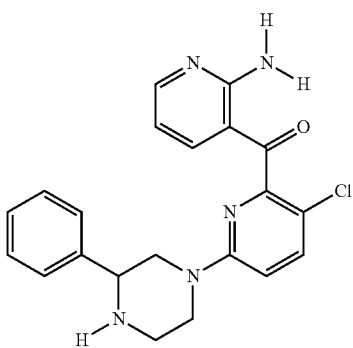
322 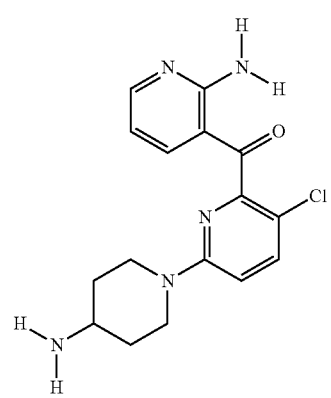
323 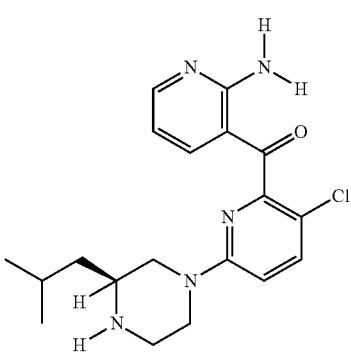
324 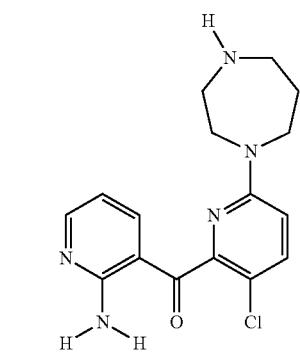

TABLE 1-continued
325 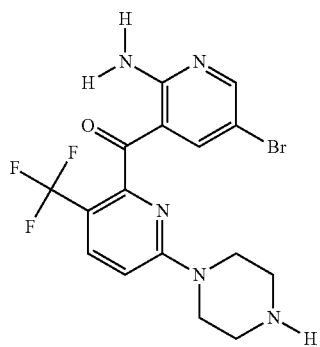
326 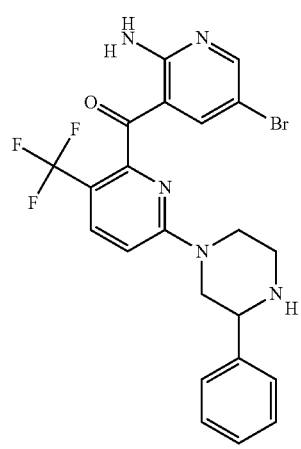
327 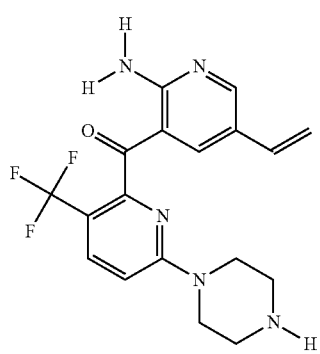
TABLE 1-continued
328 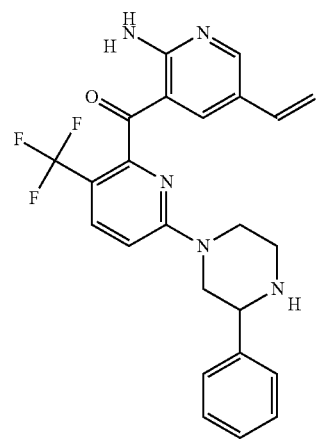
329 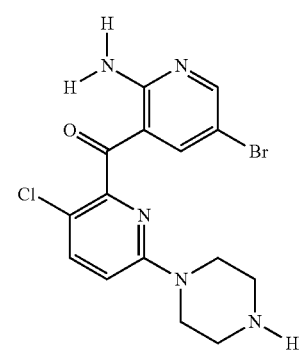
330 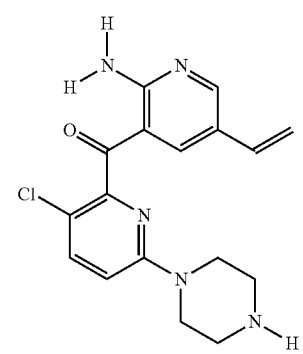

TABLE 1-continued
331 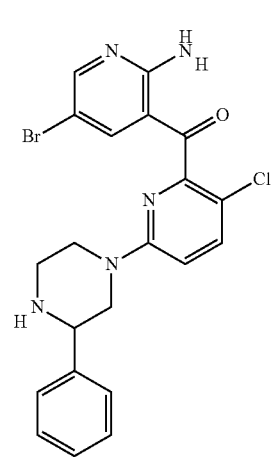
332 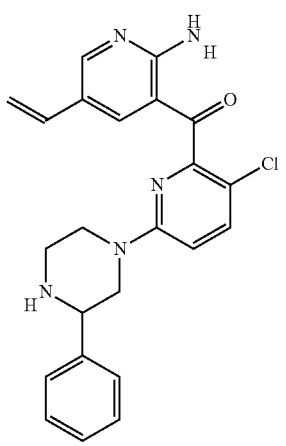
333 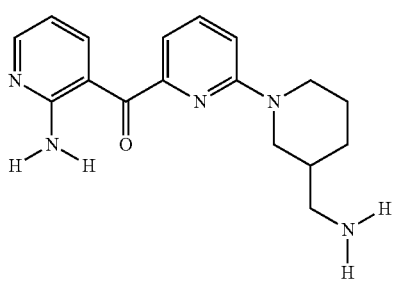
TABLE 1-continued
334 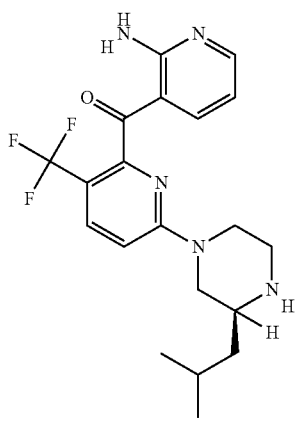
335 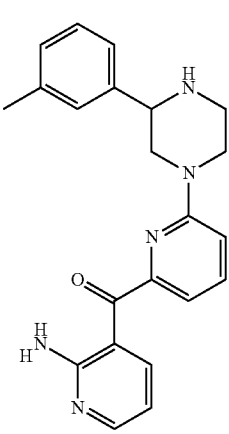
336 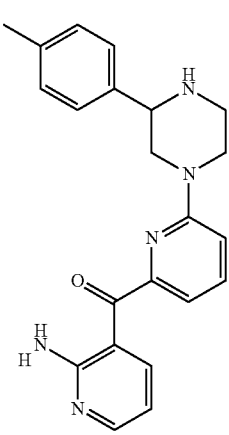

TABLE 1-continued
337 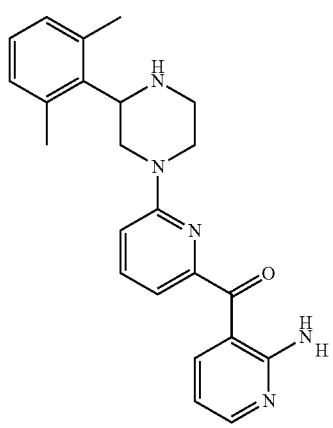
338 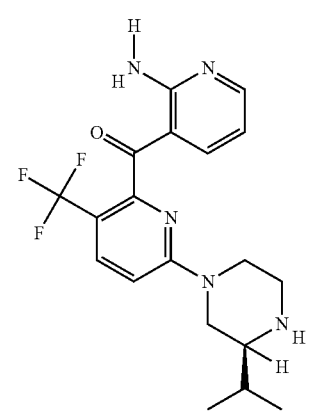
339 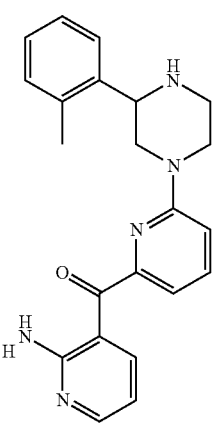
TABLE 1-continued
340 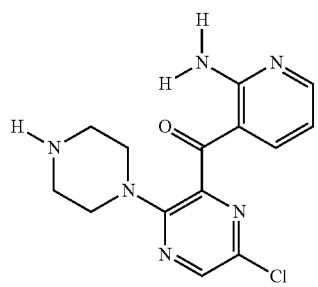
341 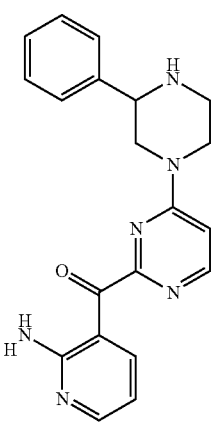
342 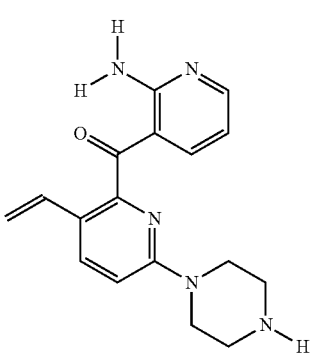
343 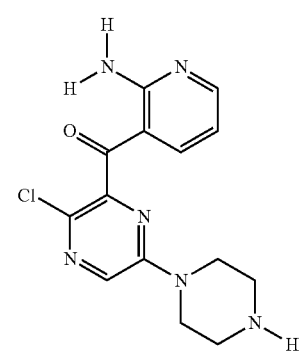

TABLE 1-continued
| | |
|---|---|
| 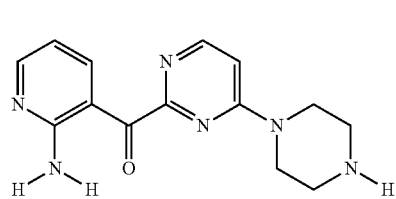 | 344 |
| 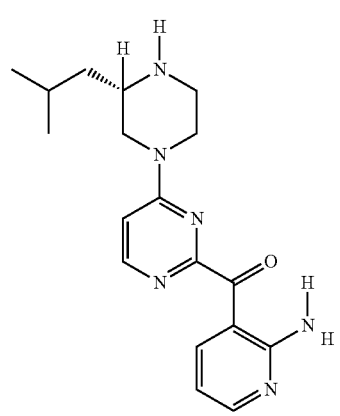 | 345 |
| 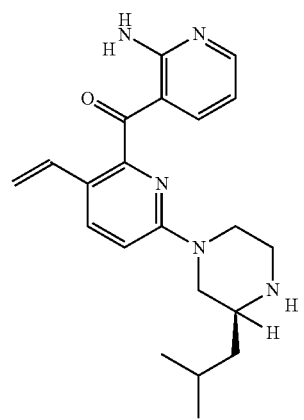 | 346 |
| 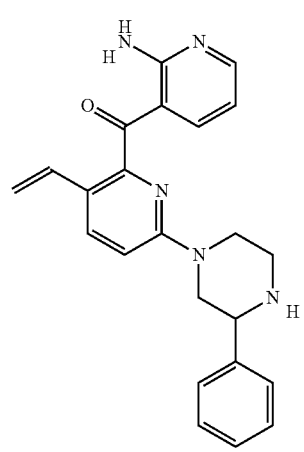 | 347 |
| 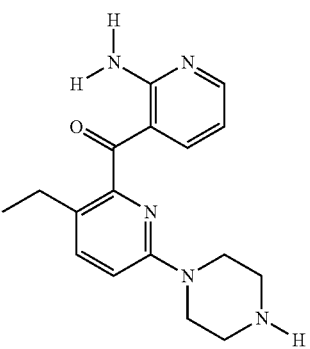 | 348 |
| 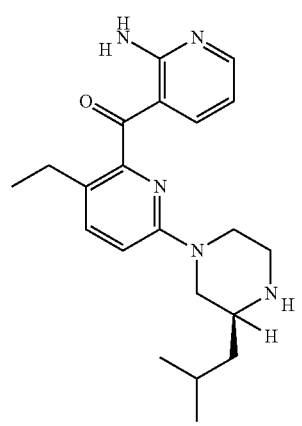 | 349 |
| 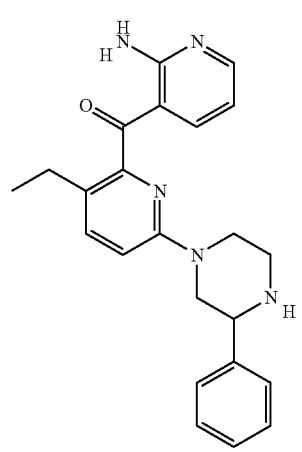 | 350 |

TABLE 1-continued
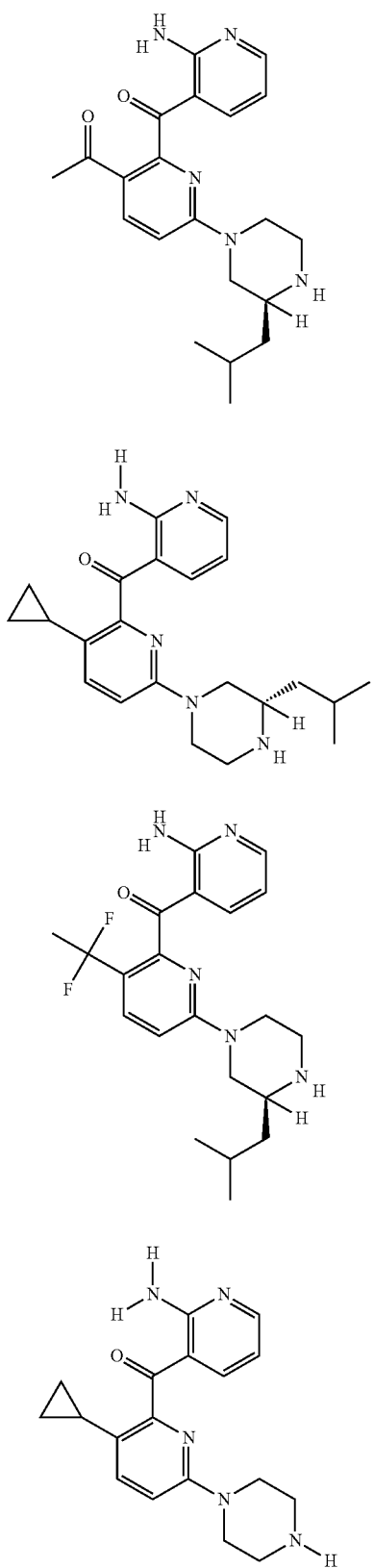
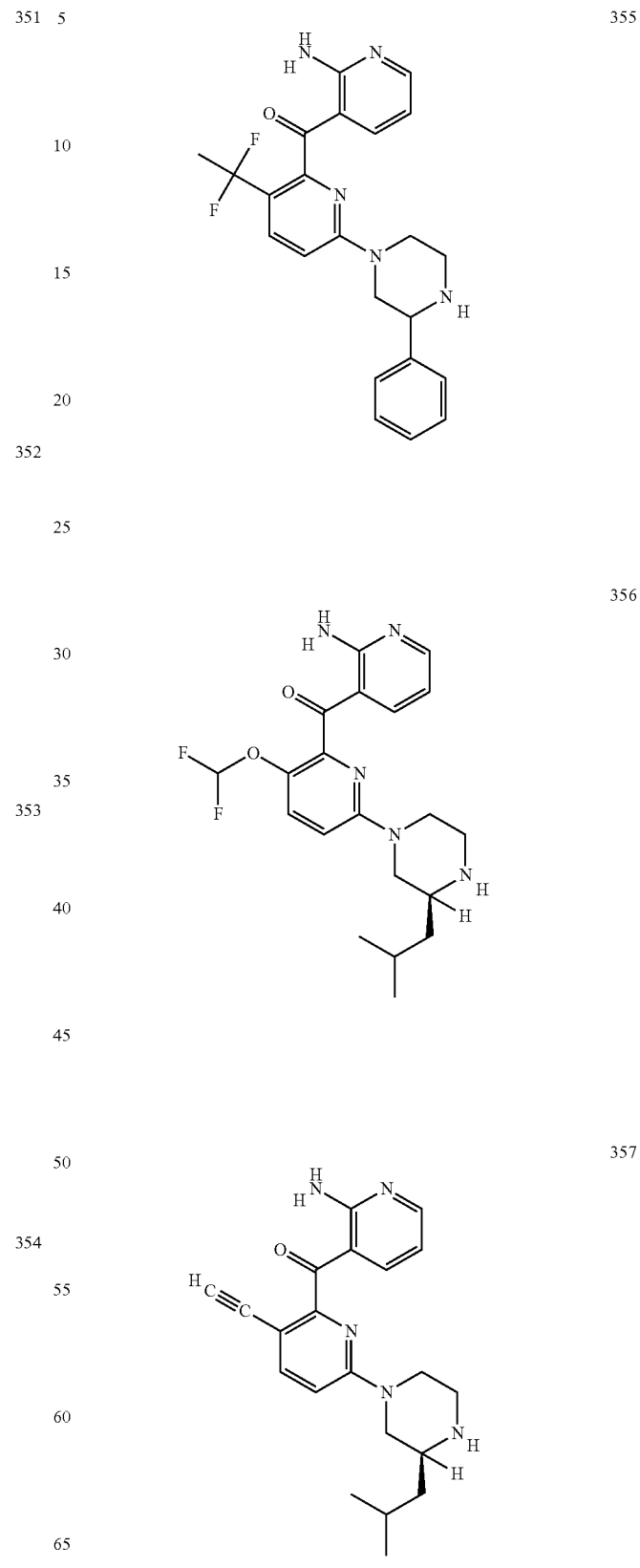

TABLE 1-continued
358 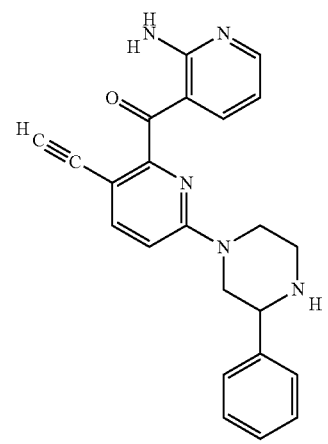
359 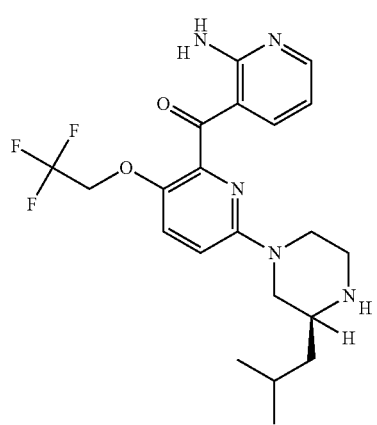
360 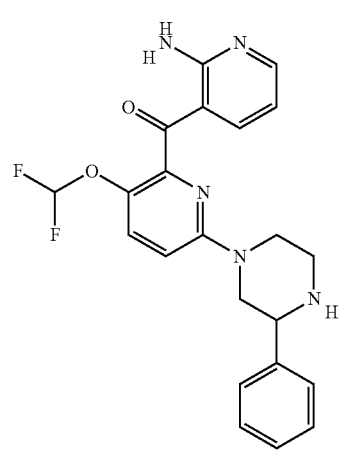
TABLE 1-continued
361 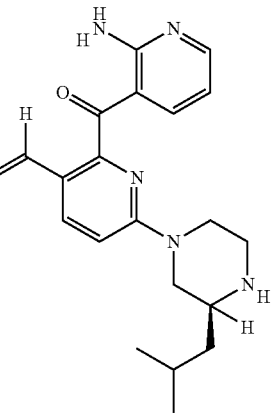
362 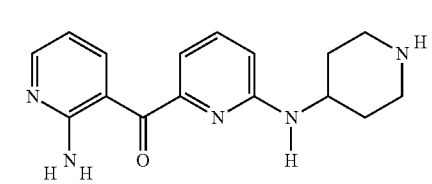
363 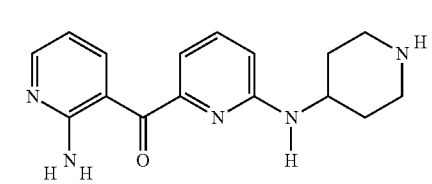
364 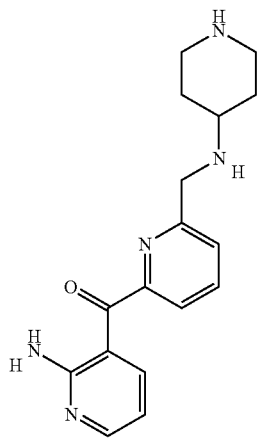

US 8,188,071 B2
187
TABLE 1-continued
188
TABLE 1-continued
365
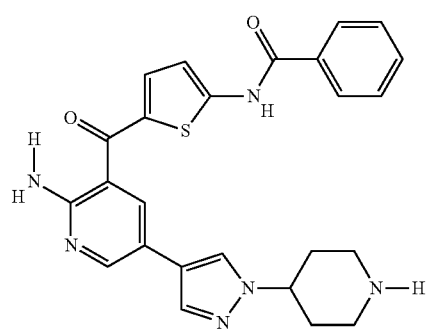
366
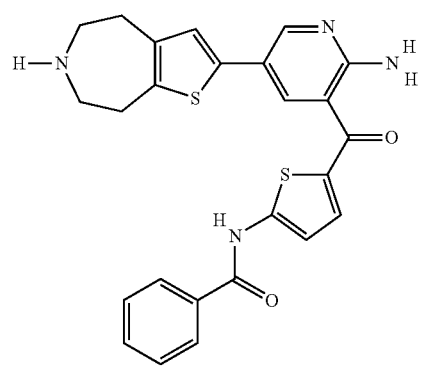
367
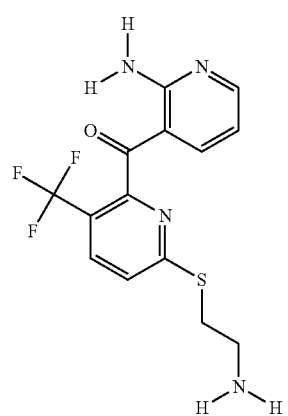
368
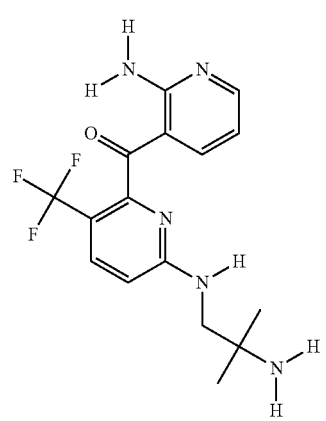
369
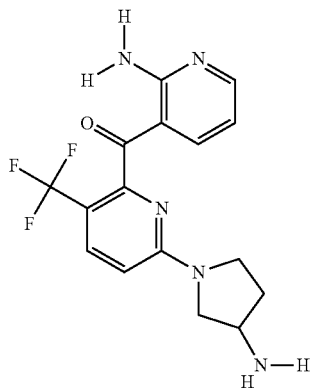
370
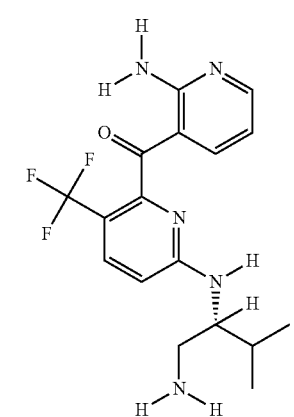
371
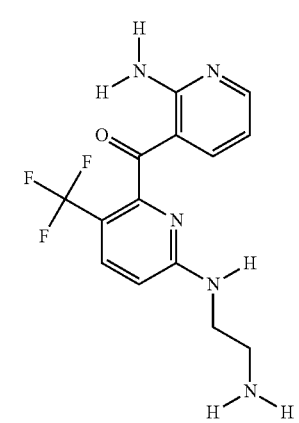

| | |
|---|---|
| 372 | 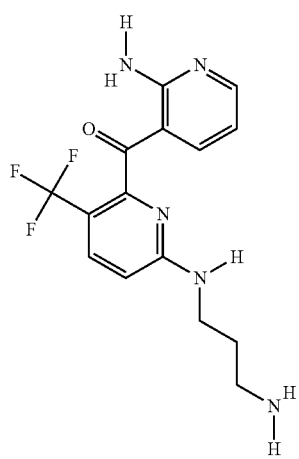 |
| 373 | 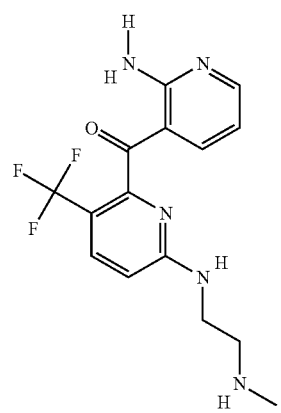 |
| 374 | 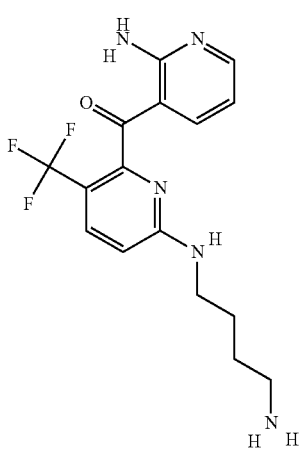 |
| 375 | 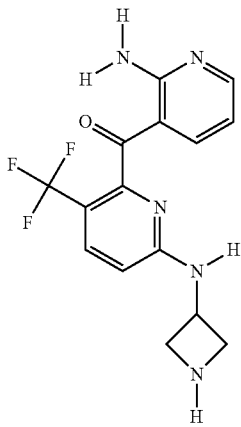 |
| 376 | 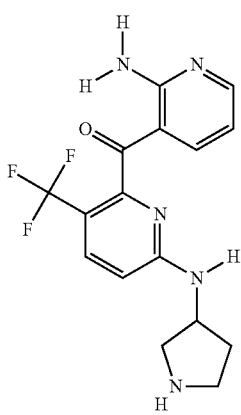 |
| 377 | 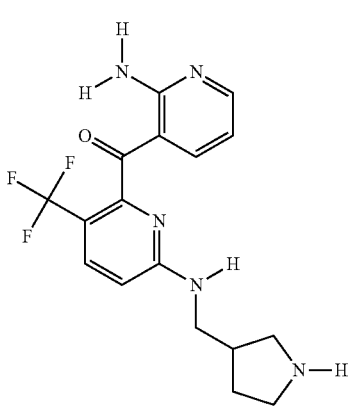 |

TABLE 1-continued
378 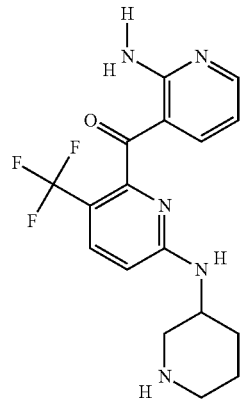
379 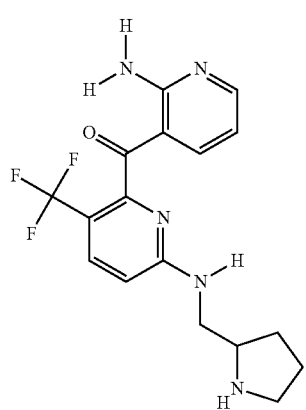
380 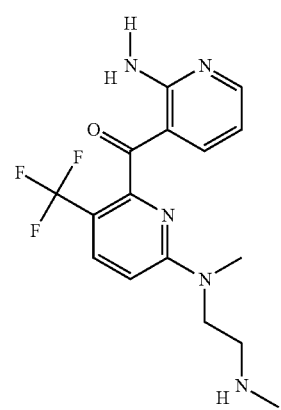
381 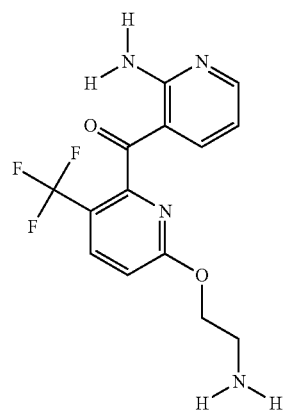
382 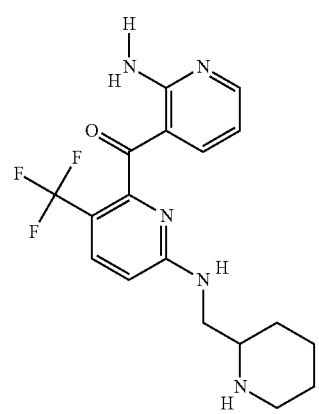
383 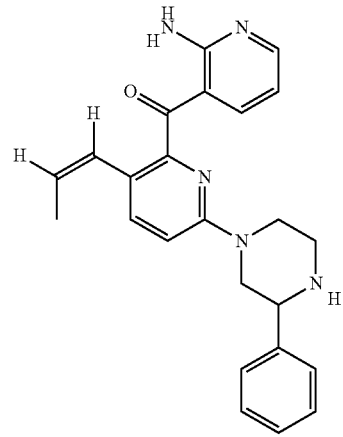

TABLE 1-continued
384 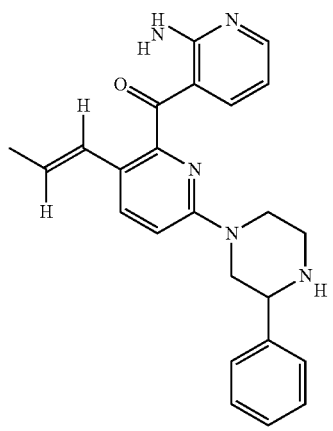
385 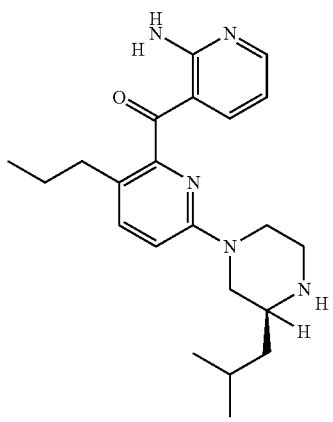
386 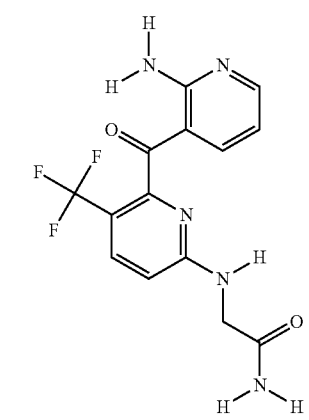
TABLE 1-continued
387 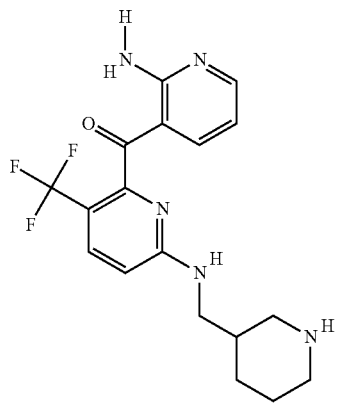
388 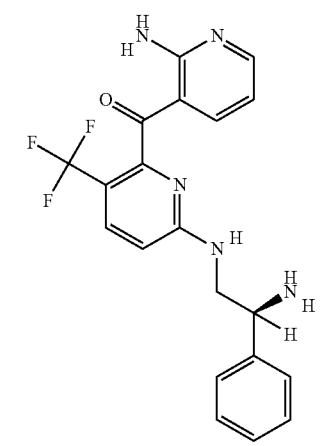
389 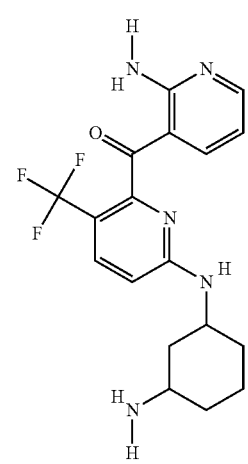

TABLE 1-continued
| | |
|---|---|
| 390 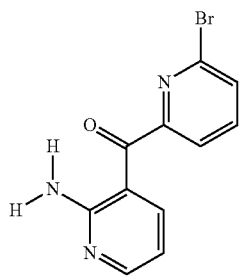 | 393 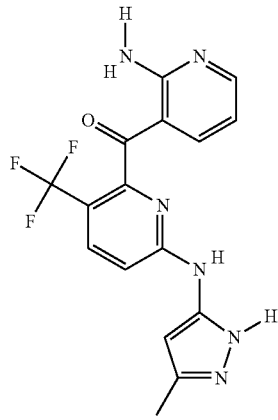 |
| 391 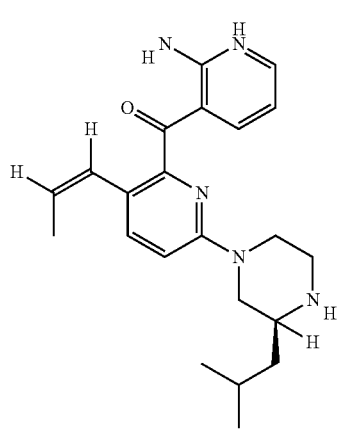 | 394 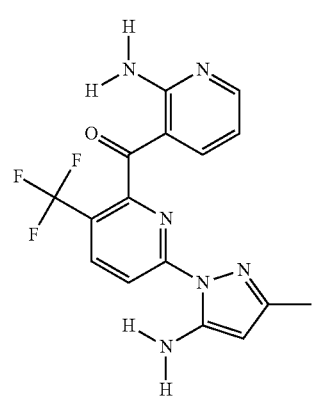 |
| 392 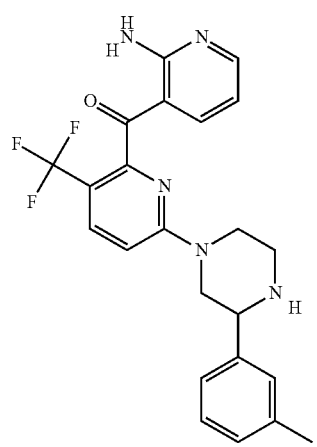 | 395 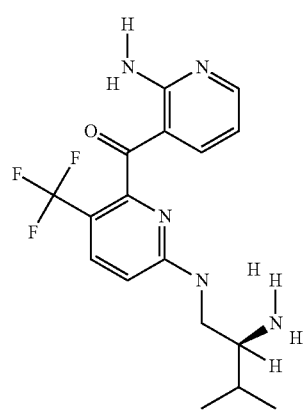 |

TABLE 1-continued
396 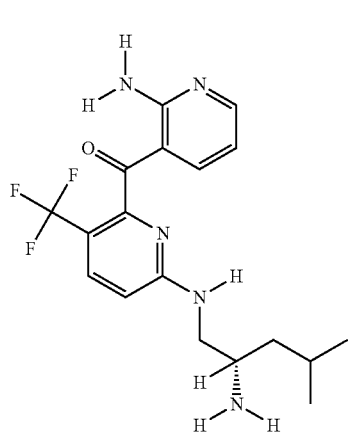
397 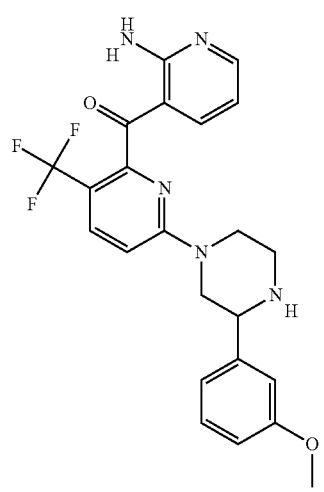
398 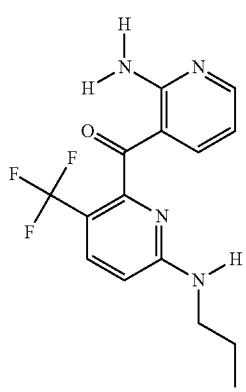
399 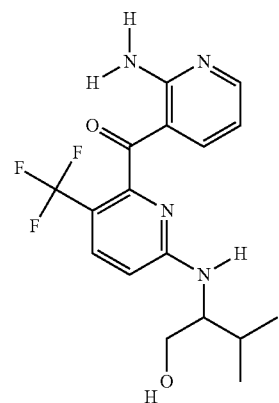
400 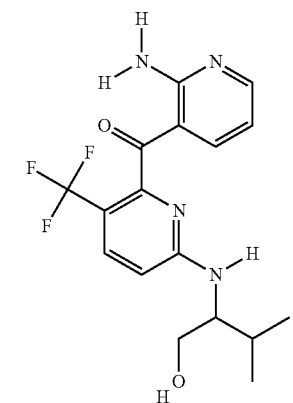
401 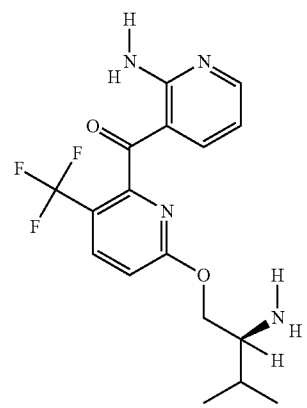

TABLE 1-continued
| | |
|---|---|
| 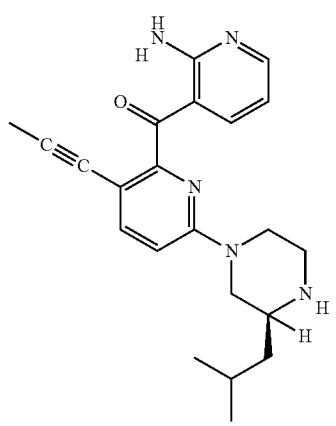 402 | 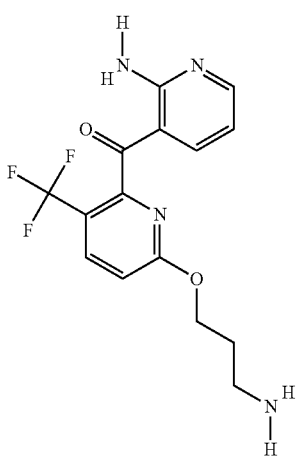 405 |
| 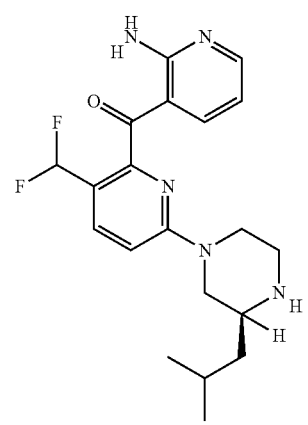 403 | 406 |
| 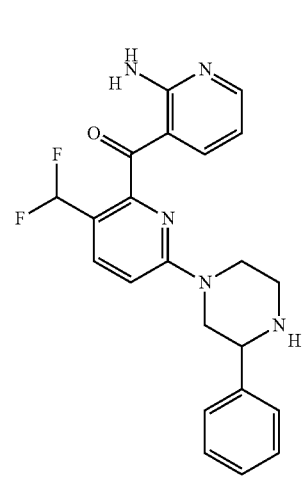 404 | 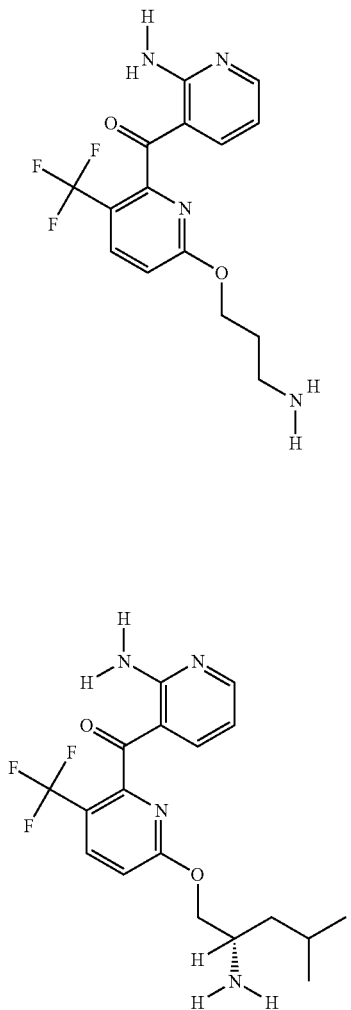 407 |
| | 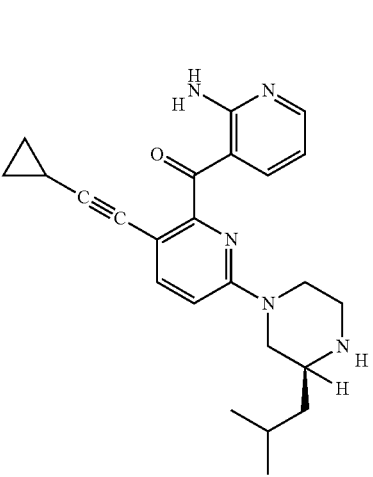 |

TABLE 1-continued
| | |
|---|---|
| 408 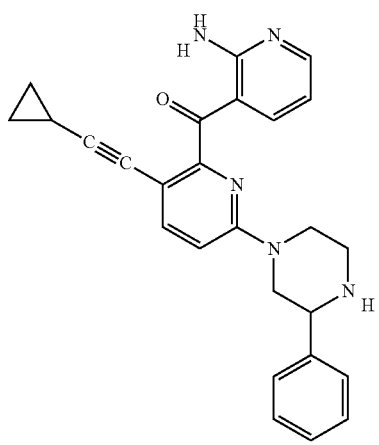 | 412 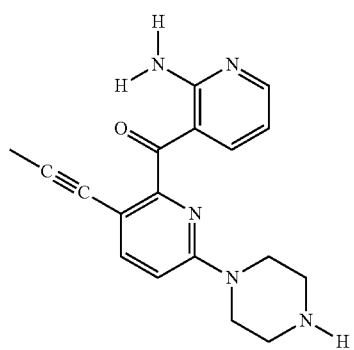 |
| 409 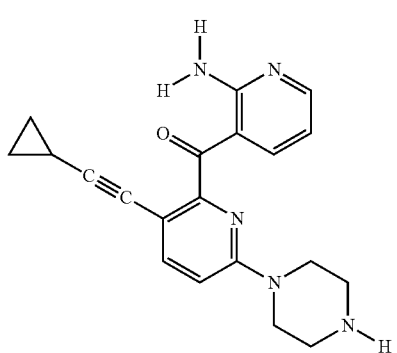 | 413 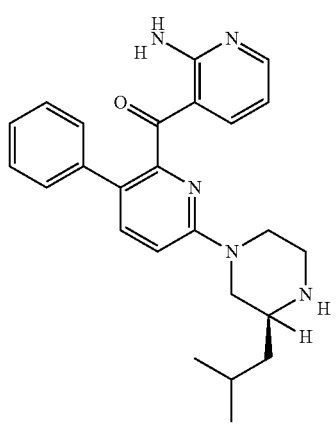 |
| 410 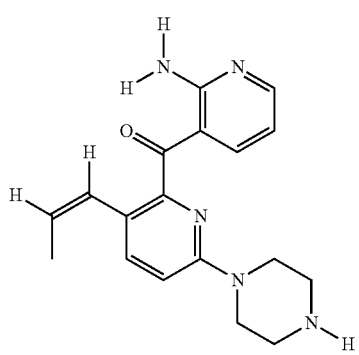 | |
| 411 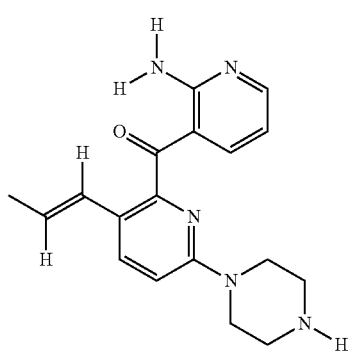 | 414 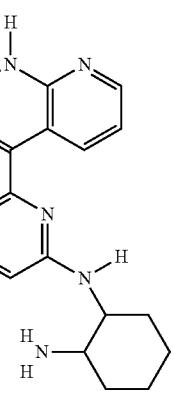 |

TABLE 1-continued
415
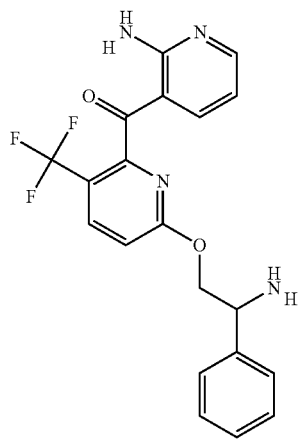
416
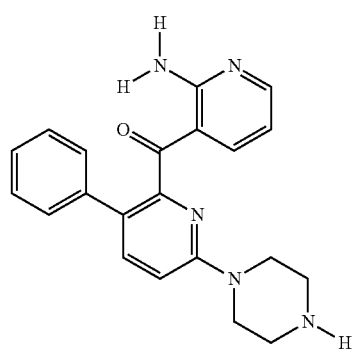
417
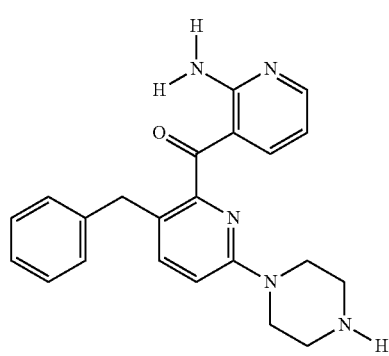
TABLE 1-continued
418
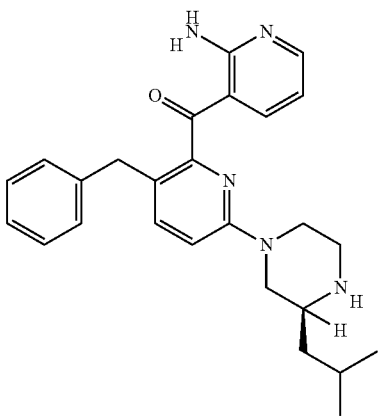
419
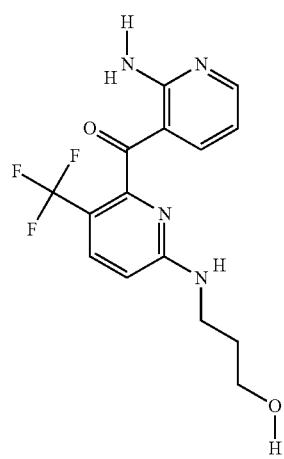
420
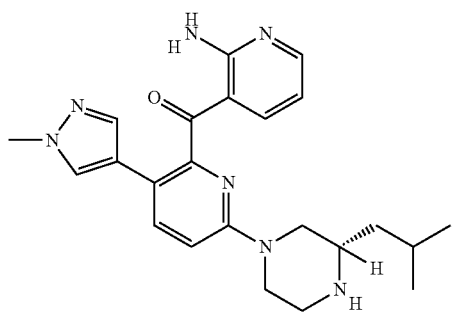

TABLE 1-continued
421
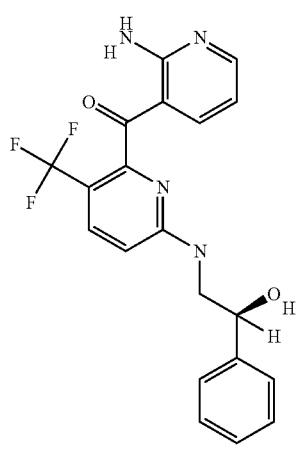
422
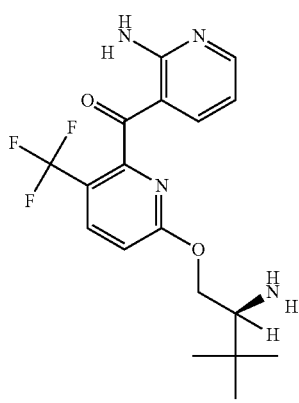
423
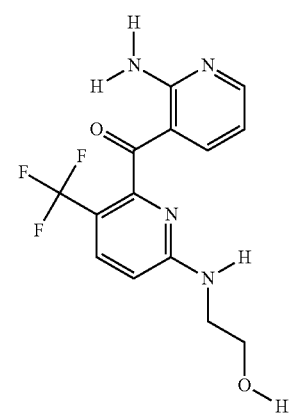
TABLE 1-continued
424
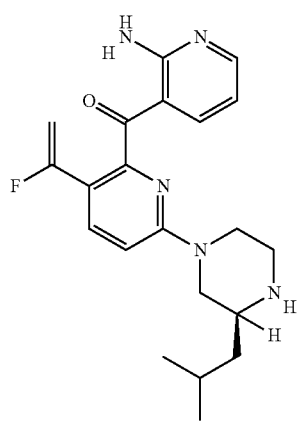
425
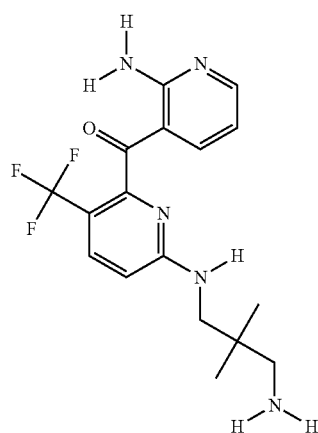
426
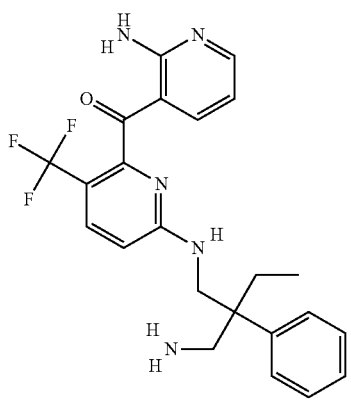

TABLE 1-continued
427
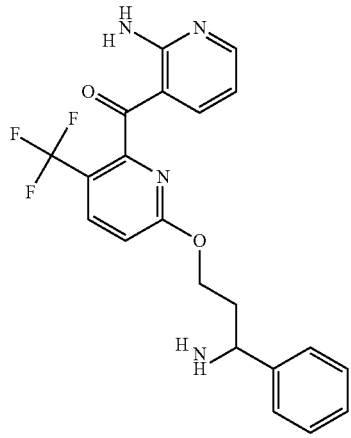
428
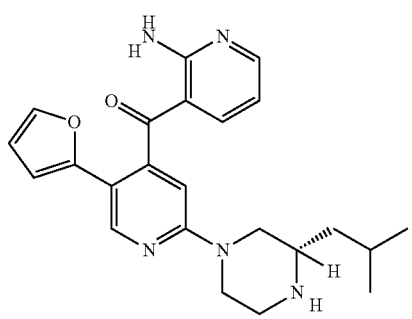
429
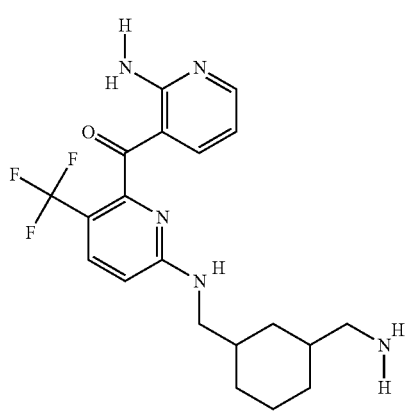
TABLE 1-continued
430
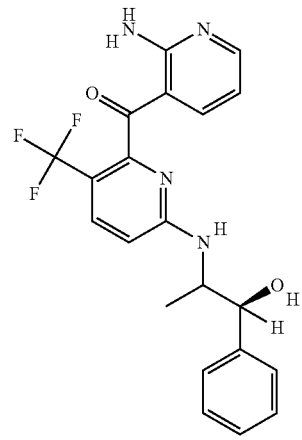
431
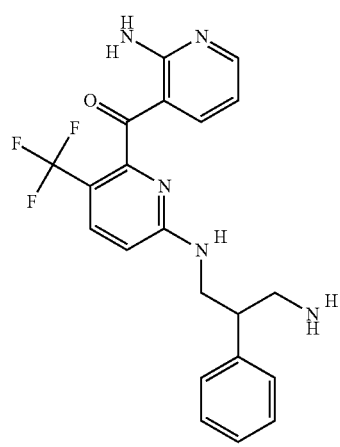
432
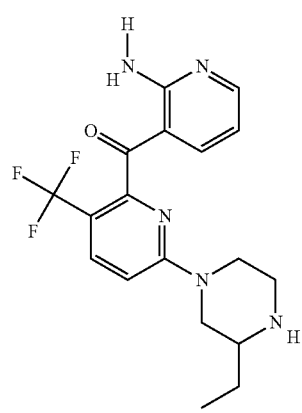

TABLE 1-continued
433 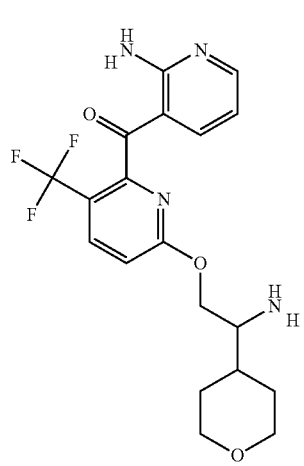
434 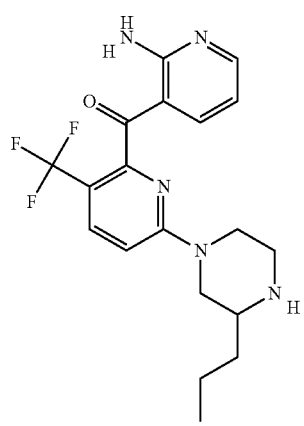
435 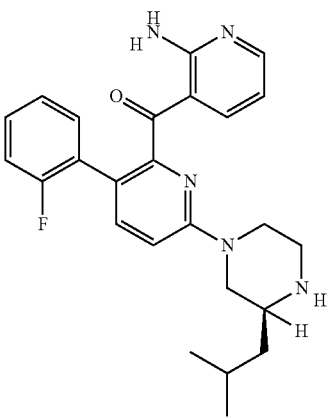
TABLE 1-continued
436 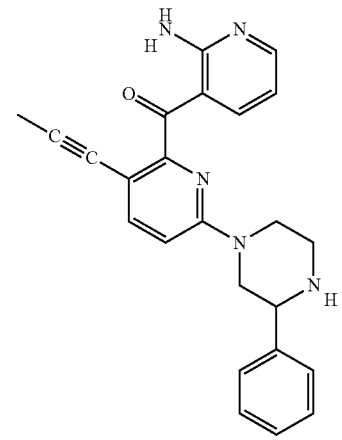
437 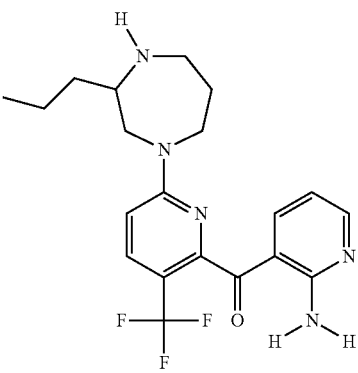
438 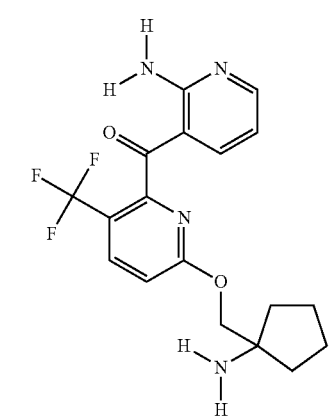

TABLE 1-continued
| 439 | 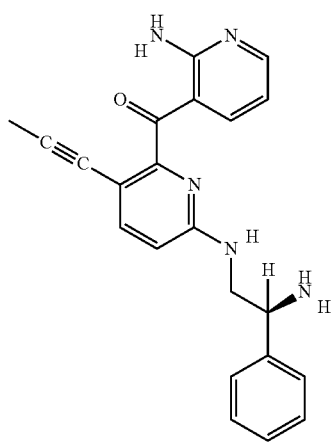 |
| --- | --- |
| 440 | 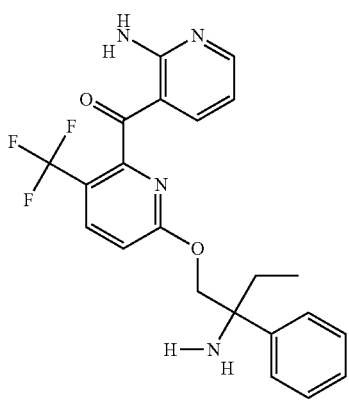 |
| 441 | 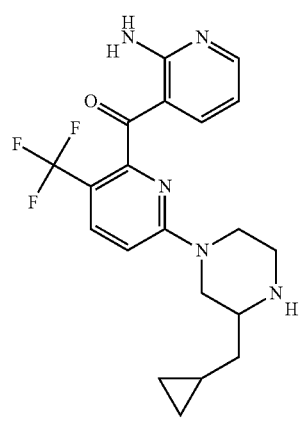 |
TABLE 1-continued
| 442 | 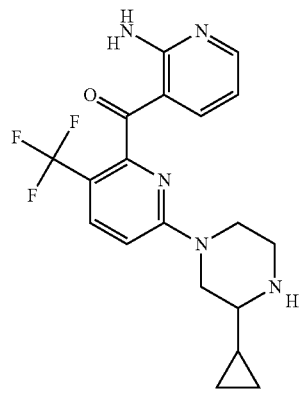 |
| --- | --- |
| 443 | 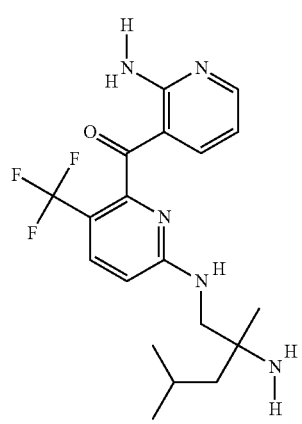 |
| 444 | 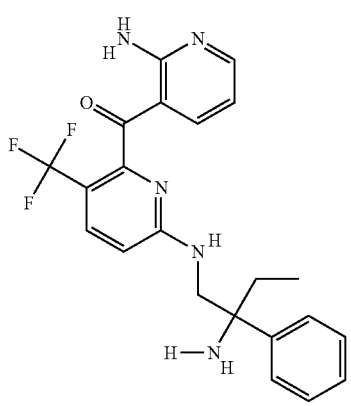 |

TABLE 1-continued
445
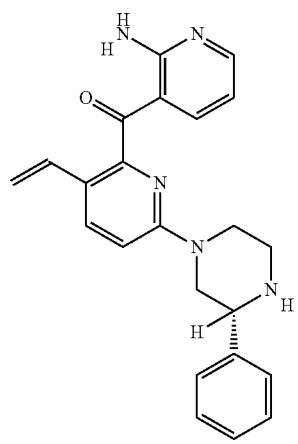
446
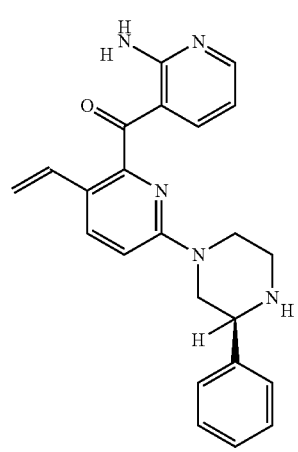
447
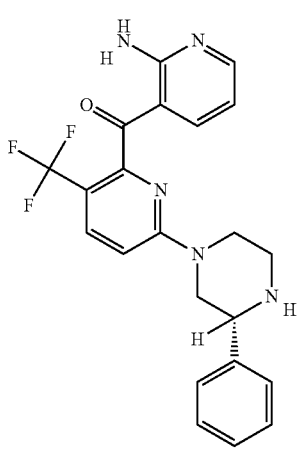
TABLE 1-continued
448
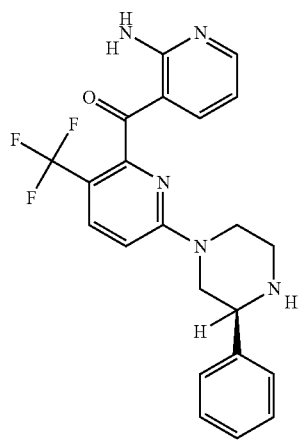
449
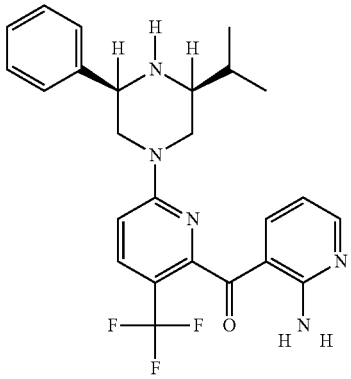
450
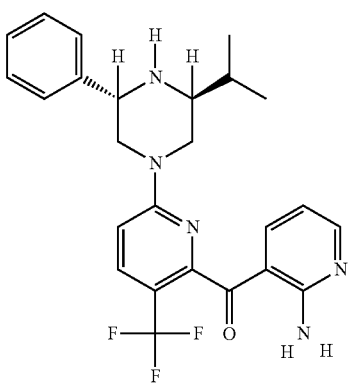

TABLE 1-continued
451 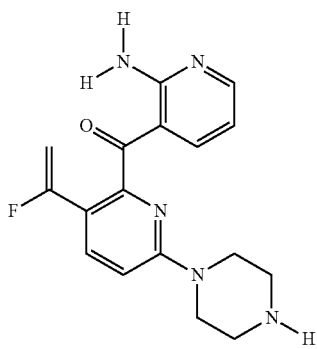
454 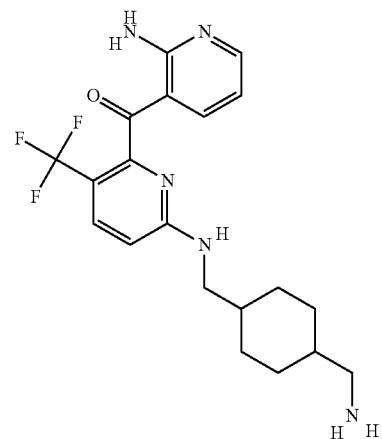
452 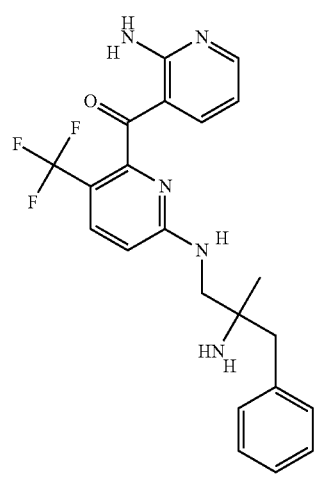
455 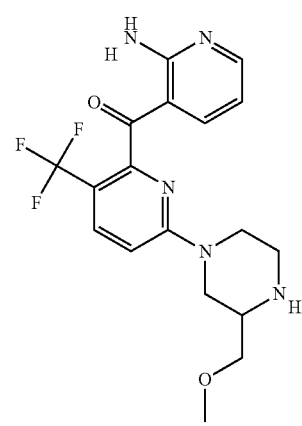
453 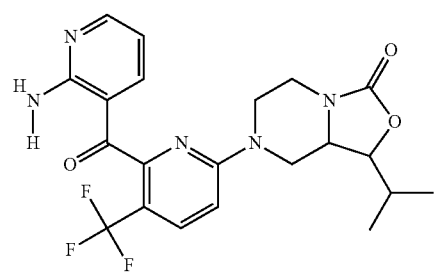
456 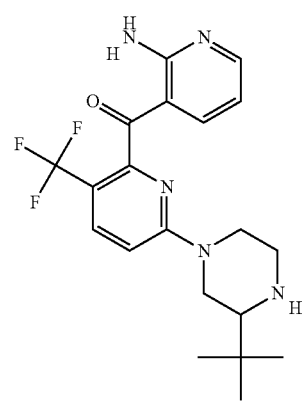

TABLE 1-continued
457 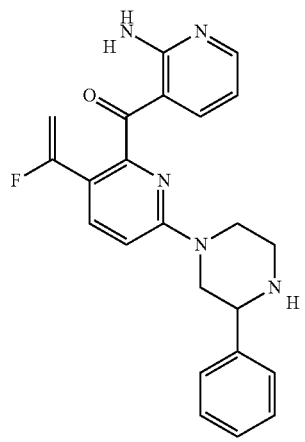
458 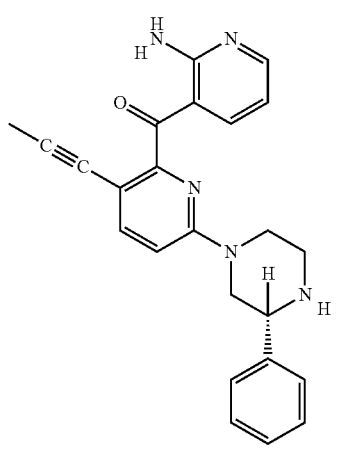
459 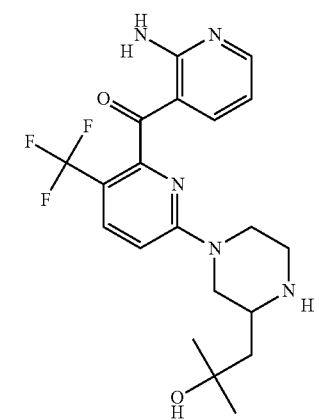
TABLE 1-continued
460 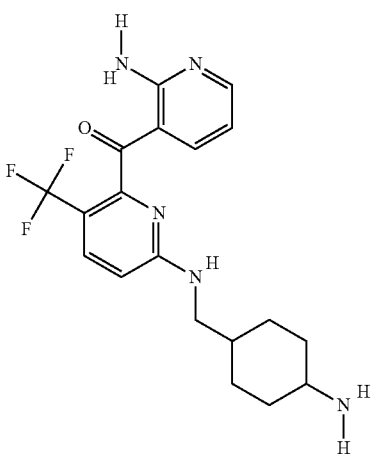
461 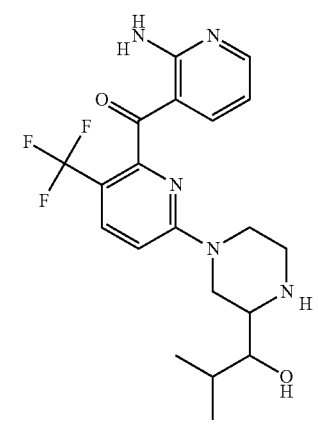
462 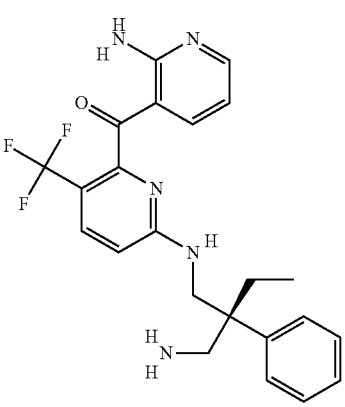

TABLE 1-continued
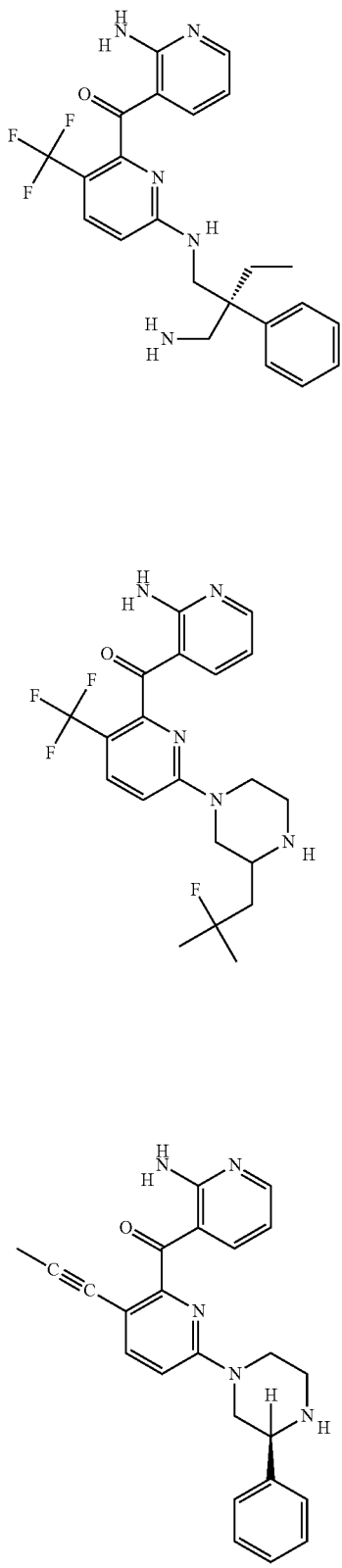
TABLE 1-continued
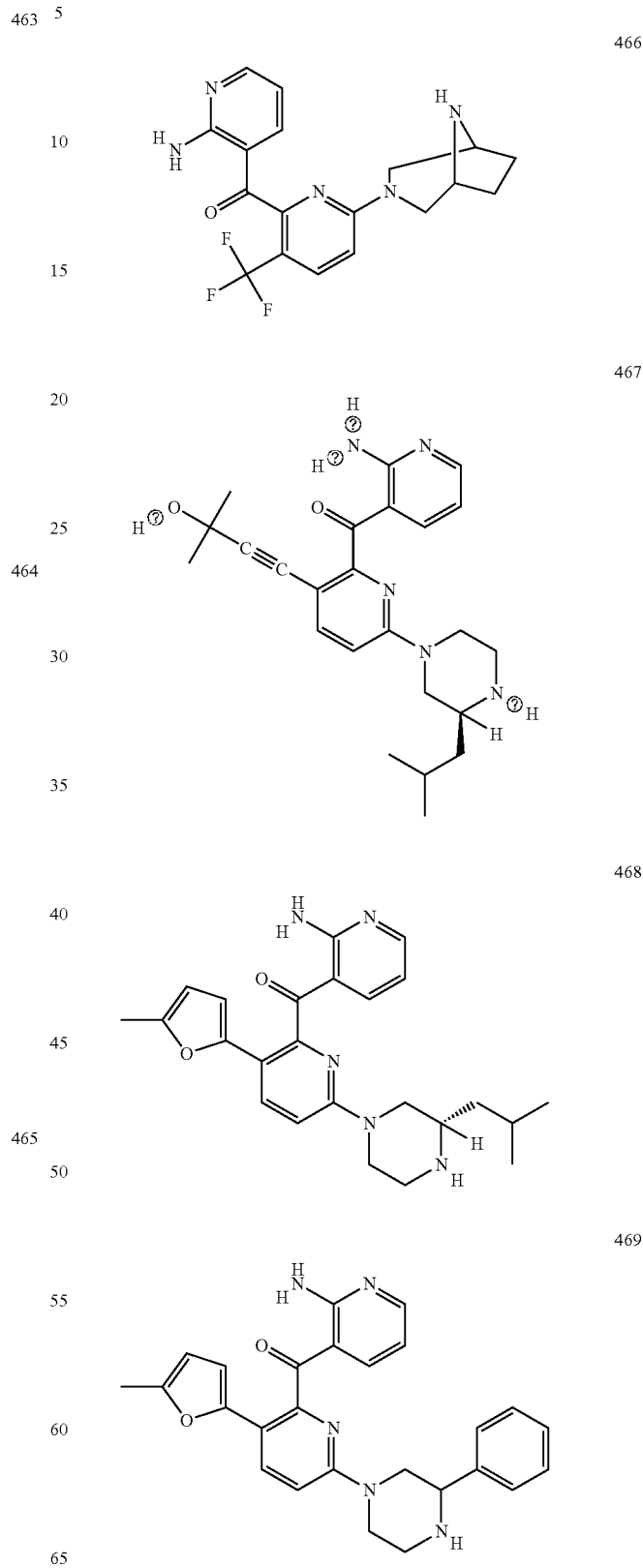

TABLE 1-continued
470 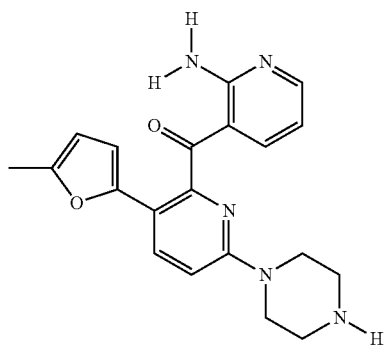
471 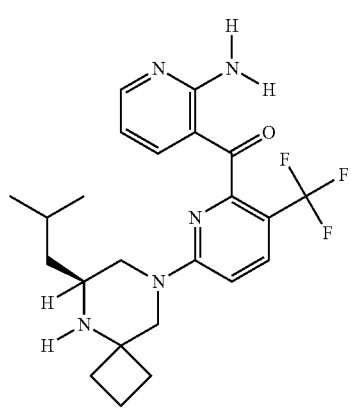
472 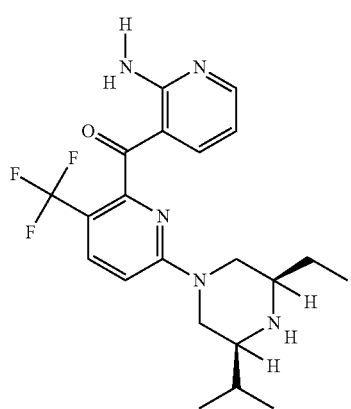
TABLE 1-continued
473 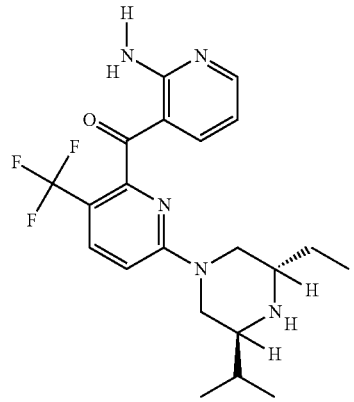
474 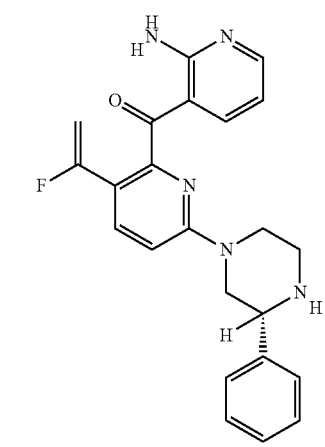
475 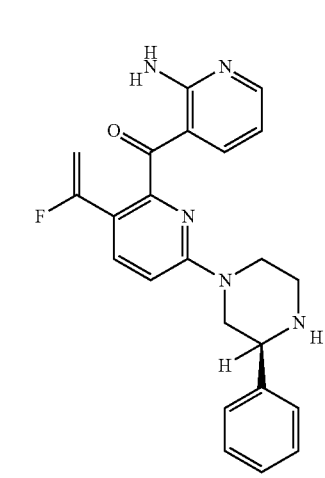

TABLE 1-continued
476
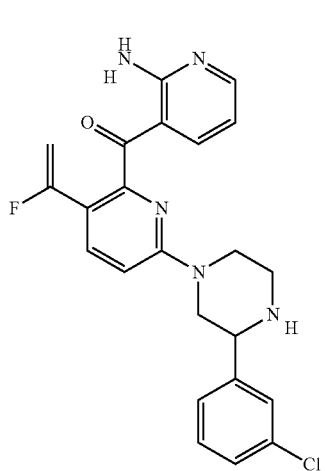
477
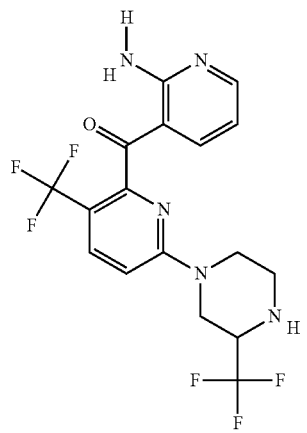
478
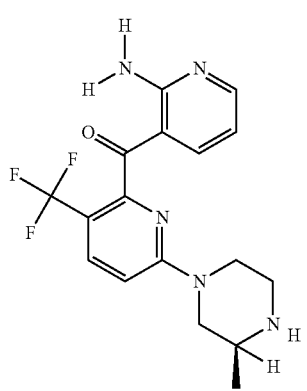
479
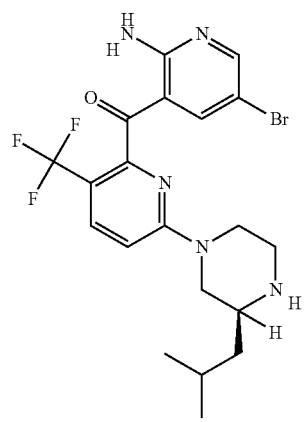
480
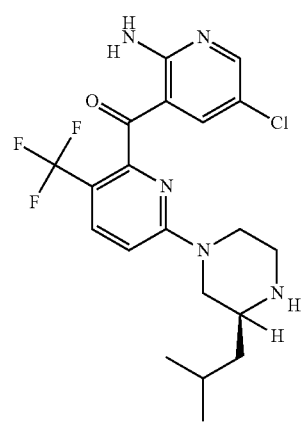
481
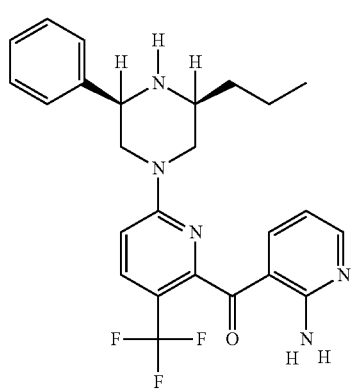

TABLE 1-continued
225
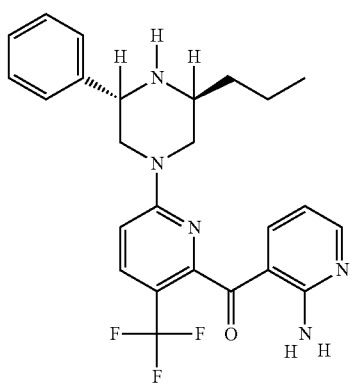
482
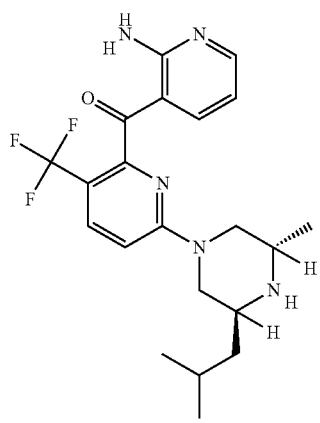
483
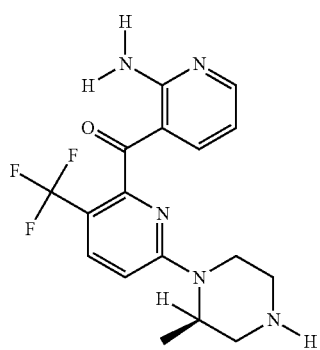
484
TABLE 1-continued
226
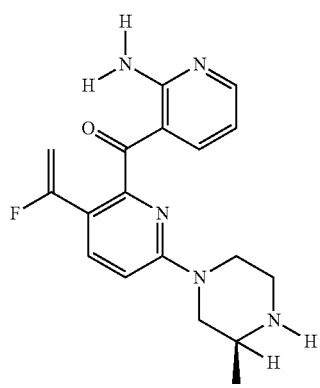
485
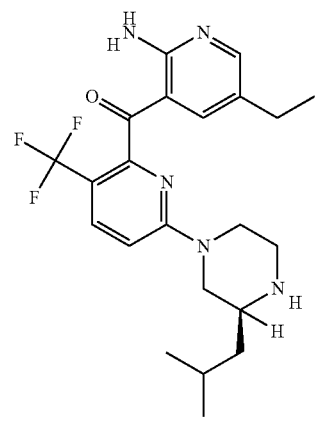
486
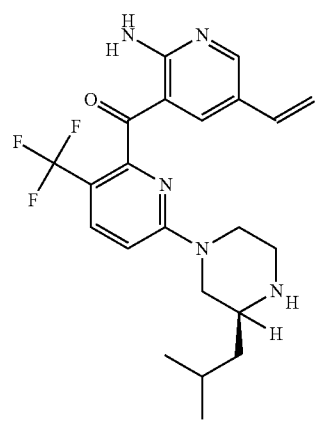
487

TABLE 1-continued
488
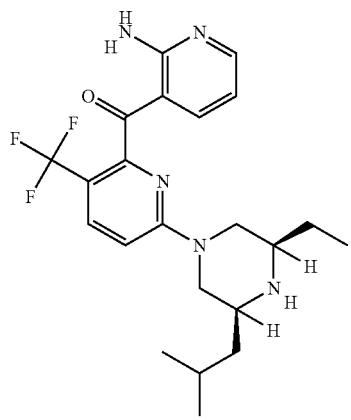
489
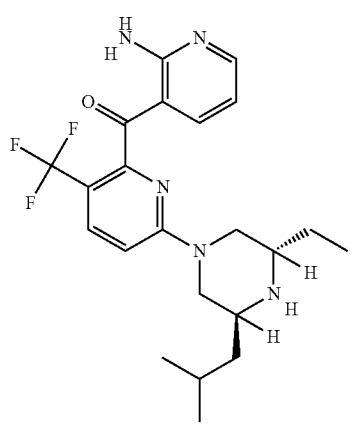
490
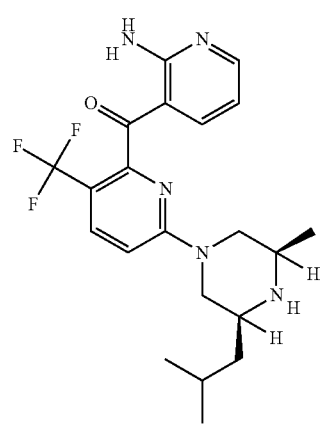
TABLE 1-continued
491
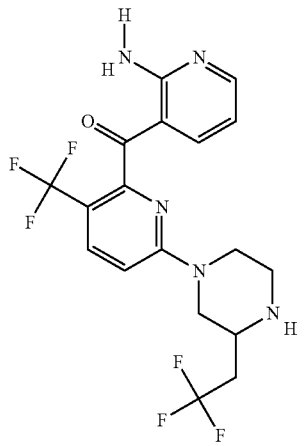
492
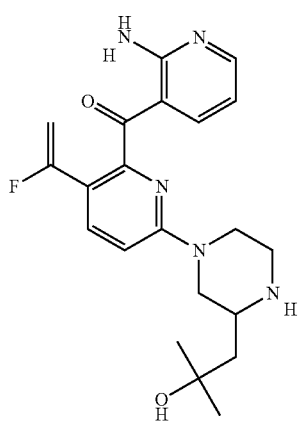
493
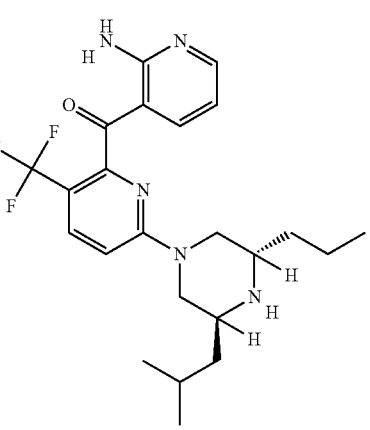

| 494 | 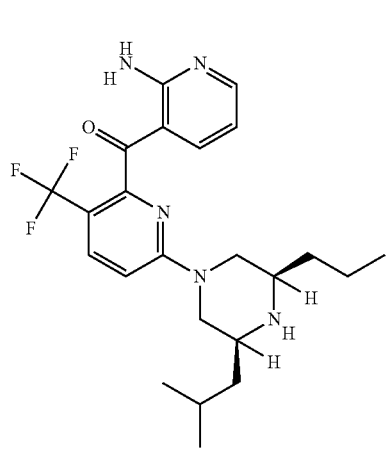 | 497 | 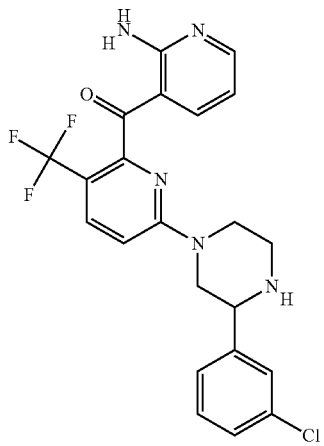 |
| 495 | 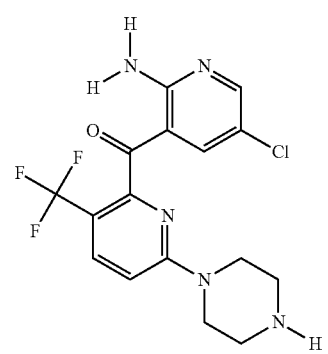 | 498 | 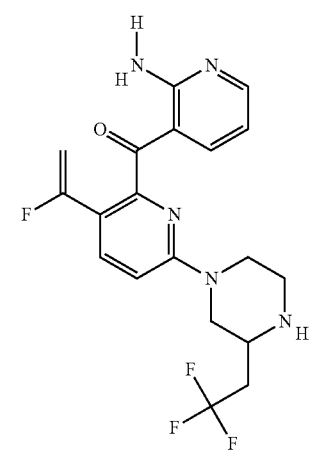 |
| 496 | 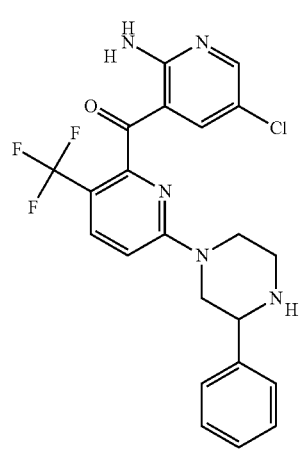 | 499 | 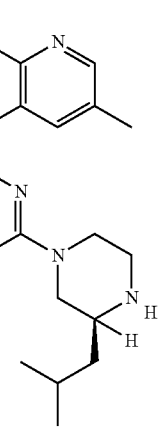 |

TABLE 1-continued
500 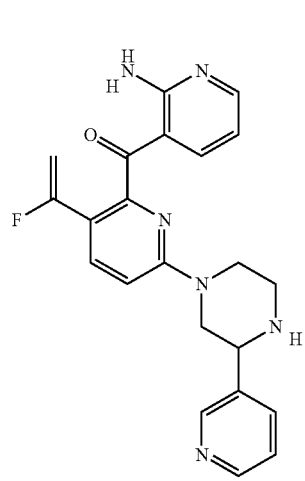
501 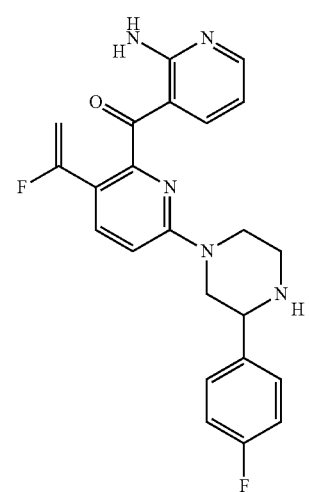
502 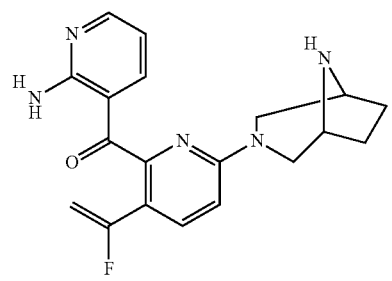
TABLE 1-continued
503 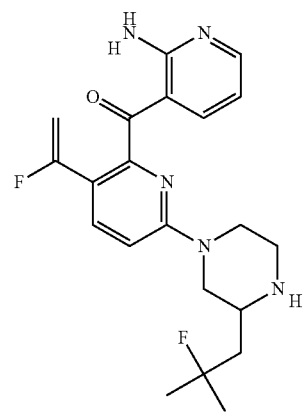
504 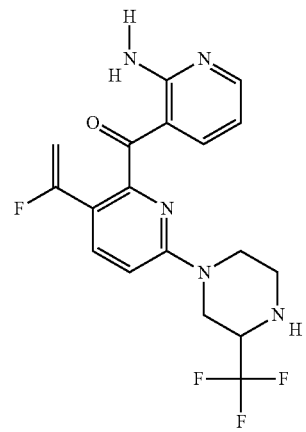
505 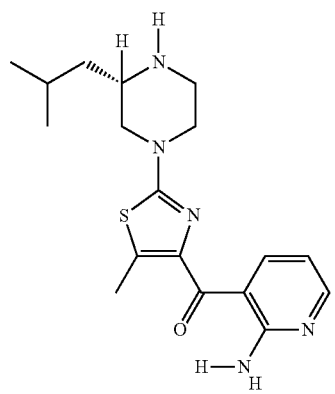

TABLE 1-continued

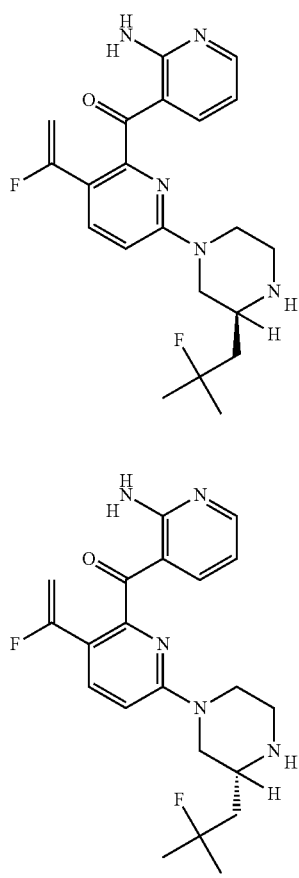

506

507

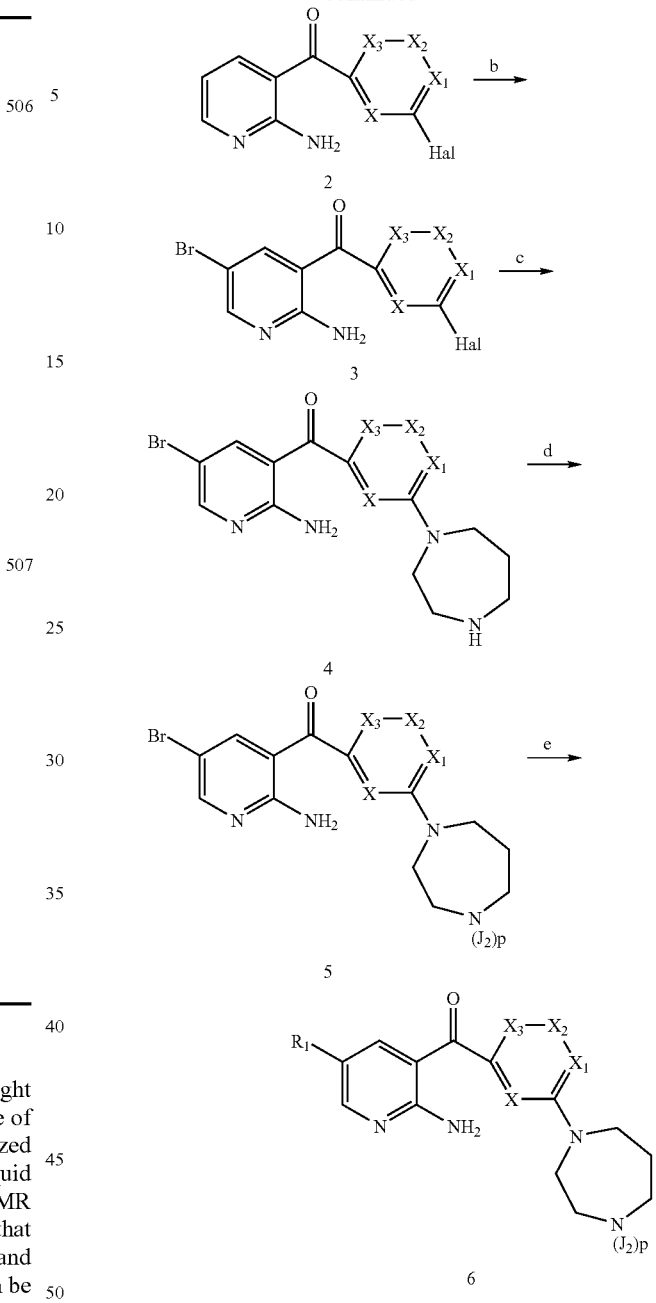

Reagents and conditions: a) n-BuLi, THF, −30° C.—r.t. (room temperature); b) NBS, CH₃CN; c) 1-Bochomopiperazine, K₂CO₃, DMF, 95° C.; HCl, dioxane; d) RCOOH, DCC, HOBt, DCM or ClCOR, THF, base or RCHO, NaCNBH3; e) R₁—Y, Pd, coupling.

Scheme I above shows a general route for the preparation of compounds of formula 6, wherein $R_1$, and J2, are as defined herein. P corresponds to q as defined above. X, X1, X2, X3, are the ring atoms required to make up B as defined herein. As shown above, the 2-amino-3-cyanopyridine is reacted with haloderivative 1 in the presence of n-butyl lithium to form a compound of formula 2. Optionally, the compound of formula 2 is then brominated using N-Bromosuccinimide (NBS) to yield derivatives 3. Compound 3 is then heated in the presence of a suitable base and a suitable solvent, with an amine (e.g. 1-Boc-homopiperazine) to form compounds that

General Synthetic Methodology

The compounds of this invention may be prepared in light of the specification using steps generally known to those of ordinary skill in the art. Those compounds may be analyzed by known methods, including but not limited to LCMS (liquid chromatography mass spectrometry) HPLC and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

General Schemes:

Scheme I

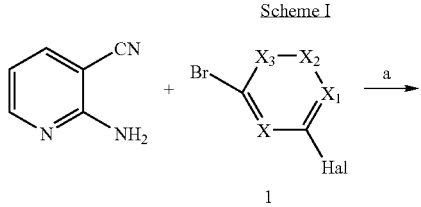

after deprotection in acidic conditions yield compounds of formula 4. Compounds of formula 4 can be further functionalized by using several methods that are well known in the art that includes amide formation, carbamate formation and reductive amination to produce compounds of formula 5. In addition, compounds of formula 5 can be further derivatized to yield compound 6 by treating them with R1-Y (Y e.g., —B(OR)$_2$, SnR3) in the presence of palladium as a catalyst by using coupling methods that are well known in the art. The reaction is amenable to a variety of substituted R1-Y.

pound 8 in the presence of n-butyl lithium or Grignard reagent to form a compound of formula 9. Compound 9 is then heated in the microwave in the presence of NH4OH to yield the amine of formula 10. The compound of formula 10 is then brominated using NBS to yield derivatives 11. In addition, compounds of formula 10 can be further derivatized to yield compound 12 by treating them with R1-Y (Y e.g., —B(OR)2, SnR3) in the presence of palladium as a catalyst by using coupling methods that are well known in the art. The reaction is amenable to a variety of substituted R1-Y.

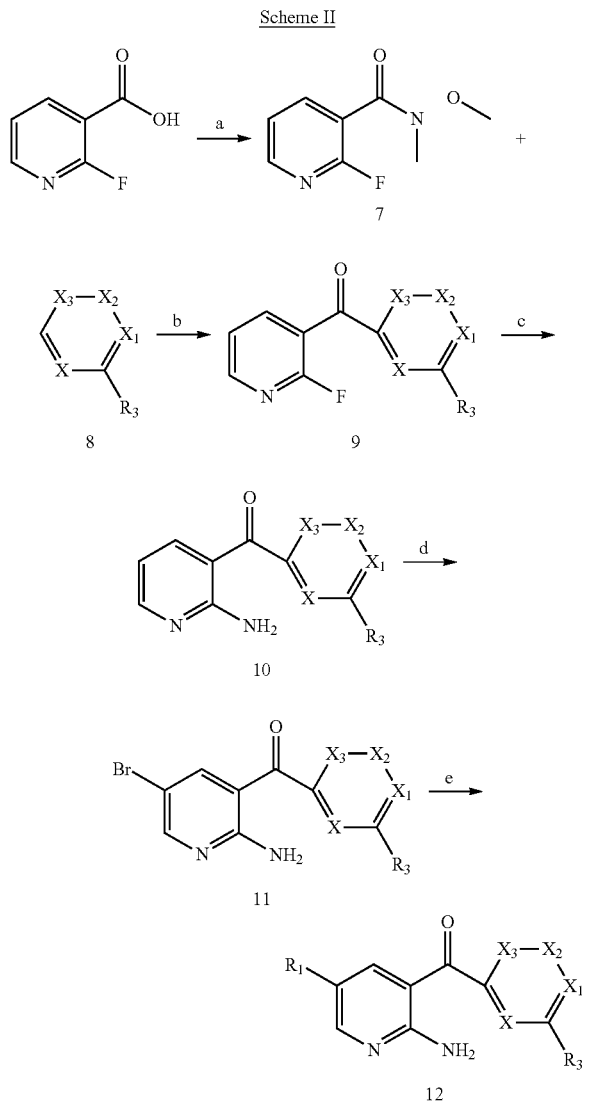

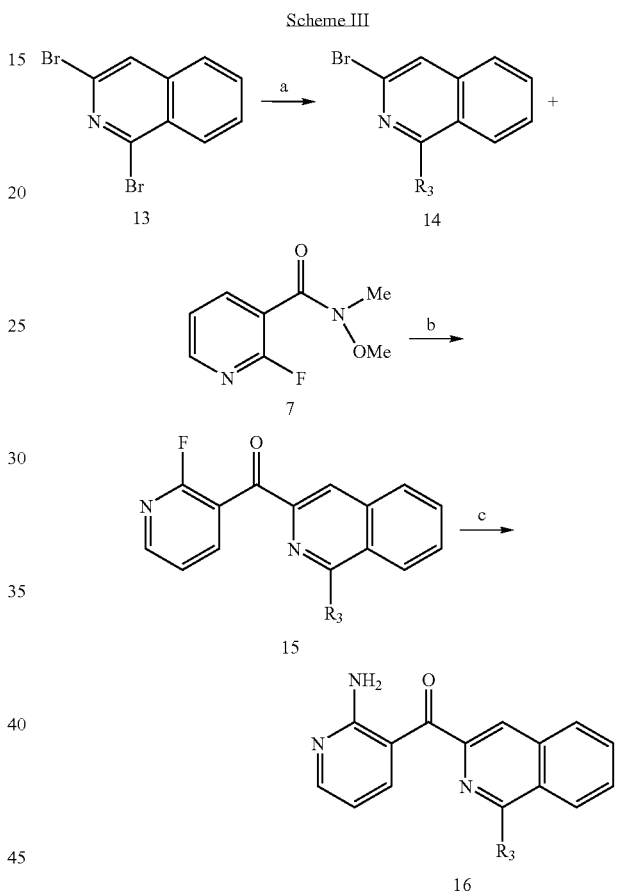

Reagents and conditions: a) TBTU, N-methoxy-N-methylamine, DIPEA, CH2Cl2.; b) n-BuLi or Grignard reagent, −78° C., THF; c) NH4OH, MW, 110° C., 25 min; d) NBS, CH3CN; e) R1-Y, Pd, coupling.

Scheme II above shows a general route for the preparation of compounds of formula 12, wherein R$_1$, and R$_3$, are as defined herein. X, X1, X2, X3, are the ring atoms required to make up ring B as defined herein. As shown above, the 2-fluoronicotinic acid is coupled with N-methoxy-N-methylamine in the presence of amide coupling agent (e.g., TBTU) to form the Weinreb amide 7. The amide 7 is then couple with com- Reagents and conditions: a) R$_3$ (amine based nucleofile), DMF, K$_2$CO$_3$, 90° C.; b) n-BuLi, −78° C., THF; c) NH$_4$OH, MW, 110° C., 25 min.

Scheme III above shows a general route for the preparation of compounds of formula 16, wherein R$_3$, are as defined herein.

As shown above, the 1,3-dibromoisoquinoline is a) heated in the presence of a suitable base and a suitable solvent, with an amine based nuclofile (e.g. 1-Boc-homopiperazine) to form compounds of formula 14. The reaction is amenable to a variety of amine based nucleofiles (R$_3$).

b) The amide 7 is then couple with compound 14 in the presence of, for example, n-butyl lithium to form a compound of formula 15.

c) Compound 15 is then heated in, for example, a microwave in the presence of, for example, NH$_4$OH to yield the amine of formula 16.

Scheme IV

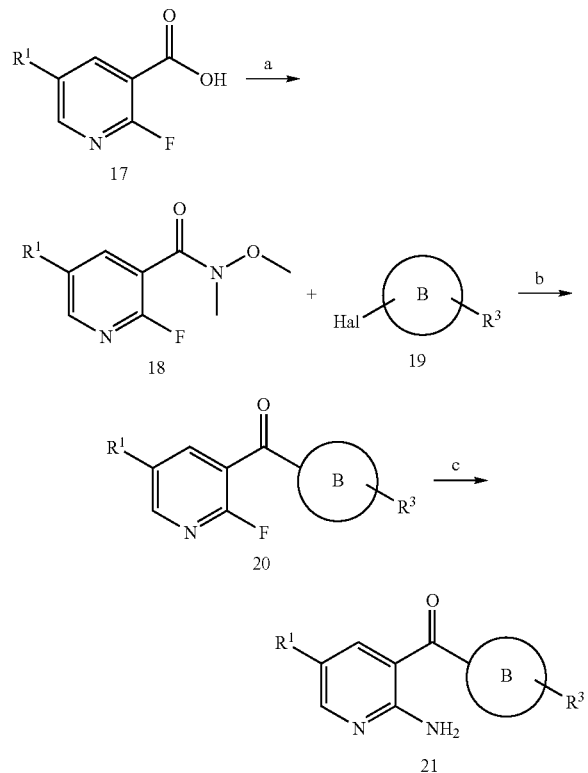

Reagents and conditions: a) TBTU, N-methoxy-N-methylamine, DIPEA, CH$_2$Cl$_2$; b) n-BuLi or Grignard reagent, −78° C., THF; c) NH$_4$OH, MW, 110° C., 25 min.

Scheme IV above shows a general route for the preparation of compounds of formula 21, wherein R$^1$, R$^3$, and ring B are as defined herein. Hal represents Br or I. As shown above, starting material 17 is coupled with N-methoxy-N-methylamine in the presence of amide coupling agent (e.g., TBTU) to form the Weinreb amide 18. The amide 18 is then coupled with compound 19 in the presence of n-butyl lithium or Grignard reagent to form a compound of formula 20. Compound 20 is then heated in the microwave in the presence of NH$_4$OH to yield the amine of formula 21.

Scheme V

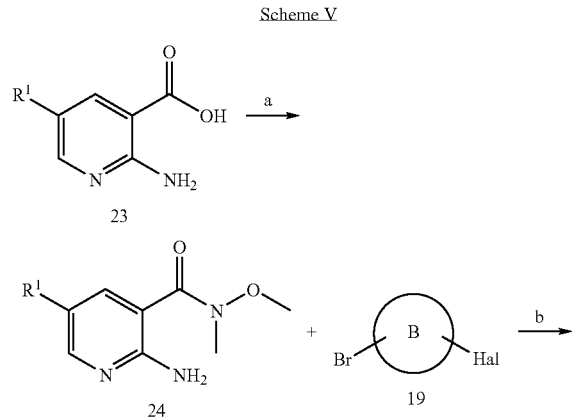

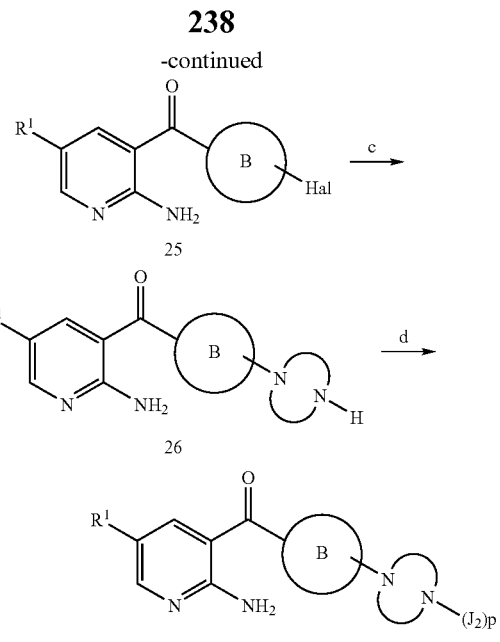

Reagents and conditions: a) TBTU, N-methoxy-N-methylamine, DIPEA, CH$_2$Cl$_2$; b) n-BuLi or Grignard reagent, −78° C., THF; c) i) Boc-amine, K$_2$CO$_3$, DMF, 95° C.; ii) HCl, dioxane; d) RCOOH, DCC, HOBt, DCM or ClCOR, THF, base or RCHO, NaCNBH$_3$.

Scheme V above shows a general route for the preparation of compounds of formula 27, wherein R$^1$, J$_2$ and ring B, are as defined herein. Hal represents an halogen. As shown above, starting material 23 is coupled with N-methoxy-N-methylamine in the presence of amide coupling agent (e.g., TBTU) to form the Weinreb amide 24. The amide 24 is then coupled with compound 19 in the presence of n-butyl lithium or Grignard reagent to form a compound of formula 25. In addition, compounds of formula 25 can be further derivatized to yield compound 26 by heating them in the presence of a suitable base and a suitable solvent, with a protected diamine (e.g. 1-Boc-homopiperazine) to form compounds that after deprotection in acidic conditions yield compounds of formula 26. Compounds of formula 26 can be functionalized by using several methods that are well known in the art that include amongst other amide formation, carbamate formation or reductive amination to produce compounds of formula 27.

Scheme VI

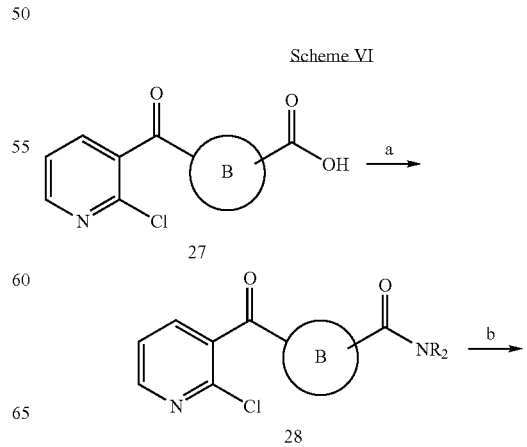

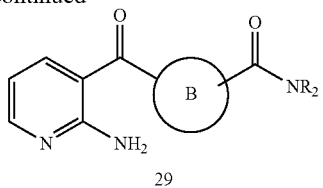

29

Reagents and conditions: a) TBTU, HNR$_2$, Et$_3$N, CH$_2$Cl$_2$; b) NH$_4$OH, MW, 160° C., 25 min.

Scheme VI above shows a general route for the preparation of compounds of formula 29, wherein ring B is as defined herein, and in C(O)NR$_2$ one R is —H and the other R is Q2 as defined herein. As shown above, starting material 27 is coupled with amine HNR$_2$ in the presence of an amide coupling agent (e.g., TBTU) to form amide 28. The reaction is amenable to a variety of amines HNR$_2$. Amide 28 is then heated in the microwave in the presence of NH$_4$OH to yield the amine of formula 29.

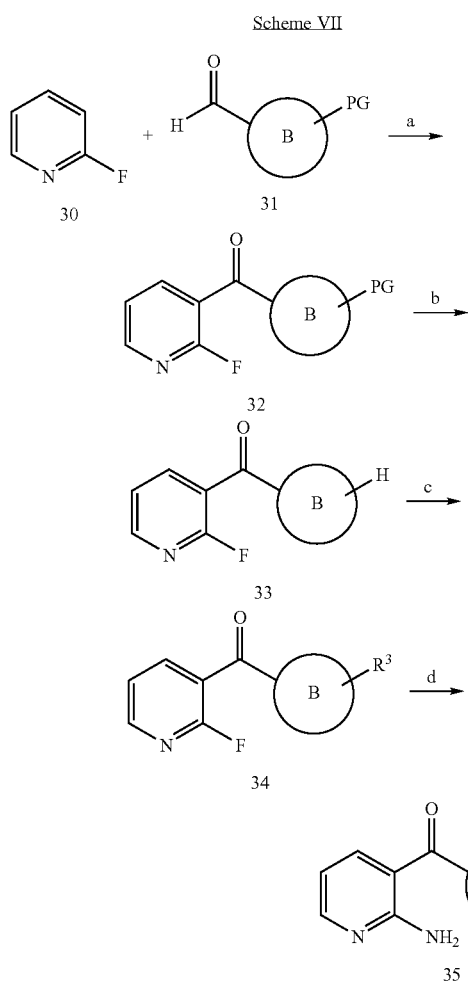

Reagents and conditions: a) i) LDA, THF, −78° C.; ii) MnO2, DCM, 75° C.; b) deprotection conditions; c) NaH, HalR$^3$, DMF; d) NH$_4$OH, MW, 100° C., 25 min.

Scheme VII above shows a general route for the preparation of compounds of formula 35, wherein R$^3$ and ring B are as defined herein. PG represents a protecting group. Compounds of formula 32, obtained via nucleophilic addition of the anion of 30 on aldehydes 31, were deprotected to form intermediates 33. 33 reacted with HalR$^3$, where Hal is a halogen, in the presence of a base (e.g., NaH) to form derivatives 34. The reaction is amenable to a variety of HalR$^3$. Compounds of formula 34 are then heated in the microwave in the presence of NH$_4$OH to yield the amines of formula 35.

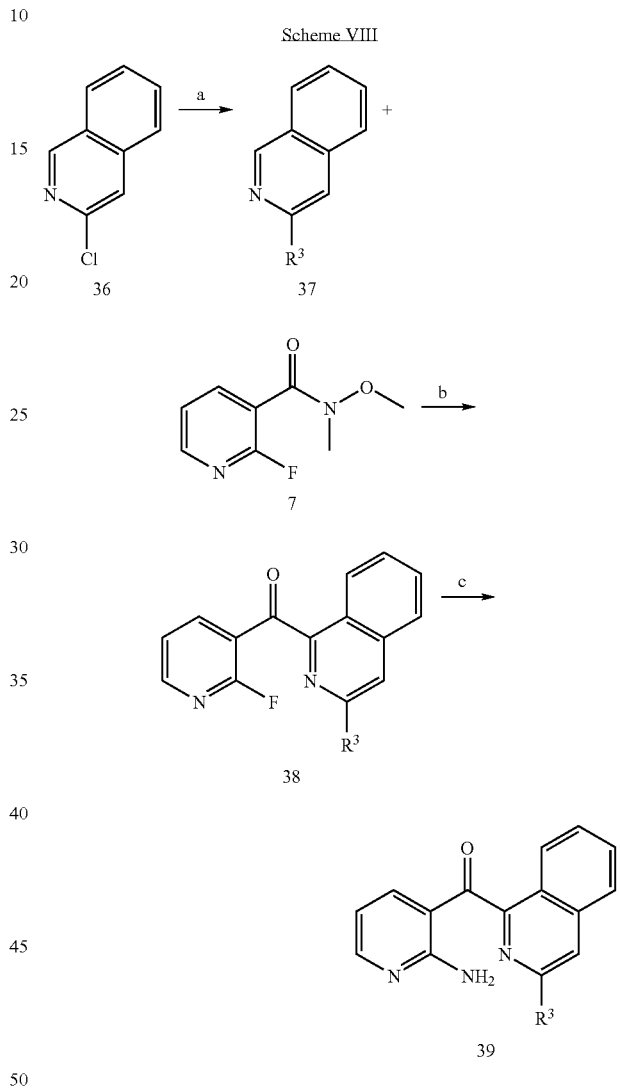

Reagents and conditions: a) R$^3$H (amine based nucleophile), ethylene glycol, 150° C.; b) "BuLi, 2-dimethylaminoethanol, THF, Hexanes, −78° C.; c) NH$_4$OH, MW, 120° C., 30 min.

Scheme VIII above shows a general route for the preparation of compounds of formula 39, wherein R$^3$ is as defined herein. 3-Chloroisoquinoline 36 is heated with an amine R$^3$H (e.g. 1-Boc-piperazine) in a suitable solvent to form compounds of formula 37. The reaction is amenable to a variety of amines. The Weinreb amide 7 is then coupled with compound 37 in the presence of "butyl lithium and 2-dimethylaminoethanol to form a compound of formula 38. Finally, compound of formula 38 is heated in the microwave in the presence of NH$_4$OH to yield the amines of formula 39.

Accordingly, this invention also provides a process for preparing a compound of this invention using the methods described above.

In one embodiment the present invention is a method of preparing the compounds described herein, comprising the steps of:

a) coupling an aminopyridine and a di-halogenated heteroaromatic compound in the presence of, for example, n-butyl lithium, alkyl lithium or gringnard reagent etc., in a suitable solvent, such as for example, tetrahydrofuran (T1), $Et_2O$, dioxane etc., at about 15° C. to about 35° C., about 20° C. to about 30° C., about 25° C. to about 30° C. to form a heteroaroyl aminopyridine;

optionally b) brominating the heteroaroyl aminopyridine with, for example, N-Bromosuccinimide or bromine in a suitable solvent, such as for example, acetonitrile, dichloromethane, trichloromethane etc., to form a heteroaroyl halogenated aminopyridine;

c) nucleofilic desplacement of the halogen from the heteroaroyl aminopyridine from step a) or the heteroaroyl halogenated aminopyridine from step b) with an optionally protected amine in the presence of suitable base, such as, potassium carbonate, diisopropylethylamine (DIPEA), triethylamine, 1,8-diazabicyclo[5.4.0]undec-7-ene (DBU) etc., in a suitable solvent, such as for example, dimethylformamide, dimethylsulfoxide (DMSO), n-butanol (n-Bu-OH) etc., at about 70° C. to about 10° C., about 80° C. to about 100° C., about 90° C. to about 100° C. to form an amine substituted heteroaroyl aminopyridine or an amine substituted heteroaroyl halogenated aminopyridine;

optionally d) the amine group from step c) can be deprotected using under acidic conditions, such as for example, using hydrochloric acid, trifluoroacetic acid etc., in a suitable solvent, such as for example, dioxane, tetrahydrofuran (THF), dichloromethane etc., to yield a deprotected amine substituted heteroaroyl aminopyridine or an amine substituted heteroaroyl halogenated aminopyridine;

optionally e) functionalizing the amine group from step d) using techniques known in the art, such as amide formation carbamate formation etc.

optionally f) derivatizing the aminopyridine group of step d) or e) by treating with R1-Y, where Y is for example —R(OR)$_2$ or —SnR3, in the presence of a catalyst, such as, palladium.

The following is an example of such a synthesis:

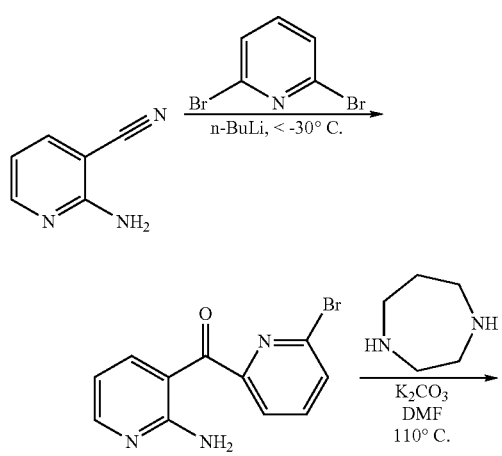

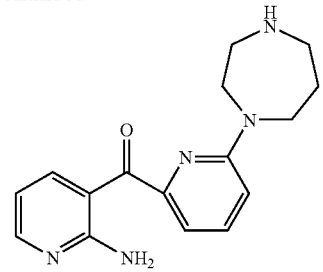

Alternatively, the present invention is a method of preparing the compounds described herein, comprising the steps of:

a) coupling a halonicotinic acid with an alkoxyamine in the presence of a coupling agent, such as, N,N,N',N'-Tetramethyl-O-(benzotriazol-1-yl)uronium tetrafluoroborate (TBTU) 1,8-dizazbicyclo[5.4.0]undec-7-ene (DBU), or N,N-dicyclohexylcarbodiimide (DCC) etc., in a suitable solvent, such as for example, dichloromethane, tetrahydrofuran (THF), dioxane etc., in the presence of a suitable base such as for example, diisopropylphosphoramidochloridite (DIPEA), triethylamine (Et3N) etc., to form a Weinreb amide;

b) heating the Weinreb amide with a heteroaromatic compound in the presence of n-butyl lithium or Grignard reagent in a suitable solvent, such as for example, tetrahydrofuran (THF), Et2O, dioxane etc., from about 10° C. to about 95° C., from about 10° C. to about 30° C. from about 20° C. to about 30° C., about 55° C. to about 95° C., about 65° C. to about 85° C., about 70° C. to about 80° C. to form a heteroaryl halopyridine;

c) heating the heteroaryl halopyridine in a microwave with, for example, ammonium hydroxide at about 80° C. to about 130° C., about 90° C. to about 120° C., about 100° C. to about 110° C. for about 5 to about 45 minutes, about 15 to about 35 minutes, or about 20 to about 30 minutes, to form a heteroaryl aminopyridine;

optionally d) brominating the heteroaroyl aminopyridine with, for example, N-Bromosuccinimide or bromine in a suitable solvent, such as for example, acetonitrile, dichloromethane, trichloromethane etc., to form a heteroaroyl brominated aminopyridine;

optionally e) derivatizing the aminopyridine group of the heteroaryl aminopyridine of step c) heteroaroyl brominated aminopyridine of step d) by treating with R1-Y, where Y is for example —R(OR)$_2$ or —SnR3, in the presence of a catalyst, such as, palladium.

EXAMPLES

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions were 5%-100% acetonitrile-methanol over 3.5 mins gradient time and 5 mins run time on an ACE C8 3.0×75 mm column. Flow rate was 1.2 ml/min. As used herein, the term "Rt(min)" refers to the LCMS retention time, in minutes, associated with the compound. Unless otherwise indicated, the LCMS method utilized to obtain the reported retention time is as detailed above.

1H-NMR spectra were recorded at 400 MHz using a Bruker DPX 400 instrument. The following compounds of formula I were prepared and analyzed as follows.

The following compounds of formula I were prepared and analyzed as follows.

Example 1

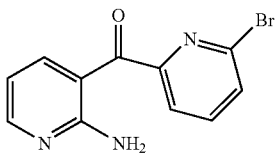

(2-aminopyridin-3-yl)(6-bromopyridin-2-yl)methanone

A mixture of 2,6-dibromopyridine (16.92 g, 71.4 mmol) and 2-amino-3-cyanopyridine (5.0 g, 42.0 mmol) in THF (150 ml) was cooled to below −30° C. before n-butyl lithium (33.6 ml, 84 mmol, 2.5 M in hexanes) was added dropwise while maintaining temperature below −30° C. On complete addition, the reaction mixture was stirred at 0° C. on an ice bath for 1.5 hours. The reaction was then quenched by the addition of 2 M HCl (until pH=~1) while keeping the temperature below 15° C., and stirred at below 15° C. for 15 mins. Additional 2M HCl (50 ml) was added and the mixture extracted with EtOAc (2×150 ml), the acidic aqueous was cooled on an ice bath before being basified by addition of 2M NaOH, causing precipitation of a brown solid. Resulting suspension was left to stand overnight, then solid product collected by filtration, washed with water and dried by suction, then under high vacuum to leave crude title compound as a brown solid (6.52 g, 56%). $^1$H NMR (DMSO-d6) 6.65 (1H, dd), 7.79 (2H, s), 7.93-7.83 (4H, m), 7.99 (1H, t), 8.28 (1H, dd). ES+ 280.80.

Example 2

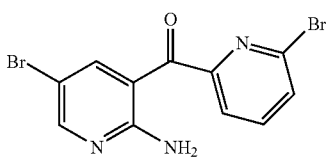

(2-amino-5-bromopyridin-3-yl)(6-bromopyridin-2-yl)methanone

To a suspension of (2-aminopyridin-3-yl)(6-bromopyridin-2-yl)methanone (5.76 g, 20.7 mmol) in acetonirile (120 ml) was added N-bromosuccinimide (4.05 g, 22.77 mmol). The resulting mixture was stirred at room temperature for 1 hour before mixture was concentrated in vacuo to approximately 20 ml. The solid was then collected by filtration and washed with minimal acetonitrile and dried to leave title compound as a brown solid (4.23 g, 57%). $^1$H NMR (DMSO-d6) 7.93-7.89 (4H, m), 8.03-7.99 (1H, m), 8.22 (1H, d), 8.36 (1H, d). ES+ 357.99.

Example 3

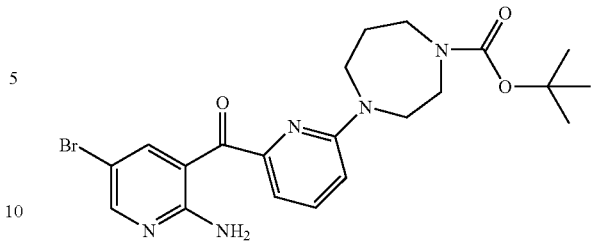

tert-butyl 4-(6-(2-amino-5-bromonicotinoyl)pyridin-2-yl)-1,4-diazepane-1-carboxylate A mixture of (2-amino-5-bromopyridin-3-yl)(6-bromopyridin-2-yl)methanone (6.0 g, 16.8 mmol), 1-Boc-homopiperazine (3.64 ml, 18.48 mmol) and K$_2$CO$_3$ (8.13 g, 58.8 mmol) in DMF (50 ml) was heated at 95° C. for 17 hours. Additional 1-Boc-homopiperazine (0.3 ml, 0.1 eq) was added and the mixture heated at 95° C. for a further 4 hours for reaction to go to completion. Reaction mixture was then allowed to cool to room temperature and solvent removed in vacuo. The resulting solid was slurried in EtOAc and filtered through a short pad of silica, washing through with EtOAc and the resulting filtrate was then concentrated to dryness in vacuo. The crude product was purified by flash chromatography on silica (5 to 25% EtOAc/Petrol) to give pure title compound as a yellow solid (2.94 g, 37%). $^1$H NMR (DMSO-d6) (quoted as a mixture of rotamers) 1.25 (9H, d), 1.91-1.77 (2H, m), 3.34 (2H, masked signal), 3.57-3.50 (2H, m), 3.65-3.62 (2H, m), 3.77-3.70 (2H, m), 6.95 (1H, dd), 7.12 (1H, dd), 7.75-7.69 (1H, m), 7.80 (2H, br s), 8.32 (1H, d), 8.60 (1H, dd). ES+ 477.98.

Example 4

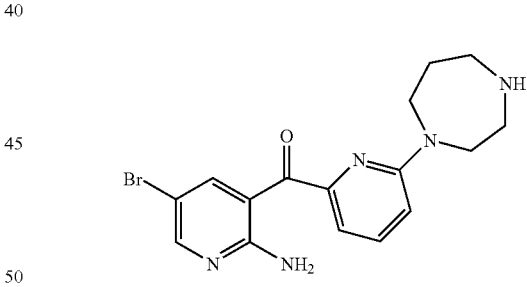

(6-(1,4-diazepan-1-yl)pyridin-2-yl)(2-amino-5-bromopyridin-3-yl)methanone

To a suspension of tert-butyl 4-(6-(2-amino-5-bromonicotinoyl)pyridin-2-yl)-1,4-diazepane-1-carboxylate (0.050 g, 0.10 mmol) in 1,4-dioxane (2 ml) was added 4 M HCl in 1,4-dioxane (1 ml) and the resulting mixture was stirred at room temperature for 5 hours. Reaction mixture was then concentrated to dryness in vacuo and the crude product purified by prep-LCMS, then freeze-dried to leave title compound as a yellow solid (13.5 mg, 36%). $^1$H NMR (DMSO-d6 1.84-1.76 (2H, m), 2.08 (1H, s), 2.71-2.68 (1H, m), 2.89-2.86 (1H, m), 3.72-3.28 (6H, masked signal), 6.89 (10.5H, d), 6.95 (0.5H, d), 7.05 (0.5H, d), 7.10 (0.5H, d), 7.74-7.68 (1H, m), 7.81 (2H, br s), 8.31 (1H, d), 8.54 (1H, d). ES+ 378.15.

Example 5

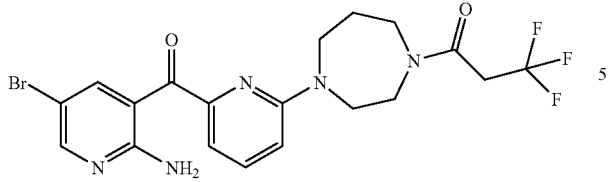

1-(4-(6-(2-amino-5-bromonicotinoyl)pyridin-2-yl)-1,
4-diazepan-1-yl)-3,3,3-trifluoropropan-1-one
(Cmpd-75)

(6-(1,4-diazepan-1-yl)pyridin-2-yl)(2-amino-5-bromopyridin-3-yl)methanone (650 mg, 1.36 mmol) was added to a stirred suspension of 3,3,3-trifluoropropionic acid (0.13 ml, 1.50 mmol), 1-hydroxybenzotriazole (184 mg, 1.36 mmol), triethylamine (1.33 ml, 9.52 mmol) and PS-carbodiimide (2.08 g, 2.72 mmol) in dichloromethane (20 ml). The resulting mixture was stirred at room temperature for 18 hours. The crude mixture was filtered and concentrated in vacuo. The residue was purified on silica gel by flash column chromatography (ISCO Companionl, 40 g column, 0-50% EtOAc/Petroleum ether) to afford the title compound as an orange solid (355 mg, 54% yield).

$^1$H NMR (DMSO-d$_6$, 400 MHz) δ 1.91-1.81 (2H, m), 3.69-3.34 (9H, m), 3.82-3.79 (1H, m), 6.99 (1H, td), 7.12 (1H, dd), 7.76-7.71 (1H, m), 7.79 (2H, s), 8.32 (1H, d), 8.46 (0.5H, d), 8.53 (0.5H, d), (rotamers); MS (ES$^+$) 487, (ES$^-$) 485.

Example 6

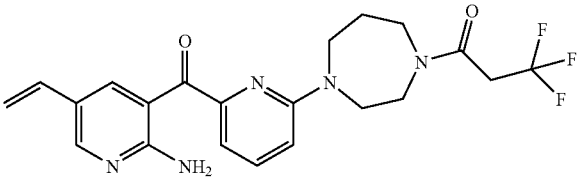

1-(4-(6-(2-amino-5-vinylnicotinoyl)pyridin-2-yl)-1,
4-diazepan-1-yl)-3,3,3-trifluoropropan-1-one
(Cmpd-107)

A mixture of 1-(4-(6-(2-amino-5-bromonicotinoyl)pyridin-2-yl)-1,4-diazepan-1-yl)-3,3,3-trifluoropropan-1-one (355 mg, 0.73 mmol), vinyl boronic acid pinacol ester (0.15 ml, 0.88 mmol), tetrakis(triphenylphosphine)palladium(0) (42 mg) and a 2M aqueous solution of sodium carbonate (2 ml) in ethanol (1 ml) and toluene (3 ml) was heated under microwave irradiation at 110° C. for 5 hours. The reaction mixture was concentrated in vacuo. The residue was slurried in ethyl acetate, filtered to remove the inorganic salts and concentrated to dryness in vacuo. The residue was purified by reverse phase preparative HPLC [Waters Sunfire C18, 10 µM, 100 Å column, gradient 10%-95% B (solvent A: 0.05% TFA in water; solvent B: CH3CN) over 16 minutes at 25 mL/min]. The fractions were collected, passed through a sodium bicarbonate cartridge and freeze-dried to give the title compound as an orange solid (68 mg, 21% yield).

$^1$H NMR (DMSO-d$_6$, 400 MHz) δ 1.85-1.76 (2H, m), 3.67-3.32 (9H, m), 3.79-3.77 (1H, m), 5.06 (1H, dd), 5.57 (1H, dd), 6.65-6.56 (1H, m), 6.97 (1H, dd), 7.04 (1H, t), 7.77-7.70 (3H, m), 8.15 (0.5H, d), 8.24 (0.5H, d), 8.42 (1H, d), (rotamers); MS (ES$^+$) 435.

Table 2 below depicts data for certain exemplary compounds made according to the method described in Scheme 1 and in Examples 1-6.:

TABLE 2

| No. | M + 1 (obs) | RT (min) | 1H-NMR |
|---|---|---|---|
| 1 | 398.1 | 2 | (d4-methanol) 8.99, 8.94, 8.91 (3d, 1H), 8.21, 8.20 (2 br s, 1H), 7.84, 7.81 (2d, 1H), 7.36, 7.30, 7.27 (3d, 1H), 7.13 (d, 1H), 7.10 (d, 1H), 4.02-3.33 (m, 8H), 2.21, 1.87 (m, 2H), 1.33, 1.30 (2s, 9H) |
| 2 | 298 | 0 | (d4-methanol) 8.93 (d, 1H), 8.21 (d, 1H), 7.86 (dd, 1H), 7.36 (d, 1H), 7.14 (d, 1H), 7.12 (dd, 1H), 4.05-3.34 (m, 8H), 2.23 (m, 2H) |
| 3 | 340.2 | 1 | (CDCl3) 8.27-8.16 (m, 2H), 7.61 (dd, 1H), 7.06 (dd, 1H), 6.87 (br s, 2H), 6.68-6.57 (m, 2H), 3.87-3.40 (m, 8H), 2.11, 2.00 (2s, 3H), 1.99-1.92 (m, 2H) |
| 6 | 412.29 | 3 | (DMSO) 0.8 (9H, d), 1.75-1.73 (1H, m), 1.83-1.80 (1H, m), 3.39-3.35 (4H, m), 3.66-3.52 (6H, m), 3.79-3.71 (2H, m), 6.62-6.58 (1H, m), 6.91 (1H, t), 6.98-6.95 (1H, m), 7.70-7.66 (3H, m), 8.12 (1H, ddd), 8.23-8.22 (1H, m). |
| 9 | 356.28 | 2 | (DMSO) 1.79-1.74 (2H, m), 3.35 (2H, masked signal), 3.54-3.47 (5H, m), 3.62 (1H, t), 3.72 (2H, t), 6.63-6.59 (1H, m), 6.90 (1H, d), 6.96 (1H, d), 7.71-7.67 (3H, m), 8.06 (1H, td), 8.22 (1H, d). |
| 10 | 370.28 | 2 | (DMSO) 1.04 (3H, dt), 1.78-1.76 (2H, m), 3.35 (2H, masked signal), 3.56-3.51 (2H, m), 3.62 (2H, br m), 3.74-3.71 (2H, m), 3.93 (2H, dq), 6.62-6.58 (1H, m), 6.90 (1H, d), 6.96 (1H, dd), 7.71-7.67 (3H, m), 8.13-8.07 (1H, m), 8.22 (1H, d). |
| 11 | 380.26 | 2 | (DMSO) 1.79-1.77 (2H, m), 3.45-3.36 (3H, masked signal), 3.56-3.54 (2H, m), 3.63 (2H, br m), 3.73-3.71 (2H, m), 4.60 (2H, dd), 6.63-6.60 (1H, m), 6.90 (1H, d), 6.96 (1H, dd), 7.71-7.66 (3H, m), 8.08 (1H, td), 8.22 (1H, d). |

TABLE 2-continued

| No. | M + 1 (obs) | RT (min) | 1H-NMR |
|---|---|---|---|
| 12 | 432.22 | 3 | (DMSO) 1.90 (2H, br m), 2.28 (3H, s), 3.52 (2H, br m), 3.76-3.73 (4H, m), 3.85 (2H, br m), 6.54-6.52 (1H, m), 6.80 (2H, br s), 6.93 (1H, d), 7.01 (1H, d), 7.10 (1H, d), 7.37 (1H, br s), 7.71 (1H, t), 8.12 (1H, d), 8.19 (1H, dd). |
| 13 | 430.29 | 2 | (DMSO) 1.77 (2H, br m), 2.94 (2H, masked signal), 3.74-3.49 (10H, m), 6.58 (1H, dd), 6.84 (1H, d), 7.02 (4H, s), 7.26 (2H, br s), 7.69-7.65 (1H, m), 8.09 (1H, d), 8.20 (1H, dd). |
| 15 | 452.18 | 3 | (DMSO) (mixture of rotamers) 1.81 (1H, br m), 1.97 (1H, br m), 3.35 (2H, masked signal), 3.90-3.50 (8H, m), 6.38-6.35 (0.5H, m), 6.53-6.50 (0.5H, m), 6.99-6.94 (2H, m), 7.25-7.03 (2H, m), 7.35-7.29 (1H, m), 7.49-7.45 (1H, m), 7.74-7.66 (3H, m), 8.20-8.06 (2H, m). |
| 16 | 400.28 | 2 | (DMSO) 1.79-1.77 (2H, brr m), 3.19 (3H, d), 3.43-3.33 (6H, masked signals), 3.56-3.53 (2H, m), 3.62 (2H, m), 3.72 (2H, m), 3.99 (1H, t), 4.07 (1H, t), 6.63-6.60 (1H, m), 6.90 (1H, d), 6.98-6.95 (1H, m), 7.71-7.67 (3H, m), 8.12-8.07 (1H, m), 8.23 (1H, d). |
| 17 | 419.09 | 3 | (DMSO) 1.86-1.82 (2H, m), 3.10 (3H, s), 3.40 (1H, t), 3.55 (1H, t), 3.70-3.61 (5H, m), 3.77-3.76 (1H, m), 4.39 (2H, d), 6.99-6.83 (1H, m), 7.01 (1H, t), 7.12 (1H, dd), 7.77-7.72 (1H, m), 8.19 (2H, br s), 8.26 (1H, dd), 8.44 (1H, dd). |
| 18 | 410.18 | 3 | |
| 19 | 385.09 | 3 | |
| 20 | 355.1 | 3 | |
| 21 | 397.16 | 3 | (DMSO) 1.94-1.74 (6H, m), 3.90-3.31 (8H, m), 4.48 (2H, t), 4.63 (1H, t), 6.89-6.82 (1H, m), 6.98 (1H, dd), 7.10 (1H, dd), 7.76-7.71 (1H, m), 8.15 (2H, br s), 8.26 (1H, d), 8.40 (1H, dd). |
| 22 | 366.06 | 3 | |
| 23 | 409.14 | 3 | (DMSO) (1.81-1.76 (2H, m), 3.38 (1H, t), 3.70-3.46 (6H, m), 3.78 (1H, t), 6.95-6.87 (1H, m), 7.03 (1H, dd), 7.15 (1H, d), 7.78-7.73 (1H, m), 8.27 (1H, dd), 8.28 (2H, masked signal), 8.50 (1H, dd). |
| 24 | 411.2 | 3 | |
| 25 | 408.14 | 3 | |
| 26 | 397.18 | 4 | |
| 27 | 423.14 | 3 | |
| 28 | 371.11 | 3 | |
| 29 | 451.1 | 4 | (DMSO) 1.74 (1H, m), 1.85 (1H, m), 3.44 (1H, t), 3.77-3.57 (6H, m), 3.85 (1H, t), 6.74-6.69 (1H, m), 6.99 (1H, dd), 7.12-7.08 (1H, m), 7.25-7.19 (3H, m), 7.3-7.30 (1H, m), 7.77-7.71 (1H, m), 8.05 (2H, br s), 8.24-8.20 8.23-8.20 (1H, m), 8.23 (1H, dd). |
| 30 | 409.21 | 2 | |
| 31 | 422.2 | 2 | |
| 32 | 402.24 | 2 | (DMSO) (rotamers) 1.58 (0.5H, m), 1.89 (0.5H, m), 3.31 (0.5H, m), 3.46 (0.5H, m), 3.81-3.60 (7H, m), 6.69 (1H, m), 7.02-6.87 (3H, m), 7.32-7.14 (3H, m) 7.41 (1H, d), 7.80-7.71 (1H, m), 8.50-8.11 (4H, m). |
| 33 | 416.24 | 2 | |
| 34 | 368.3 | 2 | |
| 35 | 380.3 | 2 | |
| 36 | 366.27 | 2 | |
| 37 | 382.3 | 2 | |
| 38 | 408.28 | 2 | |
| 39 | 422.3 | 2 | |
| 40 | 406.26 | 2 | |
| 41 | 412.29 | 2 | (DMSO) 0.84 (9H, s), 1.81-1.76 (2H, m), 3.87-3.45 (8H, m), 3.93 (1H, d), 7.03-6.91 (2H, m), 7.15 (1H, t), 7.77-7.71 (1H, m), 8.28 (1H, dd), 8.41 (2H, br s), 8.55 (1H, dd). |
| 44 | 382.38 | 4 | (DMSO) 0.85 (9H, s), 1.33-1.29 (2H, m), 1.81 (2H, m), 2.45-2.41 (2H, m), 2.55 (1H, m), 2.68 (2H, m), 3.58 (2H, t), 3.66 (2H, m), 6.58 (1H, dd), 6.82 (1H, d), 6.93 (1H, d), 7.69-7.65 (3H, m), 8.09 (1H, dd), 8.22 (1H, dd). |
| 51 | 475.26 | 4 | (DMSO) (rotamers) 1.18 (4.5H, s), 1.28 (4.5H, s), 1.60 (2H, m), 3.03 (1H, m), 3.14 (1H, m), 3.34-3.29 (2H, masked signal), 3.55-3.53 (2H, m), 3.65-3.62 (2H, m), 6.93 (1H, d), 7.13-7.09 (1H, m), 7.45-7.40 (1H, m), 7.74-7.70 (1H, m), 7.81 (2H, s), 7.94 (1H, d), 8.50 (2H, s), 8.63 (1H, d), 8.77 (1H, d). |
| 52 | 418.25 | 4 | (DMSO) (rotamers) 1.81 (1H, m), 19.2 (1H, m), 3.45 (1H, t), 3.54 (1H, t) 3.62 (1H, t), 3.88-3.70 (5H, m), 6.55-6.42 (1H, m), 6.78 (1H, d), 7.01-6.94 (3H, m), 7.20-7.14 (1H, m), 7.35-7.27 (2H, m), 7.66 (2H, s), 7.75-7.70 (1H, m), 8.12-8.01 (1H, m), 8.19-8.17 (1H, m). |
| 55 | 488.29 | 3 | (DMSO) (rotamers) 1.18 (4.5H, s), 1.27 (4.5H, s), 1.57 (2H, m), 2.19 (3H, d), 2.91 (1H, m), 3.09 (1H, m), 3.34 (2H, masked isgnal), 3.52-3.50 (2H, m), 3.62-3.60 (2H, m), 6.87 (1H, d), 7.04 (1H, dd), 7.26-7.12 (4H, m), 7.68 (1H, t), 7.75 (12H, s), 8.25-8.12 (2H, m). |
| 56 | 488.19 | 4 | (DMSO) (rotamers) 1.19 (4.5H, s), 1.30 (4.5H, s), 2.31 (3H, s), 3.03 (1H, m), 3.17 (1H, m), 3.38-3.32 (2H, masked signal), 3.67-3.53 (4H, m), 6.92 (1H, d), 7.06 (1H, t), 7.22 (2H, t), 7.40 (2H, t), 7.73-7.70 (3H, m), 8.37 (0.5H, d), 8.47 (0.5H, d), 8.56-8.55 (1H, m). |

TABLE 2-continued

| No. | M + 1 (obs) | RT (min) | 1H-NMR |
|---|---|---|---|
| 57 | 388.25 | 3 | (DMSO) 1.53-1.51 (2H, br m), 2.18 (3H, s), 2.41 (2H, t), 2.64 (2H, br m), 3.57-3.49 (4H, m), 6.79 (1H, d), 6.97 (1H, d), 7.13 (1H, d), 7.25-7.19 (3H, m), 7.64 (1H, t), 7.77 (1H, br s), 8.15 (1H, d), 8.24 (1H, d). |
| 58 | 375.32 | 3 | (DMSO) 1.54-1.52 (2H, m), 2.70-2.67 (2H, m), 3.34 (2H, masked signal), 3.59-3.53 (4H, m), 6.86 (1H, d), 7.05 (1H, d), 7.42 (1H, td), 7.70 (1H, t), 7.83 (1H, s), 7.93 (1H, d), 8.50 (1H, d), 8.53 (1H, d), 8.63 (1H, d), 8.75 (1H, d). |
| 59 | 388.31 | 4 | (DMSO) 1.68-1.65 (2H, m), 2.37 (3H, s), 2.64 (2H, t), 2.82 (2H, t), 3.68-3.63 (4H, m), 6.92 (1H, d), 7.07 (1H, d), 7.27 (2H, d), 7.45 (2H, d), 7.75 (1H, td), 7.80 (2H, s), 8.48 (1H, d), 8.61 (1H, d). |
| 60 | 424.18 | 4 | (DMSO) (rotamers)1.18 (4.5H, s), 1.31 (4.5H, s), 1.79-1.71 (2H, m), 3.34-3.23 (2H, m), 3.45 (1H, t), 3.52 (1H, t), 3.60 (2H, t), 3.75-3.68 (2H, m), 5.07 (1H, dd), 5.59 (1H, dd), 6.68-6.60 (1H, m), 6.93 (1H, t), 7.03 (1H, t), 7.74-7.68 (3H, br m), 8.23 (1H, d), 8.43 (1H, s). |
| 66 | 324.2 | 3 | (DMSO) 1.73-1.67 (2H, m), 2.65 (2H, t), 2.80 (2H, t), 3.65-3.57 (4H, m), 5.06 (1H, d), 5.53 (1H, d), 6.55 (1H, dd), 6.85 (1H, d), 6.99 (1H, d), 7.67 (1H, t), 7.75 (2H, s), 8.26 (1H, d), 8.39 (1H, d). |
| 67 | 390.05 | 3 | (DMSO) 1.90-1.88 (2H, m), 2.27 (3H, s), 2.51-2.47 (2H, masked signal), 2.62 (2H, t), 3.59 (2H, t), 3.72-3.69 (2H, m), 6.89 (1H, d), 7.06 (1H, d), 7.71 (1H, t), 7.81 (2H, s), 8.31 (1H, d), 8.52 (1H, d). |
| 69 | 434.96 | 4 | (DMSO) 1.82 (2H, m), 3.57-3.48 (7H, m), 3.65 (2H, t), 3.73 (2H, t), 6.96 (1H, d), 7.12-7.09 (1H, m), 7.72 (1H, t), 7.79 (2H, s), 8.32 (1H, d), 8.51 (1H, d). |
| 70 | 512.99 | 4 | (DMSO) (rotamers) 1.78-1.75 (1H, m), 1.85-1.82 (1H, m), 3.68-3.46 (10H, m), 6.63-6.52 (3H, m), 7.03-6.96 (2H, m), 7.12 (1H, dd), 7.74-7.69 (1H, m), 7.78 (2H, s), 8.31 (1H, d), 8.49 (1H, dd), 9.31 (1H, br s). |
| 71 | 449 | 4 | (DMSO) (rotamers) 0.82 (3H, d), 0.93 (3H, d), 1.77-1.75 (1H, m), 1.87-1.84 (1H, m), 2.72-2.65 (0.5H, m), 2.85-2.77 (0.5H, m), 3.40-3.38 (1H, m), 3.49-3.47 (1H, m), 3.68-3.54 (5H, m), 3.82-3.80 (1H, m), 6.97 (1H, dd), 7.11 (1H, t), 7.79-7.69 (3H, m), 8.32 (1H, d), 8.50 (1H, dd). |
| 72 | 497 | 4 | (DMSO) (rotamers) 1.73-1.70 (1H, m), 1.83-1.81 (1H, m), 3.40 (1H, t), 3.52 (1H, t), 3.69-3.58 (8H, m), 6.95 (1H, t), 7.24-7.09 (6H, m), 7.74-7.69 (1H, m), 7.79 (2H, s), 8.31 (1H, d), 8.47 (1H, dd). |
| 73 | 462.99 | 4 | (DMSO) 1.12 (9H, s), 1.85-1.82 (2H, m), 3.44 (2H, br m), 3.75-3.65 (6H, m), 6.96 (1H, d), 7.10 (1H, d), 7.72 (1H, t), 7.79 (2H, s), 8.32 (1H, d), 8.50 (1H, d). |
| 74 | 511.01 | 4 | (DMSO) (rotamers) 1.65-1.63 (1H, m), 1.82-1.79 (1H, m), 2.16 (1.5H, s), 2.22 (1.5H, s), 3.42 (1H, t), 3.50 (1H, t), 3.68-3.55 (8H, m), 7.01-6.91 (5H, m), 7.13 (1H, dd), 7.74-7.67 (1H, m), 7.79 (2H, d), 8.31 (1H, d), 8.47 (1H, dd). |
| 75 | 486.98 | 4 | (DMSO) (rotamers) 1.91-1.81 (2H, m), 3.69-3.34 (9H, m), 3.82-3.79 (1H, m), 6.99 (1H, td), 7.12 (1H, dd), 7.76-7.71 (1H, m), 7.79 (2H, s), 8.32 (1H, d), 8.46 (0.5H, d), 8.53 (0.5H, d). |
| 76 | 461.07 | 4 | (DMSO) 0.84 (9H, s), 1.32 (2H, t), 1.85 (2H, m), 2.43 (2H, t), 2.56-2.50 (2H, masked signal), 2.70 (2H, m), 3.60 (2H, t), 3.68 (2H, m), 6.89 (1H, d), 7.06 (1H, d), 7.70 (1H, t), 7.82 (2H, s), 8.31 (1H, d), 8.53 (1H, d). |
| 77 | 433.12 | 3 | (DMSO) (rotamers) 1.69-1.68 (1H, m), 1.79-1.78 (1H, m), 3.68-3.46 (10H, m), 6.62-6.50 (4H, m), 7.03-6.86 (3H, m), 7.70-7.65 (3H, m), 7.98 (0.5H, dd), 8.07 (0.5H, dd), 8.21 (1H, dd), 9.31 (1H, br s). |
| 82 | 313.03 | 3 | (DMSO) 1.86-1.85 (2H, m), 2.24 (3H, s), 2.56-2.43 (4H, m), 3.57-3.54 (2H, m), 3.67-3.66 (2H, m), 6.57 (1H, dd), 6.80 (1H, d), 6.93 (1H, d), 7.68-7.64 (3H, m), 8.09 (1H, d), 8.22 (1H, d). |
| 85 | 284.98 | 3 | (DMSO) 1.75-1.71 (1H, m), 2.10-2.04 (1H, m), 3.08 (1H, dd), 3.40-3.26 (2H, masked signal), 3.60-3.47 (4H, m), 6.62-6.58 (2H, m), 6.92 (1H, d), 7.69-7.65 (3H, m), 8.22-8.21 (2H, m) |
| 86 | 298.98 | 3 | (DMSO) 1.24-1.16 (1H, m), 1.36-1.28 (1H, m), 1.75-1.73 (2H, m), 2.98-2.80 (3H, m), 4.14 (2H, d), 6.61-6.58 (1H, m), 6.98 (1H, d), 7.04 (1H, d), 7.72-7.69 (3H, m), 8.08 (1H, d), 8.22 (1H, d). |
| 87 | 298.98 | 3 | (DMSO) 1.28-1.19 (1H, m), 1.47-1.38 (1H, m), 1.69-1.66 (1H, m), 1.87-1.84 (1H, m), 2.69-2.57 (2H, m), 2.86-2.79 (1H, m), 4.09 (2H, dd), 6.60 (1H, dd), 6.95 (1H, d), 7.01 (1H, d), 7.71-7.67 (3H, m), 8.06 (1H, dd), 8.22 (1H, dd). |
| 88 | 341.12 | 3 | (DMSO) 1.02 (9H, s), 2.56 (4H, t), 3.44 (4H, t), 6.60 (1H, dd), 7.02 (2H, dd), 7.74-7.68 (3H, m), 8.09 (1H, dd), 8.22 (1H, dd). |
| 89 | 417.11 | 4 | (DMSO) (110° C.) 2.04-1.76 (5H, br m), 3.45-3.23 (2H, br m), 3.90-3.40 (6H, br m), 6.47 (1H, br m), 6.94-6.86 (2H, br m), 7.24-6.98 (6H, br m), 7.69 (1H, t), 7.98 (1H, br m), 8.18 (1H, br m). |
| 90 | 408.99 | 3 | (DMSO) 1.86 (2H, m), 3.68-3.62 (4H, br m), 3.82 (4H, br m), 6.55 (1H, br m), 6.88 (1H, br m), 6.96 (1H, d), 7.03 (1H, br m), 7.35-7.26 (1H, br m), 7.64 (4H, br m), 8.05-7.87 (1H, br m), 8.20 (1H, d). |
| 91 | 407.06 | 4 | (DMSO) (ROTAMERS) 1.87 (4H, br m), 2.08-2.07 (1H, br m), 3.82-3.53 (8H, br m), 6.47-6.37 (1H, m), 6.57 (1H, br m), 6.98-6.85 (2H, br m), 7.65-7.54 (4H, br m), 8.07-8.00 (1H, br m), 8.22 (1H, s). |

TABLE 2-continued

| No. | M + 1 (obs) | RT (min) | 1H-NMR |
|---|---|---|---|
| 92 | 442.97 | 4 | (DMSO) (@110° C.) 1.90-1.86 (2H, m), 3.60-3.58 (2H, m), 3.75-3.70 (4H, m), 3.85-3.82 (2H, m), 6.55 (1H, dd), 6.88 (1H, d), 7.00 (1H, d), 7.03 (1H, d), 7.21 (2H, br s), 7.70-7.64 (2H, m), 8.09 (1H, d), 8.19 (1H, dd). |
| 93 | 423.15 | 4 | (DMSO) (rotamers) 0.65-0.60 (3H, m), 1.52-0.97 (8H, br m), 1.79-1.71 (2H, br m), 2.54-2.46 (2H, masked signal), 3.86-3.32 (8H, m), 6.62-6.60 (1H, m), 6.99-6.86 (2H, m), 7.70-7.64 (3H, br m), 8.15-8.09 (1H, m), 8.22 (1H, dd). |
| 105 | 326.97 | 3 | (DMSO) 1.14 (3H, t), 1.84-1.78 (2H, m), 2.48 (2H, q), 2.73 (1H, t), 2.88 (1H, t), 3.76-3.35 (7H, br m), 6.89 (1H, d), 7.00 (1H, d), 7.58 (2H, br s), 7.77-7.71 (1H, m), 8.09 (1H, d), 8.19 (1H, d). |
| 106 | 409.09 | 4 | (DMSO) 1.82 (2H, br m), 2.09 (3H, s), 2.59-2.57 (2H, m), 2.73-2.71 (2H, m), 3.61 (2H, t), 3.69-3.67 (4H, m), 6.54 (1H, dd), 6.80 (1H, d), 6.84 (1H, d), 6.94 (1H, d), 7.28 (1H, d), 7.70-7.66 (3H, m), 8.08 (1H, dd), 8.21 (1H, dd). |
| 107 | 435.07 | 4 | (DMSO) (rotamers) 1.85-1.76 (2H, m), 3.67-3.32 (9H, m), 3.79-3.77 (1H, m), 5.06 (1H, dd), 5.57 (1H, dd), 6.65-6.56 (1H, m), 6.97 (1H, dd), 7.04 (1H, t), 7.77-7.70 (3H, m), 8.15 (0.5H, d), 8.24 (0.5H, d), 8.42 (1H, d). |
| 112 | 418.98 | 3 | (DMSO) 0.95 (6H, d), 1.81 (2H, m), 2.54-2.50 (2H, masked signal), 2.71 (2H, br m), 2.89 (1H, br m), 3.66-3.60 (4H, m), 6.88 (1H, d), 7.06 (1H, d), 7.70 (1H, t), 7.82 (2H, s), 8.31 (1H, d), 8.53 (1H, d). |
| 113 | 430.97 | 4 | (DMSO) 0.06-0.03 (2H, m), 0.44-0.39 (2H, m), 0.82-0.78 (1H, m), 1.89-1.87 (2H, m), 2.34 (2H, d), 2.63 (2H, m), 2.78 (2H, m), 3.59-3.56 (2H, m), 3.70 (2H, m), 6.87 (1H, d), 7.05 (1H, d), 7.69 (1H, t), 7.80 (2H, s), 8.30 (1H, d), 8.51 (1H, d). |
| 114 | 481.03 | 4 | (DMSO) 1.87 (2H, br m), 2.70-2.66 (6H, m), 2.82 (2H, br m), 3.63-3.60 (2H, m), 3.71 (2H, br m), 6.89 (1H, d), 7.07 (1H, d), 7.25-7.13 (5H, m), 7.71 (1H, t), 7.82 (2H, s), 8.32 (1H, d), 8.52 (1H, d). |
| 115 | 404.94 | 3 | (DMSO) 0.99 (3H, t), 1.88 (2H, br m), 2.54-2.50 (4H, masked signal), 2.71 (2H, br, m), 3.60 (2H, t), 3.70 (2H, br m), 6.89 (1H, d), 7.07 (1H, d), 7.71 (1H, t), 7.82 (2H, s), 8.32 (1H, d), 8.52 (1H, d). |
| 116 | 341.07 | 3 | (DMSO) 0.92 (6H, d), 1.77-1.73 (2H, m), 2.54-2.47 (2H, masked signal), 2.66-2.64 (2H, m), 2.88-2.81 (1H, m), 3.63-3.59 (4H, m), 6.57 (1H, dd), 6.82 (1H, d), 6.91 (1H, d), 7.68-7.64 (3H, m), 8.09 (1H, dd), 8.22 (1H, dd). |
| 117 | 353.05 | 3 | (DMSO) 0.063-0.026 (2H, m), 0.45-0.40 (2H, m), 0.82-0.77 (1H, m), 1.85 (2H, m), 2.32 (2H, d), 2.63-2.60 (2H, m), 2.74-2.72 (2H, m), 3.58-3.55 (2H, m), 3.69-3.67 (2H, m), 6.58 (1H, dd), 6.83 (1H, d), 6.93 (1H, d), 7.69-7.65 (3H, m), 8.10 (1H, dd), 8.22 (1H, dd). |
| 118 | 447.01 | 5 | (DMSO) 0.79 (9H, s), 1.86-1.82 (2H, m), 2.25 (2H, s), 2.68 (2H, t), 2.85 (2H, t), 3.67-3.62 (4H, m), 6.90 (1H, d), 7.06 (1H, d), 7.70 (1H, t), 7.81 (2H, s), 8.31 (1H, d), 8.52 (1H, d). |
| 119 | 327.01 | 3 | (DMSO) 0.96 (3H, t), 1.84-1.80 (2H, m), 2.54-2.44 (4H, masked signal), 2.65 (2H, t), 3.57 (2H, t), 3.66 (2H, t), 6.57 (1H, dd), 6.82 (1H, d), 6.92 (1H, d), 7.68-7.64 (3H, m), 8.09 (1H, dd), 8.21 (1H, dd). |
| 120 | 403.13 | 4 | (DMSO) 1.82 (2H, m), 2.72-2.62 (6H, m), 3.59 (2H, t), 3.68 (2H, t), 6.56 (1H, dd), 6.84 (1H, d), 6.93 (1H, d), 7.25-7.13 (5H, m), 7.70-7.66 (3H, m), 8.06 (1H, dd), 8.22 (1H, dd). |
| 126 | 369.1 | 4 | (DMSO) 0.79 (9H, s), 1.78 (2H, m), 2.23 (2H, s), 2.67 (2H, m), 2.81 (2H, m), 3.65-3.59 (4H, m), 6.59-6.57 (1H, m), 6.84 (1H, d), 6.92 (1H, d), 7.68-7.64 (3H, m), 8.09 (1H, d), 8.22 (1H, d). |
| 127 | 413 | 4 | (d6-DMSO, 400 MHz) 1.06-1.21 (2H, m), 1.37 (9H, s), 1.63-1.66 (3H, m), 2.77-2.82 (4H, m), 4.22 (2H, d), 6.68 (1H, t), 6.91 (1H, t), 7.07-7.10 (2H, m), 7.73 (1H, t), 8.05 (2H, brs), 8.24-8.25 (1H, m), 8.34 (1H, d) |
| 128 | 312 | 3 | (d6-DMSO, 400 MHz) 1.08-1.15 (2H, m), 2.59 (1H, brs), 1.73 (2H, d), 2.80 (2H, t), 4.27 (2H, d), 6.60 (1H, dd), 6.98 (1H, d), 7.04 (1H, d), 7.68-7.72 (3H, m), 8.08 (1H, d), 8.21-8.23 (1H, m) |
| 129 | 409 | 3 | (d6-DMSO, 400 MHz) 1.31-1.39 (2H, m), 1.80 (2H, d), 3.04 (2H, t), 3.22 (2H, q), 4.13 (2H, d), 6.72 (1H, t), 7.07-7.13 (2H, m), 7.75 (1H, t), 7.92 (2H, brs), 8.23-8.25 (3H, m) |
| 130 | 298 | 3 | (d6-DMSO, 400 MHz) 1.68-1.73 (1H, m), 2.02-2.08 (1H, m), 2.29-2.33 (1H, m), 2.60-2.67 (1H, m), 3.07-3.12 (1H, m), 3.43-3.56 (3H, m), 6.58-6.62 (2H, m), 6.91 (1H, d), 7.65-7.69 (3H, m), 8.17 (1H, d), 8.21-8.22 (1H, m) |
| 131 | 367.17 | 3 | (DMSO) 0.93 (6H, d), 1.75 (2H, m), 2.50 (2H, masked signal), 2.64 (2H, m), 2.85 (1H, br m), 3.63-3.59 (4H, m), 5.07 (1H, d), 5.53 (1H, d), 6.57 (1H, dd), 6.85 (1H, d), 7.00 (1H, d), 7.69 (1H, t), 7.75 (2H, s), 8.25 (1H, d), 8.40 (1H, d). |
| 133 | 369.17 | 3 | (DMSO) 0.93 (6H, d), 1.08 (3H, t), 1.78 (2H, m), 2.43 (2H, q), 2.50 (2H, masked signal), 2.68 (2H, m), 2.88 (1H, m), 3.66-3.60 (4H, m), 6.83 (1H, d), 6.95 (1H, d), 7.53 (2H, s), 7.67 (1H, t), 8.04 (1H, d), 8.13 (1H, d). |
| 135 | 477 | 4 | (d6-DMSO, 400 MHz) 1.38 (9H, s), 1.79 (2H, d), 2.98 (2H, t), 3.53 (1H, brs), 4.19 (2H, d), 6.84 (1H, d), 7.10 (1H, d), 7.14 (1H, d), 7.74 (1H, t), 7.80 (2H, brs), 8.32 (1H, d), 8.57 (1H, d |

TABLE 2-continued

| No. | M + 1 (obs) | RT (min) | 1H-NMR |
|---|---|---|---|
| 136 | 377 | 3 | (d6-DMSO, 400 MHz) 1.45-1.53 (2H, m), 1.91-1.96 (2H, m), 2.98 (2H, t), 3.34 (1H, brs), 4.35 (2H, d), 7.17 (2H, t), 7.77-7.83 (5H, m), 8.34 (1H, d), 8.51 (1H, d) |
| 137 | 327 | 3 | (d6-DMSO, 400 MHz) 1.29-1.37 (2H, m), 1.79 (2H, d), 2.28-2.33 (1H, m), 2.80-2.86 (2H, m), 4.24 (2H, d), 6.58-6.61 (1H, dd), 6.99 (1H, d), 7.05 (1H, d), 7.68-7.72 (3H, m), 8.06 (1H, dd), 8.22 (1H, dd) |
| 138 | 367 | 7 | (1H, DMSO-d6): 20.02-2.10 (2H, m), 3.12-3.22 (2H, m), 3.30 (3H, s), 3.65-3.70 (2H, m), 3.85-3.90 (2H, m), 4.31 (2H, s), 7.00-7.02 (1H, d), 7.15-7.17 (1H, d), 7.63-7.80 (1H, t), 8.00-8.15 (1H, br s), 8.37 (1H, s), 8.45 (1H, s), 9.10-9.15 (2H, s). |
| 139 | 489.03 | 4 | (DMSO) 1.88-1.86 (2H, m), 2.09 (3H, s), 2.62-2.59 (2H, m), 2.77-2.74 (2H, m), 3.64 (2H, t), 3.71 (4H, m), 6.80 (1H, d), 6.90 (1H, d), 7.09 (1H, d), 7.27 (1H, d), 7.71 (1H, t), 7.79 (2H, s), 8.30 (1H, d), 8.55 (1H, d). |
| 147 | 380 | 7 | (1H, DMSO-d6): 1.54 (6H, s), 2.10-2.20 (2H, m), 3.30-3.35 (2H, m), 3.40-3.45 (2H, m), 3.80-3.85 (2H, m), 4.00-4.05 (2H, m), 7.10-7.13 (1H, d), 7.24-7.26 (1H, d), 7.88-7.92 (1H, t), 8.00-8.10 (2H, br s), 8.37 (1H, s), 8.46 (1H, s), 8.75-8.85 (2H, s). |
| 148 | 338 | 8 | (1H, DMSO-d6): 0.70-0.77 (2H, d), 0.85-0.85 (2H, m), 1.55-1.65 (2H, m), 2.05-2.15 (2H, m), 2.65-2.70 (1H, m), 2.85-2.95 (2H, m), 3.35-3.45 (1H, m), 4.28-4.35 (2H, m), 6.96-7.02 (1H, t), 7.20-7.25 (2H, m), 7.77-7.85 (1H, t), 8.30-8.35 (1H, d), 8.45-8.60 (3H, m), 9.35-9.40 (2H, s). |
| 150 | 548.08 | 4 | (DMSO) (at 120° C.) (mixture of rotamers) 1.70 (1H, br m), 1.99 (1H, br m), 2.82 (2H, masked signal), 3.35-3.27 (2H, br m), 3.59-3.71 (4H, m), 6.94 (2H, m), 7.31-7.22 (3H, br m), 7.76-7.55 (4H, br m), 8.22 (1H, br m), 8.49 (1H, br m). |
| 151 | 516.02 | 4 | (DMSO) (at 120° C.) (rotamers) 2.02-1.70 (2H, br m), 2.87-2.82 (2H, masked signal), 3.43 (2H, br m), 3.79-3.72 (4H, br m), 6.92 (1H, br m), 7.33-7.24 (7H, br m), 7.72 (1H, br m), 8.23 (1H, m), 8.55-8.52 (1H, br m). |
| 152 | 338.2 | 3 | (DMSO) 1.89-1.84 (2H, m), 2.25 (3H, s), 2.56-2.45 (4H, partially masked signal), 3.57 (2H, t), 3.68 (2H, t), 5.08 (1H, d), 5.53 (1H, d), 6.58 (1H, d), 6.86 (1H, d), 7.02 (1H, d), 7.75-7.68 (3H, m), 8.27 (1H, d), 8.39 (1H, d). |
| 153 | 340.24 | 3 | (DMSO) 1.09 (3H, t), 1.90-1.85 (2H, m), 2.26 (3H, s), 2.50-2.40 (4H, masked signals), 2.58 (2H, t), 3.58 (2H, t), 3.70 (2H, t), 6.84 (1H, d), 6.96 (1H, d), 7.52 (2H, s), 7.68 (1H, t), 8.03 (1H, d), 8.13 (1H, d). |
| 158 | 352 | 3 | (d6-DMSO, 400 MHz) 1.48-1.56 (2H, m), 1.81-1.84 (2H, m), 2.00 (2H, brs), 2.09 (2H, d), 2.87 (2H, t), 3.07-3.11 (2H, m), 3.36 (1H, brs), 3.53 (2H, brs), 4.36 (2H, d), 6.70 (1H, dd), 7.11 (1H, d), 7.17 (1H, d), 7.79 (1H, t), 7.91 (2H, brs), 8.18 (1H, d), 8.26 (1H, dd), 9.48 (1H, s) |
| 159 | 312 | 3 | (d6-DMSO, 400 MHz) 1.39-1.48 (2H, m), 2.01 (2H, d), 2.58 (3H, t), 2.89 (2H, t), 3.25 (1H, brs), 4.33 (2H, d), 6.70 (1H, m), 7.10 (1H, d), 7.15 (1H, d), 7.78 (1H, t), 7.94 (2H, brs), 8.18 (1H, d), 8.25-8.27 (1H, m), 8.45 (2H, brs) |
| 160 | 388.24 | 4 | (DMSO) 1.82 (2H, m), 2.55-2.53 (2H, m), 2.66 (2H, m), 3.63-3.60 (4H, m), 3.68 (2H, m), 6.53 (1H, dd), 6.84 (1H, d), 6.94 (1H, d), 7.31-7.22 (5H, m), 7.70-7.66 (3H, m), 8.07 (1H, d), 8.20 (1H, d). |
| 164 | 324 | 3 | (d6-DMSO, 400 MHz) 1.44-1.50 (2H, m), 1.88-1.91 (2H, m), 2.94 (2H, t), 3.36 (1H, brs), 4.30 (2H, d), 5.08 (1H, d), 5.57 (1H, d), 6.60 (1H, dd), 7.12-7.15 (2H, m), 7.76-7.81 (5H, m), 8.32 (1H, d), 8.42 (1H, d) |
| 167 | 400.21 | 4 | (DMSO) 1.77-1.70 (2H, m), 2.66 (2H, t), 2.83 (2H, t), 3.70-3.56 (4H, m), 6.88 (1H, d), 7.17-6.93 (3H, m), 7.23-7.20 (1H, m), 7.35-7.31 (2H, m), 7.53-7.49 (2H, m), 7.70 (1H, t), 7.78 (2H, s), 8.41 (1H, d), 8.53 (1H, d). |
| 168 | 413.16 | 3 | (DMSO) 1.57 (2H, m), 2.09 (1H, s), 2.57-2.50 (2H, partially masked signal), 2.75 (2H, m), 3.61-3.56 (4H, m), 6.64 (1H, s), 6.89 (1H, d), 6.97-6.94 (1H, m), 7.08-7.02 (2H, m), 7.31 (1H, d), 7.46 (1H, d), 7.71 (1H, t), 7.78 (2H, s), 8.62 (1H, s), 8.77 (1H, d), 11.39 (1H, s). |
| 169 | 389.18 | 3 | (DMSO) 1.61-1.59 (2H, m), 2.57 (2H, t), 2.75 (2H, t), 3.62-3.55 (4H, m), 5.11 (2H, br s), 6.49 (1H, dd), 6.61 (1H, d), 6.65 (1H, s), 6.85 (1H, d), 6.99 (1H, d), 7.03 (1H, t), 7.68 (1H, t), 7.73 (2H, s), 8.35 (1H, d), 8.46 (1H, d). |
| 170 | 389.19 | 3 | (DMSO) 1.64-1.62 (2H, m), 2.59 (2H, t), 2.76 (2H, t), 3.66-3.57 (4H, m), 5.14 (2H, br s), 6.58 (2H, d), 6.84 (1H, d), 6.97 (1H, d), 7.15 (2H, d), 7.61 (2H, s), 7.68 (1H, t), 8.27-8.25 (1H, m), 8.46-8.44 (1H, m). |
| 171 | 390.18 | 3 | (DMSO) 1.61-1.58 (2H, m), 2.57-2.54 (2H, m), 2.74 (2H, t), 3.64-3.55 (4H, m), 6.79 (2H, d), 6.84 (1H, d), 6.99 (1H, d), 7.29 (2H, d), 7.70-7.66 (3H, m), 8.33 (1H, d), 8.48 (1H, d), 9.51 (1H, br s). |
| 172 | 390.18 | 3 | (DMSO) 1.62-1.59 (2H, m), 2.58 (2H, t), 2.77 (2H, t), 3.64-3.57 (4H, m), 6.69 (1H, dd), 6.87-6.85 (2H, m), 6.92 (1H, t), 7.02-7.00 (1H, m), 7.69 (1H, t), 7.77 (2H, s), 8.39 (1H, d), 8.52 (1H, d). |

TABLE 2-continued

| No. | M + 1 (obs) | RT (min) | 1H-NMR |
|---|---|---|---|
| 179 | 413.17 | 3 | (DMSO) 1.93 (2H, m), 3.06 (2H, m), 3.17 (2H, m), 3.68 (2H, t), 3.90 (2H, t), 7.02-6.96 (2H, m), 7.08 (1H, d), 7.13 (1H, t), 7.43 (1H, d), 7.54 (1H, d), 7.61 (1H, d), 7.69 (2H, s), 7.79 (1H, t), 8.30 (1H, d), 8.59 (1H, d), 11.30 (1H, s). |
| 180 | 284 | 6 | DMSO-d6 3.15-3.20 (4H, m), 3.65-3.70 (4H, m), 6.65-6.69 (1H, dd), 7.16-7.18 (2H, d), 7.80-7.90 (3H, m), 8.12-8.14 (1H, d), 8.24-8.26 (1H, d), 8.70-8.80 (2H, s). |
| 181 | 404.19 | 3 | (DMSO) 1.60 (2H, m), 2.57 (2H, t), 2.72 (2H, t), 3.64-3.56 (4H, m), 4.51 (3H, s), 6.86 (1H, d), 7.02 (1H, d), 7.24 (1H, d), 7.37-7.33 (2H, m), 7.45 (1H, s), 7.69 (1H, t), 7.78 (2H, s), 8.49-8.47 (1H, m), 8.57 (1H, d). |
| 182 | 388.22 | 3 | (DMSO) 1.60-1.57 (2H, m), 2.32 (3H, s), 2.55 (2H, t), 2.73 (2H, t), 3.62-3.56 (4H, m), 6.85 (1H, d), 7.02 (1H, d), 7.11 (1H, m), 7.28 (2H, d), 7.32 (1H, s), 7.68 (1H, t), 7.77 (2H, s), 8.46 (1H, d), 8.56 (1H, d). |
| 183 | 363.19 | 3 | (DMSO at 110° C.) 1.73-1.67 (2H, m), 2.71 (2H, t), 2.83 (2H, t), 3.62 (2H, t), 3.67 (2H, t), 6.07 (1H, s), 6.19 (1H, s), 6.73 (1H, s), 6.83 (1H, d), 7.01 (1H, d), 7.14 (2H, s), 7.69-7.65 (1H, m), 8.36 (1H, d), 8.50 (1H, d). |
| 185 | 378.24 | 4 | (DMSO) 1.57-1.54 (2H, m), 1.68-1.66 (2H, m), 1.90 (2H, m), 2.10 (2H, m), 2.22 (2H, m), 2.98 (2H, m), 3.06 (2H, m), 3.67 (2H, t), 3.78 (2H, m), 5.92 (1H, m), 6.93 (1H, d), 7.03 (1H, d), 7.64 (2H, s), 7.74 (1H, t), 8.13 (1H, d), 8.33 (1H, d). |
| 186 | 404.15 | 3 | (DMSO) 1.91 (2H, m), 3.09 (2H, m), 3.18 (2H, m), 3.64 (2H, m), 3.887 (2H, m), 6.98 (3H, d), 7.14 (1H, d), 7.46 (2H, d), 7.79-7.76 (3H, m), 8.44 (1H, s), 8.55 (1H, s). |
| 187 | 402.18 | 3 | (DMSO) 1.97 (2H, m), 2.76-2.71 (4H, m), 3.07 (2H, t), 3.15 (2H, t), 3.68 (2H, t), 3.83-3.81 (2H, m), 6.94 (1H, d), 6.97 (1H, d), 7.16-7.15 (3H, m), 7.26-7.22 (2H, m), 7.54 (2H, s), 7.73 (1H, t), 7.98 (1H, d), 8.07 (1H, d). |
| 188 | 388.22 | 3 | (DMSO) 1.71-1.66 (2H, m), 2.64 (2H, t), 2.77 (2H, t), 3.53 (2H, t), 3.58 (2H, t), 3.78 (2H, s), 6.81 (1H, d), 6.92 (1H, d), 7.18-7.12 (3H, m), 7.27-7.24 (2H, m), 7.59 (2H, s), 7.64 (1H, t), 8.07 (1H, d), 8.15 (1H, d). |
| 190 | 403.21 | 3 | (DMSO) 1.77-1.73 (2H, m), 2.69 (2H, t), 2.84 (2H, t), 3.67-3.60 (4H, m), 4.10 (2H, d), 5.69 (1H, br m), 6.74 (1H, d), 6.80 (1H, d), 6.93-6.91 (2H, m), 7.34-7.18 (6H, m), 7.61 (1H, t), 7.83 (1H, d). |
| 191 | 298 | 7 | DMSO-d6 1.20-1.22 (3H, d), 3.00-3.05 (1H, m), 3.14-3.20 (2H, m), 3.30-3.35 (2H, m), 4.05-4.10 (2H, d), 4.65-4.70 (2H, m), 6.67-6.70 (1H, t), 7.09-7.16 (2H, dd), 7.80-7.90 (3H, m), 8.11-8.13 (1H, d), 8.24-8.26 (1H, d), 8.55-8.65 (1H, m), 9.00-9.10 (1H, m). |
| 192 | 310 | 7 | DMSO-d6 1.80-1.95 (4H, m), 3.14-3.18 (2H, d), 4.05-4.09 (2H, d), 4.12-4.17 (2H, s), 6.64-6.67 (1H, t), 7.06-7.08 (1H, d), 7.15-7.17 (1H, d), 7.80-7.84 (3H, m), 8.10-8.12 (1H, d), 8.25 (1H, d), 8.85-9.00 (2H, m). |
| 193 | 340 | 8 | DMSO-d6 0.81-0.88 (6H, dd), 1.39-1.46 (2H, m), 1.63-1.70 (1H, m), 2.89-2.95 (1H, t), 3.10-3.34 (4H, m), 4.26-4.29 (1H, d), 4.36-4.40 (1H, d), 6.69-6.73 (1H, t), 7.22-7.25 (2H, m), 7.83-7.87 (1H, t), 7.90-8.10 (2H, br s), 8.23-8.28 (2H, m), 8.80-8.88 (1H, m), 8.95-9.05 (1H, m). |
| 194 | 326 | 8 | DMSO-d6 0.93-0.99 (6H, dd), 1.83-1.90 (1H, m), 2.90-2.96 (1H, t), 3.03-3.21 (3H, m), 3.33-3.36 (1H, d), 4.28-4.31 (1H, d), 4.42-4.46 (1H, d), 6.69-6.73 (1H, t), 7.23-7.25 (2H, m), 7.83-7.87 (1H, t), 7.90-8.10 (2H, br s), 8.26-8.28 (1H, d), 8.77-8.85 (2H, m). |
| 195 | 364 | 8 | DMSO-d6 3.15-3.20 (4H, m), 3.70-3.75 (4H, m), 7.19-7.26 (2H, dd), 7.80-7.90 (3H, m), 8.33 (1H, s), 8.40 (1H, s), 8.75-8.85 (2H, s). |
| 199 | 363.19 | 3 | (DMSO) (mixture of rotamers) 1.73-1.66 (1.5H, m), 2.63 (1.5H, t), 3.22 (0.5H, m), 3.43 (0.5H, m), 3.66-3.59 (4H, m), 6.20 (1H, s), 6.75 (1H, d), 6.84 (1H, d), 7.01-6.91 (2H, m), 7.52 (2H, s), 7.68 (1H, t), 8.20-8.17 (1H, m), 8.48 (1H, s), 10.87 (1H, s). |
| 200 | 430.15 | 4 | (DMSO) 1.43 (2H, m), 2.33 (2H, m), 2.61 (2H, m), 3.55-3.49 (4H, m), 6.80 (1H, d), 7.02 (1H, d), 7.42-7.35 (2H, m), 7.72-7.64 (2H, m), 7.75 (1H, s), 7.85 (2H, s), 8.05 (1H, d), 8.42 (1H, d), 8.48 (1H, d). |
| 201 | 380.14 | 3 | (DMSO) (mixture of rotamers)1.65-1.59 (2H, m), 2.57 (1.5H, t), 2.73 (1.5H, m), 3.16 (0.5H, m), 3.37 (0.5H, m), 3.61-3.56 (4H, m), 6.91-6.84 (1H, m), 7.05-7.01 (1H, m), 7.35 (1H, d), 7.71-7.59 (5H, m), 8.44-8.42 (1H, m), 8.64 (1H, s). |
| 202 | 310 | 7 | DMSO-d6 3.10-3.20 (4H, m), 3.65-3.70 (4H, m), 5.23-5.26 (1H, d), 5.72-5.77 (1H, d), 6.63-6.70 (1H, dd), 7.24-7.26 (1H, d), 7.35-7.37 (1H, d), 7.86-7.90 (1H, t), 8.20-8.35 (1H, br s), 8.43 (1H, s), 8.60-8.65 (1H, s), 9.20-9.30 (2H, s). |
| 204 | 296 | 6 | DMSO-d6 1.96-1.99 (1H, d), 2.20-2.23 (1H, d), 3.20-3.35 (2H, m), 3.55-3.65 (3H, m), 4.50-4.55 (1H, s), 4.87 (1H, s), 6.67-6.70 (1H, dd), 6.89-6.91 (1H, d), 7.13-7.15 (1H, d), 7.70-7.85 (3H, m), 8.16-8.19 (1H, d), 8.30-8.32 (1H, d), 8.60-8.70 (1H, s), 9.05-9.15 (1H, s). |

TABLE 2-continued

| No. | M + 1 (obs) | RT (min) | 1H-NMR |
|---|---|---|---|
| 205 | 312 | 7 | DMSO-d6 1.25-1.27 (6H, d), 2.79-2.86 (2H, t), 3.30-3.40 (2H, s), 4.41-4.44 (2H, d), 6.70-6.73 (1H, t), 7.20-7.26 (1H, dd), 7.83-7.95 (3H, m), 8.20-8.21 (1H, d), 8.27-8.29 (1H, d), 8.55-8.65 (1H, m), 9.10-9.20 (1H, m). |
| 206 | 360 | 8 | DMSO-d6 3.05-3.15 (4H, m), 3.15-3.25 (4H, m), 7.20-7.23 (1H, d), 7.32-7.39 (2H, m), 7.46-7.50 (2H, t), 7.58-7.60 (1H, d), 7.86-7.90 (1H, t), 8.05-8.25 (2H, br s), 8.65-8.69 (2H, d), 9.10-9.15 (1H, s). |
| 207 | 399 | 8 | 1H (CD3OD) 3.05-3.08 (4H, m), 3.72-3.78 (4H, m), 7.15-7.19 (1H, t), 7.25-7.28 (2H, m), 7.51-7.53 (1H, d), 7.59-7.61 (1H, d), 7.67 (1H, s), 7.70-7.73 (1H, d), 7.91-7.95 (1H, t), 8.46 (1H, s), 9.47 (1H, s). |
| 208 | 298 | 7 | DMSO-d6 1.23-1.25 (3H, d), 2.91-2.97 (1H, m), 3.06-3.17 (2H, m), 3.30-3.35 (2H, m), 4.27-4.31 (2H, d), 6.63-6.66 (1H, t), 7.15-7.20 (2H, dd), 7.81-7.85 (3H, m), 8.09-8.11 (1H, d), 8.24-8.26 (1H, d), 8.55-8.65 (1H, m), 8.95-9.00 (1H, m). |
| 210 | 427.18 | 3 | (DMSO) 1.65 (1H, m), 2.60 (2H, t), 2.80 (2H, t), 3.64 (4H, m), 3.80 (3H, s), 6.86 (1H, d), 6.98 (1H, t), 7.03 (1H, t), 7.19 (1H, t), 7.47 (1H, d), 7.57-7.55 (2H, m), 7.65 (2H, s), 7.70 (1H, t), 8.31 (1H, d), 8.55 (1H, d). |
| 211 | 324 | 8 | DMSO-d6 1.55-1.83 (1H, m), 1.88-2.20 (3H, m), 2.90-3.20 (3H, m), 3.25-3.35 (1H, m), 3.42-3.52 (1H, m), 3.55-3.70 (2H, m), 4.45-4.50 (1H, dt), 4.66-4.69 (1H, d), 6.68-6.72 (1H, dd), 7.11-7.25 (2H, m), 7.80-8.05 (3H, m), 8.15-8.17 (1H, d), 8.25-8.27 (1H, d). |
| 214 | 360 | 9 | DMSO-d6 3.20-3.45 (5H, m), 4.40-4.50 (3H, m), 6.57-6.60 (1H, m), 7.19-7.21 (1H, d), 7.28-7.30 (1H, d), 7.45-7.60 (4H, m), 8.15-8.25 (2H, m), 9.15-9.25 (1H, m), 9.45-9.55 (1H, m). |
| 215 | 374 | 9 | DMSO-d6 2.80-2.87 (1H, m), 2.90-3.05 (2H, m), 3.10-3.15 (1H, m), 3.18-3.25 (1H, m), 4.15-4.22 (1H, m), 6.55-6.60 (1H, m), 7.08-7.10 (1H, d), 7.15-7.30 (6H, m), 7.80-8.05 (3H, m), 8.25-8.30 (1H, d), 8.90-9.05 (1H, m). |
| 216 | 298 | 8 | DMSO-d6 2.84 (3H, s), 3.00-3.20 (4H, m), 3.45-3.50 (2H, m), 3.45-3.50 (2H, m), 4.30-4.40 (2H, m), 6.69-6.72 (1H, m), 7.19-7.22 (2H, m), 7.83-8.00 (2H, m), 8.16-8.18 (1H, d), 8.25-8.27 (1H, d), 9.85-9.95 (1H, m), 8.15-8.17 (1H, d), 8.25-8.27 (1H, m). |
| 218 | 312 | 7 | DMSO-d6 1.15-1.25 (4H, dd), 2.80-2.90 (1H, m), 3.15-3.30 (4H, m), 4.23-4.26 (1H, m), 4.68-4.75 (1H, m), 6.64-6.67 (1H, dd), 7.11-7.14 (2H, m), 7.70-7.85 (3H, m), 8.07-8.09 (1H, d), 8.46-8.46 (1H, d), 8.40-8.50 (1H, m), 9.05-9.15 (1H, m). |
| 219 | 450 | 10 | DMSO-d6 0.81-0.88 (6H, dd), 1.35-1.40 (1H, m), 1.45-1.52 (1H, m), 2.90-3.15 (2H, m), 3.70-3.85 (2H, m), 4.05-4.40 (2H, m), 4.65-4.70 (1H, m), 6.62-6.66 (1H, m), 7.10-7.15 (2H, m), 7.72 (1H, s), 7.79-7.83 (1H, t), 8.11-8.14 (1H, d), 8.29-8.31 (1H, d). |
| 220 | 327.17 | 2 | (DMSO) 1.77-1.76 (2H, m), 2.56 (3H, d), 3.50 (1H, t), 3.73-3.63 (4H, m), 6.82 (1H, d), 6.88 (1H, d), 6.95-6.94 (2H, m), 7.33-7.30 (1H, m), 7.69-7.64 (1H, m), 7.82 (1H, d). |
| 222 | 312 | 7 | CD3OD 1.32-1.34 (3H, d), 1.42-1.44 (3H, d), 3.15-3.20 (1H, m), 3.42-3.59 (2H, m), 3.76-3.79 (1H, m), 4.12-4.16 (1H, d), 4.62-4.70 (1H, m), 6.88-6.92 (1H, t), 7.13-7.15 (1H, d), 7.35-7.37 (1H, d), 7.84-7.88 (1H, t), 8.19-8.21 (1H, d), 8.57-8.59 (1H, d). |
| 223 | 298 | 7 | CD3OD 1.38-1.40 (3H, d), 3.00-3.05 (1H, m), 3.20-3.25 (2H, m), 3.45-3.55 (2H, m), 4.40-4.45 (2H, d), 6.90-6.94 (1H, t), 7.21-7.23 (1H, d), 7.37-7.39 (1H, d), 7.85-7.89 (1H, t), 8.19-8.21 (1H, d), 8.61-8.63 (1H, d). |
| 224 | 394 | 8 | DMSO-d6 3.50-3.60 (8H, m), 3.65-3.75 (2H, m), 6.78-6.81 (1H, m), 7.14-7.19 (2H, m), 7.79-7.83 (1H, t), 8.00-8.10 (2H, m), 8.26-8.27 (1H, d), 8.32-8.34 (1H, d). |
| 225 | 340 | 8 | DMSO-d6 0.98 (9H, s), 2.90-3.00 (1H, m), 3.05-3.30 (4H, m), 4.30-4.35 (1H, m), 4.50-4.55 (1H, m), 6.60-6.63 (1H, dd), 7.18-7.22 (2H, m), 7.70-7.75 (2H, s), 7.80-7.85 (1H, m), 8.10-8.15 (1H, d), 8.23-8.25 (1H, d), 9.45-9.50 (1H, s). |
| 226 | 312 | 7 | CD3OD 1.45 (6H, s), 3.37-3.39 (2H, t), 3.70 (2H, s), 3.84-3.87 (2H, t), 6.95-6.98 (1H, t), 7.20-7.22 (1H, d), 7.37-7.38 (1H, d), 7.84-7.88 (1H, t), 8.19-8.21 (1H, d), 8.66-8.69 (1H, d). |
| 231 | 326 | 8 | DMSO-d6 0.93-0.99 (6H, dd), 1.83-1.90 (1H, m), 2.90-2.96 (1H, t), 3.03-3.21 (3H, m), 3.33-3.36 (1H, d), 4.28-4.31 (1H, d), 4.42-4.46 (1H, d), 6.69-6.73 (1H, t), 7.23-7.25 (2H, m), 7.83-7.87 (1H, t), 7.90-8.10 (2H, br s), 8.26-8.28 (2H, m), 8.77-8.85 (2H, m). |
| 232 | 418 | 10 | DMSO-d6 0.80-0.82 (3H, d), 0.88-0.89 (3H, d), 1.40-1.50 (2H, m), 1.65-1.75 (1H, m), 2.90-2.95 (1H, m), 3.05-3.35 (4H, m), 4.29-4.32 (2H, m), 4.38-4.41 (2H, m), 7.24-7.29 (1H, t), 7.70-7.78 (2H, br s), 7.84-7.88 (1H, t), 8.34 (1H, s), 8.40 (1H, s), 8.65-8.75 (1H, s), 8.85-8.95 (1H, s). |
| 233 | 366 | 9 | DMSO-d6 0.56-0.57 (3H, d), 0.62-0.64 (3H, d), 1.13-1.18 (2H, m), 1.45-1.55 (1H, m), 2.65-2.70 (1H, m), 2.85-3.15 (4H, m), 4.00-4.18 (2H, m), 4.85-4.89 (1H, d), 5.35-5.40 (1H, d), 6.32-6.40 (1H, dd), 7.01-7.05 (1H, t), 7.50-7.65 (1H, m), 8.09 (1H, s), 8.20 (1H, s), 8.40-8.50 (1H, s), 8.65-8.70 (1H, s). |

TABLE 2-continued

| No. | M + 1 (obs) | RT (min) | 1H-NMR |
|---|---|---|---|
| 234 | 312 | 7 | DMSO-d6 1.23-1.25 (6H, d), 1.75-1.85 (1H, m), 3.40-3.50 (2H, masked signal), 4.40-4.43 (2H, d), 6.60-6.63 (1H, m), 7.13-7.15 (1H, d), 7.20-7.22 (1H, d), 7.72-7.78 (1H, s), 7.80-7.85 (1H, t), 8.05-8.09 (1H, d), 8.24-8.26 (1H, d), 8.45-8.55 (1H, s), 9.02-9.08 (1H, s). |
| 235 | 312 | 7 | DMSO-d6 1.15-1.32 (6H, dd), 2.80-2.90 (1H, m), 3.15-3.30 (4H, m), 4.20-4.25 (1H, dd), 5.65-5.75 (1H, m), 6.60-6.65 (1H, dd), 7.09-7.14 (2H, m), 7.75-7.85 (3H, m), 8.08-8.09 (1H, d), 8.24-8.26 (1H, d), 8.40-8.50 (1H, m), 9.05-9.15 (1H, s). |
| 237 | 326 | 8 | DMSO-d6 0.96-0.98 (3H, d), 2.22-2.27 (1H, s), 2.30-2.40 (1H, t), 2.62-2.73 (3H, m), 2.88-2.95 (1H, d), 4.00-4.10 (1H, dd), 5.04-5.09 (1H, d), 5.50-5.57 (1H, d), 6.55-6.65 (1H, dd), 7.03-7.06 (1H, d), 7.08-7.12 (1H, d), 7.70-7.75 (3H, m), 8.38 (1H, s), 8.43 (1H, s). |
| 238 | 324 | 8 | DMSO-d6 0.96-0.98 (3H, d), 2.22-2.27 (1H, s), 2.30-2.40 (1H, t), 2.62-2.73 (3H, m), 2.88-2.95 (1H, d), 4.00-4.10 (1H, dd), 5.04-5.09 (1H, d), 5.50-5.57 (1H, d), 6.55-6.65 (1H, dd), 7.03-7.06 (1H, d), 7.08-7.12 (1H, d), 7.70-7.75 (3H, m), 8.38 (1H, s), 8.43 (1H, s). |
| 239 | 416 | 10 | DMSO-d6 0.73-0.76 (6H, m), 1.15-1.30 (2H, m), 1.45-1.52 (1H, m), 2.75-2.85 (1H, m), 3.10-3.30 (4H, m), 4.25-4.35 (2H, m), 7.22-7.25 (1H, d), 7.29-7.34 (2H, m), 7.38-7.45 (1H, t), 7.55-7.57 (1H, d), 7.75-7.85 (3H, m), 8.52 (1H, d), 8.60-8.65 (2H, m), 8.80-8.85 (1H, m). |
| 240 | 438 | 10 | DMSO-d6 3.20-3.45 (5H, m), 4.40-4.50 (3H, m), 7.30-7.33 (2H, t), 7.45-7.55 (5H, m), 7.75-7.88 (3H, m), 8.29 (1H, d), 8.45 (1H, d), 9.15-9.25 (1H, m), 9.50-9.55 (1H, m). |
| 241 | 386 | 9 | DMSO-d6 3.25-3.40 (4H, masked signal), 4.42-4.50 (3H, m), 5.00-5.03 (1H, d), 5.53-5.57 (1H, d), 6.48-6.55 (1H, m), 7.25-7.30 (2H, dd), 7.42-7.52 (5H, m), 7.75-7.80 (2H, s), 7.84-7.88 (1H, t), 8.30 (1H, d), 8.39 (1H, d), 9.15-9.20 (1H, s), 9.40-9.50 (1H, s). |
| 242 | 332 | 7 | DMSO-d6 2.00-2.05 (2H, m), 3.15-3.20 (2H, m), 3.25-3.30 (2H, m), 3.60-3.65 (2H, m), 3.70-3.75 (2H, m), 6.666-6.698 (1H, dd), 7.34-7.36 (1H, d), 7.75-7.85 (2H, br s), 7.98-8.00 (1H, d), 8.18-8.20 (1H, d), 8.25-8.27 (1H, d), 8.60-8.70 (2H, s). |
| 243 | 312 | 7 | DMSO-d6 0.90-0.95 (3H, t), 1.55-1.65 (1H, m), 12.90-2.97 (1H, m), 3.05-3.20 (2H, m), 3.30-3.40 (2H, m), 4.25-4.40 (2H, m), 6.60-6.65 (1H, m), 7.15-7.20 (2H, m), 7.75-7.85 (3H, m), 8.13-8.17 (1H, d), 8.22-8.25 (1H, d), 8.15-8.23 (1H, d), 8.35-8.45 (1H, s). |
| 244 | 416 | 11 | DMSO-d6 2.08 (2H, s), 2.20 (3H, s), 2.31 (6H, s), 2.43-2.46 (3H, m), 3.40-3.45 (4H, m), 6.55-6.60 (1H, m), 6.81 (2H, s), 6.98-7.05 (2H, t), 7.65-7.75 (3H, m), 8.05-8.10 (1H, d), 8.20 (1H, d). |
| 245 | 332 | 8 | DMSO-d6 2.00-2.10 (2H, m), 3.15-3.250 (4H, m), 3.65-3.70 (2H, m), 3.89-3.92 (2H, m), 7.00-7.02 (1H, d), 7.15-7.17 (1H, d), 7.76-7.80 (1H, t), 8.30 (1H, s), 8.42 (1H, s), 9.15-9.22 (2H, s). |
| 246 | 352.22 | 3 | (DMSO) 1.73-1.67 (5H, m), 1.80 (3H, s), 2.64 (2H, t), 2.79 (2H, t), 3.65-3.57 (4H, m), 6.03 (1H, s), 6.82 (1H, d), 6.92 (1H, d), 7.67-7.63 (3H, m), 7.99 (1H, d), 8.13 (1H, d). |
| 248 | 284 | 3 | (d6-DMSO, 400 MHz) 2.92 (2H, d), 3.68 (2H, t), 3.99 (2H, t), 6.54-6.60 (2H, m), 6.99 (1H, d), 7.60-7.70 (3H, m), 8.12 (1H, d), 8.22 (1H, brs) |
| 249 | 361 | 8 | DMSO-d6 3.15-3.30 (2H, m), 3.35-3.50 (2H, m), 4.40-4.50 (4H, masked), 6.64-6.68 (1H, t), 7.25-7.27 (1H, d), 7.31-7.33 (1H, d), 7.85-7.89 (1H, t), 8.01-8.03 (1H, d), 8.22-8.24 (1H, d), 8.28-8.30 (1H, d), 8.67-8.69 (1h, d), 8.76 (1H, s), 9.40-9.65 (2H, m). |
| 250 | 374 | 9 | DMSO-d6 2.80-2.87 (1H, m), 2.90-3.05 (2H, m), 3.10-3.15 (1H, m), 3.18-3.25 (1H, m), 4.15-4.22 (1H, m), 6.55-6.60 (1H, m), 7.08-7.10 (1H, d), 7.15-7.30 (6H, m), 7.80-8.05 (3H, m), 8.25-8.30 (1H, d), 8.90-9.05 (1H, m). |
| 253 | 360 | 9 | DMSO-d6 3.20-3.45 (4H, m), 4.42-4.52 (3H, m), 6.11 (3H, s), 6.51-6.55 (1H, m), 7.15-7.17 (1H, d), 7.26-7.28 (1H, d), 7.45-7.55 (5H, m), 7.63-7.68 (2H, s), 7.82-7.86 (1H, t), 8.05-8.08 (1H, d), 8.20-8.22 (1H, d), 9.10-9.40 (2H, m). |
| 254 | 360 | 9 | |
| 255 | 281 | 6 | DMSO-d6 2.70-2.77 (2H, s), 3.25-3.35 (2H, s), 3.77-3.85 (2H, s), 6.72-6.77 (1H, s), 6.90-6.95 (1H, m), 7.85-7.95 (2H, dd), 8.10-8.14 (1H, t), 8.30-8.55 (4H, m), 9.25-9.35 (2H, s). |
| 257 | 283 | 2 | DMSO-d6 1.90-2.05 (4H, m), 2.90-3.05 (2H, m), 3.06-3.15 (1H, m), 3.30-3.35 (2H, m), 7.08-7.11 (1H, t), 7.62-7.64 (1H, d), 7.90-7.92 (1H, d), 8.06-8.10 (1H, t), 8.36-8.38 (1H, d), 8.55-8.75 (3H, m), 9.05-9.20 (2H, m). |
| 258 | 394 | 10 | DMSO-d6 3.15-3.25 (1H, t), 3.30-3.40 (1H, masked), 3.45-3.50 (2H, m), 4.45-4.50 (1H, d), 4.55-4.60 (1H, d), 4.65-4.75 (1H, m), 6.57-6.60 (1H, dd), 7.18-7.20 (1H, d), 7.25-7.27 (1H, d), 7.48-7.60 (3H, m), 7.70-7.85 (4H, m), 8.09-8.11 (1H, d), 8.21-8.23 (1H, d), 8.35-8.45 (1H, s), 8.55-8.60 (1H, s). |
| 259 | 452 | 9 | DMSO-d6 3.20-3.40 (4H, m), 4.38-4.50 (3H, m), 6.83-6.86 (1H, t), 6.90-6.92 (1H, d), 7.13-7.17 (1H, d), 7.20-7.22 (1H, d), 7.25-7.27 (1H, d), 7.45 (5H, s), 7.81-7.86 (1H, m), 8.36 (1H, s), 8.44 (1H, s), 9.10-9.20 (1H, s), 9.40-9.45 (1H, s), 9.55-9.58 (1H, s). |

TABLE 2-continued

| No. | M + 1 (obs) | RT (min) | 1H-NMR |
|---|---|---|---|
| 260 | 452 | 9 | |
| 261 | 452 | 9 | |
| 262 | 436 | 4 | (d6-DMSO, 400 MHz) 3.24-3.32 (3H, m), 3.40-3.42 (1H, m), 4.40-4.50 (3H, m), 7.23-7.31 (4H, m), 7.34-7.50 (7H, m), 7.77-7.79 (2H, m), 7.85 (1H, d), 7.89 (2H, t), 8.47 (1H, d), 8.58 (1H, d), 9.21 (1H, brs), 9.47 (1H, brd) |
| 263 | 442 | 4 | (d6-DMSO, 400 MHz) 3.27-3.36 (3H, m), 3.45-3.47 (1H, m), 4.43-4.52 (4H, m), 7.10 (1H, dd), 7.29-7.33 (3H, m), 7.43-7.50 (6H, m), 7.87-7.90 (3H, m), 8.41 (1H, d), 8.60 (1H, d), 9.18 (1H, brs, 9.46 (1H, brd) |
| 264 | 442 | 4 | (d6-DMSO, 400 MHz) 3.06-3.12 (3H, m), 3.20-3.21 (1H, m), 4.12-4.29 (4H, m), 7.09 (2H, dd), 7.18 (6H, brs), 7.42 (1H, dd), 7.45 (1H, s), 7.57 (1H, brs), 7.66 (1H, t), 8.27 (1H, d), 8.44 (1H, d), 8.96 (1H, brs), 9.25 (1H, brd) |
| 265 | 492 | 4 | (d6-DMSO, 400 MHz) 3.06-3.15 (3H, m), 3.22-3.24 (1H, m), 4.21-4.33 (4H, m), 7.00 (2H, t), 7.08-7.20 (7H, brs), 7.47 (1H, s), 7.59 (1H, d), 7.66-7.74 (4H, m), 8.31 (1H, d), 8.52 (1H, d), 8.95 (1H, brs), 9.21 (1H, brd) |
| 266 | 492 | 4 | (d6-DMSO, 400 MHz) 3.18-3.36 (4H, m), 4.41-4.52 (4H, m), 7.20-7.26 (2H, m), 7.42 (7H, brs), 7.52 (1H, s), 7.72 (1H, d), 7.82-7.88 (3H, m), 8.08 (1H, d), 8.26 (1H, d), 8.50 (1H, d), 9.13 (1H, brs), 9.41 (1H, brd) |
| 267 | 475 | 4 | (d6-DMSO, 400 MHz) 3.26-3.34 (3H, m), 3.38-3.41 (1H, m), 4.37 (1H, t), 4.43-3.54 (2H, m), 6.71 (1H, s), 7.00 (1H, t), 7.09 (1H, t), 7.14 (2H, t), 7.24-7.34 (5H, m), 7.39 (1H, d), 7.81 (1H, brs), 7.92 (1H, t), 8.66 (1H, d), 8.78 (1H, d), 9.14 (1H, brs), 9.38 (1H, d), 11.44 (1H, s) |
| 268 | 475 | 4 | (d6-DMSO, 400 MHz) 3.36-3.48 (3H, m), 3.57 (1H, d), 4.53 (1H, m), 4.66-4.69 (2H, m), 7.25 (1H, t), 7.34 (1H, t), 7.14 (1H, d), 7.46 (1H, d), 7.54-7.58 (5H, m), 7.62 (1H, d), 7.72 (1H, d), 7.77 (1H, s), 7.91 (1H, brs), 8.04 (1H, t), 8.53 (1H, s), 8.74 (1H, s), 9.33 (1H, brs), 9.56 (1H, brs), 11.51 (1H, s) |
| 269 | 461 | 9 | |
| 270 | 461 | 10 | |
| 271 | 461 | 10 | |
| 275 | 437 | 9 | |
| 276 | 476 | 10 | |
| 277 | 425 | 9 | |
| 278 | 528 | 11 | |
| 279 | 374 | 10 | DMSO-d6 1.33-1.35 (3H, d), 3.30-3.40 (3H, m), 4.30-4.40 (3H, m), 4.78-4.85 (1H, s), 6.62-6.65 (1H, m), 7.18-7.24 (2H, m), 7.48-7.53 (3H, m), 7.60-7.62 (2H, d), 7.78-7.90 (3H, m), 8.18-8.23 (1H, m), 9.00-9.10 (1H, s), 9.65-9.75 (1H, s). |
| 281 | 466.21 | 4 | |
| 282 | 466.23 | 3 | |
| 283 | 466.18 | 4 | |
| 284 | 466.21 | 4 | |
| 285 | 466.23 | 4 | |
| 286 | 466.22 | 4 | |
| 287 | 420 | 3 | DMSO-d6 3.22-3.35 (4H, masked multiplet), 3.20-3.25 (6H, d), 4.40-4.45 (2H, m), 4.55-4.60 (1H, m), 6.56-6.59 (1H, m), 7.00-7.12 (4H, m), 7.18-7.24 (2H, dd), 7.75-7.85 (3H, m), 8.12-8.14 (1H, d), 8.21-8.23 (1H, d). |
| 288 | 437 | 3 | DMSO-d6 30.5-3.20 (3H, m), 3.28-3.35 (1H, m), 4.25-4.40 (3H, m), 7.20-7.30 (6H, m), 7.75-7.85 (3H, m), 7.95-8.05 (2H, s), 8.57-8.58 (2H, d), 8.68 (1H, s), 8.79 (1H, s), 9.05-9.15 (1H, s), 9.30-9.37 (1H, s). |
| 289 | 425 | 3 | DMSO-d6 3.13-3.23 (1H, m), 3.30-3.38 (1H, m), 3.32-3.40 (1H, m), 4.25-4.45 (4H, m), 6.41 (1H, s), 6.84 (1H, s), 7.27 (1H, s), 7.32-7.50 (5H, m), 7.89-7.93 (1H, t), 8.15-8.30 (2H, br s), 8.47 (1H, s), 8.78 (1H, s), 9.75-9.85 (1H, m), 10.15-10.25 (1H, m), 11.10-11.15 (1H, s). |
| 290 | 462 | 4 | DMSO-d6 3.20-3.445 (4H, m), 4.40-4.55 (3H, m), 6.95-7.15 (3H, m), 7.20-7.37 (7H, m), 7.40-7.45 (2H, d), 7.50-8.55 (2H, d), 8.40 (1H, s), 8.55 (1H, s), 9.12-9.22 (1H, m), 9.40-9.50 (1H, m). |
| 291 | 464 | 4 | DMSO-d6 2.55-2.70 (4H, m), 3.25-3.40 (3H, m), 3.45-3.50 (1H, m), 4.40-4.53 (3H, m), 7.07-7.32 (7H, m), 7.39-7.44 (2H, d), 7.50-7.52 (2H, d), 7.60-7.85 (3H, m), 8.02 (1H, s), 8.12 (1H, s), 9.20-9.30 (1H, m), 9.45-9.50 (1H, m). |
| 295 | 378 | 4 | DMSO-d6 3.15-3.45 (4H, m), 3.45-3.55 (3H, m) 6.59-6.62 (1H, m), 7.20-7.22 (1H, d), 7.28-7.30 (1H, d), 7.34-7.38 (2H, t), 7.60-7.63 (2H, t), 7.80-7.90 (3H, m), 8.15-8.20 (2H, m), 9.20-9.30 (1H, s), 9.40-9.50 (1H, s). |
| 296 | 390 | 4 | DMSO-d6 3.22-332 (3H, m), 3.40-3.45 (1H, m), 4.40-4.45 (2H, m), 4.55-4.65 (1H, m), 6.58-6.61 (1H, m), 7.07-7.11 (1H, t), 7.14-7.16 (1H, d), 7.19-7.26 (2H, dd), 7.44-7.49 (2H, m), 7.880-7.90 (3H, m), 8.15-8.17 (1H, d), 8.21-8.23 (1H, d), 8.95-9.05 (1H, br s), 9.40-9.45 (1H, m). |

TABLE 2-continued

| No. | M + 1 (obs) | RT (min) | 1H-NMR |
|---|---|---|---|
| 301 | 394 | 4 | DMSO-d6 3.15-3.38 (4H, m), 3.40-3.45 (1H, m), 4.35-4.55 (2H, m), 6.60-6.63 (1H, m), 7.21-7.23 (1H, d), 7.29-7.31 (1H, d), 7.45-7.52 (3H, m), 7.67 (1H, s), 7.80-7.90 (2H, m), 8.15-8.22 (2H, m), 9.20-9.35 (1H, s), 9.50-9.60 (1H, s). |
| 303 | 314 | 3 | (d6-DMSO, 400 MHz) 3.00-3.20 (3H, m), 3.31 (2H, d), 4.30 (2H, d), 6.64 (1H, dd), 7.16 (2H, d), 7.78-7.85 (2H, d), 8.08 (1H, d), 8.26 (1H, dd), 8.70 (1H, brs), 9.02 (1H, brs) |
| 304 | 364 | 3 | Methanol-d4 3.20-3.45 (5H, m), 3.50-3.60 (1H, d), 3.70-3.80 (1H, m), 4.30-4.50 (2H, dd), 6.90-6.92 (1H, m), 7.21-7.23 (1H, d), 7.38-7.40 (1H, d), 7.52 (1H, s), 7.86-7.90 (1H, t), 8.19-8.21 (1H, d), 8.61-8.62 (1H, d), 8.86 (1H, s). |
| 305 | 312 | 3 | (d6-DMSO, 400 MHz) 1.36 (3H, s), 1.65-1.74 (4H, m), 3.23-3.29 (2H, m), 3.99 (1H, d), 6.67 (1H, dd), 7.08 (1H, d), 7.13 (1H, d), 7.77 (1H, t), 7.91 (4H, brs), 8.15 (1h, d), 8.25 (1H, dd) |
| 306 | 374 | 3 | (d6-DMSO, 400 MHz) 2.06 (2H, m), 3.20 (2H, t), 3.93-4.02 (4H, m), 6.64 (1H, dd), 7.08 (1H, d), 7.13 (1H, d), 7.46 (1H, d), 7.53 (2H, t), 7.67 (2H, d), 7.78 (2H, t), 8.09 (1H, d), 8.24-8.28 (4H, m) |
| 307 | 394 | 4 | (1H, DMSO-d6): 3.20-3.37 (3H, m), 3.45-3.50 (1H, m), 4.40-4.55 (3H, m), 6.64-6.67 (1H, m), 7.23-7.25 (1H, d), 7.29-7.31 (1H, d), 7.84-7.88 (1H, t), 7.90-8.10 (2H, br s), 8.23-8.25 (2H, m), 9.35-9.45 (1H, br s), 9.60-9.65 (1H, be s). |
| 308 | 410 | 4 | (1H, DMSO-d6): 3.20-3.50 (4H, m), 4.40-4.55 (3H, m), 6.65-6.68 (1H, m), 7.25-7.26 (1H, d), 7.32-7.35 (1H, d), 7.57-7.65 (3H, m), 7.85-8.10 (6H, br s), 8.27-8.29 (1H, d), 8.27-8.30 (1H, d), 9.40-9.50 (1H, br s), 9.60-9.70 (1H, be s). |
| 309 | 390 | 3 | DMSO-d6 3.10-3.30 (3H, m), 3.35 (1H, d), 4.35-4.43 (3H, t), 6.60-6.63 (1H, m), 6.95-6.97 (1H, d), 7.01-7.03 (1H, d), 7.07 (1H, s), 7.18-7.20 (1H, d), 7.23-7.25 (1H, d), 7.32-7.36 (1H, t), 7.77-7.81 (1H, t), 8.00-8.10 (1H, br s), 8.15-8.17 (1H, d), 8.25-8.27 (1H, d), 9.15-9.25 (1H, s), 9.40-9.50 (1H, s) |
| 310 | 390 | 3 | DMSO-d6 3.10-3.37 (4H, m), 4.30-4.40 (3H, m), 6.56-6.60 (1H, m), 6.96-6.98 (2H, m), 7.15-7.17 (1H, d), 7.21-7.23 (1H, d), 7.38-7.40 (2H, d), 7.76-7.78 (1H, t), 7.90-8.05 (1H, br s), 8.15-8.20 (2H, m), 9.10-9.20 (1H, s), 9.35-9.40 (1H, s) |
| 311 | 376 | 3 | DMSO-d6 3.20-3.35 (3H, m), 3.40-3.45 (1H, d), 4.39-4.50 (3H, m), 6.60-6.64 (1H, m), 6.85-6.88 (1H, d), 6.95-6.99 (2H, m), 7.20-7.30 (3H, m), 7.80-7.95 (3H, m), 8.19-8.24 (2H, m), 9.05-9.15 (1H, br s), 9.40-9.50 (1H, s), 9.75-9.85 (1H, s) |
| 312 | 376 | 3 | DMSO-d6 3.20-3.41 (4H, m), 4.33-4.45 (3H, m), 6.58-6.61 (1H, m), 6.83-6.85 (2H, d), 7.18-7.20 (1H, d), 7.26-7.28 (1H, d), 7.33-7.36 (2H, d), 7.80-7.95 (3H, m), 8.17-8.23 (2H, m), 9.0-9.10 (1H, s), 9.30-9.40 (1H, s), 9.75-9.85 (1H, s) |
| 313 | 428 | 4 | DMSO-d6 3.15-3.40 (4H, m partially masked), 3.35-3.55 (3H, m), 6.50-6.55 (1H, m), 7.11-7.13 (1H, d), 7.20-7.22 (1H, d), 7.45-7.50 (1H, d), 7.80-7.92 (4H, m), 8.05-8.08 (1H, d), 8.21 (1H, d), 9.15-9.25 (1H s), 9.40-9.50 (1H, s) |
| 314 | 428 | 4 | DMSO-d6 3.21-3.51 (4H, m), 3.44-3.53 (2H, m), 3.55-3.65 (1H, m), 6.55-6.58 (1H, m), 7.18-7.22 (1H, t), 7.28-7.30 (1H, d), 7.72-7.96 (5H, m), 8.15-8.20 (2H, m), 9.35-9.45 (1H s), 9.50-9.60 (1H, s) |
| 333 | 312 | 3 | (d6-DMSO, 400 MHz) 1.12-1.21 (1H, m), 1.36-1.52 (3H, m), 1.64-1.67 (1H, m), 1.80-1.83 (1H, m), 2.64 (1H, dd), 2.83-2.89 (1H, m), 4.12-4.21 (2H, m), 6.57-6.62 (1H, m), 6.97 (1H, d), 7.03 (1H, d), 7.68-7.72 (3H, m), 8.12 (1H, dd), 8.22-8.23 (1H, m) |
| 334 | 408.2 | 3 | (DMSO) 0.84 (6H, m), 1.20 (2H, m), 1.91 (1H, m) 2.66 (3H, m), 2.93 (2H, m), 4.20 (2H, m), 6.57 (1H, m), 7.07 (1H, m), 7.43 (1H, m), 7.93 (3H, m), 8.26 (1H, m), |
| 335 | 374 | 3 | (d6-DMSO, 400 MHz) 2.35 (3H, s), 3.17-3.36 (3H, m), 3.44 (1H, d), 4.43-4.51 (3H, m), 6.63 (1H, dd), 7.22 (1H, d), 7.27-7.40 (5H, m), 7.85 (1H, t), 7.99 (1H, brs), 8.23-8.25 (2H, m), 9.25 (1H, d), 9.51 (1H, d) |
| 336 | 374 | 3 | (d6-DMSO, 400 MHz) 2.28 (3H, s), 3.22-3.36 (3H, m), 3.44 (1H, d), 4.43-4.48 (3H, m), 6.63 (1H, dd), 7.22 (1H, d), 7.28-7.31 (3H, m), 7.42 (2H, d), 7.85 (1H, t), 8.00 (2H, brs), 8.23-8.25 (2H, m), 9.24 (1H, brs), 9.51 (1H, d) |
| 337 | 388 | 4 | (d6-DMSO, 400 MHz) 2.45 (6H, brs), 3.43 (3H, brs), 3.76 (1H, t), 4.41 (1H, d), 4.49 (1H, d), 4.60-4.63 (1H, m), 6.62 (1H, t), 7.11 (2H, d), 7.20-7.23 (2H, m), 7.31 (1H, d), 7.85 (1H, t), 8.01 (2H, brs), 8.20-8.24 (3H, m), 9.90 (1H, brs) |
| 339 | 374 | 3 | (d6-DMSO, 400 MHz) 2.22 (3H, s), 3.14 (1H, t), 3.27-3.37 (2H, m), 4.37-4.51 (4H, m), 6.52 (1H, dd), 7.11 (1H, d), 7.20-7.30 (4H, m), 7.51-7.53 (1H, m), 7.75-7.81 (3H, m), 8.04 (1H, d), 8.15 (1H, dd), 9.08 (1H, brs), 9.37 (1H, d) |
| 362 | 299.2 | 2 | |
| 363 | | | |
| 364 | | | |
| 390 | | | |

Intermediate 1

2-Fluoro-N-methoxy-N-methylnicotinamide: TBTU coupling agent (13 g, 40 mmol) was added to a solution of 2-fluoronicotinic acid (5.6 g, 40 mmol), N-methoxy-N-methylamine hydrochloride (4.4 g, 45 mmol) and diisopropylethylamine (16 ml, 0.1 mol) in dichloromethane (100 ml) under nitrogen. The reaction mixture was stirred at room temperature for eighteen hours. It was diluted with more dichloromethane (200 ml), washed with a 2M aqueous hydrochloric acid solution (50 ml), a saturated sodium bicarbonate solution (100 ml), and brine (100 ml). The organic was dried over magnesium sulfate and, after filtration, concentrated in vacuo. The residue was purified by flash chromatography (120 g SiO$_2$, pentane/ethyl acetate) to afford the title compound as a colourless oil (6 g, 80%). 1H NMR (CDCl$_3$): 3.40-3.45 (3H, s), 3.55-3.65 (3H, s), 7.75-7.80 (1H, t), 7.90-7.95 (1H, t), 8.28-8.30 (1H, d).

Intermediate 2

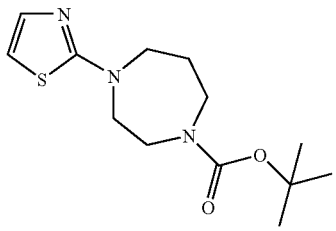

Tert-butyl-4-(thiazol-2-yl)-1,4-diazepane-1-carboxylate: A microwave vial was charged under nitrogen with 2-bromothiazole (825 mg, 5 mmol), NBoc-homopiperazine (1.2 ml, 6 mmol), sodium tert-butoxide (670 mg, 7 mmol), tris(dibenzylideneacetone) dipalladium (46 mg, 0.05 mmol), 2-dicyclohexylphosphino-2',6'-diisopropoxybiphenyl (90 mg, 0.2 mmol) and dry toluene (25 ml). The reaction mixture was stirred in the microwave under the following conditions (145° C., 90 min). The reaction mixture was diluted with ethyl acetate, then washed with brine. It was dried over magnesium sulfate, and after filtration, concentrated in vacuo. The residue was purified by flash chromatography (40 g silica gel; pentane/ethyl acetate) to give the title compound as an oil (400 mg, 30%). 1H NMR (CDCl$_3$): 1.46 (9H, s), 2.03-2.06 (2H, m), 3.35-3.50 (2H, m), 3.55-3.75 (4H, m), 6.51 (1H, d), 7.18-0.19 (1H, d). MS (ES+): 284.

Intermediate 3

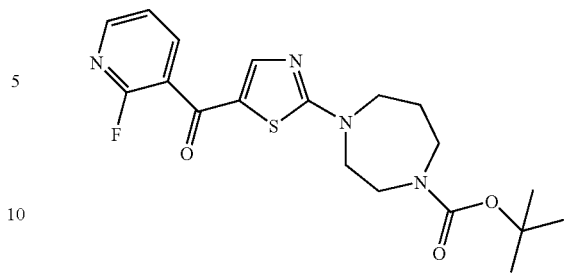

Tert-butyl 4-(5-(2-fluoronicotinoyl)thiazol-2-yl)-1,4-diazepane-1-carboxylate: A 2.5M n-butyl lithium in tetrahydrofuran solution (0.9 ml, 2.25 mmol) was added dropwise to a solution of tert-butyl-4-(thiazol-2-yl)-1,4-diazepane-1-carboxylate (570 mg, 2 mmol) in tetrahydrofuran (7 ml), cooled to −78° C. Thirty minutes later, a solution of 2-fluoro-N-methoxy-N-methylnicotinamide (370 mg, 2 mmol) in tetrahydrofuran (2 ml) added dropwise. The reaction mixture was stirred at −78° C. for one hour, then at 0° C. for an extra hour. It was quenched with a saturated sodium bicarbonate aqueous solution. The reaction mixture was diluted with ethyl acetate, then washed with brine. The organic was dried over magnesium sulfate, then concentrated in vacuo. The residue was purified by flash chromatography (40 g silica gel, pentane/ethyl acetate) to afford the title compound (300 mg, 38%). 1H NMR (CD$_3$OD): 1.42 (9H, s), 1.90-2.00 (2H, M0, 3.45-3.50 (2H, m), 3.65-6.75 (2H, m), 3.80-3.90 (2H, m), 7.46-7.49 (1H, t), 7.67-7.69 (1H, d), 8.10-8.15 (1H, t), 8.39-8.40 (1H, d). MS (ES+): 407.

Example 7

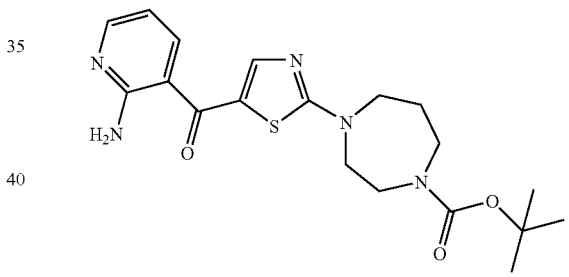

Tert-butyl-4-(5-(2-aminonicotinoyl)thiazol-2-yl)-1,4-diazepane-1-carboxylate: A microwave vial was charged with tert-butyl-4-(5-(2-fluoronicotinoyl)thiazol-2-yl)-1,4-diazepane-1-carboxylate (300 mg, 0.75 mmol) and aqueous ammonium hydroxide (1 ml). The reaction mixture was stirred in the microwave at 110° C. for 25 minutes. The reaction mixture was concentrated in vacuo to afford the title compound (300 mg, 100%). The residue was used in the next step without any further purification. MS (ES+): 405

Example 8

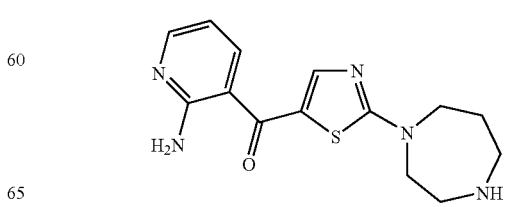

(2-(1,4-diazepan-1yl)thiazol-5-yl)(2-aminopyridin-3-ul)methanone: A solution of tert-butyl 4-(5-(2-aminonicotinoyl)thiazol-2-yl)-1,4-diazepane-1-carboxylate (100 mg, 0.25 mmol) in a dichloromethane/trifluoroacetic acid mixture (2 ml/2 ml) was stirred at room temperature for three hours. The reaction mixture was concentrated in vacuo then purified by Fractionlynx HPLC to afford the title compound as a bis TFA salt (35 mg, 25%). 1H NMR (DMSO-d6): 2.12-2.15 (2H, m), 3.20-3.25 (2H, m), 3.30-3.35 (2H, m), 3.65-3.80 (2H, m), 3.95-4.05 (2H, m), 6.80-6.83 (1H, t), 7.40-7.55 (2H, br s), 7.88 (1H, s), 8.10-8.20 (2H, m), 8.80-8.90 (2H, br s). MS (ES+): 304.

(2-(1,4-diazepan-1yl)thiazol-5-yl)(2-amino-5-bromopyridin-3-ul)methanone: N-bromosuccinimide (45 mg, 0.25 mmol) was added to a solution of tert-butyl 4-(5-(2-aminonicotinoyl)thiazol-2-yl)-1,4-diazepane-1-carboxylate (100 mg, 0.25 mmol) in acetonitrile (3 ml), stirred at room temperature under nitrogen. The reaction mixture was stirred for a further three hours. It was diluted with ethyl acetate (40 ml), washed with a saturated sodium bicarbonate solution (10 ml) and brine (10 ml), the organic was dried on magnesium sulfate then concentrated in vacuo. The residue was aken up in a dichloromethane/trifluoroacetic acid mixture (2 ml/2 ml) and stirred at room temperature for three hours. The reaction mixture was concentrated in vacuo then purified by Fractionlynx HPLC to afford the title compound as a bis TFA salt (10 mg, 10%). 1H NMR (DMSO-d6): (1H, DMSO-d6): 2.12-2.15 (2H, m), 3.20-3.25 (2H, m), 3.30-3.35 (2H, m), 3.60-4.20 (4H, m), 8.54 (1H, s), 8.80-8.83 (3H, m). MS (ES+): 380.

Table 3 below depicts data for certain exemplary compounds made according to the method described in Scheme II and in Examples 7-9.

Example 9

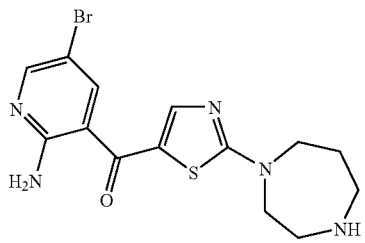

TABLE 3

| No. | M + 1 (obs) | RT (min) | 1H-NMR |
|---|---|---|---|
| 4 | 340 | 5 | 1H NMR (DMSO): 3.90 (2H, s), 6.78-6.81 (1H, m), 7.27-7.30 (5H, m), 7.90-8.00 (2H, s), 8.32-8.34 (1H, d), 9.12-9.15 (1H, d). |
| 7 | 326 | 8 | (1H, DMSO-d6): 4.30-4.70 (2H, br s), 6.82-6.86 (1H, m), 7.58-7.62 (2H, t), 7.69-7.73 (1H, t), 7.90-8.00 (1H, br s), 8.16-8.18 (1H, d), 8.34-8.36 (1H, d), 9.17-9.20 (1H, d). |
| 8 | 340 | 6 | (1H, DMSO-d6): 4.16 (3H, s), 6.78-6.81 (1H, m), 7.54-7.57 (2H, t), 7.62-7.65 (1H, t), 7.85-7.95 (2H, br s), 8.29-8.31 (2H, d), 8.35-8.36 (1H, d), 8.87-8.90 (1H, d). |
| 54 | 353 | 4 | (1H, DMSO-d6): 3.00-3.10 (1H, br s), 3.15-3.20 (2H, br s), 4.70-4.75 (2H, m), 6.75-6.85 (1H, br s), 7.20-7.45 (5H, m), 8.00-8.10 (2H, br s), 8.20-8.25 (0.5H, s), 8.32-8.37 (1H, s), 8.50-8.55 (0.5H, s), 9.20-9.30 (1H, m). |
| 62 | 418 | 4 | (1H, DMSO-d6): 4.47-4.50 (2H, d), 7.25-7.35 (4H, m), 8.00-8.05 (2H, s) 8.40 (1H, s), 8.67 (1H, s), 9.35 (1H, s), 9.50-9.55 (1H, t). |
| 64 | 432 | 4 | (1H, DMSO-d6): 2.90-3.20 (3H, m), 4.71 (2H, s), 7.20-7.50 (6H, m), 7.90-8.10 (2H, br s) 8.25-8.30 (0.5H, s), 8.35-8.40 (1H, s), 8.50-8.55 (1H, s), 9.35-9.45 (1H, m). |
| 65 | 404 | 4 | (1H, DMSO-d6): 7.15-7.20 (1H, m), 7.35-7.40 (2H, t), 7.70-7.75 (2H, d), 8.05-8.10 (2H, s) 8.40 (1H, s), 8.84 (1H, s), 9.36 (1H, s), 10.68 (1H, s). |
| 68 | 324 | 3 | (1H, DMSO-d6): 6.67-6.70 (1H, t), 6.89-6.90 (1H, d), 7.41-7.54 (5H, m), 7.88-7.90 (2H, d) 8.02-8.04 (2H, d). |
| 78 | 304 | 2 | (1H, DMSO-d6): 2.12-2.15 (2H, m), 3.20-3.25 (2H, m), 3.30-3.35 (2H, m), 3.65-3.80 (2H, m), 3.95-4.05 (2H, m), 6.80-6.83 (1H, t), 7.40-7.55 (2H, br s), 7.88 (1H, s), 8.10-8.20 (2H, m), 8.80-8.90 (2H, br s). |
| 79 | 380 | 3 | (1H, DMSO-d6): 2.12-2.15 (2H, m), 3.20-3.25 (2H, m), 3.30-3.35 (2H, m), 3.60-4.20 (4H, m), 8.54 (1H, s), 8.80-8.83 (3H, m). |
| 80 | 383 | 3 | (1H, DMSO-d6): 2.12-2.15 (2H, m), 3.20-3.25 (2H, m), 3.30-3.35 (2H, m), 3.60-3.65 (2H, m), 3.85-3.90 (2H, m), 6.85-6.88 (1H, t), 7.57 (1H, s), 7.60-7.80 (1H, br s), 8.10-8.15 (2H, m), 8.80-8.85 (2H, br s). |
| 81 | 303 | 3 | (1H, DMSO-d6): 2.12-2.15 (2H, m), 3.15-3.20 (2H, m), 3.25-3.30 (2H, m), 3.50-3.60 (2H, t), 3.75-3.80 (2H, m), 6.20-6.25 (1H, s), 6.83-6.86 (1H, s), 7.40-7.70 (3H, m), 8.04-8.06 (1H, d), 8.13-8.15 (1h, d), 8.80-8.90 (2H, br s).. |
| 83 | 383 | 3 | (1H, DMSO-d6): 2.00-2.05 (2H, m), 3.20-3.35 (6H, m), 3.45-3.55 (2H, m), 6.70-6.75 (1H, t), 7.43 (1H, s), 7.50-7.65 (2H, br s), 8.15-8.25 (2H, m), 8.70-8.80 (2H, br s). |
| 84 | 303 | 3 | (1H, DMSO-d6): 2.05-2.10 (2H, m), 3.15-3.30 (4H, m), 3.49-3.53 (2H, t), 3.65-3.70 (2H, m), 6.81-6.85 (2H, m), 7.45-7.65 (3H, m), 8.20-8.30 (2H, m), 8.65-8.75 (2H, br s).. |
| 94 | 382 | 5 | (1H, MeOD): 2.25-2.30 (2H, m), 3.25-3.30 (2H, m), 3.40-3.45 (2H, m), 3.55-3.60 (2H, m), 3.98-4.03 (2H, m), 7.00-7.05 (1H, t), 8.15-8.20 (1H, d), 9.10-9.15 (1H, d) |
| 95 | 414 | 4 | (1H, DMSO-d6): 1.85-1.95 (2H, m), 3.40-3.64 (10H, m), 6.69-6.75 (2H, m), 7.75-7.80 (2H, s), 8.27 (1H, d), 9.19-9.21 (1H, d). |

TABLE 3-continued

| No. | M + 1 (obs) | RT (min) | 1H-NMR |
|---|---|---|---|
| 96 | 416 | 4 | |
| 97 | 407 | 3 | |
| 98 | 421 | 4 | |
| 99 | 467 | 5 | |
| 100 | 405 | 4 | |
| 101 | 460 | 2 | |
| 102 | 304 | 3 | (1H, MeOD): 2.05-2.10 (2H, m), 3.20-3.25 (2H, m), 3.30-3.35 (2H, m), 3.60-3.65 (2H, m), 3.85-3.90 (2H, m), 6.59 (1H, s), 6.88-6.93 (1H, t), 8.11-8.13 (1H, d), 9.60-9.62 (1H, d) |
| 104 | 304 | 2 | (1H, DMSO-d6): 2.10-2.20 (2H, m), 3.17-3.22 (2H, m), 3.30-3.35 (2H, m), 3.60-3.80 (2H, m), 4.00-4.10 (2H, m), 6.97-7.00 (1H, t), 7.96 (1H, s), 8.22-8.35 (4H, m), 9.40-9.50 (2H, br s). |
| 109 | 318 | 3 | (1H, DMSO-d6): 2.05-2.10 (2H, m), 2.50 (3H, s), 3.15-3.30 (4H, m), 3.50-3.60 (2H, m), 3.78-3.85 (2H, m), 6.94-6.98 (1H, t), 8.27-8.28 (1H, d), 8.40-8.55 (2H, br s), 8.82-8.84 (1H, d), 9.20-9.30 (2H, br s). |
| 110 | 400 | 4 | (d6-DMSO, 400 MHz) 1.25 and 1.30 (9H, 2 × s), 1.69-1.80 (2H, m), 3.31 (2H, brs), 3.48-3.63 (3H, m), 3.77 (2H, brs), 3.87 (1H, brs), 6.61 (1H, brs), 6.84-6.88 (1H, m), 7.83 (2H, brs), 8.27 (2H, d), 8.57-8.60 (1H, m) |
| 111 | 299 | 2 | (d6-DMSO, 400 MHz) 1.67-1.74 (2H, m), 2.67-2.70 (2H, m), 2.80-2.95 (1H, brs), 3.50-3.56 (1H, brs), 3.67-3.81 (5H, m), 6.61 (1H, dd), 6.80 (1H, d), 7.82 (2H, brs), 7.97 (1H, d), 8.26-8.28 (1H, m), 8.55 (1H, d) |
| 121 | 431 | 4 | |
| 122 | 404 | 5 | |
| 123 | 363 | 3 | |
| 124 | 427 | 5 | |
| 125 | 304 | 2 | (1H, DMSO-d6): 2.10-2.15 (2H, m), 3.17-3.25 (2H, m), 3.30-3.35 (2H, m), 3.60-3.65 (2H, m), 3.90-3.95 (2H, m), 6.93-6.98 (1H, t), 7.82 (1H, s), 8.28-8.29 (1H, d), 8.40-8.50 (2H, br s), 9.02-9.04 (1H, d), 9.20-9.25 (2H, br s). |
| 141 | 404 | 5 | |
| 142 | 411 | 7 | |
| 143 | 454 | 4 | |
| 144 | 430 | 2 | |
| 145 | 437 | 7 | |
| 146 | 444 | 3 | |
| 173 | 361 | 3 | |
| 174 | 405 | 5 | |
| 175 | 458 | 5 | |
| 176 | 413 | 1 | |
| 177 | 404 | 5 | |
| 178 | 452 | 2 | |
| 184 | 272 | 2 | (d6-DMSO, 400 MHz) 2.10-2.18 (2H, m), 2.25-2.33 (2H, m), 3.05-3.14 (2H, m), 3.36-3.45 (2H, m), 4.63-4.68 (1H, m), 6.71-6.75 (1H, m), 6.89 (1H, d), 7.86 (2H, brs), 8.00 91H, d), 8.24-8.25 (1H, m), 8.40 (1H, brs), 8.64 (1H, brs), 8.83 (1H, d) |
| 196 | 376 | 2 | |
| 197 | 406 | 1 | |
| 198 | 389 | 7 | |
| 203 | 286 | 2 | (d6-DMSO, 400 MHz) 1.85-1.90 (1H, m), 1.96-2.13 (2H, m), 2.21-2.31 (3H, m), 3.22 (3H, brs), 3.33-3.41 (1H, m), 4.81 (1H, brs), 6.74 (4H, dd), 6.87 (1H, d), 7.79 (2H, brs), 7.98 (1H, d), 8.24 (1H, d), 8.61-8.65 (2H, m), 8.85 (1H, d) |
| 212 | 300 | 3 | (d6-DMSO, 400 MHz) 1.79-1.87 (1H, m), 1.95-2.05 (1H, m), 2.05-2.10 (1H, m), 2.11-2.15 (1H, m), 2.19 (3H, s), 3.05-3.21 (3H, m), 3.29 (1H, brs), 4.61 (1H, brs), 6.82 (1H, brs), 7.81 (1H, s), 7.97 (2H, brs), 8.23 (1H, d), 8.70 (1H, brs), 8.92 (2H, brs) |
| 217 | 300 | 3 | (d6-DMSO, 400 MHz) 1.83-1.91 (1H, m), 1.99-2.08 (2h, m), 2.13-2.16 (1h, m), 2.26-2.33 (2H, m), 2.36 (3h, s), 3.15-3.24 (3H, m), 3.35 (1H, brs), 4.63-4.68 (1H, m), 6.63 (1H, s), 6.72 (1H, dd), 7.78 (2H, brs), 8.23 (1H, dd), 8.54 (1H, brs), 8.61 (1H, brs), 8.81 (1H, d) |
| 227 | 298 | 7 | CD3OD 1.30-1.36 (6H, d), 3.12-3.20 (1H, m), 3.35-3.50 (4H, m), 4.30-4.35 (1H, d), 4.80-4.85 (1H, m), 7.10-7.13 (1H, t), 7.20-7.22 (1H, d), 7.45-7.47 (1H, d), 7.87-7.91 (1H, t), 8.21-8.23 (1H, d), 8.92-8.94 (1H, d). |
| 228 | 298 | 7 | CD3OD 1.30-1.36 (6H, d), 3.12-3.20 (1H, m), 3.35-3.50 (4H, m), 4.30-4.35 (1H, d), 4.80-4.85 (1H, m), 7.10-7.13 (1H, t), 7.20-7.22 (1H, d), 7.45-7.47 (1H, d), 7.87-7.91 (1H, t), 8.21-8.23 (1H, d), 8.92-8.94 (1H, d). |
| 247 | 318 | 8 | CD3OD 1.41-1.43 (3H, d), 2.67 (3H, s), 3.20-3.30 (1H, masked), 3.40-3.60 (4H, m), 3.95-3.98 (1H, d), 4.44-4.50 (1H, m), 7.07-7.10 (1H, t), 8.14-8.16 (1H, d), 9.16-9.17 (1H, d). |
| 251 | 304 | 3 | (d6-DMSO, 400 MHz) 2.47 (3H, s), 3.24 (4H, brs), 3.56-3.59 (4H, m), 6.68 (1H, dd), 7.77 (2H, brs), 8.20-8.22 (1H, m), 8.30 (1H, d), 8.81 (2H, brs) |

TABLE 3-continued

| No. | M + 1 (obs) | RT (min) | 1H-NMR |
|---|---|---|---|
| 256 | 380 | 4 | (d6-DMSO, 400 MHz) 3.38 (1H, brs), 3.45-3.56 (3H, m), 4.00 (2H, d), 4.62 (1H, brs), 6.66 (1H, q), 7.48-7.57 (4H, m), 7.81 (2H, brs), 8.20 (1H, d), 8.33 (1H, d), 9.31 (1H, brs), 9.59 (1H, brs) Methyl group masked by DMSO and TFA signal interfering with integrals of piperazine |
| 272 | 291 | 2 | |
| 273 | 291 | 3 | |
| 274 | 315 | 1 | |
| 280 | 308 | 3 | DMSO-d6 3.00-3.15 (4H, m), 3.40-3.50 (4H, m), 6.90-6.97 (1H, m), 7.94-7.96 (1H, d), 8.00-8.04 (1H, d), 8.20-8.28 (1H, t), 8.30-8.60 (4H, m), 9.20-9.40 (2H, m). |
| 292 | 279 | 1 | |
| 293 | 318 | 1 | |
| 294 | 315 | 2 | |
| 297 | 290 | 1 | |
| 298 | 314 | 2 | |
| 299 | 265 | 1 | |
| 300 | 304 | 1 | |

Intermediate 4

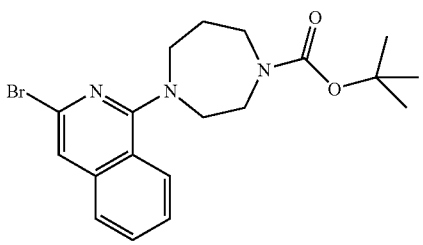

tert-butyl 4-(3-bromoisoquinolin-1-yl)-1,4-diazepane-1-carboxylate

A mixture of dibromoisoquinoline (150 mg, 0.52 mmol), tert-Butyl 1,4-diazepane-1-carboxylate (104 mg, 0.52 mmol) and potassium carbonate (144 mg, 1.04 mmol) in DMF (5 ml) was heated to 90° C. for 18 hours. The reaction mixture was allowed to cool down to room temperature and was partitioned between ethyl acetate and a saturated solution of sodium bicarbonate. The organic layer was separated, dried over sodium sulfate, filtered and concentrated in vacuo. The residue was purified on silica gel by flash column chromatography to afford the title compound as a colourless oil (160 mg, 76% yield).
$^1$H NMR (CDCl$_3$, 400 MHz) δ 1.48 and 1.49 (9H, s, rotamers), 2.02-2.18 (2H, m), 3.53-3.82 (8H, m), 7.36 (1H, d), 7.47 (1H, t), 7.62 (2H, m), 8.02 (1H, d); MS (ES$^+$) 408.

Intermediate 5

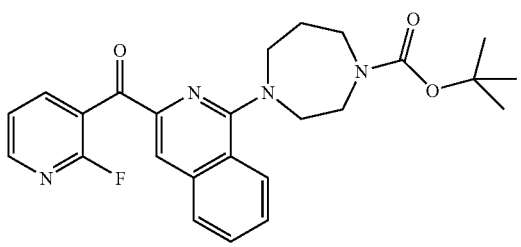

tert-butyl 4-(3-(2-fluoronicotinoyl)isoquinolin-1-yl)-1,4-diazepane-1-carboxylate A 2.5M n-butyl lithium in tetrahydrofuran solution (0.16 ml, 0.40 mmol) was added dropwise to a solution of tert-butyl 4-(3-bromoisoquinolin-1-yl)-1,4-diazepane-1-carboxylate (155 mg, 0.38 mmol) in tetrahydrofuran (8 ml), cooled to −78° C. The reaction mixture was stirred at that temperature for 10 minutes. A solution of 2-fluoro-N-methoxy-N-methylnicotinamide (70 mg, 0.38 mmol) in tetrahydrofuran (3 ml) was added dropwise. The reaction mixture was allowed to warm up to room temperature and was stirred for 2 hours. The reaction was quenched with a saturated aqueous solution of ammonium chloride and extracted into ethyl acetate. The organic phase was dried over magnesium sulfate, filtered and concentrated in vacuo. The residue was purified on silica gel by flash column chromatography to afford the title compound as a yellow solid (78 mg, 46% yield).
MS (ES$^+$) 451.

Intermediate 6

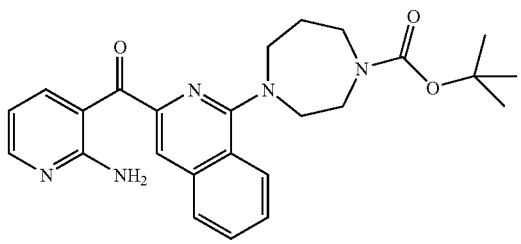

tert-butyl 4-(3-(2-aminonicotinoyl)isoquinolin-1-yl)-1,4-diazepane-1-carboxylate A microwave vial was charged with tert-butyl 4-(3-(2-fluoronicotinoyl)isoquinolin-1-yl)-1,4-diazepane-1-carboxylate (78 mg, 0.17 mmol) and a saturated aqueous solution of ammonium hydroxide (2 ml). The reaction mixture was heated under microwave irradiation at 110° C. for 25 minutes. The mixture was cooled down to room temperature, partitioned between ethyl acetate and water. The organic phase was dried over magnesium sulfate, filtered and evaporated to dryness. The residue was purified on silica gel by flash column chromatography to afford the title compound as a yellow solid (18 mg, 24% yield). MS (ES$^+$) 448.

Example 10

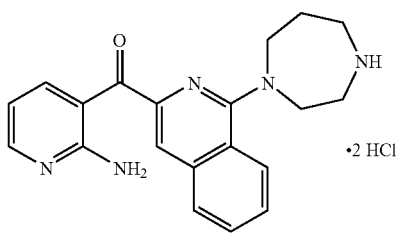

(1-(1,4-diazepan-1-yl)isoquinolin-3-yl)(2-aminopyridin-3-yl)methanone dihydrochloride (Cmpd-221)

To a suspension of tert-butyl 4-(3-(2-aminonicotinoyl)isoquinolin-1-yl)-1,4-diazepane-1-carboxylate (18 mg, 0.04 mmol) in 1,4-dioxane (1 ml) was added 4 M HCl in 1,4-dioxane (0.5 ml). The resulting mixture was stirred at room temperature for 5 hours. The reaction mixture was concentrated to dryness to leave title compound as a solid (16.6 mg, 98% yield). $^1$H NMR (CD$_3$OD, 400 MHz) δ 2.25-2.32 (2H, s), 3.40-3.45 (2H, m), 3.55-3.60 (2H, m), 3.90-3.95 (2H, m), 4.07-4.12 (2H, m), 7.14-7.17 (1H, t), 7.81-7.89 (2H, m), 8.10-8.12 (1H, d), 8.17 (1H, s), 8.22-8.24 (1H, d), 8.29-8.31 (1H, d), 8.98-9.00 (1H, d); MS (ES$^+$) 348.

Table 4 below depicts data for certain exemplary compounds made according to Example 10 and the method described in Scheme III.

| No. | M + 1 (obs) | RT (min) | 1H-NMR |
|---|---|---|---|
| 221 | 348 | 8 | CD3OD 2.25-2.32 (2H, s), 3.40-3.45 (2H, m), 3.55-3.60 (2H, m), 3.90-3.95 (2H, m), 4.07-4.12 (2H, m), 7.14-7.17 (1H, t), 7.81-7.89 (2H, m), 8.10-8.12 (1H, d), 8.17 (1H, s), 8.22-8.24 (1H, d), 8.29-8.31 (1H, d), 8.98-9.00 (1H, d). |

Intermediate 7

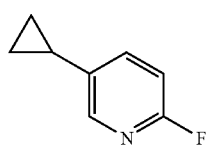

5-cyclopropyl-2-fluoropyridine

A mixture of 2-fluoro-5-bromopyridine (1.17 ml, 11.4 mmol), cyclopropylboronic acid (1.47 g, 17.1 mmol) and potassium phosphate (7.26 g, 34.2 mmol) in 1,4-dioxane (20 ml) was stirred under argon atmosphere. Chloro(di-2-norbornylphosphino)(2-dimethylaminoferrocen-1-yl)palladium (II) (67 mg, 0.11 mmol) was added. The reaction mixture was heated at 100° C. under argon atmosphere for 48 hours and then cooled down to room temperature. The crude mixture was partitioned between ethyl acetate and water. The organic phase was washed with brine, dried over magnesium sulfate, filtered and concentrated in vacuo. The residue was purified on silica gel by flash column chromatography (ISCO Companion|, 80 g column, 0-10% EtOAc/Petroleum ether) to afford the compound (70:30 mixture product: starting material; 1.55 g).

$^1$H NMR (DMSO-d$_6$, 400 MHz) δ 0.70-0.74 (2H, m), 0.95-1.00 (2H, m), 1.94-2.01 (1H, m), 7.05 (1H, dd), 7.62 (1H, dt), 8.05 (1H, s); MS (ES$^+$) 138.

Intermediate 8

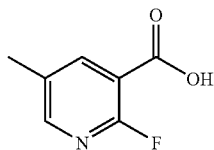

2-fluoro-5-methylnicotinic acid

A 1.6M solution of butyl lithium in hexanes (28.13 ml, 45 mmol) was added dropwise to a solution of diisopropylamine (6.36 ml, 45 mmol) in tetrahydrofuran (80 ml) keeping the temperature at −78° C. After complete addition, the mixture was allowed to warm up to 0° C., then stirred at 0° C. for 10 minutes. The resulting mixture was cooled down to −78° C. and a solution of 2-fluoro-5-methylpyridine (4.64 ml, 45 mmol) in tetrahydrofuran (15 ml) was added dropwise. The reaction mixture was stirred at −78° C. for 2 hours then quenched by addition of an excess of CO$_2$ solid. The mixture was allowed to warm up to room temperature. The mixture was acidified with 10% citric acid, diluted with ethyl acetate. The organic layer was collected, washed further with brine, dried over magnesium sulfate, filtered and concentrated in vacuo to leave the desired compound as a white solid (4.9 g, 70% yield).

$^1$H NMR (DMSO-d$_6$, 400 MHz) δ 2.34 (3H, s), 8.20-8.26 (2H, m); MS (ES$^+$) 156, (ES$^-$) 154.

Intermediate 9

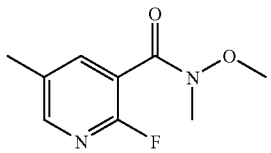

2-fluoro-N-methoxy-N,5-dimethylnicotinamide

To a solution of 2-fluoro-5-methylnicotinic acid (4.9 g, 31.6 mmol), N,O-dimethylhydroxylamine hydrochloride (4.01 g, 41.08 mmol), diisopropylethylamine (12.6 ml, 72.68 mmol) in dichloromethane (150 ml) at 0° C. was added TBTU (11.16 g, 34.76 mmol) portionwise over 30 minutes. The solution was stirred at 0° C. for a further 10 minutes then, at room temperature for 18 hours. The reaction mixture was washed with a 10 wt % solution of citric acid and brine. The organic layer was dried over magnesium sulfate, filtered and concentrated in vacuo. The residue was purified on silica gel by flash column chromatography (ISCO Companion□, 80 g

Intermediate 10

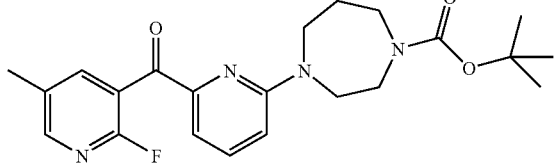

tert-butyl 4-(6-(2-fluoro-5-methylnicotinoyl)pyridin-2-yl)-1,4-diazepane-1-carboxylate To a solution of tert-butyl 4-(6-bromopyridin-2-yl)-1,4-diazepane-1-carboxylate (898 mg, 2.52 mmol) in tetrahydrofuran (10 ml) at −78° C. was added a 2.5M solution of "butyllithium in hexanes (1.01 ml, 2.52 mmol) dropwise maintaining the temperature at −78° C. After complete addition, the solution was stirred at −78° C. for a further 20 minutes. A solution of 2-fluoro-N-methoxy-N,5-dimethylnicotinamide (500 mg, 2.52 mmol) in tetrahydrofuran (5 ml) was added dropwise at −78° C. and the reaction mixture was stirred at −78° C. for 1 hour. The reaction was quenched with a saturated solution of ammonium chloride. The mixture was stirred at room temperature for 20 minutes and extracted into ethyl acetate. The organic layer was washed with brine, dried over magnesium sulfate, filtered and concentrated in vacuo. The residue was purified on silica gel by flash column chromatography (ISCO Companion□, 40 g column, 0-20% EtOAc/Petrol) to afford the title compound as a sticky green oil (906 mg, 87% yield).

$^1$H NMR (DMSO-d$_6$, 400 MHz) δ 1.18 and 1.27 (9H, 2 s, rotamers), 1.58-1.73 (2H, m), 2.35 (3H, s), 3.15-3.63 (8H, m), 7.01 (1H, d), 7.31 (1H, dd), 7.74 (1H, m), 8.00 (1H, dd), 8.24 (1H, s); MS (ES$^+$) 415.

Intermediate 11

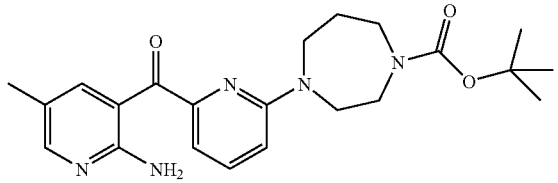

tert-butyl 4-(6-(2-amino-5-methylnicotinoyl)pyridin-2-yl)-1,4-diazepane-1-carboxylate A microwave vial was charged with tert-butyl 4-(6-(2-fluoro-5-methylnicotinoyl)pyridin-2-yl)-1,4-diazepane-1-carboxylate (280 mg, 0.68 mmol) and a saturated aqueous solution of ammonium hydroxide (1.5 ml). The reaction mixture was heated under microwave irradiation at 110° C. for 30 minutes. The mixture was cooled down to room temperature and evaporated to dryness. The residue was purified on silica gel by flash column chromatography to afford the title compound as an orange solid (49 mg, 18% yield).

$^1$H NMR (CDCl$_3$, 400 MHz) δ 1.30 and 1.37 (9H, 2 s, rotamers), 1.89 (2H, quint), 2.11 (3H, s), 3.18-3.70 (8H, m), 6.59 (1H, d), 6.74 (2H, br s), 7.01 (1H, d), 7.53 (1H, t), 8.00 (1H, s), 8.09 (1H, d); MS (ES$^+$) 412.

Example 11

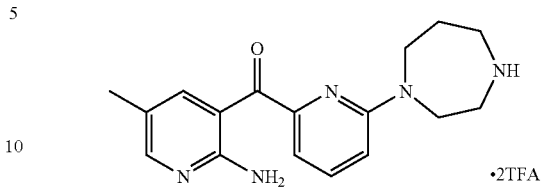

(6-(1,4-diazepan-1-yl)pyridin-2-yl)(2-amino-5-methylpyridin-3-yl)methanone bis(2,2,2-trifluoroacetate) (Cmpd-155)

To a solution of tert-butyl 4-(6-(2-amino-5-methylnicotinoyl)pyridin-2-yl)-1,4-diazepane-1-carboxylate (49 mg, 0.12 mmol) in 1,4-dioxane (1 ml) was added a 4M solution of hydrochloric acid in dioxane (2 ml). The reaction mixture was stirred at room temperature for 18 hours. The mixture was evaporated to dryness. The residue was purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. The fractions were collected and freeze-dried to give the title compound as a yellow solid (20 mg, 31% yield).

$^1$H NMR (CDCl$_3$, 400 MHz) δ 1.84 (2H, m), 1.96 (3H, s), 3.04 (4H, br m), 3.48 (2H, t), 3.68 (2H, t), 6.82 (1H, d), 6.94 (1H, d), 7.60 (1H, t), 7.65 (2H, br s), 7.94 (1H, d), 8.02 (1H, s), 8.55 (1H, s); MS (ES$^+$) 312.

Intermediate 12

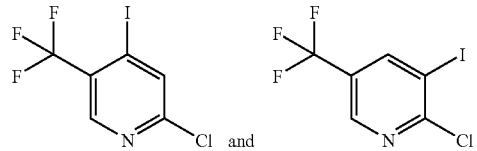

Mixture of 2-chloro-4-iodo-5-(trifluoromethyl)pyridine and 2-chloro-3-iodo-5-(trifluoromethyl)pyridine To sodium bromide (12.47 g, 3.893 mL, 121.2 mmol) in THF (200 mL) was added diisopropylamine (12.26 g, 16.98 mL, 121.2 mmol). The reaction mixture was cooled down to −78° C. "Butyl lithium in hexanes (75.75 mL of 1.6 M, 121.2 mmol) was added dropwise and the solution was allowed to warm up to 0° C. for 10 minutes before being cooled down again to −78° C. A solution of 2-chloro-5-trifluoromethylpyridine (20 g, 1110.2 mmol) in THF (20 ml) was added and the resulting solution was stirred for 1 hour. A solution of iodine (27.97 g, 5.673 mL, 110.2 mmol) in THF (50 ml) was added rapidly and the stirring was continued for 2 hours at −78° C. The reaction mixture was partitioned between water and ethyl acetate. The organic layer was washed with brine, dried over magnesium sulfate, filtered and concentrated in vacuo. The residue was purified on silica gel by flash column chromatography to afford the title compound as an off-white solid (22.47 g, 66% yield, 2:1 ratio of the 4-isomer to the 3-isomer).

Data for 2-chloro-4-iodo-5-(trifluoromethyl):

$^1$H NMR (CDCl$_3$, 400 MHz) δ 8.05 (1H, s), 8.57 (1H, s); MS (ES$^+$) 307, (ES$^−$) 305.

Data for pyridine 2-chloro-3-iodo-5-(trifluoromethyl)pyridine:
¹H NMR (CDCl₃, 400 MHz) δ 8.37 (1H, s), 8.65 (1H, s); MS (ES⁺) 307, (ES⁻) 305.

Intermediate 13

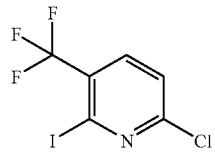

6-chloro-2-iodo-3-(trifluoromethyl)pyridine

To a solution of 2,2,6,6-tetramethylpiperidine (4.277 g, 5.110 mL, 30.28 mmol) in THF (18.00 mL) cooled to −78° C. was added "BuLi in hexanes (11.72 mL of 2.5 M, 29.30 mmol). The solution was allowed to warm up to 0° C. and was stirred for 15 minutes at that temperature before cooling it again to −78° C. Iodine (12.40 mg, 2.515 μL, 0.04884 mmol) was added followed by a dropwise addition of a solution containing a mixture of 2-chloro-3-iodo-5-(trifluoromethyl)pyridine (2 g, 6.505 mmol) and 2-chloro-4-iodo-5-(trifluoromethyl)pyridine (4.000 g, 13.01 mmol) in THF (18.00 mL). The solution was stirred at −78° C. for 2 hours. The reaction mixture was partitioned between a 1M solution of HCl and ether. The organic extract was washed with a saturated solution of sodium bicarbonate and brine, dried over magnesium sulfate, filtered and concentrated in vacuo. The residue was purified on silica gel by flash column chromatography to afford the title compound as a pale yellow oil (1.92 g, 32% yield).
¹H NMR (CDCl₃, 400 MHz) δ 7.42 (1H, d), 7.78 (1H, d).

Intermediate 14

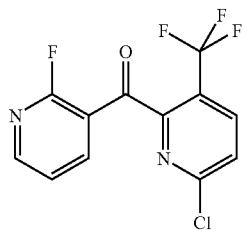

(6-chloro-3-(trifluoromethyl)pyridin-2-yl)(2-fluoropyridin-3-yl)methanone

To a solution of 6-chloro-2-iodo-3-(trifluoromethyl)pyridine (described in the literature: Eur. J. Org. Chem. 2004, 3793) (1.9 g, 6.180 mmol) in tetrahydrofuran (20 mL), cooled to −78° C., was added isopropyl magnesium chloride 2M in tetrahydrofuran (3.152 mL of 2 M, 6.304 mmol). The reaction mixture was stirred for 15 minutes. A solution of 2-fluoro-N-methoxy-N-methylnicotinamide (1.252 g, 6.798 mmol) in tetrahydrofuran (4 mL) was added and the reaction mixture was stirred at −78° C. for 1 hour. The reaction mixture was partitioned between a saturated solution of ammonium chloride and ethyl acetate. The organic extract was washed with brine, dried over magnesium sulfate, filtered and concentrated in vacuo. The residue was purified on silica gel by flash column chromatography to afford the title compound as a pale yellow oil (1.14 g, 61% yield).
¹H NMR (CDCl₃, 400 MHz) δ 7.43-7.49 (1H, m), 7.64 (1H, d), 8.12 (1H, d), 8.45-8.53 (2H, m); MS (ES⁺) 304.

Intermediate 15

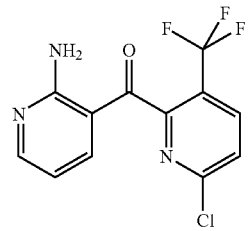

(2-aminopyridin-3-yl)(6-chloro-3-(trifluoromethyl)pyridin-2-yl)methanone

A mixture of (6-chloro-3-(trifluoromethyl)pyridin-2-yl)(2-fluoropyridin-3-yl)methanone (2.27 g, 7.452 mmol) and a saturated aqueous solution of ammonium hydroxide (20 mL, 513.6 mmol) was heated to 70° C. for 18 hours. The mixture was cooled down to room temperature and the resulting solid was filtered, washed with water and dried under vacuum to give the title compound as a pale yellow solid (2.12 g, 94% yield).
¹H NMR (DMSO-d6, 400 MHz) δ 6.59 (1H, dd), 7.53 (1H, d), 7.91 (2H, br s), 7.96 (1H, d), 8.31 (1H, dd), 8.48 (1H, d); MS (ES⁺) 302, (ES⁺) 300.

Example 12

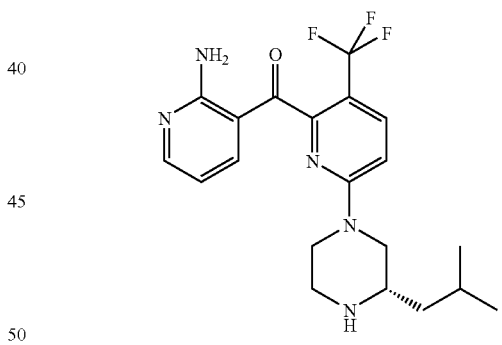

(S)-(2-aminopyridin-3-yl)(6-(3-isobutylpiperazin-1-yl)-3-(trifluoromethyl)pyridin-2-yl)methanone
(CMPD 334)

A microwave vial was charged with (2-aminopyridin-3-yl)(6-chloro-3-(trifluoromethyl)pyridin-2-yl)methanone (2.12 g, 7.028 mmol), potassium carbonate (1.166 g, 8.434 mmol), (S)-tert-butyl 2-isobutylpiperazine-1-carboxylate (1.874 g, 7.731 mmol) and dimethylformamide (4 mL). The reaction mixture was heated under microwave irradiation at 90° C. for 50 minutes. The reaction mixture was cooled down to room temperature and partitioned between a saturated solution of sodium bicarbonate and ethyl acetate. The organic extract was washed with brine, dried over magnesium sulfate, filtered and concentrated in vacuo. The residue was taken up in dichloromethane (50 ml) and trifluoroacetic acid (8 ml) was added. The reaction mixture was stirred at room temperature for 3 hours. The reaction mixture was concentrated to dryness and partitioned between dichloromethane and a saturated solution of sodium carbonate. The organic extract was dried over magnesium sulfate, filtered and concentrated in vacuo. The residue was purified on silica gel by flash column chromatography to afford the title compound as a pale yellow oil (2.203 g, 77% yield).

$^1$H NMR (DMSO-$d_6$, 400 MHz) δ 0.82 (6H, m), 1.16 (2H, m), 1.69 (1H, m), 2.58 (3H, m), 2.89 (2H, m), 4.17 (2H, m), 6.58 (1H, m), 7.04 (1H, m), 7.43 (1H, m), 7.90 (2H, br s), 8.25 (1H, m); MS (ES$^+$) 408, (ES$^+$) 406.

Intermediate 15

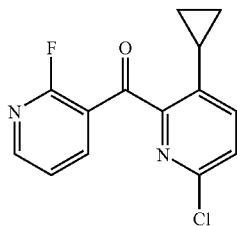

(6-chloro-3-cyclopropylpyridin-2-yl)(2-fluoropyridin-3-yl)methanone

A 2.5M solution of $^n$BuLi (10.94 ml, 27.34 mmol) was added to a solution of 2-(dimethylamino)ethanol (1.37 ml, 13.67 mmol) in hexane (15 ml) cooled to −78° C. The reaction mixture was stirred at −78° C. for 30 minutes then, a solution of 2-chloro-5-cyclopropylpyridine (700 mg, 4.56 mmol) in hexane (10 mL) was added dropwise. The reaction mixture was stirred for 90 minutes. A solution of 2-fluoro-N-methoxy-N-methylnicotinamide (3.36 g, 18.23 mmol) in tetrahydrofuran (15 mL) was added dropwise and the reaction mixture was stirred at −78° C. for 1 hour. The reaction mixture was partitioned between a saturated solution of ammonium chloride and ethyl acetate. The organic extract was washed with a saturated solution of sodium bicarbonate and brine, dried over magnesium sulfate, filtered and concentrated in vacuo. The residue was purified on silica gel by flash column chromatography to afford the title compound as a colourless oil (1.14 g, 61% yield).

$^1$H NMR (CDCl$_3$, 400 MHz) δ 0.69-0.76 (2H, m), 1.03-1.12 (2H, m), 2.35-2.45 (1H, m), 7.35-7.43 (3H, m), 8.28-8.35 (1H, m), 8.41-8.46 (1H, m); MS (ES$^+$) 277.

Table 5 below depicts data for certain exemplary compounds made according to the method described in Scheme IV and Examples 11 and 12:

TABLE 5

| No. | M + 1 (obs) | RT (min) | 1H-NMR |
|---|---|---|---|
| 108 | 322 | 3 | (1H, DMSO-d6): 2.00-2.10 (2H, m), 3.10-3.25 (4H, m), 3.65-3.70 (2H, m), 3.85-3.90 (2H, m), 4.08 (1H, s), 6.99-7.01 (1H, d), 7.13-7.17 (1H, d), 7.76-7.80 (1H, t), 7.95-8.10 (2H, br s), 8.35-8.40 (2H, m), 8.85-9.00 (2H, br s). |
| 140 | 367.08 | 3 | (DMSO) 1.77-1.72 (2H, m), 2.70-2.67 (2H, m), 2.85-2.82 (2H, m), 3.67-3.61 (4H, m), 6.91 (1H, d), 7.11 (1H, d), 7.72 (2H, t), 8.22 (2H, s), 8.56 (1H, d), 8.71 (1H, d). |
| 154 | 338.2 | 3 | (DMSO) 0.60-0.56 (2H, m), 0.88-0.84 (2H, m), 1.87-1.80 (1H, m), 2.04 (2H, br m), 3.25-3.20 (4H, br m), 3.69-3.66 (2H, masked signal), 3.89-3.87 (2H, masked signal), 7.01 (1H, d), 7.13 (1H, d), 7.81-7.77 (3H, m), 8.07 (1H, d), 8.11 (1H, s), 8.73 (1H, s). |
| 155 | 312.17 | 3 | (DMSO) 1.84 (2H, m), 1.96 (3H, s), 3.04 (4H, br m), 3.48 (2H, t), 3.68 (2H, t), 6.82 (1H, d), 6.94 (1H, d), 7.60 (1H, t), 7.65 (2H, br s), 7.94 (1H, d), 8.02 (1H, s), 8.55 (1H, s). |
| 209 | 312 | 7 | DMSO-d6 1.95-2.00 (2H, m), 2.08 (3H, s), 3.10-3.20 (4H, m), 3.55-3.60 (2H, m), 3.75-3.80 (2H, m), 6.59-6.62 (1H, m), 6.84-6.86 (1H, d), 7.56-7.58 (1H, d), 7.95-8.05 (2H, br s), 8.25-8.26 (1H, d), 8.10-8.20 (1H, s). |
| 229 | 312 | 3 | (d6-DMSO, 400 MHz) 2.08-2.11 (2H, m), 2.44 (3H, s), 3.30 (2H, brs), 3.35 (2H, brs), 3.55 (2H, t), 3.72 (2H, t), 6.77 (1H, dd), 7.46 (1H, d), 7.80 (1H, d), 7.88 (2H, brs), 8.32-8.34 (2H, m), 8.70 (1H, brs) |
| 230 | 298 | 7 | DMSO-d6 3.15-3.20 (4H, s), 3.65-3.70 (4H, m), 6.64-6.67 (1H, m), 7.08-7.10 (1H, d), 7.58-7.60 (1H, d), 7.69-7.71 (1H, d), 7.95-8.05 (2H, br s), 8.31-8.32 (1H, d), 7.72-8.80 (2H, s). |
| 236 | 298 | 3 | (d6-DMSO, 400 MHz) 2.34 (3H, s), 3.09 (4H, brs), 3.16 (4H, brs), 6.60 (1H, dd), 7.45 (1H, d), 7.65 (2H, brs), 7.76 (1H, d), 8.16-8.18 (1H, m), 8.23 (1H, dd) |
| 252 | 374 | 9 | DMSO-d6 2.10 (3H, s), 3.18-3.40 (4H, m), 4.30-4.45 (3H, m), 6.57-6.60 (1H, m), 7.12-7.16 (1H, d), 7.40-7.60 (6H, m), 7.62-7.67 (1H, d), 7.85-7.95 (2H, s), 8.20-8.23 (1H, d), 9.13-9.23 (1H, s), 9.40-9.50 (1H, s). |
| 315 | | | DMSO-d6 3.10-3.20 (4H, s), 3.70-3.80 (4H, s), 6.61-6.65 (1H, m), 7.11-7.14 (1H, d), 7.53-7.55 (1H, d), 7.85-7.87 (1H, d), 7.90-8.15 (2H, br s), 8.29-8.30 (1H, d), 8.85-8.95 (2H, s) |
| 316 | 352 | 3 | DMSO-d6 3.15-3.25 (4H, s), 3.75-3.82 (4H, s), 6.58-6.61 (1H, m), 7.17-7.19 (1H, d), 7.48-7.51 (1H, d), 7.85-8.00 (2H, s), 8.05-8.07 (1H, d), 8.27-8.29 (1H, d), 8.85-8.95 (2H, s) |
| 317 | 428 | 4 | 1H DMSO-d6 3.20-3.40 (4H, masked); 4.45-4.60 (3H, m), 6.60-6.65 (1H, m), 7.30-7.35 (1H, d), 7.48-7.53 (8H, m), 7.85 (1H. s), 8.10-8.15 (1H, d), 8.28-8.30 (1H, d), 9.20-9.30 (1H, s), 9.50-9.60 (1H, s) |
| 318 | 366 | 3 | 1H DMSO-d6 1.90-2.00 (2H, m); 3.10-3.25 (4H, s), 3.65-3.70 (2H, s), 3.85-3.90 (2H, s), 6.56-6.60 (1H, m), 6.99-7.02 (1H, d), 7.58-7.60 (1H, d), 7.95-8.20 (3H. m), 8.26-8.27 (1H, d), 8.70-8.80 (1H, s) |

TABLE 5-continued

| No. | M + 1 (obs) | RT (min) | 1H-NMR |
|---|---|---|---|
| 319 | 302 | 7 | 1H NMR (DMSO-d6) 3.10-3.20 (4H, s), 3.70-3.77 (4H, s), 6.77-6.81 (1H, m), 7.08-7.09 (1H, d), 7.92-7.94 (1H, d), 8.33-8.50 (4H, m), 9.20-9.30 (2H, s) |
| 321 | 394 | 4 | 1H (DMSO-d6) 3.18-3.40 (4H, m), 4.38-4.50 (3H, m), 6.59-6.63 (1H, m), 7.24-7.27 (1H, d), 7.45-7.55 (5H, m), 7.86-8.00 (3H, m), 8.27-8.29 (1H, d), 9.15-9.25 (1H, br s), 9.45-9.55 (1H, br s). |
| 322 | 332 | 3 | 1H (DMSO-d6) 1.39-1.47 (2H, m), 1.89-1.91 (2H, d), 2.88-2.94 (2H, t), 3.20-3.30 (1H, m), 4.23-4.27 (2H, d), 6.60-6.64 (1H, m), 7.06-7.09 (1H, d), 7.48-7.50 (1H, d), 7.76-8.10 (5H, m), 8.28-8.30 (1H, d). |
| 323 | 374 | 3 | 1H (DMSO-d6) 0.76-0.87 (6H, dd), 1.34-1.45 (2H, m), 1.67-1.74 (1H, m), 2.90-2.94 (1H, t), 3.06-3.31 (3H, m), 4.27-4.33 (3H, t), 6.59-6.62 (1H, m), 7.18-7.20 (1H, d), 7.53-7.56 (1H, d), 7.84-8.05 (3H, m), 8.28-8.30 (1H, d), 8.70-8.80 (1H, m), 8.90-9.00 (1H, m). |
| 324 | 332 | 3 | 1H (DMSO-d6) 1.95-2.05 (2H, s), 3.15-3.25 (4H, s), 3.62-3.65 (2H, m), 3.82-3.85 (2H, m), 6.60-6.63 (1H, m), 6.93-6.95 (1H, d), 7.60-7.62 (1H, d), 7.76-7.78 (1H, d), 7.90-8.10 (2H, br s), 8.28-8.30 (1H, d), 8.70-8.80 (2H, br s). |
| 325 | 432 | 9 | 1H (DMSO-d6) 3.15-3.25 (4H, s), 3.81-3.84 (4H, s), 7.18-7.21 (1H, d), 7.64 (1H, s), 8.00-8.08 (3H, m), 8.38 (1H, s), 8.85-8.95 (2H, s). |
| 326 | 508 | 3 | 1H NMR DMSO-d6 3.20-3.50 (4H, m), 4.50-4.65 (3H, m), 7.34-7.36 (1H, d), 7.45-7.55 (5H, m), 7.72 (1H, s), 8.00-8.10 (3H, m), 8.38 (1H, s), 9.20-9.30 (1H, m), 9.50-9.60 (1H, m) |
| 327 | 378 | 3 | 1H DMSO-d6 3.17 (4H, s), 3.71 (4H, s), 5.05-5.08 (1H, d), 5.54-5.59 (1H, d), 6.52-6.59 (1H, dd), 7.19-7.21 (1H, d), 7.53 (1H, s), 7.90-8.08 (3H, m), 8.50 (1H, s), 8.85-8.95 (2H, s) |
| 328 | 454 | 4 | 1H DMSO-d6 3.20-3.50 (4H, m), 4.45-4.60 (3H, m), 5.07-5.09 (1H, d), 5.58-5.63 (1H, d), 6.54-6.61 (1H, dd), 7.33-7.36 (1H, d), 7.46-7.60 (5H, m), 7.59 (1H, s), 7.95-8.10 (3H, m), 8.52 (1H, s), 9.20-9.30 (1H, m), 9.50-9.60 (1H, m) |
| 329 | 397.96 | 3 | (DMSO) 2.73 (4H, m), 3.39 (4H, m), 7.00 (1H, m), 7.59 (1H, m), 7.73 (1H, m), 8.08 (2H, m), 8.39 (1H, m) |
| 330 | 346.12 | 3 | DMSO) 2.78 (4H, m), 3.45 (4H, m), 5.14 (1H, m), 5.60 (1H, m), 6.62 (1H, m), 7.04 (1H, m), 7.56 (1H, m), 7.80 (1H, m), 8.06 (2H, m), 8.55 (1H, m) |
| 331 | 474.01 | 4 | (DMSO) 2.73 (1H, m), 2.84-2.98 (2H, m), 3.13 (1H, m) 3.78 (1H, m), 4.19 (2H, m), 7.15 (1H, m), 7.39 (3H, m), 7.48 (2H, m), 7.65 (1H, m), 7.80 (1H, m), 8.13 (2H, m), 8.43 (1H, m) |
| 332 | 420.12 | 4 | (DMSO) 2.65 (1H, m), 2.77-2.92 (2H, m), 3.04 (1H, m) 3.69 (1H, m), 4.13 (2H, m), 5.05 (1H, m), 5.52 (1H, m), 6.56 (1H, m), 7.09 (1H, m), 7.31 (3H, m), 7.40 (2H, m), 7.53 (1H, m), 7.75 (1H, m), 8.01 (2H, m), 8.48 (1H, m) |
| 338 | 394.24 | 3 | (DMSO) 0.86 (6H, m), 1.58 (1H, m), 2.33 (1H, m) 2.66 (2H, m), 2.94 (2H, m), 4.17 (2H, m), 6.57 (1H, m), 7.07 (1H, m), 7.43 (1H, m), 7.91 (3H, m), 8.26 (1H, m), |
| 340 | 319 | 3 | 1H (DMSO-d6) 3.11 (4H, s), 3.52-3.55 (4H, s), 6.71-6.74 (!H, m), 7.90-8.10 (3H, m), 8.31-8.33 (1H, d), 8.49 (1H, s), 8.90-9.00 (2H, s) |
| 341 | 361 | 3 | 1H (DMSO-d6) 3.15-3.40 (3H, m), 4.40-4.60 (4H, m), 6.62-6.65 (1H, m), 7.21-7.22 (1H, d), 7.46-7.57 (5H, m), 7.76-7.78 (1H, d), 7.95-8.05 (2H, br s), 8.27-8.30 (1H, d), 8.43-8.45 (1H, d), 9.25-9.35 (1H, m), 9.50-9.60 (1H, m) |
| 342 | 310 | 3 | 1H (CD3OD) 3.20-3.30 (4H, m), 3.83-3.86 (4H, m), 5.22-5.25 (1H, d), 5.71-5.71 (1H, d), 6.68-6.75 (1H, dd), 6.85-6.89 (1H, m), 7.14-7.16 (1H, d), 8.08-8.11 (2H, m), 8.20-8.22 (1H, d) |
| 343 | 319 | 2 | 1H CD3OD 3..32-3.37 (4H, m), 3.90-3.93 (4H, m), 6.84-6.88 (1H, m), 8.03-8.06 (1H, d), 8.26-8.28 (1H, d), 8.35 (1H, s) |
| 344 | 285 | 2 | 1H (CD3OD) 3.10-3.40 (4H, m), 3.85-4.00 (4H, m), 6.77-6.81 (1H, m), 6.85-6.91 (1H, m), 6.97-6.98 (1H, d), 8.11-8.13 (1H, d), 8.20-8.24 (1H, dd), 8.31-8.33 (1H, d). |
| 345 | 341 | 3 | 1H (CD3OD) 0.95-1.05 (6H, m), 1.53-1.65 (2H, m), 1.79-1.82 (1H, m), 3.20-3.350 (4H, m), 3.40-3.55 (3H, m), 6.97-7.04 (1H, m), 7.17-7.20 (1H, m), 7.96-7.98 (0.5H, d), 8.26-8.28 (0.5H, d), 8.33-8.37 (1H, t), 8.46-8.48 (0.5H, d), 8.62-8.64 (0.5H, d). |
| 346 | 366 | 3 | 1H (CD3OD) 0.85-0.95 (6H, m), 1.40-1.60 (2H, m), 1.70-1.80 (1H, m), 2.96-3.02 (1H, m), 3.15-3.50 (6H, masked m), 4.40-4.43 (1H, d), 4.52-4.55 (1H, d), 5.21-5.24 (1H, d), 5.70-5.74 (1H, d), 6.63-6.77 (2H, m), 7.14-7.17 (1H, d), 7.88-7.90 (1H, d), 8.07-8.10 (1H, d), 8.21-8.22 (1H, d). |
| 347 | 386 | 3 | 1H (CD3OD) 3.32-3.56 (5H, masked m), 4.46-4.50 (1H, dd), 4.59-4.65 (2H, m), 5.23-5.26 (1H, d), 5.72-5.76 (1H, d), 6.69-6.76 (1H, m), 6.81-6.84 (1H, t), 7.20-7.23 (1H, d), 7.52 (5H, s), 8.06-8.12 (2H, m), 8.17-8.19 (1H, d). |
| 348 | 312 | 3 | 1H (CD3OD) 1.18-1.22 (3H, t), 2.58-2.64 (2H, qd), 3.29-3.33 (4H, m), 3.76-3.79 (4H, m), 6.91-6.95 (1H, m), 7.11-7.13 (1H, d), 7.73-7.75 (1H, d), 8.20-8.23 (2H, m) |

TABLE 5-continued

| No. | M + 1 (obs) | RT (min) | 1H-NMR |
|---|---|---|---|
| 349 | 368 | 3 | 1H (CD3OD) 0.90-1.00 (6H, dd), 1.18-1.22 (3H, t), 1.46-1.59 (2H, m), 1.48-1.75 (1H, m), 2.58-2.64 (2H, qd), 2.92-2.98 (1H, m), 3.17-3.42 (5H, m), 4.31-4.34 (1H, d), 4.43-4.46 (1H, d), 6.91-6.94 (1H, m), 7.13-7.15 (1H, d), 7.73-7.75 (1H, d), 8.20-8.23 (2H, m) |
| 350 | 388 | 4 | 1H (CD3OD) 1.18-1.22 (3H, t), 2.59-2.65 (2H, qd), 3.32-3.54 (4H, m), 4.45-4.57 (3H, m), 6.88-6.92 (1H, m), 7.17-7.20 (1H, d), 7.75-7.78 (1H, d), 8.16-8.18 (1H, d), 8.22-8.24 (1H, d). |
| 351 | 382 | 3 | 1H (CD3OD) 0.95-0.99 (6H, m), 1.48-1.62 (2H, m), 1.77-1.80 (1H, m), 3.13-3.49 (5H, m), 4.56-4.71 (2H, m), 6.78-6.81 (1H, m), 7.12-7.15 (1H, d), 7.79 (1H, m), 8.15-8.17 (1H, d), 8.31-8.33 (1H, d) |
| 352 | 380 | 3 | 1H (CD3OD) 0.60-0.65 (4H, m), 0.85-1.00 (6H, m), 1.46-1.60 (2H, m), 1.70-1.77 (1H, m), 1.90-1.97 (1H, m)2.92-2.96 (1H, dd), 3.15-3.42 (4H, m), 4.30-4.33 (1H, d), 4.42-4.45 (1H, d), 6.90-6.94 (1H, m), 7.07-7.09 (1H, d), 7.46-7.49 (1H, d), 8.16-8.23 (2H, m). |
| 353 | 404 | 3 | 1H (CD3OD) 0.90-1.00 (6H, dd), 1.44-1.60 (2H, m), 1.71-1.78 (1H, m), 1.92-2.01 (2H, t), 3.01-3.08 (1H, dd), 3.18-3.45 (4H, m), 4.43-4.47 (1H, d), 4.54-4.58 (1H, d), 6.80-6.84 (1H, m), 7.16-7.18 (1H, d), 7.89-7.93 (2H, m), 8.21-8.23 (1H, d). |
| 354 | 324 | 3 | 1H (CD3OD) 0.60-0.64 (2H, m), 0.85-0.90 (2H, m), 1.86-1.93 (1H, m), 3.29-3.36 (4H, m), 3.76-3.78 (4H, m), 6.86-6.89 (1H, m), 7.04-7.06 (1H, d), 7.46-7.49 (1H, d), 8.06-8.08 (1H, d), 8.20-8.22 (1H, d). |
| 355 | 424 | 4 | 1H (CD3OD) 1.93-2.02 (3H, t), 3.32-3.56 (5H, m), 4.45-4.49 (1H, m), 4.63-4.68 (1H, m), 6.88-6.91 (1H, m), 7.21-7.23 (1H, d), 7.49-7.53 (5H, m), 7.91-7.93 (1H, d), 8.05-8.07 (1H, d), 8.19-8.21 (1H, d). |
| 356 | 406 | 3 | 1H NMR (DMSO) 0.82-0.88 (6H, dd), 1.39-1.45 (2H, m), 1.68-1.72 (1H, m), 2.89-2.96 (1H, m), 3.10-3.31 (5H, m), 4.24-4.31 (2H, m), 6.58-6.61 (1h, m), 6.85-7.20 (1H, t, coupling with two F), 7.21-7.22 (1H, d), 7.59-7.61 (1H, d), 7.71-7.74 (1H, d), 8.85-8.95 (2H, br s), 8.27-8.28 (1H, d), 8.65-8.78 (1H, s), 8.85-8.95 (1H, s). |
| 357 | 364 | 3 | 1H NMR (CD3OD): 0.90-1.00 (6H, m), 1.46-1.62 (2H, m), 1.73-1.80 (1H, m), 3.03-3.10 (1H, m), 3.19-3.46 (4H, m), 3.63 (1H, s), 4.43-4.47 (1H, d), 4.55-4.59 (1H, d), 6.85-6.88 (1H, m), 7.11-7.13 (1H, d), 7.84-7.86 (1H, d), 8.05-8.08 (1H, d), 8.22-8.24 (1H, d) |
| 358 | 384 | 3 | 1H NMR (CD3OD): 3.32-3.57 (5H, m), 3.63 (1H, s), 4.47-4.51 (1H, d), 4.66-4.71 (1H, m), 6.80-6.84 (1H, m), 7.15-7.17 (1H, d), 7.52-7.55 (5H, s), 7.85-7.87 (1H, d), 8.00-8.02 (1H, d), 8.20-8.22 (1H, d) |
| 359 | 438 | 3 | 1H NMR (CD3OD): 0.91-0.99 (6H, m), 1.47-1.60 (2H, m), 1.75-1.78 (1H, m), 2.92-2.98 (1H, m), 3.23-3.44 (4H, m), 4.30-4.3 (1H, d), 4.41-4.44 (1H, d), 4.51-4.58 (2H, qd), 6.80-6.83 (1H, m), 7.17-7.20 (1H, d), 7.69-7.71 (1H, d), 7.98-8.00 (1H, d), 8.21-8.23 (1H, d) |
| 360 | 426 | 3 | 1H NMR (CD3OD) 3.32-3.56 (4H, m), 4.80-4.93 (3H, m), 6.56-6.84-.6.93 (1H, t, huge J), 6.86-6.88 (1H, m), 7.24-7.26 (1H, d), 7.48-7.54 (5H, m), 7.73-7.75 (1H, d), 8.14-8.16 (1H, d), 8.21-8.22 (1H, d). |
| 361 | 380 | 4 | 1H NMR (CD3OD) 0.90-1.00 (6H, dd), 1.45-1.60 (2H, m), 1.70-1.83 (4H, m), 2.93-3.00 (1H, m), 3.15-3.33 (3H, m), 4.36-4.39 (1H, d), 4.48-4.51 (1H, d), 4.87-4.97 (1H, m), 6.18-6.27 (1H, m), 6.34-6.38 (1H, d), 6.78-6.81 (1H, m), 7.12-7.14 (1H, d), 7.93-7.95 (1H, d), 7.99-8.01 (1H, d), 8.20-8.22 (1H, d) |
| 367 | 343.12 | 7 | DMSO 8.32 (m, 1H, ArH), 8.21 (d, 1H, ArH), 8.06 (bs, 2H, NH2), 7.91 (bs, 1H, NH2), 7.76 (d, 1H, ArH), 7.56 (dd, 1H, ArH), 6.60 (dd, 1H, ArH), 3.34-3.30 (m, CH2), 3.06-3.02 (m, 2H, CH2) |
| 368 | 354.19 | 7 | DMSO 8.26 (dd, 1H, ArH), 7.92-7.74 (m, 6H, ArH, NH, 2 × NH2), 7.48 (dd, 1H, ArH), 6.81 (d, 1H, ArH), 6.59 (dd, 1H, ArH), 3.45 (d, 2H, CH2), 1.18 (s, 6H, 2 × CH3) |
| 369 | 352.2 | 7 | DMSO 8.29 (dd, 1H, ArH), 8.14 (bs, 2H, NH2), 8.05 (bs, 2H, NH2), 7.96 (d, 1H, ArH), 6.76 (d, 1H, ArH), 6.62 (dd, 1H, ArH), 3.93 (m, 1H, CH), 3.70-3.52 (m, 4H, CH2), 2.31 (m, 1H, CH), 2.10 (m, 1H, CH) |
| 370 | 368.2 | 8 | DMSO 8.06 (dd, 1H, ArH), 7.62-7.49 (m, 3H, NH, NH2), 7.31 (bs, 2H, NH2), 7.31-7.27 (m, 2H, ArH), 6.57 (d, 1H, ArH), 3.88 (bs, 1H, CH), 2.8 (bs, 1H, CH), 2.5 (bs, 1H, CH), 1.6 (m, 1H, CH), 0.63 (m, 6H, 2 × CH3). |
| 371 | 326.16 | 7 | DMSO 8.27 (d, 1H, ArH), 8.07 (bs, 1H, NH), 7.90 (d, 1H, ArH), 7.83-7.73 (bs, 4H, 2 × NH2), 7.51 (d, 1H, ArH), 6.74 (d, 1H, ArH), 6.60 (dd, 1H, ArH), 3.47-3.42 (m, 2H, CH2), 2.92-2.90 (m, 2H, CH2) |
| 372 | 340.23 | 3 | (DMSO) 1.76 (2H, m), 2.36 (2H, m), 3.24 (2H, m), 6.59 (1H, m), 6.69 (1H, m), 7.44 (1H, m), 7.63-7.67 (4H, br m), 7.82 (2H, br m), 8.28 (1H, m) |
| 373 | 340.19 | 3 | (DMSO) 2.53 (3H, s), 3.03 (2H, m), 3.52 (2H, m), 6.61 (1H, m), 6.71 (1H, m), 7.51 (1H, m), 7.73-7.91 (4H, br m), 8.43 (3H, br m) |
| 374 | 354.23 | 3 | (DMSO) 1.52 (4H, m), 2.74 (2H, m), 3.22 (2H, m), 6.59 (1H, m), 6.67 (1H, m), 7.45 (1H, m), 7.60-7.67 (4H, br m), 7.87 (2H, br m), 8.27 (1H, m) |
| 375 | 338.15 | 3 | (DMSO) 3.68-3.88 (4H, br m), 4.85 (1H, m), 6.57 (1H, m), 6.75 (1H, m), 7.45 (1H, m), 7.86-7.97 (3H, br m), 8.26 (2H, m) |
| 376 | 352.22 | 3 | (DMSO) 1.87 (1H, m), 2.12 (1H, m), 2.98 (1H, m), 3.20-3.36 (3H, br m), 4.45 (1H, m), 6.58 (1H, m), 6.76 (1H, m), 7.46 (1H, m), 7.86-7.93 (3H, br m), 8.26 (2H, m), 8.64 (1H, m), 8.78 (1H, m) |

TABLE 5-continued

| No. | M + 1 (obs) | RT (min) | 1H-NMR |
|---|---|---|---|
| 377 | 366.23 | 3 | (DMSO) 1.59 (1H, m), 1.97 (1H, m), 2.82 (1H, m), 3.08 (1H, m), 3.20-3.26 (5H, br m), 6.58 (1H, m), 6.73 (1H, m), 7.45 (1H, m), 7.76 (3H, br m), 8.26 (1H, m), 8.58 (2H, m) |
| 378 | 327.13 | 3 | (DMSO) 3.21 (2H, m), 4.43 (2H, m), 6.58 (1H, m), 7.17 (1H, m), 7.49 (1H, m), 7.91 (3H, br m), 8.30 (2H, m) |
| 379 | 366.23 | 7 | 1H NMR (400.0 MHz, DMSO) d 1.55-1.65 (m, 1H), 1.77-1.97 (m, 3H), 3.10-3.14 (m, 2H), 3.51 (t, J = 5.8 Hz, 2H), 3.62 (t, J = 6.2 Hz, 1H), 6.65 (dd, J = 5.0, 7.7 Hz, 1H), 6.80 (d, J = 9.0 Hz, 1H), 7.63 (d, J = 7.1 Hz, 1H), 7.87 (d, J = 8.9 Hz, 1H), 7.93 (s, 1H), 8.10 (s, 2H), 8.29-8.30 (m, 1H), 8.37 (s, 1H) and 9.02 (s, 1H) ppm |
| 380 | 354.22 | 3 | (DMSO) 3.08 (6H, m), 3.79 (4H, m), 6.58 (1H, m), 6.92 (1H, m), 7.50 (1H, m), 7.91 (3H, br m), 8.27 (2H, m) |
| 381 | 366.23 | 3 | (DMSO) 1.54 (2H, br m), 1.94 (2H, br m), 2.67 (1H, m), 2.85 (1H, m), 3.27 (1H, m), 3.44 (1H, m), 4.08 (1H, m), 6.58 (1H, m), 6.73 (1H, m), 7.47 (1H, m), 7.71 (1H, m), 7.84 (2H, m), 8.26 (1H, m), 8.50 (2H, m) |
| 382 | 380.24 | 3 | (DMSO) 1.24 (3H, br m), 1.71 (3H, br m), 2.74 (1H, m), 3.16 (2H, m), 3.43 (2H, m), 6.59 (1H, m), 6.78 (1H, m), 7.53 (1H, m), 7.85 (3H, m), 8.01 (1H, m), 8.27 (1H, m), 8.38 (1H, m) |
| 383 | 400 | 4 | 1H (CD3OD) 1.75-1.77 (6H, d), 3.33-3.57 (7H, m), 4.47-4.51 (1H, d), 4.58-4.65 (2H, m), 5.76-5.84 (1H, m), 6.33-6.36 (1H, d, J = 11.5), 6.84-6.87 (1H, m), 7.19-7.21 (1H, d), 7.50-7.54 (5H, s), 7.79-7.81 (1H, d), 8.12-8.14 (1H, d), 8.18 (1H, d), |
| 384 | 400 | 4 | 1H (CD3OD) 1.82-1.84 (6H, d), 3.33-3.57 (7H, m), 4.45-4.49 (1H, d), 4.55-4.61 (2H, m), 6.21-6.27 (1H, m), 6.37-6.41 (1H, d, J = 16), 6.80-6.84 (1H, m), 7.17-7.19 (1H, d), 7.51 (5H, s), 8.01-8.06 (2H, m), 8.17-8.19 (1H, d). |
| 385 | 382 | 9 | 1H (CD3OD) 0.88-0.98 (9H, m), 1.45-1.62 (3H, m), 1.69-1.74 (1H, m), 2.52-2.56 (2H, t), 2.90-2.97 (1H, dd), 3.15-3.42 (4H, m), 4.32-4.35 (1H, d), 4.44 4.47 (1H, d), 6.79-6.82 (1H, m), 7.10-7.12 (1H, d), 7.70-7.72 (1H, m), 7.98-8.00 (1H, d), 8.20-8.23 (1H, d). |
| 386 | 340.11 | 7 | 1H NMR (400.0 MHz, DMSO) d 8.27 (dd, J = 1.6, 4.8 Hz, 1H), 8.06 (s, 1H), 7.82 (d, J = 8.7 Hz, 2H), 7.63 (d, J = 7.6 Hz, 1H), 7.36 (s, 1H), 7.02 (s, 1H), 6.86 (s, 1H), 6.66 (dd, J = 5.0, 7.8 Hz, 1H) and 3.80 (s, 2H) ppm |
| 387 | 380.2 | 7 | 1H NMR (400.0 MHz, DMSO) d 8.68 (d, J = 10.1 Hz, 1H), 8.34 (d, J = 9.7 Hz, 1H), 8.29 (dd, J = 1.4, 4.7 Hz, 1H), 8.07 (s, 2H), 7.79 (s, 2H), 7.58 (d, J = 7.7 Hz, 1H), 6.74 (d, J = 9.0 Hz, 1H), 6.67 (dd, J = 4.9, 7.8 Hz, 1H), 3.26-3.10 (m, 4H), 2.73 (dd, J = 11.6, 22.8 Hz, 1H), 2.62-2.50 (m, 1H), 1.90 (s, 1H), 1.73 (m, 2H), 1.53 (t, J = 12.7 Hz, 1H) and 1.14 (t, J = 11.5 Hz, 1H) ppm |
| 388 | 402.19 | 8 | 1H NMR (400.0 MHz, DMSO) d 8.30-8.29 (m, 4H), 7.89 (s, 1H), 7.84 (d, J = 9.1 Hz, 1H), 7.78 (s, 1H), 7.49 (d, J = 7.6 Hz, 1H), 7.39-7.38 (m, 3H), 7.30 (s, 2H), 6.73 (d, J = 9.0 Hz, 1H), 6.62 (dd, J = 4.6, 7.9 Hz, 1H), 4.40 (s, 1H) and 3.65 (s, 2H) ppm |
| 389 | 380.16 | 8 | |
| 391 | 380 | 2 | 1H NMR (CD3OD): 0.93-0.98 (6H, m), 1.49-1.57 (2H, m), 1.72-1.78 (4H, m), 2.96-3.03 (1H, m), 3.20-3.43 (4H, m), 4.38-4.42 (1H, d), 4.50-4.54 (1H, d), 5.78-5.81 (1H, m), 6.31-6.34 (1H, dd, J = 11 Hz), 6.82-8.86 (1H, m), 7.14-7.16 (1H, d), 7.78-7.80 (1H, d), 8.04-8.06 (!H, d), 8.20-8.22 (1H, d). |
| 392 | 442 | 2 | 1H NMR (CD3OD) 2.41 (3H, s), 3.38-3.57 (4H, m), 4.42-4.46 (1H, m), 4.70-4.75 (2H, m), 6.78-6.81 (1H, m), 7.24-7.42 (5H, m), 7.89-7.91 (1H, d), 8.03-8.05 (1H, d), 8.22-8.24 (1H, d). |
| 393 | 363.14 | 8 | 1H NMR (400.0 MHz, DMSO) d 8.42 (d, J = 9.0 Hz, 1H), 8.30 (dd, J = 1.9, 4.6 Hz, 1H), 8.05 (d, J = 9.0 Hz, 1H), 6.60 (dd, J = 4.8, 7.9 Hz, 1H), 5.27 (s, 1H) and 2.11 (s, 3H) ppm |
| 394 | 363.12 | 8 | 1H NMR (400.0 MHz, DMSO) d 8.35 (d, J = 9.0 Hz, 1H), 8.30 (dd, J = 1.8, 4.8 Hz, 1H), 8.07 (s, 2H), 7.89 (d, J = 9.1 Hz, H), 7.79 (dd, J = 1.8, 7.9 Hz, 1H), 6.64 (dd, J = 4.9, 8.0 Hz, 1H), 5.69 (d, J = 0.7 Hz, 1H) and 2.33 (s, 3H) ppm |
| 395 | | | 1H NMR (400.0 MHz, DMSO) d 8.28 (dd, J = 1.8, 4.7 Hz, 1H), 7.96 (s, 2H), 7.86 (d, J = 9.0 Hz, 1H), 7.78 (s, 3H), 7.55 (dd, J = 1.7, 7.9 Hz, 1H), 6.79 (d, J = 9.0 Hz, 1H), 6.62 (dd, J = 4.8, 7.9 Hz, 1H), 3.56 (s, 1H), 3.29 (s, J = 7.0 Hz, 1H), 3.08 (m, 1H), 1.85 (d, J = 6.3 Hz, 1H) and 0.84 (dd, J = 6.8, 15.9 Hz, 6H) ppm |
| 396 | 382.26 | 8 | 1H NMR (400.0 MHz, DMSO) d 8.28 (dd, J = 1.9, 4.9 Hz, 1H), 7.96 (s, 2H), 7.86 (d, J = 8.9 Hz, 1H), 7.72 (s, 2H), 7.54 (dd, J = 1.7, 7.8 Hz, 1H), 6.78 (d, J = 8.9 Hz, 1H), 6.60 (dd, J = 4.8, 7.9 Hz, 1H), 3.53-3.50 (m, 1H), 3.27-3.17 (m, 2H), 1.59 (qn, J = 6.6 Hz, 1H), 1.39-1.23 (m, 2H) and 0.72 (dd, J = 6.4, 17.7 Hz, 6H) ppm |
| 397 | 458.29 | 9 | 1H NMR (400.0 MHz, DMSO) d 8.28 (dd, J = 1.9, 4.9 Hz, 1H), 8.07 (d, J = 9.2 Hz, 1H), 7.99 (s, 2H), 7.60 (dd, J = 1.8, 7.9 Hz, 1H), 7.40 (t, J = 7.9 Hz, 1H), 7.33 (d, J = 9.1 Hz, 1H), 7.12 (s, 1H), 7.09-7.01 (m, 2H), 6.62 (dd, J = 4.8, 7.9 Hz, 1H), 4.60-4.47 (m, 4H), 3.77 (s, 3H) and 3.48-3.42 (m, 3H) ppm. 9.62 (s, 1H) 9.34 (s, 1H) |

TABLE 5-continued

| No. | M + 1 (obs) | RT (min) | 1H-NMR |
|---|---|---|---|
| 398 | 325 | 3 | (d6-DMSO, 400 MHz) 0.86 (3H, t), 1.44-1.53 (3H, m), 3.15 (2H, m), 6.63-6.70 (2H, m), 7.56 (1H, dd), 7.65 (1H, brs), 7.77 (1H, d), 7.98 (2H, brs), 8.27 (1H, dd) |
| 399 | 369.21 | 3 | (DMSO) 0.87 (6H, br m), 1.86 (1H, m), 3.30 (2H, m), 3.81 (1H, m), 6.58 (1H, m), 6.63 (1H, m), 7.39 (1H, br s), 7.71 (1H, m), 7.79 (1H, m), 8.25 (2H, br s), 8.27 (1H, m) |
| 400 | 369.21 | 3 | (DMSO) 0.85 (6H, br m), 1.97 (1H, m), 3.30 (1H, m), 4.31 (1H, m), 4.48 (1H, m), 6.58 (1H, m), 7.20 (1H, m), 7.47 (1H, m), 7.91-7.99 (4H, br s), 8.30 (1H, m) |
| 401 | 404 | 3 | 1H (CD3OD): 0.92-0.97 (6H, dd), 1.45-1.57 (2H, m), 1.67-1.73 (1H, m), 2.95-3.01 (1H, dd), 3.17-3.43 (4H, m), 4.35-4.39 (1H, m), 4.47-4.50 (1H, m), 5.94-6.10 2H, dt) 6.85-6.89 (1H, m), 7.16-7.18 (1H, d), 7.77-7.79 (1H, d), 8.18-8.23 (2H, m). |
| 402 | 378 | 3 | 1H (CD3OD): 0.95-0.99 (6H, dd), 1.48-1.58 (2H, m), 1.74-1.76 (1H, m), 1.90 (3H, s), 2.98-3.04 (1H, dd), 3.22-3.45 (4H, m), 4.41-4.45 (1H, m), 4.53-4.57 (1H, m), 6.81-6.84 (1H, m), 7.08-7.10 (1H, d), 7.75-7.77 (1H, d), 7.97-7.99 (1H, d), 8.22-8.24 (1H, d). |
| 403 | 390 | 3 | 1H (CD3OD): 0.95-0.99 (6H, dd), 1.55-1.59 (2H, m), 1.69-1.76 (1H, m), 3.03-3.09 (1H, dd), 3.21-3.47 (4H, m), 4.44-4.48 (1H, m), 4.56-4.60 (1H, m), 6.82-7.10 (1H, t), 6.87-6.91 (1H, m), 7.24-7.26 (1H, d), 8.04-8.06 (1H, d), 8.24-8.26 (21H, m). |
| 404 | 410 | 3 | 1H (CD3OD): 3.32-3.44 (2H, m), 3.53-3.58 (1H, m), 4.65-4.72 (2H, m), 6.83-7.10 (2H, m), 7.29-7.31 (1H, d), 7.53 (5H, s), 8.05-8.07 (1H, d), 8.19-8.21 (1H, d), 8.24-8.26 (1H, d. |
| 405 | 341.18 | 7 | E14942__31A 1H NMR (400.0 MHz, DMSO) d 8.31-8.25 (m, 2H), 7.93 (s, 2H), 7.71 (s, 2H), 7.49 (dd, J = 1.9, 8.0 Hz, 1H), 7.18 (d, J = 9.0 Hz, 1H), 6.60 (dd, J = 4.8, 7.9 Hz, 1H), 4.30 (t, J = 6.2 Hz, 2H), 2.95 (dd, J = 6.1, 13.0 Hz, 2H) and 1.98 (dd, J = 6.5, 20.5 Hz, 2H) ppm |
| 406 | 383.21 | 8 | E14942__32B 1H NMR (400.0 MHz, DMSO) d 8.31 (dd, J = 3.5, 5.1 Hz, 2H), 7.98 (s, 4H), 7.51 (dd, J = 1.4, 7.9 Hz, 1H), 7.20 (d, J = 8.8 Hz, 1H), 6.59 (dd, J = 4.7, 7.9 Hz, 1H), 4.49 (dd, J = 3.0, 11.7 Hz, 1H), 4.23 (dd, J = 7.0, 11.8 Hz, 1H), 3.53 (s, 1H), 1.63 (qn, J = 6.7 Hz, 1H), 1.48-1.40 (m, 2H) and 0.81 (dd, J = 6.5, 10.1 Hz, 6H) ppm |
| 407 | 404 | 3 | 1H (CD3OD) 0.45-0.51 (2H, m), 0.77-0.82 (2H, m), 0.95-0.99 (6H, m), 1.30-1.34 (1H, m), 1.49-1.58 (2H, m), 1.75-1.77 (1h, m), 2.98-3.05 (1H, m), 3.22-3.45 (4H, m), 4.41-4.45 (1H, d), 4.53-4.57 (1H, d), 6.84-6.88 (1H, m), 7.07-7.09 1H, d), 7.71-7.73 (1H, d), 8.01-8.03 (1H, d), 8.22-8.25 (1H, d). |
| 408 | 424 | 4 | 1H (CD3OD) 0.43-0.45 (2H, m), 0.80-0.82 (2H, m), 1.30-1.36 (1H, m), 3.32-3.57 (4H, m), 4.46-4.50 (1H, m), 4.62-4.69 (2H, m), 6.85-6.88 (1H, m), 7.12-7.14 (1H, d), 7.50-7.54 (5H, m), 7.73-7.75 (1H, d), 8.04-8.06 (1H, d), 8.21-8.23 (1H, d). |
| 409 | 348 | 33 | 1H (CD3OD) 0.50-0.53 (2H, m), 0.78-0.82 (2H, m), 1.30-1.36 (1H, m), 3.85-3.88 (4H, m), 4.88-4.93 (4H, m), 6.89-6.92 (1H, m), 7.05-7.08 (1H, d), 7.71-7.74 (1H, d), 8.07-8.09 (1H, d), 8.23-8.25 (1H, d). |
| 410 | 324 | 3 | 1H (CD3OD) 1.74-1.77 (3H, d), 3.29-3.35 (4H, m), 3.80-3.85 (4H, m), 5.75-5.84 (1H, m), 6.33-6.36 (1H, dd, J = 11 Hz), 6.89-6.92 91H, m), 7.13-7.15 (1H, d), 7.78-7.80 (1H, d), 8.15-8.21 (2H, m). |
| 411 | 324 | 3 | 1H (CD3OD) 1.82-1.84 (3H, d), 3.29-3.35 (4H, m), 3.80-3.85 (4H, m), 6.19-6.28 (1H, m), 6.38-6.43 (1H, dd, J = 16 Hz), 6.88-6.91 (1H, m), 7.11-7.15 (1H, d), 8.00-8.02 (1H, d), 8.12-8.14 (1H, d), 8.20-8.22 (1H, d). |
| 412 | 322 | 3 | 1H (CD3OD) 1.91 (3H, s), 3.20-3.34 (4H, m), 3.85-3.88 (4H, m), 6.90-6.93 (1H, m), 7.07-7.09 (1H, d), 7.75-7.77 (1H, d), 8.12-8.14 (1H, d), 8.22-8.24 (1H, d). |
| 413 | 416 | 3 | 1H (CD3OD) 0-97-1-01 (6H, m), 1.51-1.62 (2H, m), 1.77-1.81 (1H, m), 3.02-3.08 (1H, m), 3.26-3.48 (4H, m), 4.45-4.49 (1H, m)< 4.58-4.62 (1H, m), 6.77-6.80 (1H, m), 7.24-7.35 (6H, m), 7.85-7.87 (1H, d), 8.07-8.13 (2H, m). |
| 414 | 380.28 | 3 | (DMSO) 0.97 (2H, br m), 1.17 (1H, br m), 1.35-1.38 (4H, br m), 1.62 (1H, br m), 2.91-3.35 (1H, m), 3.69-4.24 (1H, m), 6.73-6.89 (2H, m), 7.54-7.76 (2H, br m), 7.83-7.96 (2H, br m), 8.21 (1H, m) |
| 415 | 403.24 | 3 | (DMSO) 4.54 (1H, m), 4.67 (2H, br m), 6.59 (1H, m), 7.21 (1H, m), 7.41 (5H, m), 7.51 (1H, m), 7.98 (2H, br s), 8.30 (2H, m), 8.64 (2H, brs |
| 416 | 360 | 3 | 1H (CD3OD) 3.15-3.36 (4H, m), 4.87-5.02 (4H, m), 6.67-6.70 (1H, m), 7.20-7.33 (6H, m), 7.84-7.89 (2H, m), 8.10-8.12 (1H, d). |
| 417 | 374 | 3 | 1H (CD3OD) 3.28-3.35 (4H, m), 3.77-3.80 (4H, m), 3.96 (2H, s), 6.72-6.75 (1H, m), 7.01-7.16 (6H, m), 7.71-7.73 (1H, d), 7.84-7.86 (1H, d), 8.10-8.12 (1H, d). |
| 418 | 430 | 4 | 1H (CD3OD) 0.88-0.95 (6H, m), 1.46-1.59 (2H, m), 1.69-1.75 (1H, m), 2.91-2.97 (1H, m), 3.20-3.40 (4H, m), 3.95 (2H, s), 4.33-4.36 (1H, m), 4.45-4.48 (1H, m), 6.67-6.70 (1H, m), 7.01-7.16 (6H, m), 7.70 7.72 (1H, d), 7.76-7.78 (1H, d), 8.11-8.13 (1H, d). |
| 419 | 341.26 | 8 | 1H NMR (400.0 MHz, DMSO) d 8.28 (dd, J = 1.8, 5.0 Hz, 1H), 8.09 (s, 2H), 7.78 (d, J = 8.0 Hz, 1H), 7.62 (d, J = 6.8 Hz, 2H), 6.70-6.64 (m, 2H), 3.43 (t, J = 6.2 Hz, 2H), 3.23 (d, J = 4.0 Hz, 2H) and 1.63 (qn, J = 6.4 Hz, 2H) ppm |

TABLE 5-continued

| No. | M + 1 (obs) | RT (min) | 1H-NMR |
|---|---|---|---|
| 420 | 420 | 3 | 1H (CDCL3) 0.97-1.00 (6H, m), 1.60-1.64 (2H, m), 1.81-1.85 (1H, m), 2.99-3.46 (5H, m), 4.09 (3H, s), 4.20-4.23 (1H, m), 4.40-4.43 (1H, m), 6.50-6.53 (1H, m), 6.61-6.63 (1H, d), 7.28-7.30 (1H, masked), 7.69 (1H, s), 7.92-7.96 (2H, m), 8.06 (1H, s). |
| 421 | 402.99 | 9 | 1H NMR (400.0 MHz, DMSO) d 8.28 (dd, J = 1.8, 5.0 Hz, 1H), 8.11 (s, 2H), 7.84 (s, 1H), 7.78 (d, J = 9.0 Hz, 1H), 7.65 (d, J = 7.6 Hz, 1H), 7.26-7.21 (m, 5H), 6.79 (d, J = 9.0 Hz, 1H), 6.69 (dd, J = 5.0, 7.9 Hz, 1H), 4.68 (dd, J = 4.1, 7.6 Hz, 1H), 3.44 (d, J = 12.9 Hz, 1H) and 3.25 (s, 1H) ppm |
| 422 | 383.02 | 3.15 | (DMSO) 0.94 (9H, m), 3.30 (1H, m), 4.23 (1H, m), 4.60 (1H, m), 6.58 (1H, m), 7.22 (1H, m), 7.48 (1H, m), 7.91 (4H, m), 8.30 (1H, m), |
| 423 | 326.96 | 2.95 | (DMSO) 2.55 (2H, m), 2.66 (2H, m), 6.62 (1H, m), 6.72 (1H, m), 7.50 (1H, m), 7.51 (1H, m), 7.67 (1H, m), 8.03 (2H, m), 8.10 (1H, m), |
| 424 | 384 | 3.29 | H (CD3OD) 9.94-0.8 (6H, m), 1.47-1.62 (2H, m), 1.73-1.78 (1H, m), 3.03-3.09 (1H, m), 3.20-3.46 (4H, masked), 4.45-4.49 (1H, m), 4.57-4.60 !H, m), 4.80-5.02 (3H, masked), 6.82-6.86 (1H, m), 7.15-7.17 (1H, d), 7.95-8.00 (2H, m), 8.21-8.23 (1H, d). |
| 425 | 368 | 2.87 | (d6-DMSO, 400 MHz) 0.91 (6H, s), 2.67-2.68 (2H, m), 3.20 (2H, d), 6.60 (1H, dd), 6.80 (1H, d), 7.43 (1H, dd), 7.60-7.66 (4H, brm), 7.80 (1H, d), 7.90 (2H, brs), 8.27 (1H, dd) |
| 426 | 444 | 3.35 | (d6-DMSO, 400 MHz) 0.56 (3H, t), 1.71-1.75 (2H, m), 3.21 (2H, brs), 3.73 (2H, brm), 6.61 (1H, dd), 6.79 (1H, d), 7.26-7.28 (1H, m), 7.29-7.42 (6H, m), 7.57 (3H, brs), 7.78 (1H, d), 7.88 (1.5H, brs), 8.27 (1H, dd) |
| 427 | 416.99 | 8.42 | 1H NMR (400.0 MHz, DMSO) d 8.38 (d, J = 3.4 Hz, 2H), 8.30-8.24 (m, 2H), 7.97 (s, 2H), 7.45-7.35 (m, 5H), 7.13 (d, J = 8.8 Hz, 1H), 6.57 (dd, J = 4.7, 7.9 Hz, 1H), 4.42 (dd, J = 5.2, 8.5 Hz, 1H), 4.24 (dd, J = 5.4, 11.1 Hz, 1H), 4.21 (s, 1H), 4.07-4.01 (m, 1H), 2.33 (m, 1H) and 2.24 (m, 1H) ppm |
| 428 | 406 | 3.37 | 1H (CD3OD) 0.93-.096 (6H, m), 1.34-1.56 (2H, m), 1.72-1.77 (1H, m), 2.90-2.97 (1H, m), 3.14-3.39 (4H, m), 4.39-4.42 (1H, m), 4.55-4.58 (1H, m), 6.89-6.96 (3H, m), 7.40 (1H, d), 7.97-8.00 (1H, d), 8.05-8.07 (1H, d), 9.57-9.62 (2H, m). |
| 429 | 408.1 | 3.2 | (DMSO) 0.48 (1H, m), 0.76 (2H, m), 1.16-1.47 (4H, m), 1.68 (3H, m), 2.33 (2H, m), 3.06 (2H, m), 6.55 (1H, m), 6.69 (1H, m), 7.40 (1H, m), 7.62 (1H, m), 7.80 (3H, m), 8.26 (1H, m), |
| 430 | 416.99 | 8.97 | 1H NMR (400.0 MHz, CDCl3) d 10.50 (s, 1H), 9.00 (s, 1H), 8.05 (d, J = 6.8 Hz, 2H), 7.77 (d, J = 9.0 Hz, 1H), 7.39-7.28 (m, 5H), 6.80 (t, J = 6.9 Hz, 1H), 6.64 (d, J = 9.0 Hz, 1H), 5.30 (s, 1H), 4.94 (d, J = 3.0 Hz, 1H), 4.31 (s, 1H) and 1.08 (d, J = 6.8 Hz, 3H) ppm |
| 431 | 416 | 3.12 | (d6-DMSO, 400 MHz) 3.14 (3H, brs), 3.37 (1H, brs), 3.50 (1H, brs), 6.63 (1H, dd), 6.70 (1H, d), 7.05-7.31 (5H, m), 7.48 (1H, d), 7.67-7.95 (7H, m), 8.28 (1H, dd) |
| 432 | 380.04 | 8.12 | 1H NMR (400.0 MHz, MeOH) d 8.25 (dd, J = 1.7, 5.7 Hz, 1H), 8.04-8.01 (m, 2H), 7.22 (d, J = 9.1 Hz, 1H), 6.87 (dd, J = 5.7, 7.8 Hz, 1H), 4.59 (m, 2H), 3.49-3.32 (m, 2H), 3.28-3.13 (m, 3H), 1.74 (qn, J = 7.3 Hz, 2H) and 1.06 (t, J = 7.6 Hz, 3H) ppm |
| 433 | 411.02 | 7.39 | 1H NMR (400.0 MHz, MeOH) d 8.30-8.26 (m, 2H), 8.17 (dd, J = 1.7, 7.7 Hz, 1H), 7.29 (d, J = 8.5 Hz, 1H), 6.96 (dd, J = 6.0, 7.6 Hz, 1H), 4.65 (dd, J = 3.1, 12.2 Hz, 1H), 4.50 (dd, J = 6.4, 12.1 Hz, 1H), 4.02-3.93 (m, 2H), 3.47-3.32 (m, 3H), 2.11-2.02 (m, 1H), 1.71 (d, J = 12.4 Hz, 2H) and 1.52-1.37 (m, 2H) ppm |
| 434 | 394.04 | 8.52 | 1H NMR (400.0 MHz, MeOH) d 8.27-8.20 (m, 2H), 8.04 (d, J = 9.2 Hz, 1H), 7.23 (d, J = 9.1 Hz, 1H), 6.97 (dd, J = 6.1, 7.8 Hz, 1H), 4.50 (m, 2H), 3.48 (m, 2H), 3.33 (qn, J = 1.6 Hz, 1H), 3.20-3.17 (m, 2H), 1.69-1.64 (m, 2H), 1.47 (dd, J = 2.8, 7.3 Hz, 2H) and 0.98 (t, J = 7.3 Hz, 3H) ppm |
| 435 | 434 | 9.14 | 1H (CD3OD) 0.90-1.00 (6H, m), 1.49-1.63 (2H, m), 1.72-1.79 (1H, m), 3.03-3.09 (1H, m), 3.23-3.47 (3H, m), 6.85-6.88 (1H, m), 7.04-7.36 (4H, m), 7.31-7.36 (1H, m), 8.17-8.19 (1H, d), 8.26-8.28 (1H, d). |
| 436 | 398 | 3.43 | 1H (CD3OD) 1.91 (3H, s), 3.32-3.56 (4H, m), 4.46-4.49 (1H, m), 4.60-4.67 (2H, m), 6.86-6.89 (1H, m), 7.13-7.15 (1H, d), 7.52 (5H, s), 7.76-7.78 (1H, d), 8.09-8.11 (1H, d), 8.19-8.21 (1H, d). |
| 437 | 408.04 | 8.14 | 1H NMR (400.0 MHz, MeOH) d 8.27 (dd, J = 1.4, 6.0 Hz, 1H), 8.20 (dd, J = 1.2, 7.6 Hz, 1H), 8.00 (d, J = 9.2 Hz, 1H), 7.04 (d, J = 9.2 Hz, 1H), 6.97 (dd, J = 6.1, 7.6 Hz, 1H), 4.40 (d, 1H), 3.90 (m, 1H), 3.63-3.47 (m, 3H), 3.17-3.11 (m, 1H), 2.32 (m, 2H), 1.60-1.54 (m, 2H), 1.41-1.32 (m, 1H), 1.28 (m, 1H) and 0.84 (t, J = 7.2 Hz, 3H) ppm |
| 438 | 381.07 | 2.95 | (DMSO) 1.39 (2H, m), 1.56 (4H, m), 1.73 (2H, m), 4.09 (2H, s), 6.56 (1H, m), 7.16 (1H, m), 7.43 (1H, m), 7.86 (2H, br s), 8.21 (1H, m), 8.29 (1H, m), |
| 439 | 372 | 7.93 | 1H (MeOD-d4) 1.85 (3H, s), 3.73-3.79 (2H, m), 4.54-4.57 (1H, m), 6.65-6.67 (1H, d), 6.81-6.84 (1H, m), 7.31-7.35 (2H, m), 7.40-7.41 (3H, m), 7.53-7.56 (1H, d), 8.01-8.03 (1H, d), 8.20-8.21 (1H, d). |
| 440 | 431.05 | 3.59 | (DMSO) 0.74 (3H, m), 2.01-2.14 (2H, m), 4.67 (2H, m), 6.59 (1H, m), 7.14 (1H, m), 7.38-7.47 (6H, m), 7.90 (2H, br s), 8.29 (2H, m), 8.71 (2H, br s), |

TABLE 5-continued

| No. | M + 1 (obs) | RT (min) | 1H-NMR |
|---|---|---|---|
| 441 | 406.1 | 8.72 | 1H NMR (400.0 MHz, MeOH) d 8.08 (dd, J = 1.4, 5.8 Hz, 1H), 7.95 (d, J = 7.6 Hz, 1H), 7.87 (d, J = 9.1 Hz, 1H), 7.08-7.04 (m, 1H), 6.76 (dd, J = 6.1, 7.4 Hz, 1H), 4.50 (d, 1H), 4.38 (d, 1H), 3.33-3.19 (m, 3H), 3.10-3.00 (m, 2H), 1.51 (qn, J = 7.1 Hz, 1H), 1.39 (q, J = 7.1 Hz, 1H), 0.65-0.57 (m, 1H), 0.43-0.35 (m, 2H) and 0.04-0.00 (m, 2H) ppm |
| 442 | 392.1 | 8.23 | 1H NMR (400.0 MHz, MeOH) d 8.26 (d, J = 5.4 Hz, 1H), 8.18 (d, J = 7.7 Hz, 1H), 8.03 (d, J = 9.1 Hz, 1H), 7.23 (d, J = 9.1 Hz, 1H), 6.98-6.94 (m, 1H), 4.60 (d, 1H), 4.50 (d, 1H), 3.50-3.44 (m, 3H), 3.21-3.14 (m, 1H), 2.62 (td, J = 10.1, 4.3 Hz, 1H), 1.05-1.00 (m, 1H), 0.76-0.71 (m, 2H), 0.59 (s, 1H), 0.57 (t, J = 4.7 Hz, 1H) and 0.47-0.41 (m, 1H) ppm |
| 443 | 396.09 | 3.15 | 1H NMR (400.0 MHz, DMSO) d 0.85 (dd, J = 3.7, 6.4 Hz, 6H), 1.16 (s, 3H), 1.43 (t, J = 5.5 Hz, 2H), 1.69 (m, 1H), 3.40-3.47 (m, 2H), 6.56 (dd, J = 4.6, 7.9 Hz, 1H), 6.85 (d, J = 9.0 Hz, 1H), 7.40-7.42 (m, 1H), 7.83 (d, J = 8.7 Hz, 3H) and 8.26 (dd, J = 1.7, 4.5 Hz, 1H) ppm |
| 444 | 430.07 | 3.45 | (400.0 MHz, DMSO) d 0.65 (6H, m), 1.91 (1H, m), 2.13 (1H, m), 3.87 (2H, m), 6.58 (1H, dd), 6.80 (1H, d), 7.37-7.49 (7H, m), 7.82 (3H, m) and 8.30 (3H, m) |
| 445 | 386.08 | 8.97 | 1H NMR (400.0 MHz, MeOH) d 8.06 (dd, J = 1.7, 4.7 Hz, 1H), 7.84 (d, J = 9.0 Hz, 1H), 7.50 (dd, J = 1.8, 7.9 Hz, 1H), 7.31 (d, J = 7.2 Hz, 2H), 7.25-7.15 (m, 3H), 6.87 (d, J = 9.1 Hz, 1H), 6.49-6.41 (m, 2H), 5.48 (s, 1H), 5.00 (d, J = 11.1 Hz, 1H), 4.18 (d, J = 12.3 Hz, 2H), 3.71 (dd, J = 2.7, 10.7 Hz, 1H), 3.04 (d, J = 11.0 Hz, 1H) and 2.95-2.73 (m, 3H) ppm |
| 446 | 386.08 | 8.95 | 1H NMR (400.0 MHz, MeOH) d 8.06 (dd, J = 1.7, 4.7 Hz, 1H), 7.84 (d, J = 9.0 Hz, 1H), 7.50 (dd, J = 1.8, 7.9 Hz, 1H), 7.31 (d, J = 7.2 Hz, 2H), 7.25-7.15 (m, 3H), 6.87 (d, J = 9.1 Hz, 1H), 6.49-6.41 (m, 2H), 5.48 (s, 1H), 5.00 (d, J = 11.1 Hz, 1H), 4.18 (d, J = 12.3 Hz, 2H), 3.71 (dd, J = 2.7, 10.7 Hz, 1H), 3.04 (d, J = 11.0 Hz, 1H) and 2.95-2.73 (m, 3H) ppm |
| 447 | 428.07 | 9.14 | 1H NMR (400.0 MHz, MeOH) d 8.08 (d, J = 3.7 Hz, 1H), 7.76 (d, J = 9.2 Hz, 1H), 7.44 (d, J = 7.3 Hz, 1H), 7.31 (d, J = 7.4 Hz, 2H), 7.22 (dd, J = 7.1, 24.7 Hz, 3H), 6.91 (d, J = 9.2 Hz, 1H), 6.50 (dd, J = 4.9, 7.7 Hz, 1H), 4.29 (d, J = 12.6 Hz, 2H), 3.70 (d, J = 10.6 Hz, 1H), 3.05 (d, J = 12.9 Hz, 2H), 2.88 (s, 2H) and 2.84 (dd, J = 7.8, 11.5 Hz, 2H) ppm |
| 448 | 428.07 | 9.12 | 1H NMR (400.0 MHz, MeOH) d 8.10-8.08 (m, 1H), 7.77 (d, J = 9.2 Hz, 1H), 7.45 (dd, J = 1.7, 7.9 Hz, 1H), 7.31 (d, J = 7.2 Hz, 2H), 7.27-7.17 (m, 3H), 6.92 (d, J = 9.2 Hz, 1H), 6.51 (dd, J = 4.8, 7.8 Hz, 1H), 4.30 (d, J = 12.6 Hz, 2H), 3.71 (dd, J = 2.7, 10.8 Hz, 1H), 3.07-2.96 (m, 2H) and 2.88-2.81 (m, 2H) ppm |
| 449 | 470.07 | 10.28 | 1H NMR (400.0 MHz, MeOH) d 8.20-8.19 (m, 1H), 7.86 (d, J = 9.2 Hz, 1H), 7.59 (dd, J = 1.6, 7.8 Hz, 1H), 7.45 (d, J = 7.2 Hz, 2H), 7.36-7.26 (m, 3H), 7.00 (d, J = 9.2 Hz, 1H), 6.61 (dd, J = 4.8, 7.8 Hz, 1H), 4.50 (d, J = 12.6 Hz, 1H), 4.37 (d, J = 12.7 Hz, 1H), 3.83 (dd, J = 2.7, 10.8 Hz, 1H), 2.90-2.84 (m, 1H), 2.77-2.71 (m, 1H), 2.62-2.57 (m, 1H), 1.73 (q, J = 6.7 Hz, 1H) and 1.01 (dd, J = 2.8, 6.7 Hz, 6H) ppm |
| 450 | 470.07 | 10.09 | 1H NMR (400.0 MHz, MeOH) d 8.20 (d, J = 3.5 Hz, 1H), 7.84 (d, J = 9.2 Hz, 1H), 7.55-7.53 (m, 1H), 7.45 (d, J = 7.4 Hz, 2H), 7.35-7.25 (m, 3H), 6.98 (d, J = 9.2 Hz, 1H), 6.62 (dd, J = 4.9, 7.7 Hz, 1H), 4.15 (s, 1H), 4.12-4.10 (m, 1H), 4.00 (d, J = 13.0 Hz, 1H), 3.65 (dd, J = 8.5, 12.6 Hz, 1H), 3.52 (dd, J = 2.3, 13.1 Hz, 1H), 2.58 (t, J = 4.3 Hz, 1H), 1.94 (dd, J = 7.0, 14.8 Hz, 1H), 1.90 (s, 1H) and 0.94 (dd, J = 6.6, 19.0 Hz, 6H) ppm |
| 451 | 408.1 | 3.09 | 1H NMR (400.0 MHz, DMSO) d 0.89 (dd, J = 10.5, 19.8 Hz, 1H), 1.34-1.43 (m, 6H), 1.70-1.75 (m, 3H), 2.63-2.70 (m, 2H), 3.07 (d, J = 5.8 Hz, 1H), 3.16 (t, J = 6.0 Hz, 1H), 6.59-6.63 (m, 1H), 6.70 (d, J = 8.9 Hz, 1H), 7.47 (dt, J = 7.8, 2.4 Hz, 1H), 7.64 (d, J = 4.9 Hz, 3H), 7.76 (d, J = 8.0 Hz, 1H), 7.86 (s, 1H) and 8.26 (dd, J = 1.9, 4.7 Hz, 1H) ppm |
| 452 | 430.08 | 3.22 | 1H NMR (400.0 MHz, DMSO) d 1.14 (s, 3H), 2.86 (d, J = 5.8 Hz, 2H), 3.49 (d, J = 5.9 Hz, 2H), 6.51 (dd, J = 4.7, 7.9 Hz, 1H), 6.87 (d, J = 9.0 Hz, 1H), 7.21-7.33 (m, 5H), 7.44 (d, J = 7.9 Hz, 2H), 7.76 (d, J = 12.2 Hz, 5H), 7.88 (d, J = 9.0 Hz, 1H) and 8.25 (d, J = 3.0 Hz, 1H) ppm |
| 453 | 450 | 3.52 | (d6-DMSO, 400 MHz) 0.79 (3H, d), 0.85 (3H, d), 1.77-1.84 (1H, m0, 2.94 (1H, t), 3.03 (2H, d), 3.55-3.63 (2H, m), 3.93 (1H, t), 4.34 (1H, d), 4.48 (1H, d), 6.57 (1H, dd), 7.18 (1H, d), 7.49 (1H, d), 7.80 (2H, brs), 7.99 (1H, d), 8.26 (1H, d) |
| 454 | 328 | 7 | 1H NMR (CD3OD) 3.30-3.32 (4H, masked), 3.89-3.92 (4H, m), 4.80-5.03 (2H, m), 6.89-6.92 (1H, m), 7.13-7.15 (1H, dd), 7.95-7.97 (1H, d), 8.08-8.10 (1H, d), 8.21-8.23 (1H, d) |
| 455 | 396.05 | 7.95 | 1H NMR (400.0 MHz, MeOH) d 8.26 (d, J = 1.5, 6.0 Hz, 1H), 8.16-8.14 (m, 1H), 8.05 (dd, J = 3.4, 9.1 Hz, 1H), 7.25-7.21 (m, 1H), 6.95 (dd, J = 6.1, 7.7 Hz, 1H), 4.55 (d, 2H), 3.70-3.51 (m, 3H) and 3.48-3.20 (m, 8H) ppm |

TABLE 5-continued

| No. | M + 1 (obs) | RT (min) | 1H-NMR |
|---|---|---|---|
| 456 | 408.11 | 8.89 | 1H NMR (400.0 MHz, MeOH) d 8.25 (dd, J = 1.6, 5.5 Hz, 1H), 8.04 (d, J = 9.1 Hz, 1H), 7.98 (d, 1H), 7.21 (d, J = 9.1 Hz, 1H), 6.81 (d, 1H), 4.80 (d, 1H), 4.55 (d, 1H), 3.33 (m, 5H) and 1.08 (s, 9H) ppm |
| 457 | 404 | 3.43 | 1H NMR (CD3OD) 3.33-3.56 (5H, masked), 4.47-4.50 (1H, m), 4.68-4.71 (2H, m), 4.79-4.99 (2H, m), 6.72-6.75 (1H, m), 7.17-7.19 (1H, d), 7.52 (5h, s), 7.81-7.83 (1H, d), 7.95-7.97 (1H, d), 8.19-8.20 (1H, d) |
| 458 | 398 | 8.78 | |
| 459 | 424.05 | 7.67 | 1H NMR (400.0 MHz, MeOH) d 8.25 (dd, J = 1.5, 6.0 Hz, 1H), 8.19 (dd, J = 1.4, 7.7 Hz, 1H), 8.03 (d, J = 9.2 Hz, 1H), 7.21 (d, J = 9.2 Hz, 1H), 6.96 (dd, J = 6.1, 7.6 Hz, 1H), 4.59 (d, J = 12.9 Hz, 1H), 4.51 (d, 1H), 3.64-3.59 (m, 1H), 3.45-3.32 (m, 2H), 3.28-3.16 (m, 2H), 1.84 (dd, J = 8.5, 14.9 Hz, 1H), 1.75 (dd, J = 4.0, 14.9 Hz, 1H) and 1.30 (d, J = 3.6 Hz, 6H) ppm |
| 460 | 394.1 | 2.97 | 1H NMR (400.0 MHz, DMSO) d 0.98 (t, J = 12.0 Hz, 2H), 1.22 (dd, J = 12.0, 23.0 Hz, 2H), 1.43 (s, 1H), 1.74 (d, J = 11.9 Hz, 2H), 1.89 (d, J = 10.5 Hz, 2H), 2.90 (s, 1H), 3.08 (s, 2H), 6.63 (dd, J = 4.8, 7.9 Hz, 1H), 6.70 (d, J = 9.0 Hz, 1H), 7.52 (dd, J = 1.7, 7.9 Hz, 1H), 7.67 (s, 1H), 7.78 (s, 2H), 7.95 (s, 2H) and 8.27 (dd, J = 1.8, 4.7 Hz, 1H) ppm |
| 461 | 424 | 3.17 | (d6-DMSO, 400 MHz) 0.75 (3H, d), 0.86 (3H, d), 1.69-1.73 (1H, m), 3.11-3.39 (6H, m), 4.38 (1H, s), 4.41 (1H, s), 5.68 (1H, brs), 6.56 (1H, dd), 7.23 (1H, d), 7.50 (1H, dd), 7.85 (2H, brs), 8.05 (1H, d), 8.27 (1H, dd), 8.65-8.76 (2H, m) |
| 462 | 444.08 | 8.73 | 1H NMR (400.0 MHz, MeOH) d 8.21-8.20 (m, 1H), 7.69 (d, J = 9.0 Hz, 1H), 7.54 (d, J = 7.7 Hz, 1H), 7.38-7.30 (m, 4H), 7.24 (t, J = 6.6 Hz, 1H), 6.73 (d, J = 9.0 Hz, 1H), 6.64 (dd, J = 4.8, 7.8 Hz, 1H), 3.78 (dd, 2H), 2.89 (d, J = 10.2 Hz, 2H), 1.73 (q, J = 7.4 Hz, 2H) and 0.66 (t, J = 7.4 Hz, 3H) ppm |
| 463 | 444.08 | 8.75 | 1H NMR (400.0 MHz, MeOH) d 8.21 (d, J = 4.4 Hz, 1H), 7.69 (d, J = 9.0 Hz, 1H), 7.54 (d, J = 7.7 Hz, 1H), 7.35 (dd, J = 7.9, 14.7 Hz, 4H), 7.29 (s, 4H), 7.23 (t, J = 6.6 Hz, 1H), 6.72 (d, J = 9.0 Hz, 1H), 6.64 (dd, J = 4.9, 7.8 Hz, 1H), 3.88 (dd, 2H), 2.88 (d, J = 9.8 Hz, 2H), 1.73 (q, J = 7.5 Hz, 2H) and 0.66 (t, J = 7.4 Hz, 3H) ppm |
| 464 | 426.06 | 8.53 | 1H NMR (400.0 MHz, MeOH) d 8.26 (dd, J = 1.6, 5.9 Hz, 1H), 8.12 (dd, J = 1.3, 7.9 Hz, 1H), 8.05 (d, J = 9.2 Hz, 1H), 7.20 (d, J = 9.1 Hz, 1H), 6.92 (dd, J = 6.0, 7.7 Hz, 1H), 4.69 (d, 1H), 4.54 (d, 1H), 3.70-3.63 (m, 1H), 3.46-3.22 (m, 3H), 3.16 (dd, J = 10.7, 14.6 Hz, 1H), 2.07-2.04 (m, 1H), 2.00 (d, J = 6.4 Hz, 1H), 1.47 (d, J = 6.7 Hz, 3H) and 1.41 (d, J = 7.0 Hz, 3H) ppm |
| 465 | 398 | 8.77 | |
| 466 | 378 | 3 | (d6-DMSO, 400 MHz) 1.78-1.81 (2H, m), 1.92-1.94 (2H, m), 3.22 (1H, s), 3.25 (1H, s), 4.14-4.21 (4H, m), 6.59 (1H, dd), 7.10 (1H, d), 7.47 (1H, dd), 7.89 (2H, brs), 8.04 (1H, d), 8.27 (1H, dd), 8.96 (1H, brs), 9.02 (1H, brs) |
| 467 | 422 | 7.52 | 1H NMR (CD3OD) 0.96-1.00 (6H, m), 1.36 (6H, s), 1.45-1.65 (2H, m), 1.70-1.80 (1H, m), 3.05-3.09 (1H, m), 3.20-3.43 (4H, m), 4.40-4.45 (1H, m), 4.55-4.60 (1H, m), 6.86-6.90 (1H, m), 7.10-7.12 (1H, d), 7.76 = 7.78 (1H, d), 8.04-8.06 (1H, d), 8.23-8.25 (1H, d) |
| 468 | 422 | 7.52 | 1H NMR (CD3OD) 0.96-1.00 (6H, m), 1.45-1.65 (2H, m), 1.70-1.80 (1H, m), 2.17 (3H, s), 3.02-3.08 (1H, m), 3.24-3.47 (4H, m), 4.44-4.47 (1H, m), 4.56-4.59 (1H, m), 6.01 (1H, d), 6.41 (1H, d), 6.81-6.84 (1H, m), 7.18-7.20 (1H, m), 7.98-8.02 (2H, m), 8.17-8.19 (1H, d). |
| 469 | 440 | 9.23 | 1H NMR (CD3OD) 2.17 (3H, s), 3.40-3.59 (4H, m), 4.48-4.52 (1H, m), 4.63-4.71 (2H, m), 6.01 (1H, d), 6.42 (1H, d), 6.81-6.85 (1H, m), 7.22-7.22 (1H, d), 7.50-7.57 (5H, m), 8.00-8.04 (2H, m), 8.15-8.17 (1H, d). |
| 470 | 364 | 7.45 | 1H NMR (CD3OD) 2.17 (3H, s), 3.32-3.34 (4H, masked), 3.87-3.90 (4H, m), 6.01 (1H, d), 6.42 (1H, d), 6.81-6.84 (1H, m), 7.15-7.17 (1H, d), 7.96-8.03 (2H, m), 8.17-8.19 (1H, d). |
| 471 | 448.1 | 9.75 | 1H NMR (400.0 MHz, MeOH) d 8.26 (dd, J = 1.6, 5.7 Hz, 1H), 8.03 (d, J = 9.0 Hz, 2H), 7.31 (d, J = 9.2 Hz, 1H), 6.87 (dd, J = 5.8, 7.7 Hz, 1H), 4.85 (d, 1H), 4.68 (d, 1H), 3.34-3.23 (m, 2H), 2.97 (dd, J = 11.1, 14.3 Hz, 1H), 2.42-2.34 (m, 1H), 2.31-2.26 (m, 1H), 2.18-2.00 (m, 4H), 1.79 (dt, J = 14.8, 5.3 Hz, 1H), 1.62-1.46 (m, 2H) and 0.96 (dd, J = 6.5, 14.0 Hz, 6H) ppm |
| 472 | 422.11 | 9.34 | 1H NMR (400.0 MHz, MeOH) d 8.24 (dd, J = 1.8, 5.2 Hz, 1H), 8.04 (d, J = 9.1 Hz, 1H), 7.79 (d, J = 4.2 Hz, 1H), 7.23 (d, J = 9.2 Hz, 1H), 6.75-6.71 (m, 1H), 4.76 (d, 2H), 3.25-3.20 (m, 1H), 3.15-3.08 (m, 2H), 3.04-2.96 (m, 1H), 2.00 (q, J = 6.7 Hz, 1H), 1.89-1.83 (m, 1H), 1.73-1.66 (m, 1H) and 1.10 (q, J = 7.0 Hz, 9H) ppm |
| 473 | 422.11 | 9.28 | H NMR (400.0 MHz, MeOH) d 8.26 (dd, J = 1.6, 6.0 Hz, 1H), 8.16 (dd, J = 1.3, 7.6 Hz, 1H), 8.03 (d, J = 9.2 Hz, 1H), 7.21 (d, J = 9.2 Hz, 1H), 6.95 (dd, J = 6.1, 7.7 Hz, 1H), 4.22-4.14 (m, 2H), 3.79-3.67 (m, 2H), 3.52 (dd, J = 5.1, 8.8 Hz, 1H), 3.49 (s, 1H), 3.34-3.27 (m, 1H), 2.03 (dd, J = 7.0, 14.2 Hz, 1H), 1.82-1.72 (m, 2H) and 1.12-1.02 (m, 9H) ppm |
| 474 | 404 | 8.73 | |
| 475 | 404 | 8.72 | |

TABLE 5-continued

| No. | M + 1 (obs) | RT (min) | 1H-NMR |
|---|---|---|---|
| 476 | 438 | 9.34 | 1H (CDCl3) 3.32-3.57 (5H, m), 4.50-4.52 (1H, m), 4.67-4.73 (2H, m), 4.80-5.02 (1H, m), 6.79-6.82 (1h< m), 7.19-7.21 (1H, d), 7.46-7.55 (4H, m), 7.93-7.99 (2H, m), 8.20-8.22 (1H, d). |
| 477 | 420.03 | 3.38 | 1H NMR (400.0 MHz, DMSO d 2.98-3.03 (m, 1H), 3.22-3.30 (m, 1H), 3.35 (dd, J = 10.0, 13.5 Hz, 2H), 4.12 (s, 1H), 4.20 (s, 1H), 4.46 (s, 1H), 6.60 (dd, J = 4.7, 7.9 Hz, 1H), 7.26 (d, J = 9.2 Hz, 1H), 7.55 (dd, J = 1.6, 7.9 Hz, 1H), 7.95 (s, 1H), 8.06 (d, J = 9.2 Hz, 1H) and 8.28 (dd, J = 1.8, 4.7 Hz, 1H) ppm |
| 478 | 366.1 | 2.95 | 1H NMR (400.0 MHz, DMSO) d 1.23 (d, J = 6.5 Hz, 3H), 3.04 (dd, J = 10.7, 14.1 Hz, 2H), 3.21 (t, J = 11.7 Hz, 2H), 3.35 (d, J = 12.1 Hz, 2H), 4.37-4.42 (m, 2H), 6.61 (dd, J = 4.7, 7.9 Hz, 1H), 7.21-7.25 (m, 1H), 7.51 (dd, J = 1.7, 7.9 Hz, 1H), 7.95 (s, NH), 8.06 (d, J = 9.2 Hz, 1H), 8.28 (dd, J = 1.8, 4.8 Hz, 1H), 8.79 (d, J = 10.4 Hz, 1H) and 9.13 (d, J = 9.3 Hz, NH) ppm |
| 479 | 487.96 | 3.77 | 1H NMR (400.0 MHz, DMSO d 0.81 (d, J = 6.5 Hz, 6H), 1.37-1.46 (m, 2H), 1.70 (dd, J = 6.5, 13.4 Hz, 1H), 3.06 (dd, J = 10.8, 14.1 Hz, 2H), 3.14-3.19 (m, 1H), 3.27-3.33 (m, 2H), 4.43 (m, 2H), 7.26 (d, J = 9.2 Hz, 1H), 7.58 (d, J = 2.7 Hz, 1H), 8.01 (s, 2H), 8.07 (d, J = 9.2 Hz, 1H) and 8.33 (d, J = 2.7 Hz, 1H) ppm |
| 480 | 442.07 | 3.73 | 1H NMR (400.0 MHz, DMSO d 0.81 (d, J = 6.5 Hz, 6H), 1.37-1.46 (m, 2H), 1.70 (dd, J = 6.5, 13.4 Hz, 1H), 3.06 (dd, J = 10.8, 14.1 Hz, 1H), 3.14-3.19 (m, 1H), 3.27-3.33 (m, 3H), 4.39 (m, 2H), 7.26 (d, J = 9.2 Hz, 1H), 7.58 (d, J = 2.7 Hz, 1H), 8.01 (s, 2H), 8.07 (d, J = 9.2 Hz, 1H), 8.33 (d, J = 2.7 Hz, 1H), 8.80 (d, J = 7.8 Hz, 1H) and 9.00 (d, J = 8.3 Hz, 1H) ppm |
| 481 | 470.07 | 10.03 | 1H NMR (400.0 MHz, MeOH) d 8.24 (dd, J = 1.7, 5.7 Hz, 1H), 8.06-8.04 (m, 2H), 7.58-7.47 (m, 5H), 7.29 (d, J = 9.1 Hz, 1H), 6.88 (dd, J = 5.8, 7.7 Hz, 1H), 4.84 (d, 1H), 4.75 (d, 1H), 4.50 (dd, J = 3.2, 11.8 Hz, 1H), 3.60-3.47 (m, 2H), 3.16 (dd, J = 11.5, 14.5 Hz, 1H), 1.74 (dd, J = 7.9, 14.8 Hz, 2H), 1.57-1.44 (m, 2H) and 1.02 (t, J = 8.0 Hz, 3H) ppm |
| 482 | 470.07 | 9.95 | 1H NMR (400.0 MHz, MeOH) d 8.09 (dd, J = 1.8, 4.8 Hz, 1H), 7.74 (d, J = 9.2 Hz, 1H), 7.43 (dd, J = 1.9, 7.9 Hz, 1H), 7.32 (d, J = 7.3 Hz, 2H), 7.24-7.14 (m, 3H), 6.88 (d, J = 9.2 Hz, 1H), 6.50 (dd, J = 4.8, 7.9 Hz, 1H), 4.04 (dd, J = 3.4, 8.3 Hz, 1H), 3.94 (dd, J = 3.4, 13.1 Hz, 1H), 3.86-3.83 (m, 1H), 3.53-3.41 (m, 2H), 2.96 (s, 1H), 2.92 (t, J = 3.5 Hz, 1H), 1.51-1.39 (m, 2H), 1.26 (td, J = 15.0, 7.5 Hz, 2H), 1.19 (s, 2H) and 0.79 (t, J = 7.3 Hz, 3H) ppm |
| 483 | 422.11 | 8.97 | 1H NMR (400.0 MHz, MeOH) d 8.26 (dd, J = 1.6, 5.7 Hz, 1H), 8.03 (d, J = 9.1 Hz, 2H), 7.25 (d, J = 9.1 Hz, 1H), 6.88 (dd, J = 5.8, 7.7 Hz, 1H), 4.78 (d, 1H), 4.62 (d, 1H), 3.47-3.41 (m, 1H), 3.38-3.32 (m, 1H), 3.05 (dd, J = 11.6, 14.5 Hz, 1H), 2.92 (dd, J = 11.5, 14.4 Hz, 1H), 1.77 (dt, J = 14.7, 5.3 Hz, 1H), 1.61-1.46 (m, 2H), 1.39 (d, J = 6.5 Hz, 3H), 0.97 (d, J = 6.5 Hz, 3H) and 0.91 (d, J = 6.6 Hz, 3H) ppm |
| 484 | 366 | 3.05 | (d6-DMSO, 400 MHz) 1.21 (3H, d), 3.00-3.05 (1H, m), 3.19-3.33 (4H, m), 4.33 (1H, d), 4.77 (1H, s), 6.59 (1H, dd), 7.12 (1H, d), 7.43 (1H, dd), 7.86 (2H, brs), 8.05 (1H, d), 8.28 (1H, dd), 8.62 (1H, brs), 9.02 (1H, brs) |
| 485 | 342 | 2.73 | 1H (CD3OD) 1.37.139 (3H, d), 3.02-3.09 (1H, m), 3.17-3.49 (4H, m), 4.48-4.53 (2H, m), 4.79-5.01 (2H, m), 6.83-6.86 (1h< m), 7.13-7.16 (1H, d), 7.94-7.99 (2H, m), 8.21-8.23 (1H, d) |
| 486 | 436.11 | 3.67 | 1H NMR (400.0 MHz, DMSO d 0.81 (d, J = 6.5 Hz, 6H), 1.03 (t, J = 7.5 Hz, 3H), 1.41 (dd, J = 7.4, 14.2 Hz, 2H), 1.68 (dd, J = 6.6, 13.7 Hz, 1H), 2.41 (q, J = 7.6 Hz, 2H), 3.04 (dd, J = 10.8, 14.2 Hz, 1H), 3.12 (d, J = 12.0 Hz, 1H), 3.30 (t, J = 11.9 Hz, 3H), 4.41 (m, 2H), 7.26 (d, J = 9.2 Hz, 1H), 7.38 (d, J = 2.3 Hz, 1H), 7.76 (s, NH2), 8.07 (d, J = 9.2 Hz, 1H), 8.19 (d, J = 2.4 Hz, 1H), 8.77 (d, J = 8.4 Hz, NH) and 8.96 (s, 1H) ppm |
| 487 | 434.1 | 3.63 | 1H NMR (400.0 MHz, DMSO) d 0.81 (t, J = 6.6 Hz, 6H), 1.23 (s, 2H), 1.65 (s, 1H), 2.75 (m, 3H), 3.01 (m, 2H), 4.27 (m, 2H), 5.05 (d, J = 11.2 Hz, 1H), 5.50 (m, 1H), 6.54 (m, 1H), 7.10 (m, 1H), 7.51 (d, J = 2.3 Hz, 1H), 7.95 (d, J = 9.3 Hz, 1H + NH2) and 8.48 (d, J = 2.3 Hz, 1H) ppm |
| 488 | 436.11 | 9.35 | 1H NMR (400.0 MHz, MeOH) d 8.26 (dd, J = 1.6, 5.9 Hz, 1H), 8.12 (dd, J = 1.1, 7.8 Hz, 1H), 8.03 (d, J = 9.2 Hz, 1H), 7.21 (d, J = 9.2 Hz, 1H), 6.93 (dd, J = 6.0, 7.7 Hz, 1H), 3.99 (dq, J = 3.6, 14.5 Hz, 2H), 3.91-3.81 (m, 2H), 3.58 (t, J = 3.3 Hz, 1H), 3.48 (q, J = 3.0 Hz, 1H), 1.80-1.64 (m, 4H), 1.50-1.43 (m, 1H), 1.04 (t, J = 7.5 Hz, 3H) and 0.95 (t, J = 6.1 Hz, 6H) ppm |
| 489 | 436.11 | 9.44 | 1H NMR (400.0 MHz, MeOH) d 8.25 (dd, J = 1.8, 5.4 Hz, 1H), 8.04 (d, J = 9.1 Hz, 1H), 7.86 (dd, J = 1.6, 7.8 Hz, 1H), 7.25 (d, J = 9.1 Hz, 1H), 6.78 (dd, J = 5.4, 7.8 Hz, 1H), 4.79 (1, 1H), 4.70 (d, 1H), 3.29-3.21 (m, 1H), 3.06-2.91 (m, 2H), 1.82-1.65 (m, 3H), 1.62-1.48 (m, 2H), 1.08 (t, J = 7.5 Hz, 3H), 0.97 (d, J = 6.6 Hz, 3H) and 0.91 (d, J = 6.6 Hz, 3H) ppm |
| 490 | 422.11 | 8.85 | 1H NMR (400.0 MHz, MeOH) d 8.24 (dd, J = 1.7, 5.4 Hz, 1H), 8.01 (d, J = 9.2 Hz, 1H), 7.84 (dd, J = 1.6, 7.8 Hz, 1H), 7.18 (d, J = 9.1 Hz, |

TABLE 5-continued

| No. | M + 1 (obs) | RT (min) | 1H-NMR |
|---|---|---|---|
| | | | 1H), 6.78 (dd, J = 5.4, 7.8 Hz, 1H), 4.07 (d, J = 11.0 Hz, 1H), 3.93 (d, J = 4.7 Hz, 2H), 3.74-3.70 (m, 2H), 3.67-3.59 (m, 1H), 1.74-1.64 (m, 2H), 1.45-1.37 (m, 4H) and 0.98-0.91 (m, 6H) ppm |
| 491 | 434.03 | 8.75 | 1H NMR (400.0 MHz, MeOH) d 8.26 (d, J = 5.9 Hz, 1H), 8.14 (d, J = 7.6 Hz, 1H), 8.08 (d, J = 9.1 Hz, 1H), 7.23 (d, J = 9.0 Hz, 1H), 6.94-6.91 (m, 1H), 4.67 (d, 1H), 4.46 (d, 1H), 3.79 (d, J = 4.8 Hz, 1H), 3.54-3.51 (m, 2H), 3.33-3.28 (m, 2H), 2.84-2.77 (m, 1H) and 2.73-2.65 (m, 1H) ppm |
| 492 | 400.13 | 7.17 | 1H NMR (400.0 MHz, MeOH) d 8.22 (dd, J = 1.6, 5.9 Hz, 1H), 8.12 (dd, J = 1.7, 7.8 Hz, 1H), 7.97 (d, J = 9.1 Hz, 1H), 7.15 (dd, J = 1.4, 9.1 Hz, 1H), 6.91 (dd, J = 6.0, 7.7 Hz, 1H), 5.04 (d, J = 3.9 Hz, 1H), 4.85 (d, J = 3.8 Hz, 1H), 4.56 (d, 1H), 4.48 (d, 1H), 3.63-3.58 (m, 1H), 3.44-3.40 (m, 1H), 3.36-3.23 (m, 2H), 3.13 (dd, J = 10.6, 14.3 Hz, 1H), 1.86-1.72 (m, 2H) and 1.30 (d, J = 3.5 Hz, 6H) ppm |
| 493 | 450.14 | 9.84 | 1H NMR (400.0 MHz, MeOH) d 8.25 (dd, J = 1.7, 5.5 Hz, 1H), 8.04 (d, J = 9.2 Hz, 1H), 7.93 (dd, J = 1.7, 7.8 Hz, 1H), 7.25 (d, J = 9.1 Hz, 1H), 6.82 (dd, J = 5.5, 7.8 Hz, 1H), 4.78 (d, 1H), 4.70 (d, 1H), 3.06-2.93 (m, 2H), 1.79-1.43 (m, 8H), 1.01-0.96 (m, 8H) and 0.91 (d, J = 6.6 Hz, 2H) ppm |
| 494 | 450.14 | 9.78 | 1H NMR (400.0 MHz, MeOH) d 8.25 (dd, J = 1.7, 5.4 Hz, 1H), 8.01 (d, J = 9.2 Hz, 1H), 7.82 (dd, J = 1.7, 7.8 Hz, 1H), 7.18 (d, J = 9.2 Hz, 1H), 6.77 (dd, J = 5.4, 7.8 Hz, 1H), 4.01-3.94 (m, 2H), 3.90-3.81 (m, 2H), 3.56 (d, J = 4.9 Hz, 2H), 1.75-1.59 (m, 3H), 1.50-1.40 (m, 3H) and 0.99-0.94 (m, 10H) ppm |
| 495 | 386.03 | 3.29 | 1H NMR (400.0 MHz, DMSO) d 3.19 (s, 4H), 3.81-3.84 (m, 4H), 7.20 (d, J = 9.2 Hz, 1H), 7.55 (d, J = 2.6 Hz, 1H), 8.05 (t, J = 9.3 Hz, 1H + NH), 8.33 (d, J = 2.6 Hz, 1H) and 8.86 (s, NH2) ppm |
| 496 | 462.04 | 3.79 | 1H NMR (400.0 MHz, DMSO) d 3.36 (d, J = 12.9 Hz, 2H), 3.46 (t, J = 10.2 Hz, 2H), 4.49-4.55 (m, 3H), 7.35 (d, J = 9.1 Hz, 1H), 7.44-7.53 (m, 5H), 7.63 (d, J = 2.6 Hz, 1H), 8.02 (s, NH2), 8.08 (d, J = 9.2 Hz, 1H), 8.33 (d, J = 2.5 Hz, 1H), 9.30 (d, J = 9.0 Hz, 1H) and 9.60 (d, J = 7.2 Hz, 1H) ppm |
| 497 | 462 | 9.57 | 1H NMR 3.35-3.59 (4H, m), 4.50-4.54 (1H, m), 4.71-4.77 (2H, m), 6.82-6.85 (1H, m), 7.26-7.28 (1H, d), 7.46-7.56 (5H, m), 7.94-7.96 (1H, d), 8.04-8.06 (1H, d), 8.23-8.25 (1H, d). |
| 498 | 410.12 | 8.5 | 1H NMR (400.0 MHz, MeOH) d 8.23 (dd, J = 1.7, 5.8 Hz, 1H), 8.10 (dd, J = 1.7, 7.7 Hz, 1H), 7.99 (dd, J = 1.0, 9.0 Hz, 1H), 7.16 (dd, J = 1.4, 9.1 Hz, 1H), 6.89 (dd, J = 5.8, 7.8 Hz, 1H), 5.05-5.02 (m, 1H), 4.87 (d, J = 3.9 Hz, 1H), 4.61 (dd, J = 2.0, 14.4 Hz, 1H), 4.43 (d, 1H), 3.82-3.75 (m, 1H), 3.54-3.42 (m, 2H), 3.34-3.27 (m, 2H) and 2.88-2.62 (m, 2H) ppm |
| 499 | 422.11 | 3.7 | (DMSO) 0.80 (6H, m), 1.40 (2H, m), 1.68 (1H, m), 2.07 (3H, s), 3.04 (2H, m), 3.25 (3H, m), 4.43 (2H, m), 7.24 (1H, m), 7.40 (1H, m), 7.79 (NH2), 8.05 (1H, m), 8.16 (1H, m), |
| 500 | 405 | 7.69 | |
| 501 | 422 | 8.75 | |
| 502 | 354 | 7.07 | 1H NMR (MeOD) 1.74-1.93 (4H, m), 3.04-3.07 (2H, dd), 3.63 (2H, s), 4.00-4.02 (2H, dd), 4.68-4.74 (2H, m), 6.58-6.61 (1H, m), 6.84-6.89 (1H, d), 7.55-7.57 (1H, d), 7.79-7.81 (1H, d), 8.17-8.19 (1h, d) |
| 503 | 402.08 | 8.19 | 1H NMR (400.0 MHz, MeOH) d 8.18 (dd, J = 1.8, 4.8 Hz, 1H), 7.81 (dd, J = 0.7, 9.1 Hz, 1H), 7.58 (dd, J = 1.8, 7.8 Hz, 1H), 6.92 (dd, J = 1.2, 9.1 Hz, 1H), 6.60 (dd, J = 4.9, 7.9 Hz, 1H), 4.73 (d, J = 4.0 Hz, 1H), 4.68 (d, J = 3.7 Hz, 1H), 4.37 (d, J = 12.5 Hz, 1H), 4.24 (s, 1H), 3.03-2.95 (m, 3H), 2.86-2.80 (m, 1H), 2.64 (dd, J = 10.4, 13.0 Hz, 1H), 1.77-1.70 (m, 2H), 1.40 (d, J = 2.1 Hz, 3H) and 1.35 (d, J = 2.3 Hz, 3H) ppm |
| 504 | 396 | 8.34 | 1H NMR (MeOD): 3.14-3.21 (1H, m), 3.26-3.44 (4H, m), 4.04-4.10 (1H, m), 4.35-4.38 (1H, d), 4.68-4.73 (1H, dd), 4.81-5.04 (2H, m), 6.88-6.91 (1H, m)7.16-7.19 (1H, d), 7.96-7.98 (1H, d), 8.09-8.11 (1H, d), 8.21-8.23 (1H, s), |
| 505 | 360.14 | 3.37 | (DMSO) 0.88 (t, 3H), 1.27-1.12 (m, 2H), 1.77-1.66 (m, 1H), 2.29 (br s, 1H), 2.41 (s, 3H), 2.58 (t, 1H), 2.75-2.65 (m, 2H), 2.97-2.91 (m, 2H), 3.64-3.57 (m, 2H), 6.60 (dd, 1H), 7.60 (br s, 2H), 8.19 (dd, 1H), 8.23 (dd, 1H). |
| 506 | 402.1 | 8.18 | 1H NMR (400.0 MHz, MeOH) d 8.18 (dd, J = 1.8, 4.8 Hz, 1H), 7.81 (d, J = 9.0 Hz, 1H), 7.58 (dd, J = 1.8, 7.8 Hz, 1H), 6.93 (dd, J = 1.2, 9.1 Hz, 1H), 6.60 (dd, J = 4.9, 7.9 Hz, 1H), 4.73 (dd, J = 0.9, 3.7 Hz, 1H), 4.69 (d, J = 3.6 Hz, 1H), 4.37 (d, J = 12.7 Hz, 1H), 4.25 (s, 1H), 3.04-2.95 (m, 3H), 2.87-2.80 (m, 1H), 2.64 (dd, J = 10.4, 13.0 Hz, 1H), 1.78-1.67 (m, 2H), 1.41 (d, J = 2.3 Hz, 3H) and 1.35 (d, J = 2.5 Hz, 3H) ppm |
| 507 | 402.1 | 8.2 | 1H NMR (400.0 MHz, MeOH) d 8.18 (dd, J = 1.8, 4.8 Hz, 1H), 7.81 (d, J = 9.0 Hz, 1H), 7.58 (dd, J = 1.8, 7.8 Hz, 1H), 6.93 (dd, J = 1.2, 9.1 Hz, 1H), 6.60 (dd, J = 4.9, 7.9 Hz, 1H), 4.73 (dd, J = 0.9, 3.7 Hz, 1H), 4.69 (d, J = 3.6 Hz, 1H), 4.37 (d, J = 12.7 Hz, 1H), 4.25 (s, 1H), |

TABLE 5-continued

| No. | M + 1 (obs) | RT (min) | 1H-NMR |
|---|---|---|---|
| | | | 3.04-2.95 (m, 3H), 2.87-2.80 (m, 1H), 2.64 (dd, J = 10.4, 13.0 Hz, 1H), 1.78-1.67 (m, 2H), 1.41 (d, J = 2.3 Hz, 3H) and 1.35 (d, J = 2.5 Hz, 3H) ppm |

Intermediate 16

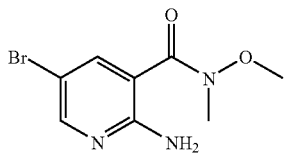

2-amino-5-bromo-N-methoxy-N-methylnicotinamide

To a solution of 2-amino-5-bromonicotinic acid (7 g, 32.3 mmol), N,O-dimethylhydroxylamine (5.99 g, 61.37 mmol) in N-methylmorpholine (60 ml) and dichloromethane (500 ml) at 0° C. was added PyBop (25.2 g, 48.45 mmol) portionwise. The solution was allowed to warm to room temperature and the mixture was stirred at room temperature for 18 hours. The reaction mixture was washed with a 2M aqueous solution of NaOH and with a 10 wt % solution of citric acid. The organic layer was dried over magnesium sulfate, filtered and concentrated in vacuo. The resulting oil was dissolved in ether and the formed solid was filtered off. The mother liquors were concentrated in vacuo to approximatively half of the original volume. This solution was diluted with dichloromethane and stirred vigorously while adding a 2M HCl solution in diethylether until complete formation of the precipitate. The solid was filtered off and partitioned between a 2M aqueous solution of NaOH and EtOAc. The organic layer was collected, dried over sodium sulfate, filtered and concentrated to dryness to afford the title compound as a cream solid (5.26 g, 63% yield).

$^1$H NMR (DMSO-d$_6$, 400 MHz) δ 3.24 (3H, s), 3.55 (3H, s), 6.35 (2H, s), 7.70 (1H, d), 8.10 (1H, d); MS (ES$^+$) 260, 262.

Intermediate 17

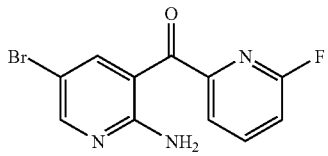

(2-amino-5-bromopyridin-3-yl)(6-fluoropyridin-2-yl)methanone

To a solution of 2-bromo-6-fluoropyridine (7.5 g, 42.6 mmol) in tetrahydrofuran (50 ml) at 0° C. was added a 2 M solution of isopropylmagnesium chloride in ether (21.3 ml, 42.6 mmol) over a period of 10 minutes. The ice-bath was removed and the reaction mixture was stirred at room temperature for 2 hours. The resulting solution was added dropwise to a solution of 2-amino-5-bromo-N-methoxy-N-methylnicotinamide (3 g, 11.5 mmol) in tetrahydrofuran (40 ml) at room temperature over a period of 30 minutes. The resulting solution was stirred at room temperature for 18 hours. The solution was quenched by addition of an aqueous saturated solution of ammonium chloride at 0° C. and the mixture was stirred at room temperature for 20 minutes. Water was added and the mixture was extracted with ethyl acetate. The organic layer was dried over magnesium sulfate, filtered and concentrated in vacuo. The residue was purified on silica gel by flash column chromatography (ISCO Companion□, 80 g column, 0-100% EtOAc/Petrol) to give an orange sticky solid which was slurried in ether/MeOH, collected by filtration and dried. The desired compound was obtained as a yellow solid (196 mg, 6% yield). $^1$H NMR (DMSO-d$_6$, 400 MHz) δ 7.48 (1H, dd), 7.84 (1H, dd), 7.87 (1H, br s), 8.22-8.30 (2H, m), 8.36 (1H, d), 9.27 (1H, dd); MS (ES$^+$) 296, 298.

Example 13

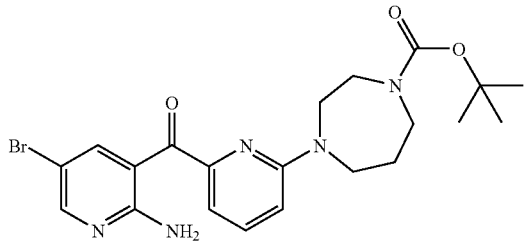

tert-butyl 4-(6-(2-amino-5-bromonicotinoyl)pyridin-2-yl)-1,4-diazepane-1-carboxylate (Cmpd-5)

A mixture of (2-amino-5-bromopyridin-3-yl)(6-fluoropyridin-2-yl)methanone (190 mg, 0.64 mmol), 1-Boc-homopiperazine (0.14 ml, 0.70 mmol) and potassium carbonate (310 mg, 2.24 mmol) in dimethylfonmamide (4 ml) was heated at 95° C. for 48 hours. The reaction mixture was cooled down to room temperature and concentrated in vacuo. The residue was slurried in EtOAc and K$_2$CO$_3$ was filtered off. The mother liquors were concentrated in vacuo. The resulting residue was purified on silica gel by flash column chromatography (ISCO Companion|, 12 g column, 0-20% EtOAc/Petrol) to give the title compound as a yellow solid (180 mg, 59% yield).

$^1$H NMR (DMSO-d$_6$, 400 MHz) δ 1.25 (9H, d), 1.91-1.77 (2H, m), 3.34 (2H, masked signal), 3.57-3.50 (2H, m), 3.65-3.62 (2H, m), 3.77-3.70 (2H, m), 6.95 (1H, dd), 7.12 (1H, dd), 7.75-7.69 (1H, m), 7.80 (2H, br s), 8.32 (1H, d), 8.60 (1H, dd); MS (ES$^+$) 478.

Example 14

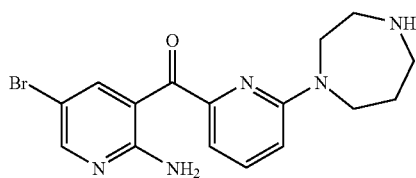

(6-(1,4-diazepan-1-yl)pyridin-2-yl)(2-amino-5-bromopyridin-3-yl)methanone (Cmpd-14)

To a suspension of tert-butyl 4-(6-(2-amino-5-bromonicotinoyl)pyridin-2-yl)-1,4-diazepane-1-carboxylate (50 mg, 0.1 mmol) in 1,4-dioxane (2 ml) at 0° C. was added 4 M HCl in 1,4-dioxane (1 ml). The resulting mixture was stirred at room temperature for 5 hours. The reaction mixture was concentrated to dryness to leave an orange solid which was further purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. The fractions were collected, passed through a sodium bicarbonate cartridge and freeze-dried to give the title compound as a yellow solid (13.5 mg, 36% yield).

$^1$H NMR (DMSO-d$_6$, 400 MHz) δ 1.84-1.76 (2H, m), 2.08 (1H, s), 2.71-2.68 (1H, m), 2.89-2.86 (1H, m), 3.72-3.28 (6H, masked signal), 6.89 (10.5H, d), 6.95 (0.5H, d), 7.05 (0.5H, d), 7.10 (0.5H, d), 7.74-7.68 (1H, m), 7.81 (2H, br s), 8.31 (1H, d), 8.54 (1H, d); MS (ES$^+$) 378.

Table 6 below depicts data for certain exemplary compounds made according to the method described in Scheme V and in Examples 13 and 14.

TABLE 6

| No. | M + 1 (obs) | RT (min) | 1H-NMR |
|---|---|---|---|
| 5 | 478.13 | 4 | (DMSO) 1.25 (9H, d), 1.91-1.77 (2H, m), 3.34 (2H, masked signal), 3.57-3.50 (2H, m), 3.65-3.62 (2H, m), 3.77-3.70 (2H, m), 6.95 (1H, dd), 7.12 (1H, dd), 7.75-7.69 (1H, m), 7.80 (2H, br s), 8.32 (1H, d), 8.60 (1H, dd). |
| 14 | 378.15 | 2 | (DMSO) 1.84-1.76 (2H, m), 2.08 (1H, s), 2.71-2.68 (1H, m), 2.89-2.86 (1H, m), 3.72-3.28 (6H, masked signal), 6.89 (10.5H, d), 6.95 (0.5H, d), 7.05 (0.5H, d), 7.10 (0.5H, d), 7.74-7.68 (1H, m), 7.81 (2H, br s), 8.31 (1H, d), 8.54 (1H, d). |
| 43 | 474.3 | 4 | (DMSO at 80° C.) 1.29 (9H, s), 1.70-1.67 (2H, m), 3.19 (2H, m), 3.41-3.83 (2H, m), 3.62-3.59 (2H, m), 3.69-3.66 (2H, m), 6.90 (1H, d), 7.09 (1H, d), 7.30 (1H, T), 7.51-7.39 (6H, m), 7.71 (1H, t), 8.50 (1H, d), 8.55 (1H, d). |
| 45 | 374.2 | 3 | (DMSO) 1.57-1.54 (2H, m), 2.72-2.70 (2H, m), 3.34 (2H, masked signal), 3.61-3.54 (4H, m), 6.85 (1H, d), 7.02 (1H, d), 7.30 (1H, t), 7.40 (2H, t), 7.51-7.49 (2H, m) 7.69 (1H, t), 7.77 (2H, br s), 8.45 (1H, d), 8.58 (1H, d). |
| 132 | 382 | 8 | (1H, DMSO-d6): 2.10-2.15 (2H, m), 3.15-3.35 (4H, m), 3.60-3.65 (2H, m), 3.82-3.87 (2H, m), 6.80 (1H, s), 8.38 (1H, s), 9.10-9.20 (1H, br s), 9.45 (1H, s). |
| 134 | 385 | 8 | (1H, DMSO-d6): 1.60-1.70 (2H, m), 1.95-2.05 (2H, m), 2.90-3.00 (2H, m), 3.20-3.30 (1H, br s), 3.92-3.95 (2H, d), 7.01 (1H, s), 7.90-8.20 (4H, m), 8.39 (1H, s), 9.44 (1H, s). |
| 149 | 379 | 7 | DMSO) 1.40-1.50 (2H, m), 2.57-2.67 (4H, m), 3.05-3.10 (2H, m), 3.25-3.30 (2H, m), 7.48 (1H, s), 7.56 (1H, s), 7.61 (1H, s), 7.77 (1H, s). |
| 156 | 391 | 8 | DMSO-d6 2.10-2.20 (2H, m), 2.80-2.85 (3H, s), 3.20-3.80 (7H, m), 4.05-4.11 (1H, m), 7.90-7.95 (2H, m), 8.26 (1H, s), 8.36 (1H, s), 8.42 (1H, s), 8.48 (1H, s), 9.5-9.6 (1H, s). |
| 157 | 299 | 8 | DMSO-d6 2.05-2.15 (2H, m), 3.15-3.23 (4H, m)3.70-3.75 (2H, m), 3.90-3.95 (2H, m), 6.99-7.02 (1H, t), 8.31 (1H, s), 8.38-8.39 (1H, d), 8.53 (1H, s), 8.70-8.80 (2H, m), 9.5-9.6 (2H, s). |
| 161 | 299 | 5 | DMSO_d6 1.451.55 (2H, m), 1.95-2.05 (2H, m), 3.00-3.10 (2H, m), 4.35-4.45 (2H, m), 6.75-6.80 (1H, m), 8.00-8.15 (4H, m), 8.22-8.27 (2H, m), 8.30-8.32 (1H, d), 8.61 (1H, s) |
| 162 | 445 | 9 | DMSO_d6 2.00-2.10 (2H, m), 3.20-3.30 (4H, m), 3.75-3.80 (2H, m), 3.95-4.00 (2H, m), 6.5-6.8 (1H, br s), 7.27-7.295 (2H, d), 7.85-7.95 (2H, br s), 8.36 (1H, s), 8.45 (1H, s), 9.10-9.15 (2H, s). |
| 163 | 398 | # | DMSO-d6: 2.10-2.20 (2H, m), 2.82-2.87 (3H, d), 3.15-3.70 (7H, m), 4.00-4.10 (1H, m), 6.79 (1H, s), 7.90-8.00 (2H, s), 8.38 (1H, s), 9.42 (1H, d), 9.55-9.60 (1H, br s) |
| 165 | 325 | 7 | DMSO-d6 2.05-2.15 (2H, m), 3.18-3.25 (4H, m), 3.70-3.75 (2H, m), 3.85-3.90 (2H, m), 5.15-5.20 (1H, d), 5.71-5.76 (1H, d), 6.62-6.67 (1H, m), 8.05-8.10 (1H, br s), 8.27 (1H, s), 8.43-8.46 (1H, d), 8.50 (1H, s), 9.00-9.10 (1H, s), 9.3-9.5 (1H, br s). |
| 166 | 392 | 9 | DMSO-d6 1.95-2.05 (2H, m), 3.10-3.20 (4H, m), 3.67-3.75 (2H, m), 3.90-3.95 (2H, m), 5.21-5.24 (1H, d), 5.76-5.80 (1H, d), 6.62-6.69 (1H, m), 7.31-7.36 (2H, d), 8.15-8.35 (2H, br s), 8.45-8.55 (2H, d), 9.10-9.20 (2H, s). |
| 189 | 312 | 7 | DMSO-d6 2.00-2.08 (2H, m), 2.32-2.37 (3H, m), 3.10-3.20 (4H, m), 3.57 (2H, s), 3.63-3.66 (2H, m), 3.80-3.85 (2H, m), 6.91-6.96 (2H, m), 7.09 (1H, s), 8.31-8.33 (1H, d), 8.45-8.35 (1H, br s), 8.61-8.63 (1H, d), 9.10-9.20 (2H, s). |

TABLE 6-continued

| No. | M + 1 (obs) | RT (min) | 1H-NMR |
|---|---|---|---|
| 213 | 414.25 | 3 | (DMSO) 1.61 (2H, m), 2.54-2.50 (2H, masked signal), 3.70-3.64 (4H, m), 7.00 (1H, t), 7.12 (1H, t), 7.42 (1H, d), 7.57-7.55 (2H, m), 7.72 (2H, s), 8.12 (1H, s), 8.34-8.32 (2H, m), 8.60 (1H, d), 11.28 (1H, s). |
| 302 | 323 | 3 | DMSO-d6 2.00-2.10 (2H, m), 3.15-3.30 (4H, m), 3.65-3.70 (2H, m), 3.85-3.903 (2H, m), 7.01-7.03 (1H, d), 7.17-7.19 (1H, d), 7.77-7.81 (1H, t), 8.30-8.40 (2H, s), 8.61 (1H, s), 8.69 (1H, s), 8.80-8.90 (2H, s). |

Example 15

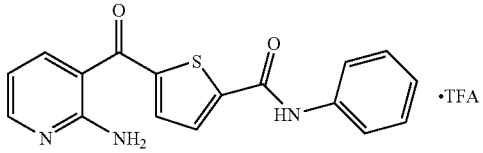

5-(2-aminonicotinoyl)-N-phenylthiophene-2-carboxamide 2,2,2-trifluoroacetate (Cmpd-46)

To 2-chloro-3-(5-ethoxycarbonyl-2-thenoyl)pyridine (5 g, 17 mmol) in tetrahydrofuran (50 ml) and ethanol (5 ml) was added a solution of sodium hydroxide (1.4 g, 40 mmol) in water (15 ml). The reaction mixture was stirred at room temperature for 18 hours. The solution was acidified to pH 2-3 by addition of concentrated HCl and extracted into ethyl acetate. The organic layer was washed with brine, dried over magnesium sulfate, filtered and concentrated in vacuo to give the acid (4.3 g, 94% yield).

To a solution of 5-(2-chloronicotinoyl)thiophene-2-carboxylic-acid (150 mg, 0.61 mmol), aniline (112 mg, 1.2 mmol) and triethylamine (0.14 ml, 1 mmol) in dichloromethane (2 ml) was added o-benzotriazol-1-yl-N,N,N',N'-tetramethyluronium tetrafluoroborate (209 mg, 0.65 mmol). The solution was stirred at room temperature for 18 hours. The reaction mixture was diluted with dichloromethane and washed with a 1M aqueous solution of HCl, an aqueous saturated solution of sodium bicarbonate and brine. The organic layer was dried over magnesium sulfate, filtered and concentrated in vacuo. The compound was used in the next step without any further purification.

A microwave vial was charged with 5-(2-chloronicotinoyl)-N-phenylthiophene-2-carboxamide (0.61 mmol) and a saturated aqueous solution of ammonium hydroxide (2 ml). The reaction mixture was heated under microwave irradiation at 160° C. for 25 minutes. The mixture was evaporated to dryness. The residue was and purified by reverse phase preparative HPLC [Waters Sunfire C18, 10 μM, 100 Å column, gradient 10%-95% B (solvent A: 0.05% TFA in water; solvent B: CH3CN) over 16 minutes at 25 mL/min]. The fractions were collected and freeze-dried to give the title compound as a solid (10 mg, 4% yield).

$^1$H NMR (DMSO-$d_6$, 400 MHz) δ 6.81-6.85 (1H, t), 7.13-7.17 (1H, t), 7.37-7.41 (2H, t), 7.74-7.81 (4H, m), 8.10-8.11 (1H, d), 8.24-8.28 (2H, m), 10.51 (1H, s); MS (ES$^+$) 324.

Table 7 below depicts data for certain exemplary compounds made according to the method described in Scheme VI and Example 15.

TABLE 7

| No. | M + 1 (obs) | RT (min) | 1H-NMR |
|---|---|---|---|
| 46 | 324 | 3 | (1H, DMSO-d6): 6.81-6.85 (1H, t), 7.13-7.17 (1H, t), 7.37-7.41 (2H, t), 7.74-7.81 (4H, m), 8.10-8.11 (1H, d), 8.24-8.28 (2H, m), 10.51 (1H, s). |
| 47 | 352 | 3 | (1H, DMSO-d6): 2.84-2.87 (2H, t), 3.46-3.51 (2H, m), 6.67-6.81 (1H, dd), 7.19-7.33 (4H, m), 7.60-7.80 (3H, m), 8.19-8.26 (2H, 2d), 8.90-8.93 (1H, t). |
| 48 | 380 | 4 | (1H, DMSO-d6): 1.17-1.18 (6H, d), 4.39-4.42 (1H, m), 4.65-4.75 (2H, br s), 6.79-6.82 (1H, t), 7.20-7.35 (5H, m), 7.4-7.5 (1H, br s), 7.55-7.80 (2H, m), 8.20-8.30 (2H, m). |
| 49 | 332 | 2 | (1H, DMSO-d6): 2.75-2.90 (5H, m), 3.05-3.20 (2H, br s), 3.35-3.45 (2H, br s), 3.80-3.90 (2H, br s), 7.03-7.06 (1H, dd), 7.63-7.64 (1H, d), 7.78-7.78 (1H, d), 7.88-7.90 (1H, d), 8.41-8.43 (1H, d), 9.90-10.50 (1H, br s). |
| 50 | 331 | 2 | (1H, DMSO-d6): 1.95-2.05 (2H, br s), 3.15-3.35 (4H, br m), 3.60-3.75 (4H, br s), 6.75-6.78 (1H, dd), 7.45-7.65 (3H, m), 8.14-8.16 (1H, d), 8.26-8.28 (1H, d), 8.70-8.85 (2H, br s). |
| 61 | 262 | 3 | (1H, DMSO-d6): 2.79-2.80 (3H, d), 6.80-6.83 (1H, t), 7.68-7.78 (4H, m), 8.22-8.26 (2H, m), 8.78-8.79 (1H, d). |
| 103 | 352 | 4 | (1H, DMSO-d6): 2.90-3.20 (3H, m), 4.65-4.80 (2H, br s), 6.60-6.70 (1H, s), 7.20-7.40 (8H, m), 7.50-7.60 (2H, s), 8.00-8.10 (1H, d), 8.25-8.26 (1H, d). |

Intermediate 18

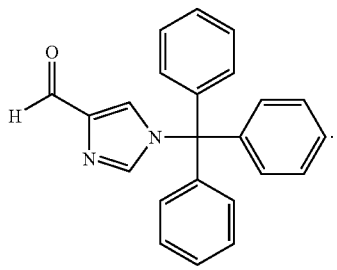

1-trityl-1H-imidazole-4-carbaldehyde

Triethylamine (3.05 ml, 21.86 mmol) was added to a solution of 1H-imidazole-4-carbaldehyde (2 g, 20.82 mmol) and triphenylmethyl chloride (5.80 g, 20.82 mmol) in N,N-dimethylformamide (20 ml). The reaction mixture was stirred at room temperature for 18 hours. The crude mixture was concentrated in vacuo and partitioned between ethyl acetate and water. The organic phase was washed dried over sodium sulfate, filtered and concentrated in vacuo. The residue was recrystallised from dichloromethane and hexanes to afford the title compound as a cream solid (4.7 g, 67% yield).

$^1$H NMR (DMSO-$d_6$, 400 MHz) δ 7.10-7.16 (6H, m), 7.36-7.57 (9H, m), 7.63 (1H, s), 7.64 (1H, s), 9.91 (1H, s).

Intermediate 19

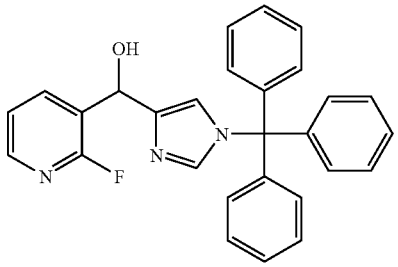

(2-fluoropyridin-3-yl)(1-trityl-1H-imidazol-4-yl)methanol

A 2.5M n-butyl lithium in hexanes solution (6 ml, 15 mmol) was added dropwise to a solution of diisopropylamine (2.12 ml, 15 mmol) in tetrahydrofuran (30 ml), cooled to −78° C. The reaction mixture was allowed to warm up to 0° C. for 30 minutes before being cooled down to −78° C. 2-Fluoropyridine (1.36 g, 14 mmol) in tetrahydrofuran (10 ml) was added dropwise. The reaction mixture was stirred at −78° C. for 1 hour. A solution of 1-trityl-1H-imidazole-4-carbaldehyde (4.5 g, 13.3 mmol) in tetrahydrofuran (10 ml) was added dropwise. The reaction mixture was allowed to warm up to room temperature and was stirred for 18 hours. The reaction was quenched with a saturated aqueous solution of sodium bicarbonate and extracted into ethyl acetate. The organic phase was washed with brine, dried over magnesium sulfate, filtered and concentrated in vacuo. The residue was purified on silica gel by flash column chromatography to afford the title compound (1.3 g, 22% yield).

MS (ES$^+$) 436.

Intermediate 20

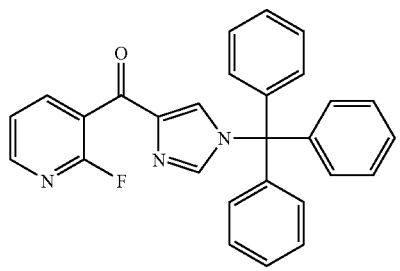

(2-fluoropyridin-3-yl)(1-trityl-1H-imidazol-4-yl)methanone

Manganese dioxide (5 g, 57.51 mmol) was added to a solution of (2-fluoropyridin-3-yl)(1-trityl-1H-imidazol-4-yl)methanol (1.3 g, 2.99 mmol) in dichloromethane (25 ml). The reaction mixture was heated to 75° C. and stirred for 18 hours. The crude mixture was cooled down to room temperature and filtered through a path of celite. The mother liquors were concentrated in vacuo to afford the title compound (1.1 g, 85% yield).

Intermediate 21

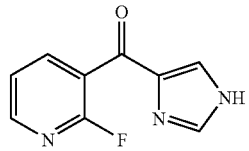

(2-fluoropyridin-3-yl)(1H-imidazol-4-yl)methanone

Trifluoroacetic acid (5 ml) was added to (2-fluoropyridin-3-yl)(1-trityl-1H-imidazol-4-yl)methanone (1.1 g, 2.54 mmol). The reaction mixture was stirred for 18 hours. The crude mixture was concentrated in vacuo and treated with a 2N aqueous solution of HCl. The aqueous phase was extracted with diethyl ether and basified with NaOH pellets. The compound was extracted with ethyl acetate. The organic phase was washed with brine, dried over sodium sulfate, filtered and concentrated in vacuo to afford the title compound (250 mg, 51% yield).

MS (ES$^+$) 192.

Intermediate 22

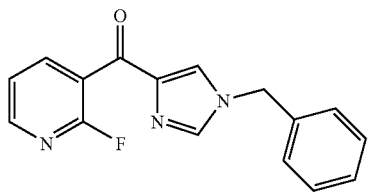

(1-benzyl-1H-imidazol-4-yl)(2-fluoropyridin-3-yl)methanone

Sodium hydride (60% in mineral oil, 23 mg, 0.58 mmol) was added to a solution of (2-fluoropyridin-3-yl)(1H-imidazol-4-yl)methanone (100 mg, 0.52 mmol) in tetrahydrofuran (3 ml), cooled to 0° C. The reaction mixture was then stirred for 30 minutes. Benzyl bromide (0.062 ml, 0.52 mmol) was added and the mixture was warmed up to room temperature. The reaction mixture was stirred for 18 hours, diluted with ethyl acetate and washed with a saturated aqueous solution of sodium bicarbonate and brine. The organic phase was dried over magnesium sulfate, filtered and concentrated in vacuo. The residue was purified on silica gel by flash column chromatography to afford the title compound (100 mg, 68% yield).

$^1$H NMR (CDCl$_3$, 400 MHz) δ 5.15 (2H, s), 7.20-7.30 (3H, m), 7.35-7.40 (3H, m), 7.15-7.25 (2H, m), 8.10-8.20 (1H, t), 8.30-8.35 (1H, d); MS (ES$^+$) 282.

Example 16

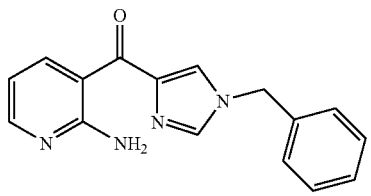

(2-aminopyridin-3-yl)(1-benzyl-1H-imidazol-4-yl)methanone (Cmpd-42)

A microwave vial was charged with (1-benzyl-1H-imidazol-4-yl)(2-fluoropyridin-3-yl)methanone (50 mg, 0.18 mmol) and a saturated aqueous solution of ammonium hydroxide (1 ml). The reaction mixture was heated under microwave irradiation at 160° C. for 25 minutes. The mixture was evaporated to dryness. The residue was and purified on silica gel by flash column chromatography to give the title compound as a solid (15 mg, 30% yield).

$^1$H NMR (CDCl$_3$, 400 MHz) δ 5.05-5.10 (2H, s), 6.80-6.85 (1H, t), 7.10-7.20 (1H, m), 7.30-7.35 (1H, s), 7.50 (1H, s), 7.75 (1H, s), 7.84-7.89 (1H, d), 8.80-9.10 (2H, br s), 9.95-9.97 (1H, d); MS (ES$^+$) 279.

Table 8 below depicts data foe certain exemplary compounds made according to the method described in Scheme VII and Example 16.

TABLE 8

| No. | M + 1 (obs) | RT (min) | 1H-NMR |
|---|---|---|---|
| 42 | 279 | 2.11 | (1H, CDCl3: 5.05-5.10 (2H, s), 6.80-6.85 (1H, t), 7.10-7.20 (1H, m), 7.30-7.35 (1H, s), 7.50 (1H, s), 7.75 (1H, s), 7.84-7.89 (1H, d), 8.80-9.10 (2H, br s), 9.95-9.97 (1H, d). |
| 53 | 280 | 2.35 | (1H, DMSO-d6): 6.89-6.90 (1H, m), 7.38-7.39 (2H, d), 8.10-8.15 (1H, s), 8.23-8.25 (2H, m), 8.64-8.66 (2H, d), 9.29-9.31 (1H, d). |
| 63 | 360 | 3.02 | (1H, DMSO-d6): 5.58 (2H, s), 7.38-7.39 (2H, d), 7.65-7.90 (2H, br s), 8.12 (1H, s), 8.20 (1H, s), 8.29 (1H, s), 8.75-8.77 (2H, d), 9.41-9.42 (1H, s). |

Intermediate 23

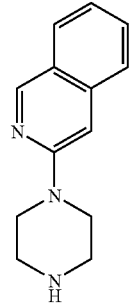

3-(piperazin-1-yl)isoquinoline

A mixture of 3-chloroisoquinoline (200 mg, 1.22 mmol) and piperazine (2.10 g, 24.4 mmol) in ethylene glycol (2 ml) was heated to 150° C. and stirred at that temperature for 24 hours. The reaction was allowed to cool down to room temperature. The crude mixture was partitioned between water and ethyl acetate. The organic layer was washed with brine, dried over magnesium sulfate, filtered and concentrated under vacuo. The residue was and purified on silica gel by flash column chromatography to give the title compound as a pale brown solid (131 mg, 50% yield).

$^1$H NMR (CDCl$_3$, 400 MHz) δ 3.18 (4H, t), 3.67 (4H, t), 6.81 (1H, s), 7.31 (1H, t), 7.54 (1H, t), 7.62 (1H, d), 7.82 (1H, d), 8.97 (1H, s); MS (ES$^+$) 214.

Intermediate 24

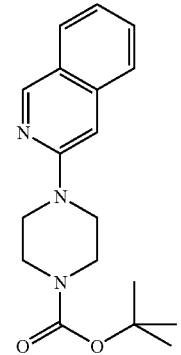

tert-butyl 4-(isoquinolin-3-yl)piperazine-1-carboxylate

To a solution of 3-(piperazin-1-yl)isoquinoline (130 mg, 0.61 mmol) in dichloromethane (5 ml) was added triethylamine (92.5 mg, 0.91 mmol) followed by di-tert-butyl dicarbonate (160 mg, 0.73 mmol). The solution was stirred at room temperature for 18 hours. The crude mixture was partitioned between dichloromethane and a saturated solution of sodium bicarbonate. The organic extract was washed further with brine, dried over magnesium sulfate, filtered and concentrated under vacuo. The residue was and purified on silica gel by flash column chromatography to give the title compound as a pale green solid (151 mg, 79% yield).

$^1$H NMR (CDCl$_3$; 400 MHz) δ 1.58 (9H, s), 3.52-3.71 (8H, m), 6.83 (1H, br s), 7.33 (1H, t), 7.51-7.67 (2H, m), 7.84 (1H, d), 9.00 (1H, s); MS (ES$^+$) 314.

Intermediate 25

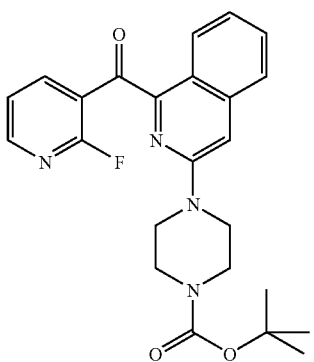

tert-butyl 4-(1-(2-fluoronicotinoyl)isoquinolin-3-yl)piperazine-1-carboxylate A solution of 2-dimethylaminoethanol (0.072 ml, 0.72 mmol) in hexanes (3 ml) was cooled down to −40° C. A 2.5M solution of $^n$butyl lithium in tetrahydrofuran (0.574 ml, 1.44 mmol) was added dropwise. The solution was stirred for 20 minutes. A suspension of tert-butyl 4-(isoquinolin-3-yl)piperazine-1-carboxylate (0.75 mg, 0.24 mmol) in hexanes (8 ml) was added and the resulting solution was stirred for 1 hour. The solution was cooled down to −78° C. A solution of 2-fluoro-N-methoxy-N-methylnicotinamide (176.3 mg, 0.96 mmol) in THF (40 ml) was added dropwise. The reaction mixture was warmed up to −50° and stirred for 1 hour, then the mixture was stirred at 0° C. for a further 1 hour. The crude mixture was partitioned between water and ethyl acetate. The organic extract was dried over magnesium sulfate, filtered and concentrated under vacuo. The residue was and purified on silica gel by flash column chromatography to give the title compound as a yellow oil (8 mg, 8% yield).

MS (ES$^+$) 437.

Intermediate 26

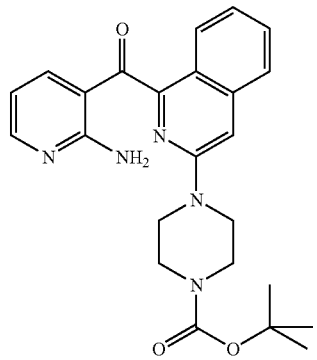

tert-butyl 4-(1-(2-aminonicotinoyl)isoquinolin-3-yl)piperazine-1-carboxylate A microwave vial was charged with tert-butyl 4-(1-(2-fluoronicotinoyl)isoquinolin-3-yl)piperazine-1-carboxylate (8 mg, 0.018 mmol) and a saturated aqueous solution of ammonium hydroxide (3 ml). The reaction mixture was heated under microwave irradiation at 120° C. for 30 minutes. The mixture was cooled down to room temperature, partitioned between ethyl acetate and water. The organic phase was dried over magnesium sulfate, filtered and evaporated to dryness. The residue was purified on silica gel by flash column chromatography to afford the title compound as a yellow solid (6 mg, 76% yield).

MS (ES$^+$) 434.

Example 17

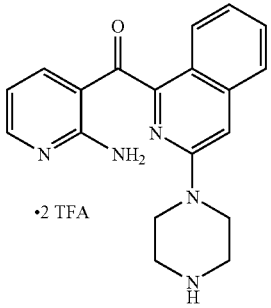

(2-aminopyridin-3-yl)(3-(piperazin-1-yl)isoquinolin-1-yl)methanone bis(2,2,2-trifluoroacetate) (Cmpd 320)

To a solution of tert-butyl 4-(1-(2-aminonicotinoyl)isoquinolin-3-yl)piperazine-1-carboxylate (6 mg, 0.014 mmol) in dichloromethane (2 ml) was added trifluoroacetic acid (0.5 ml). The solution was stirred at room temperature for 1 hour. The resulting mixture was concentrated in vacuo and triturated twice with ether and dried to leave the compound as an orange solid (2 mg, 26% yield).

$^1$H NMR (DMSO-d$_6$, 400 MHz) δ 3.24 (3H, br s), 3.74 (2H, br s), 6.52 (1H, dd), 7.31-7.34 (2H, m), 7.44 (1H, d), 7.63-7.68 (2H, m), 7.82 (1H, d), 8.02 (2H, br s), 8.74 (2H, br s); MS (ES$^+$) 334.

Table 9 below depicts data for certain exemplary compounds made according to the method described in Scheme VIII and in Example 17.

TABLE 9

| No. | M + 1 (obs) | RT (min) | 1H-NMR |
|---|---|---|---|
| 320 | 334 | 3.04 | (d6-DMSO, 400 MHz) 3.24 (3H, brs), 3.74 (2H, brs), 6.52 (1H, dd), 7.31-7.34 (2H, m), 7.44 (1H, d), 7.63-7.68 (2H, m), 7.82 (1H, d), 8.02 (2H, brs), 8.74 (2H, brs) some signals of piperazine are masked by TFA signal |

Example 18

PKC Theta I

An assay buffer solution was prepared which consisted of 100 mM HEPES (pH 7.5), 10 mM $MgCl_2$, 25 mM NaCl, 0.1 mM EDTA and 0.01% Brij. An enzyme buffer containing reagents to final assay concentrations of 0.00001% Triton X-100, 200 μg/mL Phosphatidylserine, 20 μg/mL Diacylglycerol, 360 μM NADH, 3 mM phosphoenolpyruvate, 70 μg/mL pyruvate kinase, 24 μg/mL lactate dehydrogenase, 2 mM DTT, 100 μM substrate peptide (ERMRPRKRQGSVRRRV) and 18 nM PKC theta kinase was prepared in assay buffer. To 60 μL of this enzyme buffer, in a 384 well plate, was added 2 μL of VRT stock solution in DMSO. The mixture was allowed to equilibrate for 10 mins at 30° C. The enzyme reaction was initiated by the addition of 5 μL stock ATP solution prepared in assay buffer to a final assay concentration of 240 μM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 μM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.). Ki values are represented as A<0.05 μM, B<0.5 μM, C<2.8 μM, D>2.8 M.

A compounds are: 14, 23, 45, 66, 67, 102, 105, 107, 112, 132, 136, 149, 152, 164, 165, 170, 172, 179, 180, 188, 191-195, 199, 200, 202, 206, 207, 210, 213, 214, 225, 227, 232, 235, 238, 240, 241, 246, 252, 253, 258, 268, 279, 296, 301, 305, 306, 311, 313-317, 321-325, 327-332, 334, 335, 338, 342, 346, 347, 349-353, 355-358, 360, 361, 366, 383-385, 388, 391, 392, 396, 397, 401-404, 406, 410-413, 415, 416, 421, 424, 426, 427, 431, 434, 435, 436, 437, 439, 441, 442, 443, 444, 446, 448, 450, 454, 457, 458, 459, 461, 462, 463, 464, 466, 468, 469, 471, 473, 474, 475, 476, 478, 479, 480, 482, 485, 487, 488, 490, 492, 494, 495, 496, 497, 498, 499, 500, 501, 502, 503, 504, 505, 506, and 507.

B compounds are: 2, 20, 27, 31, 33-35, 37, 44, 47, 50, 53, 57-59, 62, 70, 71, 75, 76, 82, 89, 92, 93, 98, 100, 106, 108, 109, 113, 115-117, 119-121, 126, 133, 134, 138, 140, 146, 150, 151, 153, 154-157, 161, 163, 167, 169, 171, 181-183, 186, 187, 201, 205, 208, 209, 211, 218, 219, 222, 223, 226, 228, 230, 231, 233, 237, 239, 243, 245, 247, 249, 251, 254-256, 260-266, 269-271, 276, 277, 280, 282, 283, 285-291, 295, 302, 303, 307-310, 312, 318, 320, 326, 336, 339, 341, 343, 345, 348, 359, 367, 371, 372, 377, 379, 357, 395, 400, 422, 425, 429, 432, 433, 440, 445, 447, 451, 452, 455, 456, 460, 465, 470, 477, 483, 484, 486, and 491.

C compounds are: 9, 15, 19, 22, 26, 29, 32, 36, 38, 39, 41, 48, 52, 60, 69, 72-74, 77, 83-85, 87, 88, 90, 91, 95-97, 99, 101, 103, 110, 111, 114, 118, 122-125, 128-130, 135, 137, 139, 141-145, 147, 148, 159, 160, 168, 174, 177, 184, 185, 189, 190, 196, 203, 212, 215-217, 220, 224, 229, 234, 236, 242, 248, 250, 257, 259, 275, 281, 304, 319; 337, 354, 368-370, 373-376, 378, 380-382, 386, 389, 390, 393, 394, 398, 399, 405, 407-409, 414, 417, 418, 419, 420, 423, 428, 430, 438, 449, 453, 467, 472, 481, 489, and 493.

D compounds are: 4-8, 10-13, 16-18, 21, 24, 25, 28, 30, 40, 42, 43, 46, 47, 49-51, 53-56, 61, 63-66, 68, 78-81, 94, 104, 127, 129, 135, 137, 141-143, 145, 158, 162, 166, 173, 175, 176, 178, 179, 193, 194, 197, 198, 204, 207, 210, 213, 221, 244, 253, 267, 272-274, 278, 292-294, 297-300, 330, 333, 340, 344, 346, 357, and 361.

No Data: 1, 3, and 362-366.

In general, compounds of the invention, including compounds in Table 1-9, are effective for the inhibition of PKC-theta.

PKC Theta II 33P i

An assay buffer solution was prepared which consisted of 100 mM HEPES (pH 7.5), 10 mM $MgCl_2$, 25 mM NaCl, 0.1 mM EDTA and 0.01% Brij. An enzyme buffer containing reagents to final assay concentrations of 0.002% Triton X-100, 200 μg/mL Phosphatidylserine, 20 μg/mL Diacylglycerol, 2 mM DTT, 150 μM substrate peptide (ERMRPRKRQGSVRRRV) and 0.5 nM PKC theta kinase was prepared in assay buffer. To 22 μL of this enzyme buffer, in a 96 well plate, was added 2 μL of VRT stock solution in DMSO. The mixture was allowed to equilibrate for 10 mins at 25° C. The enzyme reaction was initiated by the addition of 16 μL stock ATP solution prepared in assay buffer to a final assay concentration of 240 μM and 23 nCi/μL [$\gamma$-$^{33}$P] ATP.

The reaction was stopped after 60 minutes by the addition of 100 μL 10 mM phosphoric acid. A phosphocellulose 96 well plate (Millipore, Cat no. MAPHNOB) was washed with 200 μL 100 mM phosphoric acid prior to the addition of the reaction mixture (120 μL) and was left to soak for at least 30 minutes, prior to wash steps (4×200 μL 100 mM phosphoric acid). After drying, 100 μL Optiphase 'SuperMix' liquid scintillation cocktail (PerkinElmer) was added to the well prior to scintillation counting (1450 Microbeta Liquid Scintillation Counter, Wallac).

For each Ki determination, 11 data points covering the VRT concentration range of 0-0.25 μM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.). A compounds are 14, 45, 67, 75, and 107. B compounds are: 23, 66, 164, 179, 180, 191, 193, 194, 210, 213, 301, 346, 357, 361, 391 and 402.

PKC Theta III

Compounds tested in an assay similar to PKC theta I above with a fluorescence read out rather than a UV read out gave the following results: D compounds are (2-aminopyridin-3-yl)(6-(1-benzylpiperidin-4-ylamino)pyridin-2-yl)methanone, and (2-aminopyridin-3-yl)(6-(2,3-dihydroxypropylamino)pyridin-2-yl)methanone (naming by ChemDraw Ultre version 10.0).

Example 19

PKC Delta

An assay buffer solution was prepared which consisted of 100 mM HEPES (pH 7.5), 10 mM MgCl$_2$, 25 mM NaCl, 0.1 mM EDTA and 0.01% Brij. An enzyme buffer containing reagents to final assay concentrations of 0.002% Triton X-100, 200 µg/mL Phosphatidylserine, 20 µg/mL Diacylglycerol, 360 µM NADH, 3 mM phosphoenolpyruvate, 70 µg/mL pyruvate kinase, 24 µg/mL lactate dehydrogenase, 2 mM DTT, 150 µM substrate peptide (ERMRPRKRQGSVRRRV) and 46 nM PKC delta kinase was prepared in assay buffer. To 16 µL of this enzyme buffer, in a 384 well plate, was added 1 µL of VRT stock solution in DMSO. The mixture was allowed to equilibrate for 10 mins at 30° C. The enzyme reaction was initiated by the addition of 16 µL stock ATP solution prepared in assay buffer to a final assay concentration of 150 µM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 µM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.).

A compounds are: 108, 112, 131, 132, 136, 164, 179, 191, 192, 193, 194, 202, 210, 213, 227, 235, 238, 279, 301, 306, 311, 323, 327, 330, 334, 346, 347, 349, 353, 357, 358, 361, 366, 383-385, 388, 391, 402, 403, 410, 411, 413, 415, 416, 421, 424, 426, 431, 435, 436, 439, 446, 454, 457, 458, 463, 468, 475, 476, 482, 485, 488, 490, 492, 494, 497, 498, 500, 501, 502, 503, 504, and 507.

B compounds are: 2, 14, 23, 33, 45, 58, 59, 62, 66, 67, 75, 86, 98, 100, 102, 105, 107, 113, 115, 116, 117, 121, 134, 138, 140, 149, 150, 152, 154, 156, 157, 163, 165, 167, 169, 170, 171, 172, 180, 181, 182, 183, 186, 187, 188, 195, 199, 200, 201, 206, 208, 211, 214, 218, 222, 223, 225, 226, 228, 232, 233, 237, 240, 241, 243, 245, 246, 249, 252, 253, 258, 260, 263, 268, 269, 270, 271, 280, 282, 283, 284, 286, 289, 290, 295, 296, 303, 305, 310, 312, 313, 314, 315, 316, 317, 318, 321, 322, 324, 325, 326, 328, 329, 331, 332, 335, 338, 339, 342, 343, 348, 350, 352, 355, 356, 360, 377, 387, 392, 396, 397, 401, 404, 406, 412, 425, 427, 429, 432, 434, 437, 440, 441, 442, 443, 444, 448, 450, 452, 459, 461, 462, 464, 465, 466, 469, 470, 471, 473, 474, 477, 478, 479, 480, 484, 486, 487, 495, 496, 499, 505, and 506.

C compounds are: 9, 20, 27, 31, 34, 37, 57, 70, 71, 76, 82, 92, 106, 109, 119, 120, 126, 151, 153, 155, 161, 184, 203, 209, 217, 230, 231, 239, 247, 254, 256, 262, 264, 265, 266, 288, 302, 304, 307, 309, 336, 351, 354, 359, 367-376, 378-382, 386, 389, 390, 393-395, 398-400, 405, 407-409, 414, 417-420, 422, 438, 445, 447, 455, 460, 483, 489, 491, and 493.

D compounds are: 19, 32, 35, 39, 41, 44, 89, 90, 93, 219, 244, 292, 293, 294, 333, 337, 340, 341, 344, 345, 423, 428, 430, 433, 449, 451, 453, 456, 467, 472, and 481.

Example 20

PKC Alpha

An assay buffer solution was prepared which consisted of 100 mM HEPES (pH 7.5), 10 mM MgCl$_2$, 25 mM NaCl, 0.1 mM EDTA, 100 µM CaCl$_2$ and 0.01% Brij. An enzyme buffer containing reagents to final assay concentrations of 0.002% Triton X-100, 100 µg/mL Phosphatidylserine, 20 µg/mL Diacylglycerol, 360 µM NADH, 3 mM phosphoenolpyruvate, 70 µg/mL pyruvate kinase, 24 µg/mL lactate dehydrogenase, 2 mM DTT, 150 µM substrate peptide (RRRRRKGSFKRKA) and 4.5 nM PKC alpha kinase was prepared in assay buffer. To 16 µL of this enzyme buffer, in a 384 well plate, was added 1 µL of VRT stock solution in DMSO. The mixture was allowed to equilibrate for 10 mins at 30° C. The enzyme reaction was initiated by the addition of 16 µL stock ATP solution prepared in assay buffer to a final assay concentration of 130 µM. Initial rate data was determined from the rate of change of absorbance at 340 nM (corresponding to stoichiometric consumption of NADH) using a Molecular Devices Spectramax plate reader (Sunnyvale, Calif.) over 15 mins at 30° C. For each Ki determination 12 data points covering the VRT concentration range of 0-20 µM were obtained in duplicate (DMSO stocks were prepared from an initial 10 mM VRT stock with subsequent 1:2 serial dilutions). Ki values were calculated from initial rate data by non-linear regression using the Prism software package (Prism 4.0a, Graphpad Software, San Diego, Calif.).

A compounds are: 14, 45, 66, 108, 179, 187, 188, 202, 210, 240, 241, 246, 323, 325, 326, 327, 328, 330, 332, 388, 392, 402, 413, 415, 424, 431, 435, 457, 463, 475, 476, 487, 488, 490, 494, 495, and 497.

B compounds are: 2, 102, 105, 140, 154, 155, 164, 180, 190, 191, 193, 194, 214, 227, 235, 245, 252, 253, 305, 306, 309, 311, 312, 313, 314, 315, 316, 317, 318, 321, 322, 324, 329, 331, 334, 335, 346, 347, 349, 353, 356, 357, 358, 361, 366, 383, 384, 391, 396, 397, 403, 404, 406, 410-412, 416, 421, 426, 427, 432, 434, 436, 437, 439, 440, 441, 442, 443, 444, 446, 448, 450, 454, 455, 458, 459, 461, 462, 466, 468, 471, 473, 474, 478, 479, 480, 482, 484, 485, 486, 492, 496, 498, 499, 500, 501, 502, 503, 505, and 507.

C compounds are: 89, 92, 109, 157, 161, 184, 203, 209, 220, 230, 243, 303, 307, 310, 336, 337, 338, 339, 342, 343, 345, 350, 352, 355, 359, 360, 367-382, 385-387, 389, 390, 393-395, 398-401, 405, 407-409, 414, 417-420, 425, 445, 447, 452, 464, 465, 469, 483, 504, and 506.

D compounds are: 217, 304, 333, 340, 341, 344, 348, 351, 354, 422, 423, 428, 429, 430, 433, 438, 449, 451, 453, 456, 460, 467, 470, 472, 477, 481, 489, 491, and 493.

Example 21

GSK-3 Inhibition Assay

Compounds of the present invention were screened for their ability to inhibit GSK-3β (AA 1-420) activity using a standard coupled enzyme system (Fox et al., Protein Sci. 1998, 7, 2249). Reactions were carried out in a solution containing 100 mM HEPES (pH 7.5), 10 mM MgCl2, 25 mM NaCl, 300 µM NADH, 1 mM DTT and 1.5% DMSO. Final substrate concentrations in the assay were 20 µM ATP (Sigma Chemicals, St Louis, Mo.) and 300 µM peptide (American Peptide, Sunnyvale, Calif.). Reactions were carried out at 30° C. and 20 nM GSK-3β. Final concentrations of the components of the coupled enzyme system were 2.5 mM phosphoenolpyruvate, 300 µM NADH, 30 µg/ml pyruvate kinase and 10 µg/ml lactate dehydrogenase.

An assay stock buffer solution was prepared containing all of the reagents listed above with the exception of ATP and the test compound of the present invention. The assay stock-buffer solution (175 µl) was incubated in a 96 well plate with 5 µl of the test compound of the present invention at final concentrations spanning 0.002 µM to 30 µM at 30° C. for 10 min. Typically, a 12-point titration was conducted by preparing serial dilutions (from 10 mM compound stocks) with DMSO of the test compounds of the present invention in daughter plates. The reaction was initiated by the addition of 20 µl of ATP (final concentration 20 µM). Rates of reaction were obtained using a Molecular Devices Spectramax plate reader (Sunnyvale, Calif.) over 10 min at 30° C. The Ki values were determined from the rate data as a function of inhibitor concentration. Compounds of the invention were found to inhibit GSK 3.

In general, compounds of the invention, including compounds in Table 1-9, are effective for the inhibition of GSK-3β.

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A compound represented by the following structural formula:

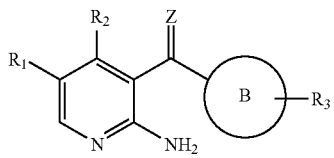

or a pharmaceutically acceptable salt thereof, wherein:
B is pyridyl, wherein B is optionally and independently substituted with $R_{12}'$ and independently optionally and independently substituted with one or more $R_{12}$ groups in addition to $R_3$;
Z is O;
$R_1$ is —H, halogen, —CN, —NO$_2$, or -T1-Q1;
T1 is absent or C1-10 aliphatic, wherein up to three methylene units of T1 are optionally and independently replaced by G wherein G is —O—, —S—, —S(O)—, —S(O)$_2$—, —N(R$_4$)—, or —C(O)—; T1 is optionally and independently substituted with one or more JT1;
Q1 is absent, a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein Q1 is optionally and independently substituted with J1 and independently optionally and independently substituted with one or more $R_{13}$ groups;
J1 is —Y1-M1;
Y1 is absent, oxo, or C1-10 aliphatic wherein up to three methylene units of Y1 are optionally and independently replaced with G1 wherein G1 is —N(R$^\$$)—, —O—, —S—, —C(O)—, —S(O)—, or —S(O)$_2$—, Y1 is optionally and independently substituted with one or more JT1;
M1 is C1-6 aliphatic, C3-8 cycloaliphatic, haloC1-4 aliphatic, —O(haloC1-4 aliphatic), 3-8 membered heterocyclyl, 5-6 membered heteroaryl, phenyl, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, —NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$; M1 is optionally and independently substituted with one or more J; or M1 is absent, halogen, —N(O)$_2$, or —CN;
$R_2$ is —H, halogen, —CN, —N(O)$_2$, or optionally and independently substituted C1-C6 alkyl;
$R_3$ is -T2-Q2;
T2 is absent;
Q2 is 1,4-diazepane ring, wherein Q2 is optionally and independently substituted with J2 and independently optionally and independently substituted with one or more $R_{13}$ groups;
J2 is —Y2-M2;
Y2 is absent, oxo, or C1-10 aliphatic, wherein up to three methylene units of Y2 are optionally and independently replaced with G1' wherein G1' is —N(O)—, —O—, —S—, —C(O)—, —S(O)—, or —S(O)$_2$—, Y2 is optionally and independently substituted with one or more JT2;
M2 is C1-6 aliphatic, C3-8 cycloaliphatic, haloC1-4 aliphatic, —O(haloC1-4 aliphatic), 3-8 membered heterocyclyl, heteroaryl, aryl, —OR$^\$$, —SR$^\$$, —N(R$^\$$)$_2$, —C(O)R$^\$$, —C(O)$_2$R$^\$$, —C(O)N(R$^\$$)$_2$, —OC(O)R$^\$$, —OC(O)N(R$^\$$)$_2$, —NR$^\$$C(O)R$^\$$, —NR$^\$$C(O)$_2$R$^\$$, —NR$^\$$C(O)N(R$^\$$)$_2$, —SO$_2$N(R$^\$$)$_2$, —NR$^\$$S(O)$_2$R$^\$$, —S(O)R$^\$$, —S(O)$_2$R$^\$$, —P(O)R$^\$$, —P(O)$_2$R$^\$$, —P(O)(R$^\$$)$_2$, or —PO(OR$^\$$)$_2$; wherein M2 is optionally and independently substituted with one or more J; or M2 is absent, halogen, —N(O)$_2$, or —CN;
each J is independently halogen, C1-6 aliphatic, C3-6 cycloaliphatic, —NO$_2$, —CN, —N(R$^\$$)$_2$, —OR$^\$$, —C(O)R$^\$$, —C(O)N(R$^\$$)$_2$, —C(O)$_2$R$^\$$, oxo, —O(haloC1-4 aliphatic), or halo C1-4 aliphatic;
$R_4$ is —H or an optionally and independently substituted C1-C6 alkyl;
each JT1 is independently halogen, —CN, —N(O)$_2$, or hydroxy;
each JT2 is independently halogen, —CN, —N(O)$_2$, or hydroxy;
each R$^\$$ is independently —H or C1-C6 alkyl;
each $R_{12}$ is independently halogen, amino, aminoalkyl, alkylaminoalkyl, alkoxy, hydroxy, —CN, —NO$_2$, or optionally and independently substituted C1-C6 alkyl;
each $R_{12}'$ is independently halogen, amino, aminoalkyl, alkylaminoalkyl, alkoxy, hydroxy, —CN, —NO$_2$, or optionally and independently substituted C1-C10 aliphatic wherein up to three methylene units are optionally and independently replaced by G' wherein G' is —O—, —S(O)$_p$—, —N(R$_4$)—, or —C(O)—, and each methylene unit is optionally and independently substituted with one or more JT3; or each $R_{12}'$ is cycloaliphatic, phenyl, heteroaryl, each independently and optionally substituted with one or more JT4;
each JT3 is independently halogen, —CN, —NO$_2$, cycloaliphatic, or phenyl;
each JT4 is independently halogen, C1-C6 alkyl, or C1-C6 alkoxy;
each $R_{13}$ is independently halogen, amino, aminoalkyl, alkylaminoalkyl, alkoxy, hydroxy, —CN, —NO$_2$, oxo or optionally and independently substituted C1-C6 alkyl; and
p is 0, 1 or 2.

2. The compound of claim 1 wherein:

$R_2$ is —H, halogen, —CN, —N(O)$_2$, or C1-C6 alkyl optionally and independently substituted with one or more $R_{13}$.

3. The compound of claim 2 wherein:

$R_2$ is —H.

4. The compound of claim 3 wherein:

$R_1$ is —H, halogen, or -T1-Q1;

T1 is absent or C1-10 aliphatic, wherein up to three methylene units of T1 are optionally and independently replaced by G wherein G is —O—, —N(R$_4$)—, or —C(O)—; T1 is optionally and independently substituted with one or more JT1;

Q1 is absent, or a 3-8-membered saturated, partially unsaturated, or fully unsaturated monocyclic ring having 0-3 heteroatoms independently selected from nitrogen, oxygen, and sulfur, or an 8-12 membered saturated, partially unsaturated, or fully unsaturated bicyclic ring system having 0-5 heteroatoms independently selected from nitrogen, oxygen, and sulfur, wherein Q1 is independently optionally and independently substituted with J1;

J1 is —Y1-M1;

Y1 is absent, oxo, or C1-10 aliphatic wherein up to three methylene units of Y1 are optionally and independently replaced with G1 wherein G1 is —N(R$^\$$)—, —O—, —C(O)—, or —S(O)$_2$—, Y1 is optionally and independently substituted with one or more JT1; and M1 is C3-8 cycloaliphatic, 3-8 membered heterocyclyl, 5-6 membered heteroaryl, phenyl, —OR$^\$$, —SR$^\$$, —N(R$^\$$)$_2$, —P(O)R$^\$$, —P(O)$_2$R$^\$$, P(O)(R$^\$$)$_2$, or PO(OR$^\$$)$_2$, wherein M1 is optionally and independently substituted with one or more J; or M1 is absent, —CN, —NO$_2$, or halogen.

5. The compound of claim 4 wherein:

T1 is absent or C1-10 aliphatic wherein up to three methylene units of T1 are optionally and independently replaced by G wherein G is —O—, or —N(R$_4$)—; T1 is optionally and independently substituted with one or more JT1;

Y1 is absent or C1-10 aliphatic wherein up to three methylene units of Y1 are optionally and independently replaced with G1 wherein G1 is —N(R$^\$$)—, —O— —C(O)—, or —S(O)$_2$; Y1 is optionally and independently substituted with one or more JT1; and M1 is C3-8 cycloaliphatic, 3-8 membered heterocyclyl, 5-6 membered heteroaryl, phenyl, —N(R$^\$$)$_2$, or —OR$^\$$; wherein M1 is optionally and independently substituted with one or more J; or M1 is absent, —CN, or halogen.

6. The compound of claim 5 wherein:

each J is independently halogen, C1-6 aliphatic, —NO$_2$, —CN, —N(R$^\$$)$_2$, —OR$^\$$, —C(O)R$^\$$, —C(O)N(O)$_2$, —C(O)$_2$R$^\$$, oxo, or haloC1-4 aliphatic.

7. The compound of claim 6 wherein:

T1 is absent, C1-C10 alkyl, C2-10 alkenyl, or C2-C10 alkynyl wherein up to three methylene units of T1 are optionally and independently replaced by G wherein G is —O—, or —N(R$_4$)—; T1 is optionally and independently substituted with one or more JT1;

Q1 is absent, phenyl, indolyl, quniolyl, isoindolyl, isoquinolyl, indazolyl, cyclobutyl, cyclopentyl, cyclohexyl, cyclohexenyl, cyclopropyl, pyrrolyl, pyrazolyl, imidazolyl, thienyl, benzothienyl, furyl, benzofuryl, piperidinyl, piperizinyl, pyrrolodinyl, pyrazinyl, pyrimidinyl, or pyridyl; wherein Q1 is optionally and independently substituted with J1;

Y1 is absent or C1-10 alkyl group wherein up to three methylene units of Y1 are optionally and independently replaced with G1 wherein G1 is —O—, Y1 is optionally and independently substituted with one or more JT1; and M1 is phenyl, —N(R$^\$$)$_2$, or —OR$^\$$; wherein M1 is optionally and independently substituted with one or more J; or M1 is absent, or —CN.

8. The compound of claim 4 wherein:

$R_1$ is —H, or halogen.

9. The compound of claim 7 wherein ring B is substituted with $R_3$ and independently optionally substituted with $R_{12}'$ and independently and optionally and independently substituted with one or more $R_{12}$ groups.

10. The compound of claim 9 wherein:

Y2 is absent, oxo, or C1-10 aliphatic wherein up to three methylene units of Y2 are independently and optionally replaced with G1' wherein G1' is —N(R$^\$$)—, —O—, —C(O)—, or —S(O)$_2$—, Y2 is optionally and independently substituted with one or more JT2;

M2 is C1-6 aliphatic, C3-8 cycloaliphatic, 3-8 membered heterocyclyl, 5-12 membered heteroaryl, 5-12 membered aryl, —N(R$^\$$)$_2$, —OR$^\$$, —C(O)R$^\$$, —C(O)$_2$R$^\$$, —S(O)R$^\$$, or —S(O)$_2$R$^\$$ wherein M2 is optionally and independently substituted with one or more J; or M2 is absent, —NO$_2$, or —CN; and each J is independently halogen, C1-6 aliphatic, —NO$_2$, —CN, N(R$^\$$)$_2$, —OR$^\$$, —COR$^\$$, —CON(R$^\$$)$_2$, —CO$_2$R$^\$$, oxo or haloC1-4 aliphatic.

11. The compound of claim 10 wherein:

M2 is —OR$^\$$, —N(R$^\$$)$_2$, —C(O)R$^\$$, —C(O)$_2$R R$^\$$, —S(O) R$^\$$, or —S(O)$_2$R$^\$$, pyridyl, pyrazinyl, pyrimidinyl, pyrrolyl, imidazolyl, pyrazolyl, furyl, tetrahydrofuryl, thienyl, tetrahydrothienyl, pyranyl, tetrahydropyranyl, isooxazolyl, piperidinyl, pyrrolidinyl, cyclopentyl, cyclohexyl, cyclopropyl, naphthyl, or phenyl, wherein M2 is optionally and independently substituted with one or more J; or M2 is absent, —N(O)$_2$, or —CN; and each J is independently halogen, C1-6 aliphatic, —NO$_2$, —CN, —N(R$^\$$)$_2$, —OR$^\$$, oxo, or haloC1-4 aliphatic.

12. The compound of claim 1 wherein Q2 is represented by the following structural formula:

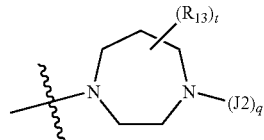

t is 0 or 1; and q is 0 or 1.

13. The compound of claim 12 wherein the compound is represented by a structural formula selected from the group consisting of:

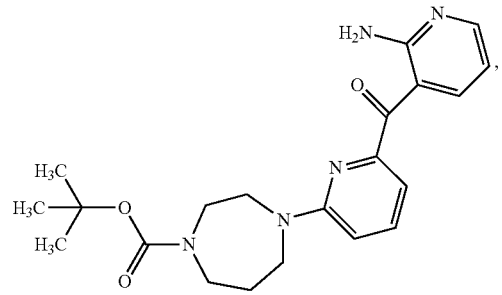

319
-continued
320
-continued
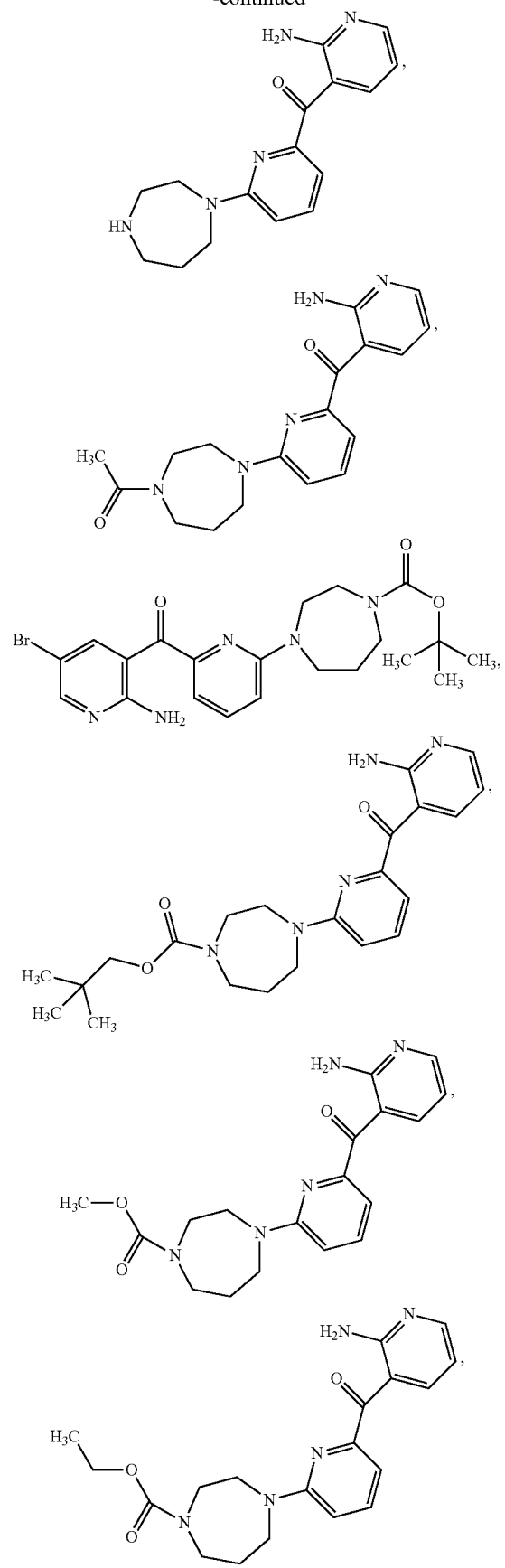
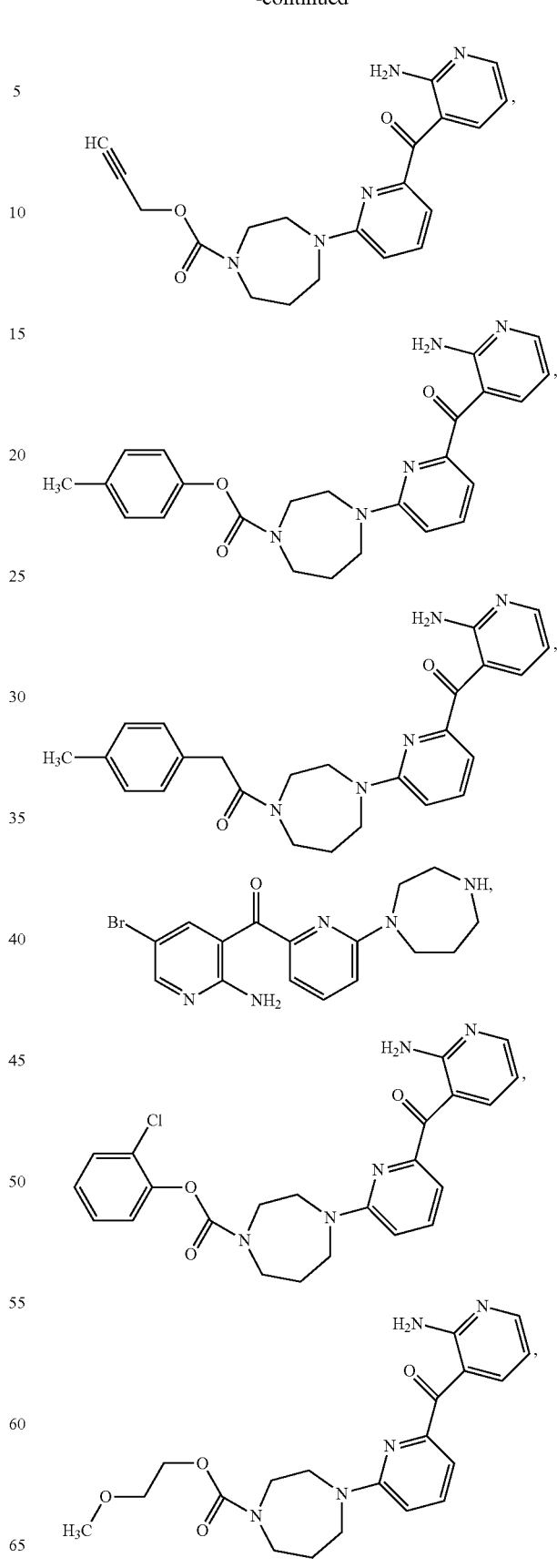

321
-continued
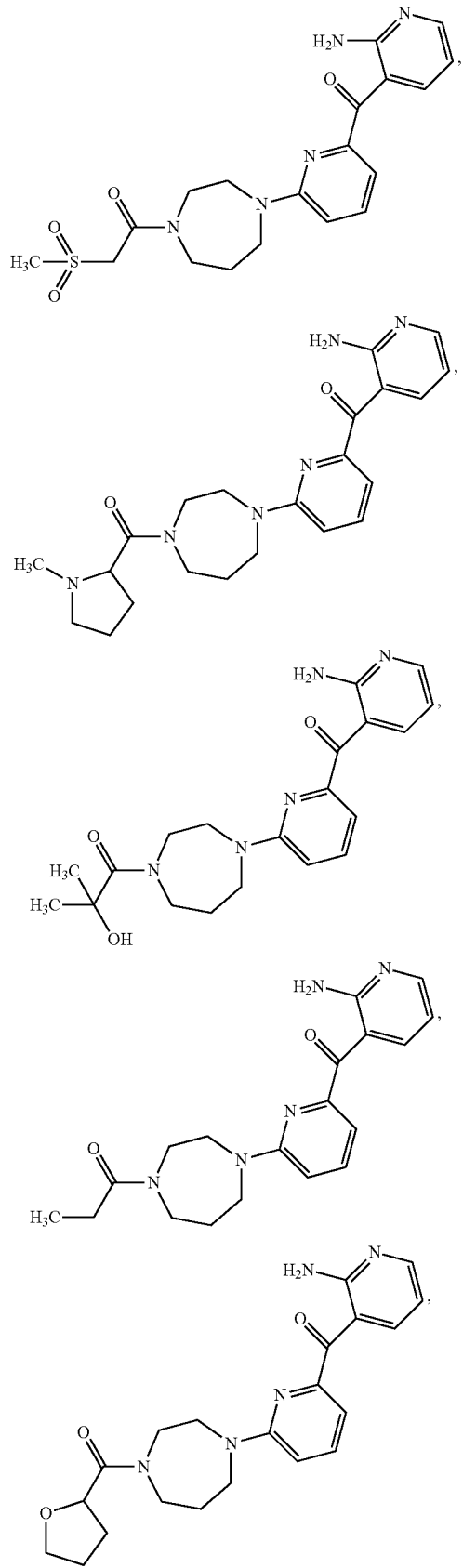
322
-continued
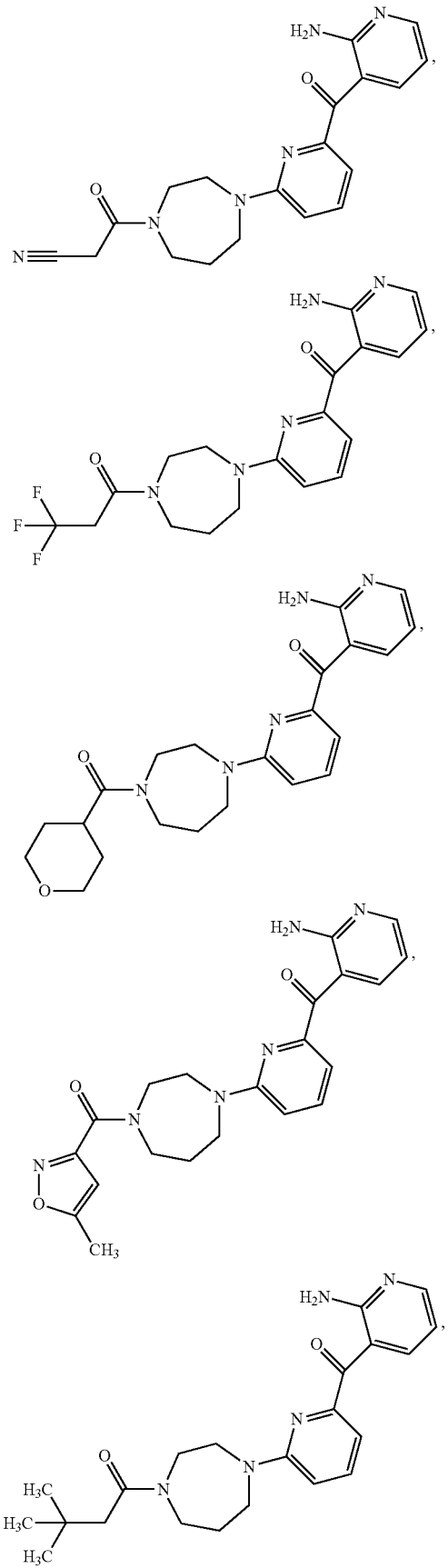

323
-continued
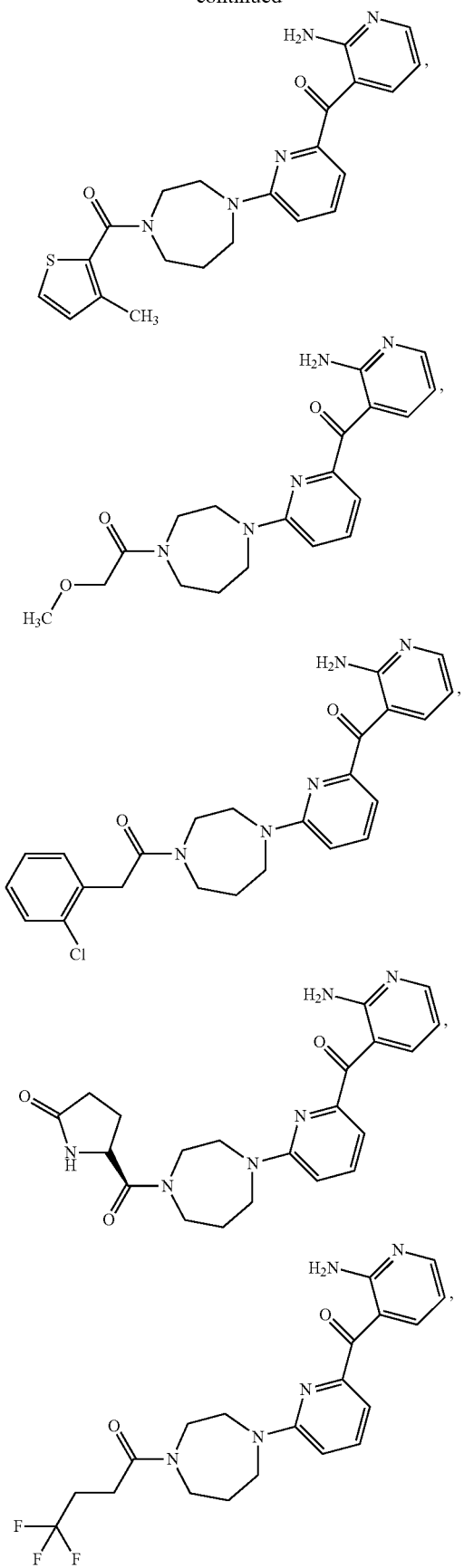
324
-continued
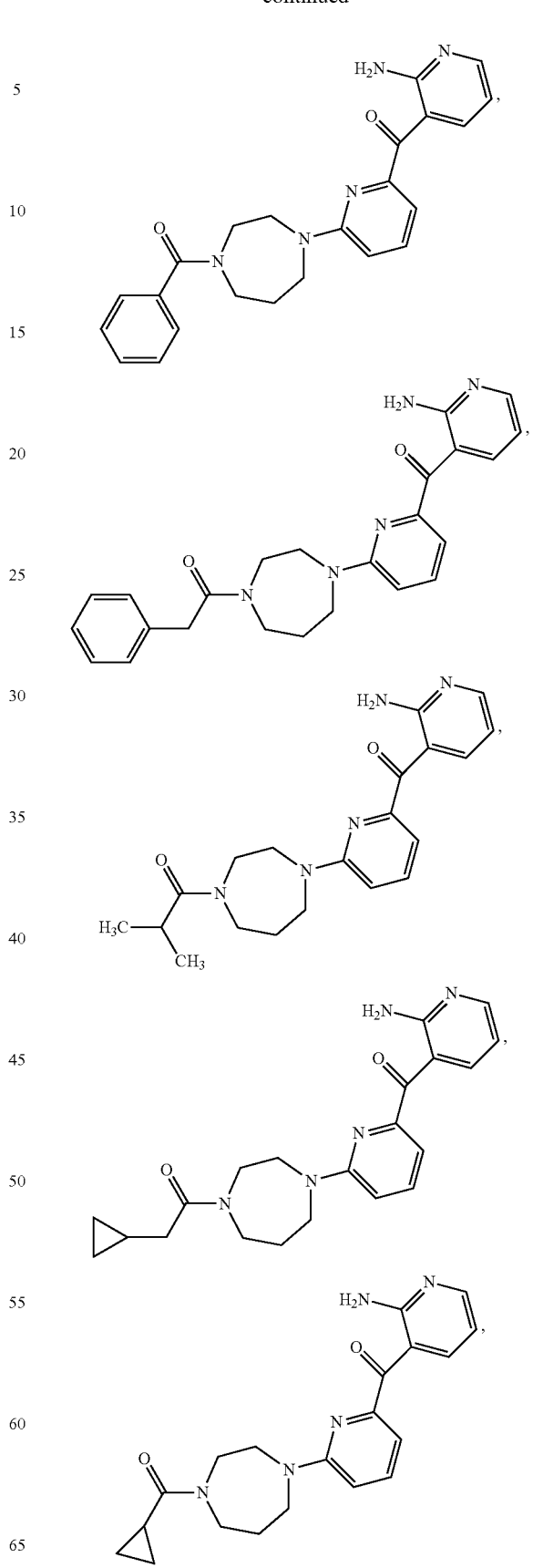

325
-continued
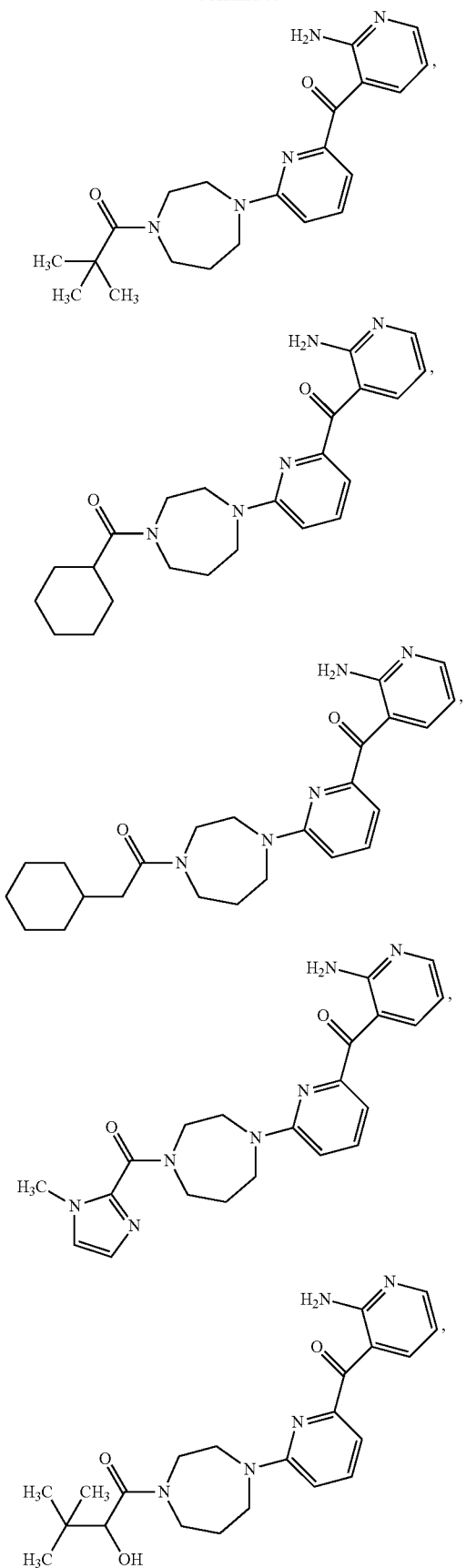
326
-continued
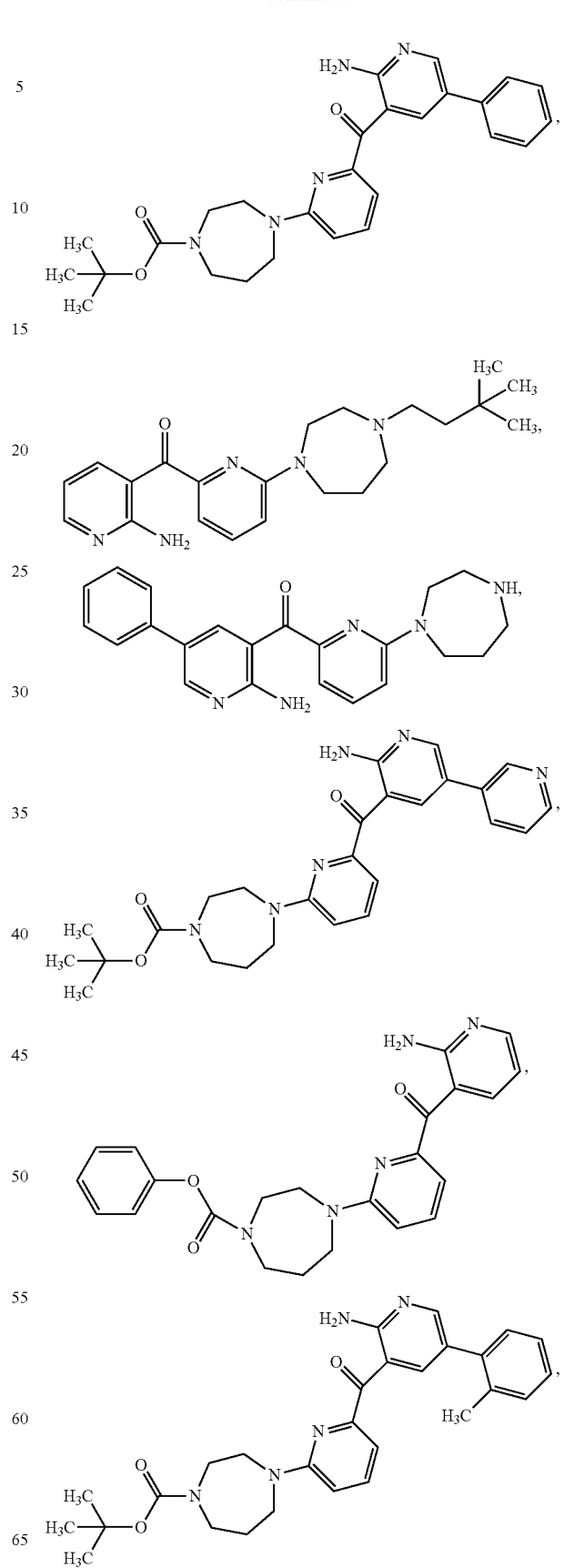

327
-continued
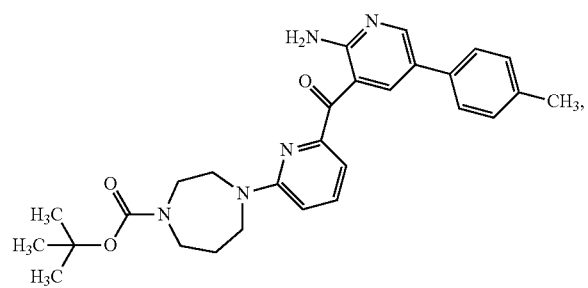
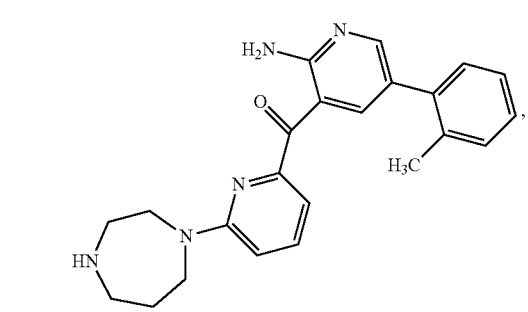
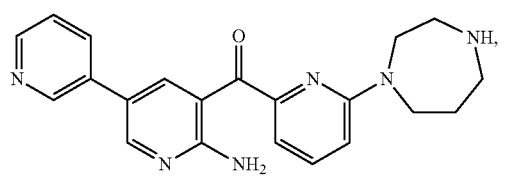
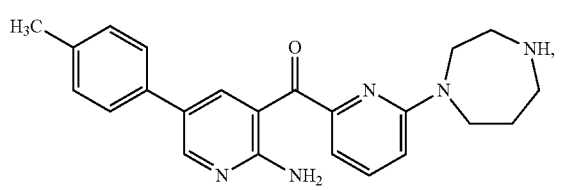
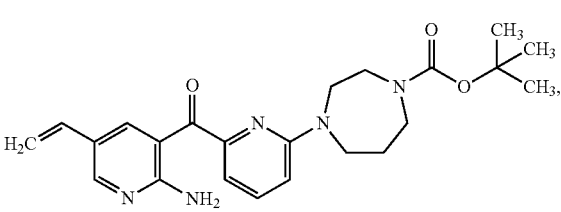
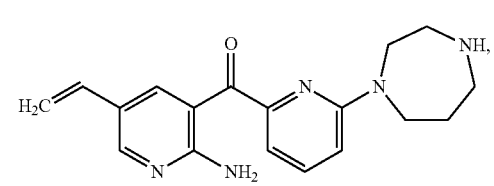
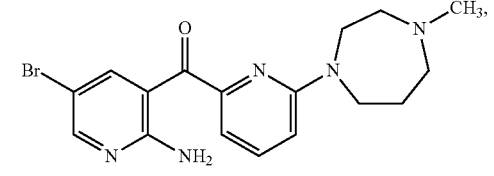
328
-continued
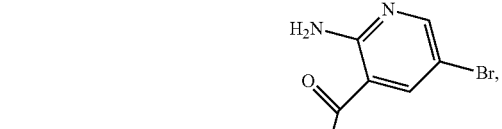
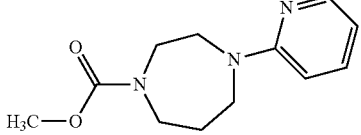
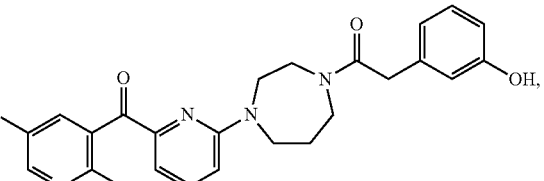
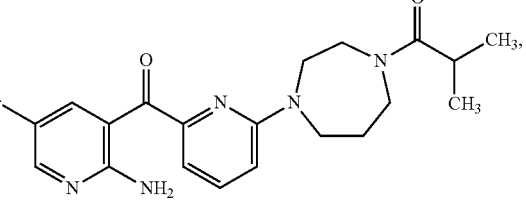
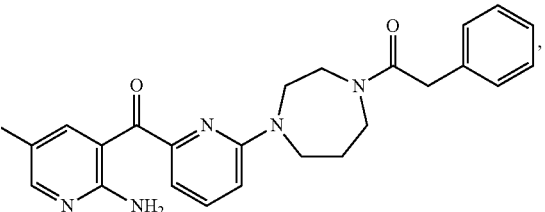
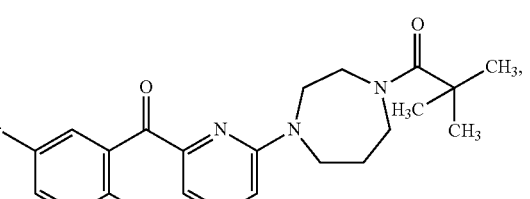
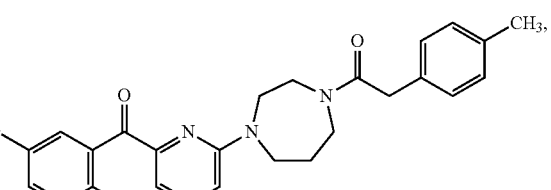
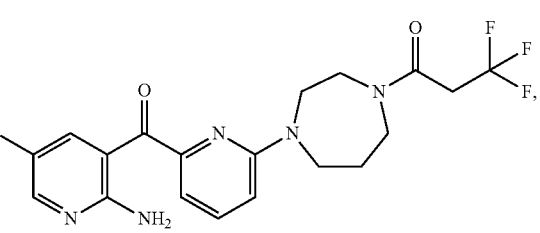

-continued
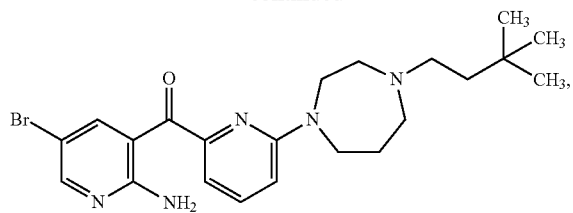
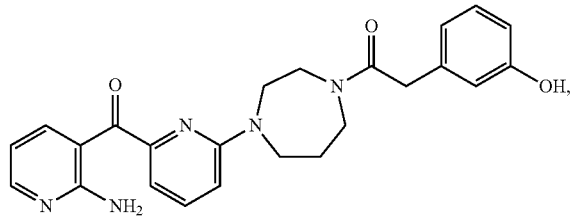
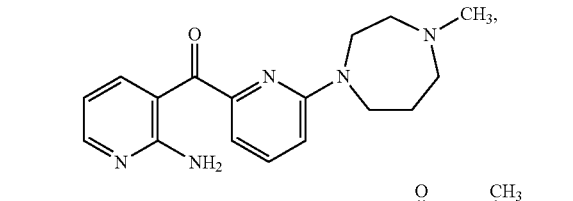
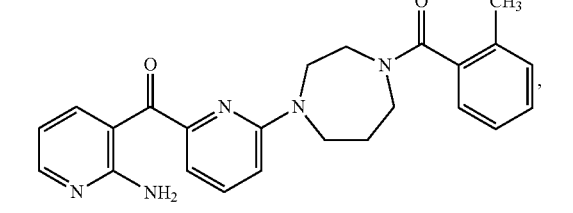
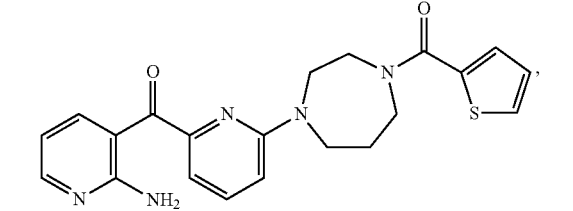
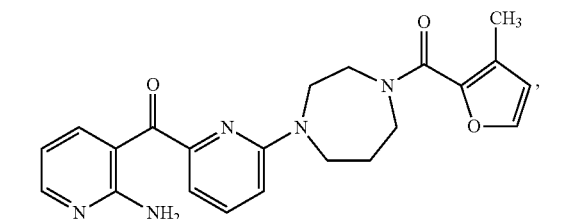
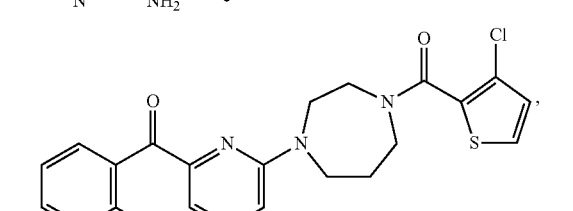
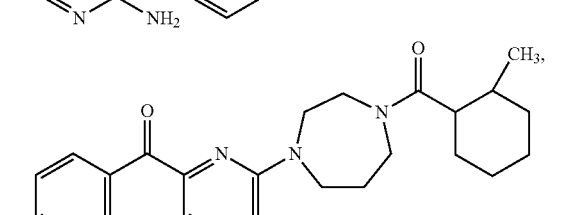
-continued
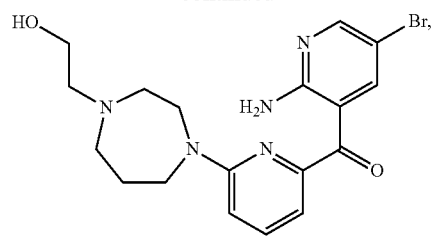
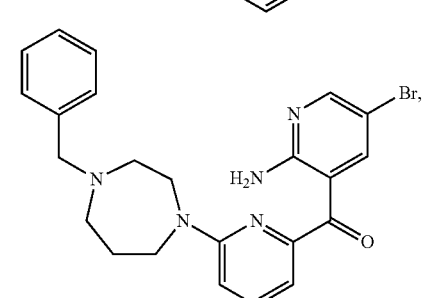
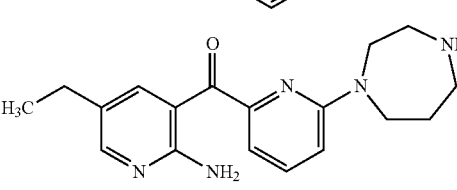
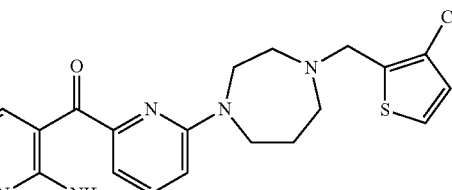
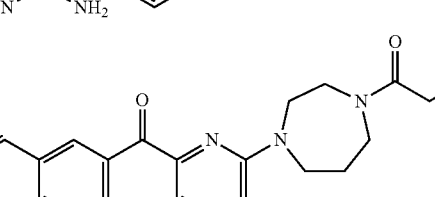
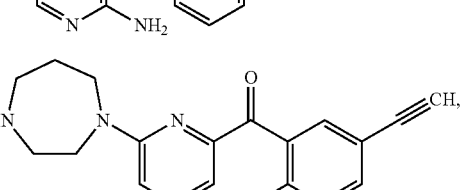
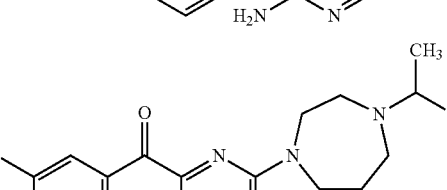
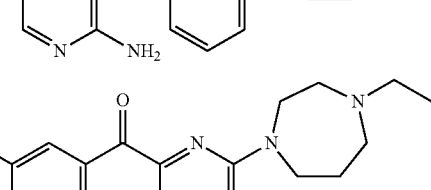
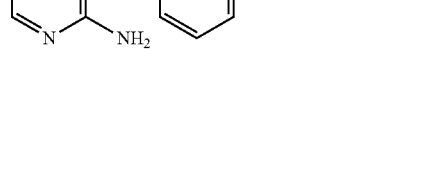

331
-continued
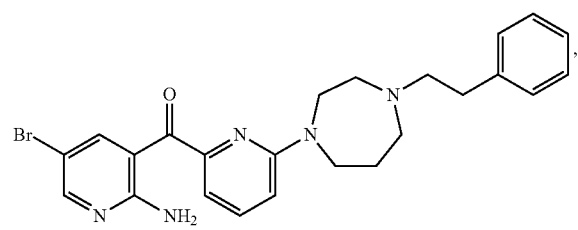
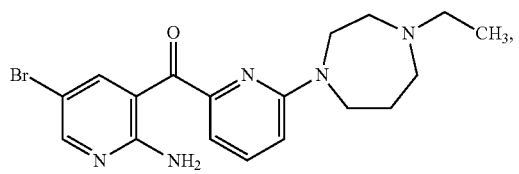
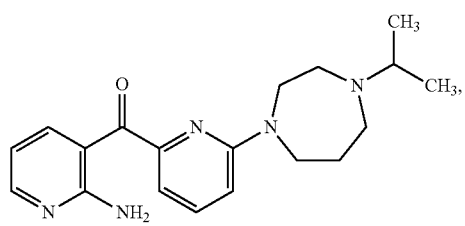
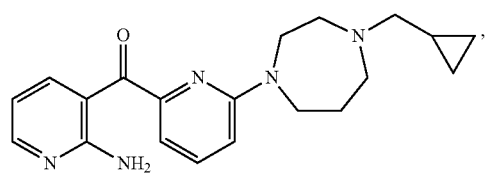
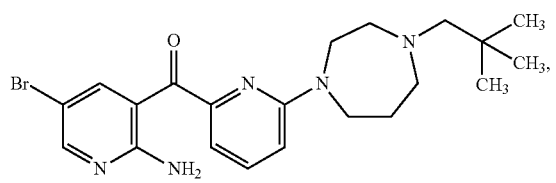
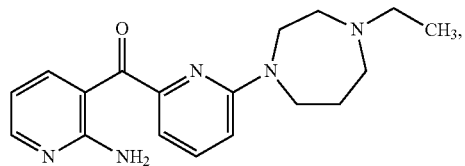
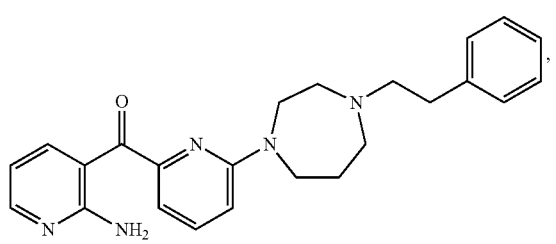
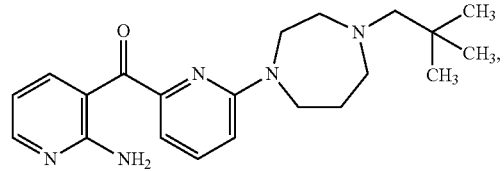
332
-continued
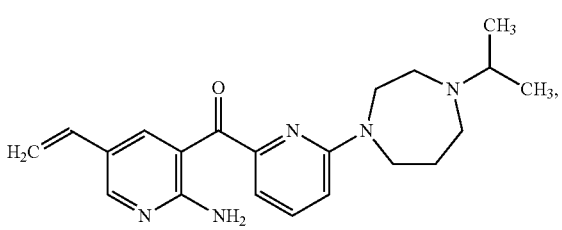
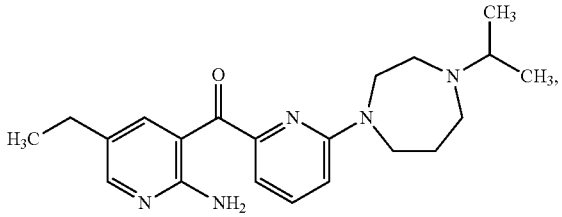
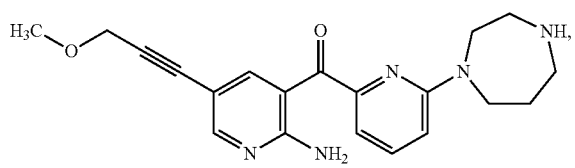
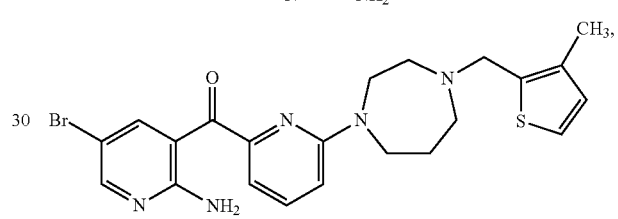
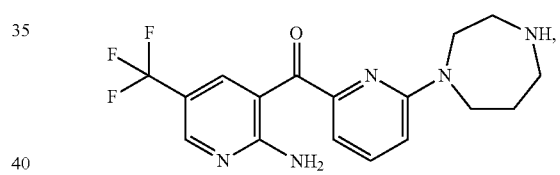
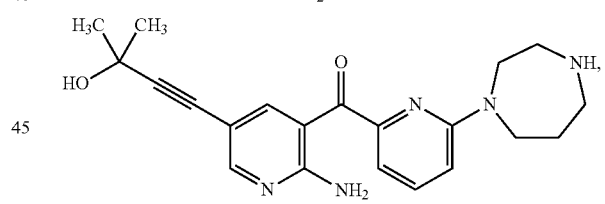
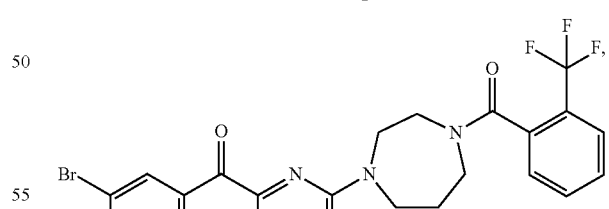
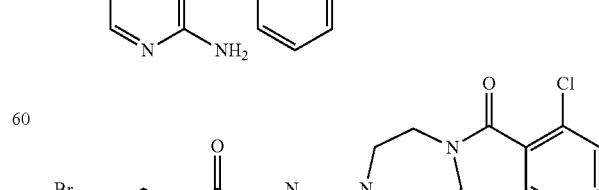
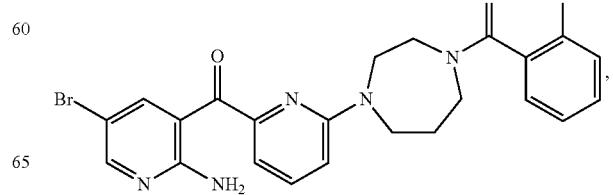

333
-continued
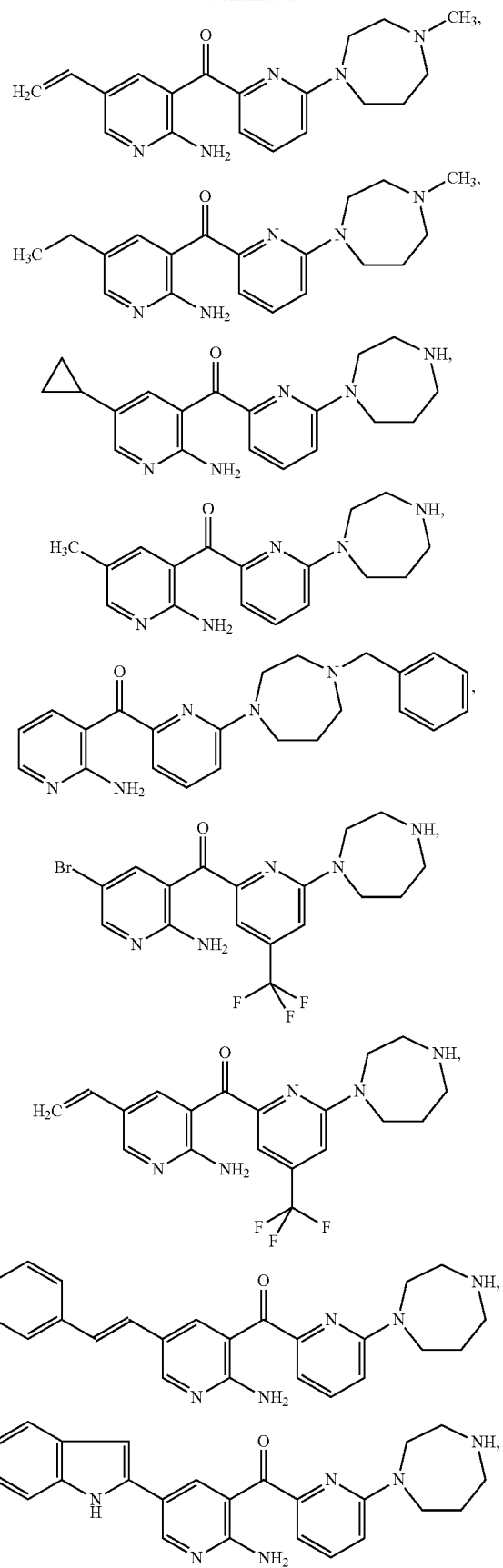
334
-continued
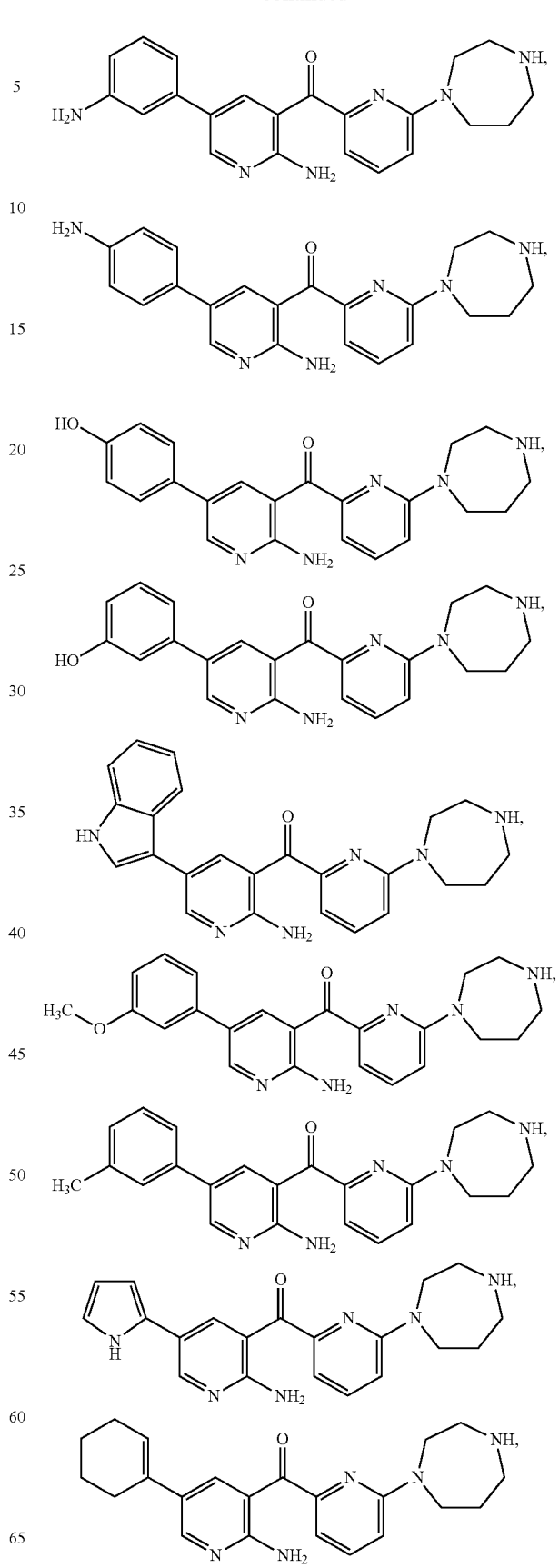

335
-continued
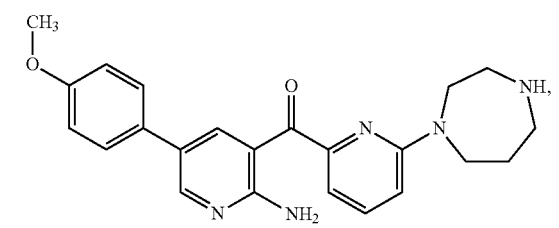
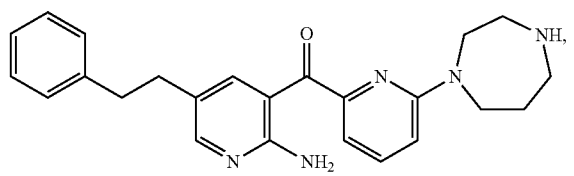
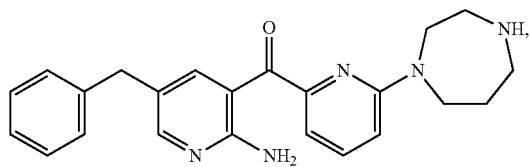
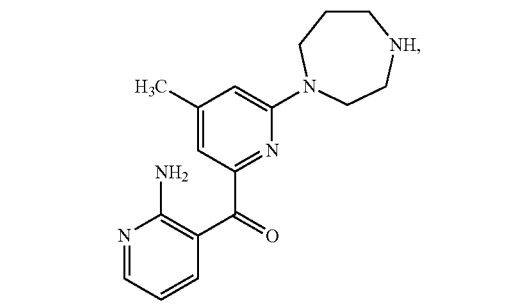
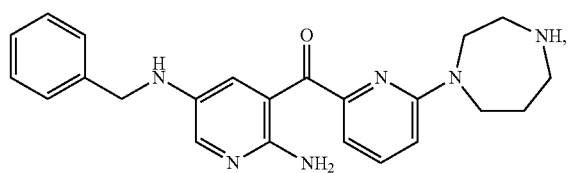
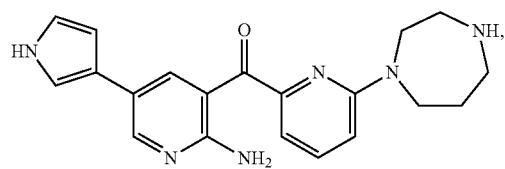
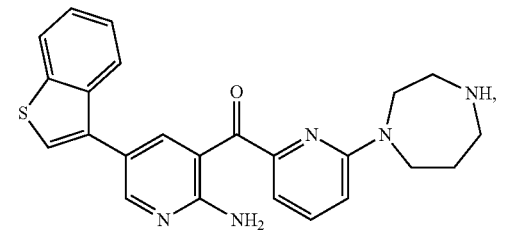
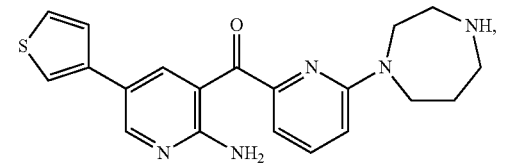
336
-continued
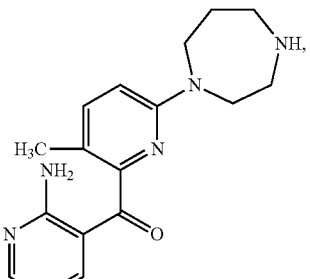
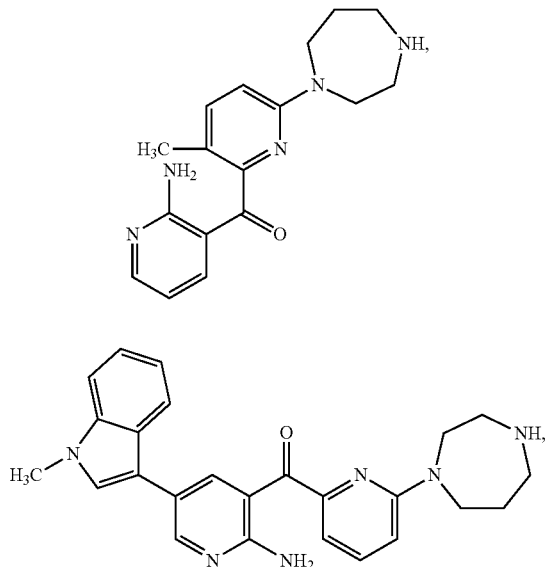
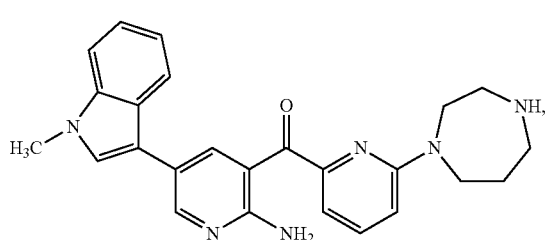
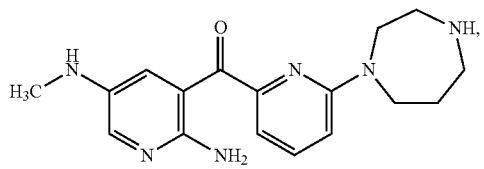
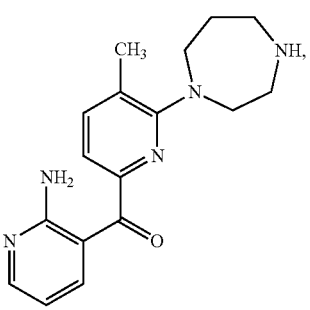
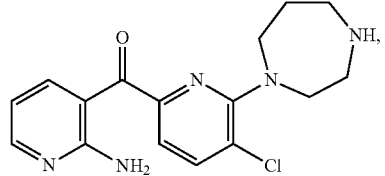
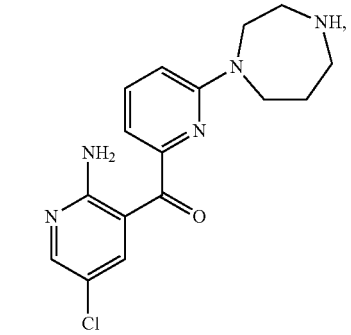

337
-continued
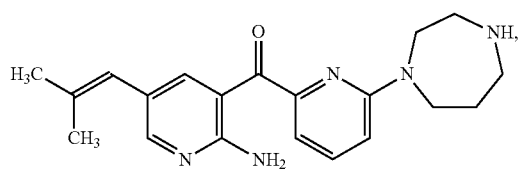
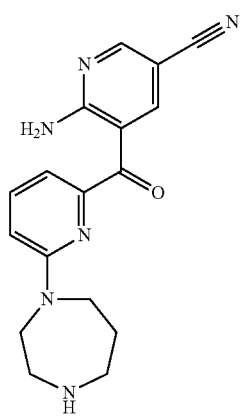
338
-continued
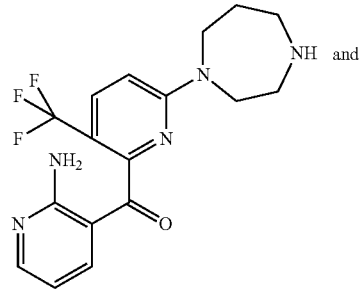
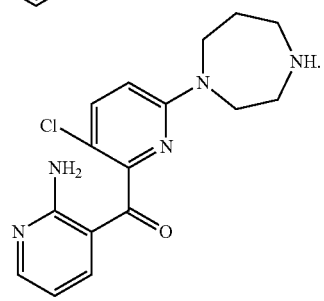
14. A composition comprising a compound of pharmaceutically acceptable salt thereof according to claim 1, and a pharmaceutically acceptable carrier, adjuvant, or vehicle.
* * * * *